US009121855B2

(12) United States Patent
Golding et al.

(10) Patent No.: US 9,121,855 B2
(45) Date of Patent: Sep. 1, 2015

(54) METHOD FOR THE DETECTION OF HIV-1 ANTIBODIES UTILIZING A PEPTIDE CONTAINING A NOVEL GP41 EPITOPE

(75) Inventors: Hana Golding, Rockville, MD (US); Surender Khurana, Haryana (IN)

(73) Assignee: The United States of America, as represented by the Secretary, Department of Health and Human Services, Washington, DC (US)

( * ) Notice: Subject to any disclaimer, the term of this patent is extended or adjusted under 35 U.S.C. 154(b) by 1209 days.

(21) Appl. No.: 12/977,411

(22) Filed: Dec. 23, 2010

(65) Prior Publication Data
US 2013/0143202 A1 Jun. 6, 2013

Related U.S. Application Data

(62) Division of application No. 11/662,370, filed as application No. PCT/US2005/031287 on Sep. 2, 2005, now Pat. No. 7,888,003.

(60) Provisional application No. 60/676,931, filed on May 3, 2005, provisional application No. 60/607,579, filed on Sep. 8, 2004.

(51) Int. Cl.
*G01N 33/68* (2006.01)
*G01N 33/569* (2006.01)
*C07K 14/16* (2006.01)
*C07K 14/005* (2006.01)

(52) U.S. Cl.
CPC .......... *G01N 33/6854* (2013.01); *C07K 14/005* (2013.01); *C07K 14/161* (2013.01); *C07K 14/162* (2013.01); *C07K 14/163* (2013.01); *G01N 33/56988* (2013.01); *C12N 2740/16111* (2013.01); *C12N 2740/16122* (2013.01); *C12N 2740/16222* (2013.01); *C12N 2740/16322* (2013.01); *G01N 2333/162* (2013.01); *G01N 2469/20* (2013.01)

(58) Field of Classification Search
CPC ........... C07K 14/005; G01N 33/56988; G01N 2333/162
See application file for complete search history.

(56) References Cited

U.S. PATENT DOCUMENTS

| | | |
|---|---|---|
| 3,791,932 A | 2/1974 | Schuurs et al. |
| 4,016,043 A | 4/1977 | Schuurs et al. |
| 4,185,084 A | 1/1980 | Mochida et al. |
| 4,243,749 A | 1/1981 | Sadeh et al. |
| 4,313,734 A | 2/1982 | Leuvering |
| 4,373,932 A | 2/1983 | Gribnau et al. |
| 4,401,764 A | 8/1983 | Smith |
| 4,661,444 A | 4/1987 | Li |
| 4,746,631 A | 5/1988 | Clagett |
| 5,156,949 A | 10/1992 | Luciw et al. |
| 5,260,189 A | 11/1993 | Formoso et al. |
| 5,459,060 A | 10/1995 | Cotropia |
| 5,462,852 A | 10/1995 | Arthur et al. |
| 5,476,765 A | 12/1995 | Wang |
| 5,501,985 A | 3/1996 | Baugher et al. |
| 5,563,036 A | 10/1996 | Peterson et al. |
| 5,576,421 A | 11/1996 | Saito et al. |
| 5,580,739 A | 12/1996 | Alizon et al. |
| 5,599,662 A | 2/1997 | Respess |
| 5,627,080 A | 5/1997 | Cheng et al. |
| 5,633,141 A | 5/1997 | Lee et al. |
| 5,637,453 A | 6/1997 | Jehuda-Cohen |
| 5,660,979 A | 8/1997 | Romano et al. |
| 5,679,525 A | 10/1997 | Peterson et al. |
| 5,681,696 A | 10/1997 | Wang |
| 5,691,147 A | 11/1997 | Draetta et al. |
| 5,695,930 A | 12/1997 | Weinstein et al. |
| 5,697,525 A | 12/1997 | O'Reilly et al. |
| 5,698,411 A | 12/1997 | Lucas et al. |
| 5,705,331 A | 1/1998 | Arthur et al. |

(Continued)

FOREIGN PATENT DOCUMENTS

| | | |
|---|---|---|
| CA | 2539325 | 3/2005 |
| EP | 177191 B1 | 9/1986 |

(Continued)

OTHER PUBLICATIONS

Selvey, L. A., et al., 1990, Identification of B-epitopes in the human papillomavirus 18 E7 open reading frame protein, J. Immunol. 145(9):3105-3110.*
Zwick, M. B., et al., 2001, Broadly neutralizing antibodies targeted to the membrane-proximal external region of human immunodeficiency virus type 1 glycoprotein gp41, J. Virol. 75(22):10892-10905.*
Alcaro, M.C., et al., "Synthetic peptides in the diagnosis of HIV infection," Curr. Protein Pept. Sci., 2003, 4(4), 285-290.
Arnold, C., et al., "At least five HIV-1 sequence subtypes (A, B, C, D, A/E) occur in England," Aids Res. Hum. Retroviruses, 1995, 11(3), 427.
Baillou, A., et al., "Fine serotyping of human immunodeficiency virus serotype 1 (HIV-1) and HIV-2 infections by using synthetic oligopeptides representing an immunodominant domain of HIV-1 and HIV2/simian immunodeficiency virus," J. Clin. Microbiol., 1991, 29(7), 1387-1391.
Beristain, C.N., et al., "Evaluation of a dipstick method for the detection of human immunodeficiency virus infection," J. Clin. Lab. Anal., 1995, 9(6), 347-350.
Berzofsky, J.A., et al., "Novel approaches to peptide and engineered protein vaccines for HIV using defined epitopes: advances in 1994-1995," AIDS, 1995, 9(Suppl. A), S143-S157.

(Continued)

*Primary Examiner* — Jeffrey Parkin
(74) *Attorney, Agent, or Firm* — Baker & Hostetler, LLP

(57) ABSTRACT

This invention concerns methods for detecting the presence of an anti-HIV-1 antibody in a biological sample, the method comprising conducting an immunoassay comprising: (a) contacting the biological sample with at least one epitope that is recognized by the anti-HIV-1 antibody, wherein the contacting being under conditions sufficient to permit the anti-HIV-1 antibody if present in the sample to bind to the epitope and form an epitope-anti-HIV-1 antibody complex; (b) contacting the formed epitope-anti-HIV-1 antibody complex with an anti-HIV-1 antibody binding molecule, the contacting being under conditions sufficient to permit the anti- HIV-1 antibody binding molecule to bind to anti-HIV-1 antibody of the formed epitope-anti-HIV-1 antibody complex and form an extended complex; and (c) determining the presence or concentration of the anti-HIV-1 antibody in the biological sample by determining the presence or concentration of the formed extended complex; the epitope being present on a peptide comprising SEQ ID No. 55.

10 Claims, 8 Drawing Sheets

(56) References Cited

U.S. PATENT DOCUMENTS

| | | | |
|---|---|---|---|
| 5,712,385 A | 1/1998 | McDonough et al. | |
| 5,721,095 A | 2/1998 | Chan et al. | |
| 5,747,352 A | 5/1998 | Yan et al. | |
| 5,759,781 A | 6/1998 | Ward et al. | |
| 5,811,526 A | 9/1998 | Davidson | |
| 5,830,641 A | 11/1998 | Montagnier et al. | |
| 5,849,494 A | 12/1998 | Heneine et al. | |
| 5,851,778 A | 12/1998 | Oh et al. | |
| 5,856,088 A | 1/1999 | McDonough et al. | |
| 5,876,935 A | 3/1999 | Pankratz et al. | |
| 5,891,623 A | 4/1999 | Primi | |
| 5,925,513 A | 7/1999 | Primi | |
| 5,928,642 A | 7/1999 | Primi | |
| 5,976,822 A | 11/1999 | Landrum et al. | |
| 6,004,925 A | 12/1999 | Dasseux et al. | |
| 6,008,044 A | 12/1999 | Cotropia | |
| 6,048,685 A | 4/2000 | Alizon et al. | |
| 6,194,221 B1 * | 2/2001 | Rehg et al. | 436/514 |
| 6,245,737 B1 | 6/2001 | Boyd et al. | |
| 6,252,059 B1 | 6/2001 | McDonough et al. | |
| 6,270,959 B1 | 8/2001 | Dekaban et al. | |
| 6,352,826 B1 | 3/2002 | Jehuda-Cohen | |
| 6,399,307 B1 | 6/2002 | Pasloske et al. | |
| 6,429,289 B1 | 8/2002 | Krieger et al. | |
| 6,458,527 B1 | 10/2002 | Luciw et al. | |
| 6,492,104 B1 * | 12/2002 | Cloyd et al. | 435/5 |
| 6,531,276 B1 | 3/2003 | Luciw et al. | |
| 6,534,285 B1 | 3/2003 | Berman et al. | |
| 6,541,609 B2 | 4/2003 | Essex et al. | |
| 6,582,920 B2 | 6/2003 | Yang et al. | |
| 6,586,177 B1 | 7/2003 | Shuber | |
| 6,589,734 B1 | 7/2003 | Kacian et al. | |
| 6,623,920 B1 | 9/2003 | Bee et al. | |
| 6,649,749 B2 | 11/2003 | McDonough et al. | |
| 6,689,879 B2 | 2/2004 | Barnett et al. | |
| 7,101,676 B2 | 9/2006 | Buechter et al. | |
| 7,157,225 B2 | 1/2007 | Charneau et al. | |
| 8,048,431 B2 * | 11/2011 | Haynes | 424/208.1 |
| 2005/0058992 A1 | 3/2005 | Groat et al. | |

FOREIGN PATENT DOCUMENTS

| | | |
|---|---|---|
| EP | 0439077 B1 | 5/2000 |
| GB | 2084317 A | 4/1982 |
| WO | WO90/08162 A1 | 7/1990 |
| WO | WO92/00997 A1 | 1/1992 |
| WO | WO95/33206 A1 | 12/1995 |
| WO | WO01/54701 A1 | 8/2001 |
| WO | WO 03/059262 A2 | 7/2003 |
| WO | WO03/073992 A2 | 9/2003 |
| WO | WO2004/052924 A1 | 6/2004 |

OTHER PUBLICATIONS

Berzofsky, J.A., et al., "Approaches to improve engineered vaccines for human immunodeficiency virus and other viruses that cause chronic infections," Immunol Rev., 1999, 170, 151-172.

Brattegaard, K., et al., "Insensitivity of a synthetic peptide-based test (PEPTI-LAV 1-2) for the diagnosis of HIV infection in African children," AIDS, 1995, 9(6), 656-657.

Brutlag, et al., "Improved sensitivity of biological sequence database searches," Comp. App. Biosci., 1990, 6, 237-245.

Buckler, C.E., et al., Sequence P12493, 1988, 5 pages.

Chan, D.C., et al., "Core structure of GP41 from the HIV envelope glycoprotein," Cell, 1997, 89(2), 263-273.

Cho, M.W., "Subunit protein vaccines: theoretical and principal considerations for HIV-1," Curr. Mol. Med., 2003, 3(3), 243-263.

Choppin, J., et al., "Characteristics of HIV-1 nef regions containing multiple CD8+T cell epitopes: wealth of HLA-binding motifs and sensitivity to proteasome degradation," J. Immunol., 2001, 166(10), 6164-6169.

Costa, G.L., et al., "Polishing with T4 or pfu polymerase increases the efficiency of cloning of PCR fragments," Nucleic Acids Res., 1994, 22(12), 2423.

Döpel, S.H., et al., "Comparison of four anti-HIV screening assays which belong to different test generations," Eur. J. Clin. Chem. Clin. Biochem., 1991, 29, 331-337.

Döpel, S.H., et al., "Fine mapping of an immunodominant region of the transmembrane protein of the human immunodeficiency virus (HIV-1)," J. Virol. Meth., 1990, 25, 167-178.

Fang, H., et al., "Unique insertion sequence and pattern of CD4 expression in variants selected with immunotoxins from human immunodeficiency virus type 1-infected T cells," J. Virol., 1995, 69(1), 75-81.

Gnann, J.W., Jr., et al., "Custom-designed synthetic peptide immunoassays for distinguishing HIV type 1 and type 2 infections," Methods Enzymol., 1989, 178, 693-715.

Gombert, F.O., et al., "Antigenic epitopes of NEF proteins from different HIV-1 strains as recognized by sera from patients with manifest and latent HIV infection," Virology, 1990, 176, 458-466.

Gueye-Ndiaye, A., et al., "Cost-effictive diagnosis of HIV-1 and HIV-2 by recombinant-expressed env peptide (566/996) dot-blot analysis," AIDS, 1993, 7(4), 475-481.

Ho, D et al; Geneseq [Online] Sep. 25, 2001; HIV Nef-1 CTL epitope; XP002451124; retrieved from EBI accession No. GSP:AAB98916.

Ishikawa, E., et al., "Enzyme-labeling of antibodies and their fragments for enzyme immunoassay and immunohistochemical staining," J. Immunoassay, 1983, 49(3), 209-327.

Manocha, M., et al, "Comparing modified and plain peptide linked enzyme immunosorbent assay (ELISA) for detection of human immunodeficiency virus type-1 (HIV-1) and type-2 (HIV-2) antibodies," Immunol. Lett., 2003, 85(3), 275-278.

McDougal, J.S., et al., "Binding of HTLV-III/LAV TO T4+T cells by a complex of the 110K viral protein and the T4 molecule," Science, 1986, 231, 382-385.

Sabatier, J.M., et al., "Use of synthetic peptides for the detection of antibodies against the nef regulating protein in sera of HIV-infected patients," AIDS, 1989, 3(4), 215-220.

Schneider, T., et al., "Epitopes of the HIV-1-negative factor (nef) reactive with murine monoclonal antibodies and human HIV-1-positive sera," Aids Res. Hum. Retroviruses, 1991, 7(1), 37-44.

Schnölzer, M., et al., "Constructing proteins by dovetailing unprotected synthetic peptides: backbone-engineering HIV protease," Science, 1992, 256(5054), 221-225.

Smith, R.S., et al., "Synthetic peptide assays to detect human immunodeficiency virus types 1 and 2 in seropositive individuals," Arch Pathol. Lab Med., 1990, 114(3), 254-258.

Broliden et al., "Specific synthetic peptides for detection of and discrimination between HIV-1 and HIV-2 infection," J. Acquir. Immune Defic. Syndr., 1991, 4(10), 952-958.

Fack et al., "Epitope mapping by phage display: random versus gene-fragment libraries," J. Immunol. Methods, Aug. 1997, 206(1-2), 43-52.

Ngai et al., "Protein A antibody-capture ELISA (PACE): an ELISA format to avoid denaturation of surface-adsorbed antigens," J. Immunol. Methods, Feb. 1993, 158(2), 267-276.

Niedrig et al., "Characterization of murine monoclonal antibodies directed against the core proteins of human immunodeficiency virus types 1 and 2," J. Virol., Aug. 1991, 65(8), 4529-4533.

Ostrowski et al., "Detection assays for HIV proteins," Curr. Protocols Immunol., John Wiley & Sons, Inc., 2005, Unit 12.5 (Supplement 70), pp. 12.5.1-12.5.23.

Ribeiro-Rodrigues et al., "Performance Characteristics of a Rapid New Immunochromatographic Test for Detection of Antibodies to Human Immunodeficiency Virus," Clin. Diagn. Lab. Immunol., Mar. 2003, 10(2), 303-307.

Thongcharoen et al., "Immunoglobulin G antibody capture enzyme-linked immunosorbent assay: a versatile assay for detection of anti-human immunodeficiency virus type 1 and 2 antibodies in body fluids," J. Clin. Microbiol., Dec. 1992, 30(12), 3288-3289.

Sprengers et al., "A Micro-Elisa System for the Detection of Both Anti-HIV-1 and Anti-HIV-2 Antibodies", Journal of Immunological Methods, 1991, 139(1), 77-82.

* cited by examiner (c) p6

(d) gp41

(a) MULTIPLE TRIALS

(b) VAX-003

(c) VAX-004

METHOD FOR THE DETECTION OF HIV-1 ANTIBODIES UTILIZING A PEPTIDE CONTAINING A NOVEL GP41 EPITOPE

CROSS-REFERENCE TO RELATED APPLICATIONS

This application is a divisional application of U.S. patent application Ser. No. 11/662,370, filed Jan. 24, 2008, which is the National Stage of International Application No. PCT/US2005/031287, filed Sep. 2, 2005, which claims the benefit of the filing date of U.S. Provisional Application No. 60/607,579, filed Sep. 8, 2004, and U.S. Provisional Patent Application No. 60/676,931, filed May 3, 2005. The entire contents of these patent applications are hereby incorporated by reference.

FIELD OF THE INVENTION

This invention relates to compositions and methods for the detection of immunodeficiency virus infection, especially human immunodeficiency virus-1 (HIV-1) infection. The invention particularly concerns compositions and methods that may be used in HIV vaccine recipients whose sera may contain vaccine-generated anti-HIV-1 antibodies.

BACKGROUND OF THE INVENTION

The human immunodeficiency virus (HIV) is a pathogenic retrovirus (Varmus, H. (1988) "RETROVIRUSES," Science 240: 1427-1439; Cowley S. (2001) "THE BIOLOGY OF HIV INFECTION" Lepr Rev. 72(2):212-20). HIV-1 is the causative agent of acquired immune deficiency syndrome (AIDS) and related disorders (Gallo, R. C. et al. (1983) "Isolation of human T-cell leukemia virus in acquired immune deficiency syndrome (AIDS)," Science 220(4599):865-7; Barre-Sinoussi, F. et al. "ISOLATION OF A T-LYMPHOTROPIC RETROVIRUS FROM A PATIENT AT RISK FOR ACQUIRED IMMUNE DEFICIENCY SYNDROME (AIDS)," (1983) Science 220:868-870; Gallo, R. et al. (1984) "FREQUENT DETECTION AND ISOLATION OF CYTOPATHIC RETROVIRUSES (HTLV-III) FROM PATIENTS WITH AIDS AND AT RISK FOR AIDS," Science 224:500-503; Teich, N. et al. (1984) "RNA TUMOR VIRUSES," Weiss, R. et al. (eds.) Cold Spring Harbor Press (NY) pp. 949-956).

Since 1987, more than 25,000 individuals have received immunizations with human immunodeficiency virus (HIV) preventive vaccines. Currently, most of the HIV vaccine candidates are complex products containing multiple viral genes or proteins. Prime-boost strategies are under way to optimize cellular and humoral immune responses. Consequently, vaccine recipients' sera are often reactive in licensed HIV sero-detection assays, generating patterns indistinguishable from HIV-infected individuals (Ackers, M. L. et al. (2003) "HUMAN IMMUNODEFICIENCY VIRUS (HIV) SEROPOSITIVITY AMONG UNINFECTED HIV VACCINE RECIPIENTS," J Infect Dis 187:879-986; Pitisuttithum, P. et al. (2003) "SAFETY AND IMMUNOGENICITY OF COMBINATIONS OF RECOMBINANT SUBTYPE E AND B HUMAN IMMUNODEFICIENCY VIRUS TYPE 1 ENVELOPE GLYCOPROTEIN 120 VACCINES IN HEALTHY THAI ADULTS," J Infect Dis 188:219-227; Chuenchitra, T. et al. (2003) "LONGITUDINAL STUDY OF HUMORAL IMMUNE RESPONSES IN HIV TYPE 1 SUBTYPE CRF01_AE (E)-INFECTED THAI PATIENTS WITH DIFFERENT RATES OF DISEASE PROGRESSION," AIDS Res Hum Retroviruses 19:293-305; Schwartz, D. H. et al. (1995) "UTILITY OF VARIOUS COMMERCIALLY AVAILABLE HUMAN IMMUNODEFICIENCY VIRUS (HIV) ANTIBODY DIAGNOSTIC KITS FOR USE IN CONJUNCTION WITH EFFICACY TRIALS OF HIV-1 VACCINES," Clin Diagn Lab Immunol 2, 268-271). This will have a negative impact on future prophylactic vaccine trials, in which early detection of HIV infections is of paramount importance. Furthermore, long-term HIV seropositivity will exclude vaccine trial participants from the pool of blood and plasma donors, and will contribute to a plethora of socio-economic harms including denied employment, health insurance, travel, immigration, and recruitment to the armed forces (Belshe, R. B. et al. (1994) "INTERPRETING HIV SERODIAGNOSTIC TEST RESULTS IN THE 1990S: SOCIAL RISKS OF HIV VACCINE STUDIES IN UNINFECTED VOLUNTEERS," NIAID AIDS Vaccine Clinical Trials Group. Ann Intern Med 121:584-589; Allen, M. et al. (2001) "TRIAL-RELATED DISCRIMINATION IN HIV VACCINE CLINICAL TRIALS. AIDS RES HUM RETROVIRUSES," 17:667-674). Therefore, the prospect of seroconversion could deter potential trial participants and severely curtail recruitment into large scale trials around the globe (Gross, M. et al. (1996) "INTEREST AMONG GAY/BISEXUAL MEN IN GREATER BOSTON IN PARTICIPATING IN CLINICAL TRIALS OF PREVENTIVE HIV VACCINES," J Acquir Immune Defic Syndr Hum Retrovirol 12:406-412; Sheon, A. R. et al. (1998) "PREVENTING DISCRIMINATION AGAINST VOLUNTEERS IN PROPHYLACTIC HIV VACCINE TRIALS: LESSONS FROM A PHASE II TRIAL," J Acquir Immune Defic Syndr Hum Retrovirol 19:519-526; Koblin, B. A. et al. (1998) "READINESS OF HIGH-RISK POPULATIONS IN THE HIV NETWORK FOR PREVENTION TRIALS TO PARTICIPATE IN HIV VACCINE EFFICACY TRIALS IN THE UNITED STATES," Aids 12:785-793. Currently, there is no HIV detection assay that differentiates between vaccine generated antibodies and those produced after true HIV infection during HIV vaccine trials.

HIV-2 (also known as the West African AIDS Virus) is closely related to the simian immunodeficiency virus, and infected individuals are found primarily in West Africa (Smith, R. S. et al. (1990) "SYNTHETIC PEPTIDE ASSAYS TO DETECT HUMAN IMMUNODEFICIENCY VIRUS TYPES 1 AND 2 IN SEROPOSITIVE INDIVIDUALS," Arch Pathol Lab Med. 114(3):254-258; Baillou, A. et al. (1991) "FINE SEROTYPING OF HUMAN IMMUNODEFICIENCY VIRUS SEROTYPE 1 (HIV-1) AND HIV-2 INFECTIONS BY USING SYNTHETIC OLIGOPEPTIDES REPRESENTING AN IMMUNODOMINANT DOMAIN OF HIV-1 AND HIV-2/SIMIAN IMMUNODEFICIENCY VIRUS," J Clin Microbiol. 29(7):1387-1391).

HIV acts to compromise the immune system of infected individuals by targeting and infecting the CD-4$^+$ T lymphocytes that would otherwise be the major proponents of the recipient's cellular immune system response (Dalgleish, A. et al. (1984) "THE CD4 (T4) ANTIGEN IS AN ESSENTIAL COMPONENT OF THE RECEPTOR FOR THE AIDS RETROVIRUS," Nature 312: 767-768, Maddon et al. (1986) "THE T4 GENE ENCODES THE AIDS VIRUS RECEPTOR AND IS EXPRESSED IN THE IMMUNE SYSTEM AND THE BRAIN," Cell 47:333-348; McDougal, J. S. et al. (1986) "BINDING OF HTLV-III/LAV TO T4+ T CELLS BY A COMPLEX OF THE 110K VIRAL PROTEIN AND THE T4 MOLECULE," Science 231: 382-385). HIV infection is pandemic and HIV-associated diseases represent a major world health problem.

Infection of cells by HIV-1 requires membrane attachment of the virion and subsequent fusion of the viral and cellular membranes. The fusion process is mediated by the viral outer envelope glycoprotein complex (gp120/gp41) and target cell receptors (McGaughey, G. B. et al. (2004) "PROGRESS TOWARDS THE DEVELOPMENT OF A HIV-1 GP41-DIRECTED VACCINE," Curr HIV Res. 2(2):193-204). The envelope glycoprotein is synthesized as a precursor protein (gp160) that is proteolytically cleaved into two non-covalently associated protein subunits, a surface subunit (gp120) and a transmembrane subunit (gp41). The gp120 envelope protein is responsible for binding to the CD4 cell-surface receptor and a chemokine co-receptor, CCR5 or CXCR4. Following receptor binding, the membrane-anchored gp41 mediates fusion of the viral and target cell membranes. The gp41 ectodomain contains a hydrophobic, glycine-rich fusion peptide (amino acids 512-527) at the amino terminus that is essential for membrane fusion (numbering based on HXB2 gp160 variant as described in Chan, D. C. et al. (1997) "CORE STRUCTURE OF GP41 FROM THE HIV ENVELOPE GLYCOPROTEIN," Cell 89(2):263-273). Two 4,3 hydrophobic repeat regions following the fusion peptide are defined by a heptad repeat (abcdefg)n, where the residues occupying the a and d positions are predominantly hydrophobic. The two heptad repeat regions are referred to as the N36 (residues 546-581) and C34 (residues 628-661) peptides. A loop region containing a disulfide linkage separates the two heptad repeat regions. The region of the gp41 ectodomain proximal to the viral membrane is abundant in the amino acid tryptophan (amino acids 665-683) and has been shown to be critical for the membrane fusion mechanism of HIV-1. Gp41 exists in two distinct conformations, a native or non-fusogenic state and a fusion-active state (fusogenic state) (McGaughey, G. B. et al. (2004) "PROGRESS TOWARDS THE DEVELOPMENT OF A HIV-1 GP41-DIRECTED VACCINE," Curr HIV Res. 2(2):193-204). On the surface of free virions, gp41 exists in the native state with the N-terminal fusion peptide largely inaccessible. Following interaction of the gp120/gp41 complex with cell-surface receptors, gp41 undergoes a series of conformational changes leading to the fusion-active conformation (Chan, D. C. et al. (1998) HIV ENTRY AND ITS INHIBITION," Cell 93(5):681-684). The transition from the native non-fusogenic to fusion-competent state proceeds through a nascent species termed the prehairpin intermediate. In this transient conformation, the N- and C-terminal regions of gp41 become separated; the N-terminal fusion peptide is inserted into the target cell membrane and the C-terminal region is anchored to the viral membrane. The prehairpin intermediate ultimately folds into the fusion-active conformation bringing the viral and target membranes into proximity allowing viral entry into the target cell (Chan, D. C. et al. (1998) HIV ENTRY AND ITS INHIBITION," Cell 93(5):681-684).

The detection of HIV infection may be accomplished by either identifying viral proteins in the sera of infected individuals, by identifying viral nucleic acids in plasma or cells, or by detecting host antibodies that are produced by such individuals in response to viral infection. Strategies involving the detection of viral proteins are complicated by the low levels of such proteins during HIV infection, and by high assay cost. Thus, the detection of HIV infection is typically accomplished by detecting host anti-HIV antibodies (Manocha, M. et al. (2003) "COMPARING MODIFIED AND PLAIN PEPTIDE LINKED ENZYME IMMUNOSORBENT ASSAY (ELISA) FOR DETECTION OF HUMAN IMMUNODEFICIENCY VIRUS TYPE-1 (HIV-1) AND TYPE-2 (HIV-2) ANTIBODIES," Immunol Lett. 85(3):275-278). Such detection is however, complicated by the etiology of HIV infection, in which a significant initial "eclipse" period precludes detection of elicited antibodies (Mortimer, P. P. (1991) "THE FALLIBILITY OF HIV WESTERN BLOT," Lancet 11:286-286), and by persistent false positive results (Gnann, J. W. Jr. et al. (1989) "CUSTOM-DESIGNED SYNTHETIC PEPTIDE IMMUNOASSAYS FOR DISTINGUISHING HIV TYPE 1 AND TYPE 2 INFECTIONS," Methods Enzymol. 178:693-714). Due to these problems, more sensitive and expensive tests, such as the Western blot are often needed to confirm positive screening test results or to detect low level of circulating virus. However, Western blot analyses sometimes give indeterminate results so that a combination of screening tests (ELISA or Rapid tests) is required to confirm the diagnosis (Mortimer, P. P. (1991) "THE FALLIBILITY OF HIV WESTERN BLOT," Lancet 11:286-286; Brattegaard, K. et al. (1995) "INSENSITIVITY OF A SYNTHETIC PEPTIDE-BASED TEST (PEPTI-LAV 1-2) FOR THE DIAGNOSIS OF HIV INFECTION IN AFRICAN CHILDREN," AIDS 9(6):656-657). Additionally, different HIV proteins are expressed at different times during infection. For example, the env-gene products of HIV have been found to induce an immune response that precedes the immune response of HIV's gag-related gene products (Döpel, S. H. et al. (1991) "COMPARISON OF FOUR ANTI-HIV SCREENING ASSAYS WHICH BELONG TO DIFFERENT TEST GENERATIONS," Eur. J. Clin. Chem. Clin. Biochem. 29:331-337).

The most common screening method for the diagnosis of infection with human immunodeficiency virus (HIV) is the detection (by sandwich ELISA) of virus-specific antibodies elicted by infected individuals in response to the infection (Döpel, S. H. et al. (1991) "COMPARISON OF FOUR ANTI-HIV SCREENING ASSAYS WHICH BELONG TO DIFFERENT TEST GENERATIONS," Eur. J. Clin. Chem. Clin. Biochem. 29:331-337; Manocha, M. et al. (2003) "COMPARING MODIFIED AND PLAIN PEPTIDE LINKED ENZYME IMMUNOSORBENT ASSAY (ELISA) FOR DETECTION OF HUMAN IMMUNODEFICIENCY VIRUS TYPE-1 (HIV-1) AND TYPE-2 (HIV-2) ANTIBODIES," Immunol Lett. 85(3):275-278; Alcaro, M. C. et al. (2003) "SYNTHETIC PEPTIDES IN THE DIAGNOSIS OF HIV INFECTION," Curr Protein Pept Sci. 4(4):285-290; Beristain, C. N. et al. (1995) "EVALUATION OF A DIPSTICK METHOD FOR THE DETECTION OF HUMAN IMMUNODEFICIENCY VIRUS INFECTION," J. Clin. Lab. Anal. 9(6):347-350). "First generation" assays used purified viral proteins obtained from infected cells to bind, and identify, such antibodies. However, since diagnostically relevant viral proteins, such as those encoded by the HIV-1 env gene were difficult to obtain in large quantities, "second generation" assays were soon developed that employed recombinantly produced HIV antigens.

Unfortunately, the use of such recombinant products requires extensive protein purification in order to avoid false positive results. Thus, it has been proposed that synthetic peptides be used to bind to and detect HIV-1 antibodies (Döpel, S. H. et al. (1991) "COMPARISON OF FOUR ANTI-HIV SCREENING ASSAYS WHICH BELONG TO DIFFERENT TEST GENERATIONS," Eur. J. Clin. Chem. Clin. Biochem. 29:331-337; Manocha, M. et al. (2003) "COMPARING MODIFIED AND PLAIN PEPTIDE LINKED ENZYME IMMUNOSORBENT ASSAY (ELISA) FOR DETECTION OF HUMAN IMMUNODEFICIENCY VIRUS TYPE-1 (HIV-1) AND TYPE-2 (HIV-2) ANTIBODIES," Immunol Lett. 85(3):275-278; Alcaro, M. C. et al. (2003) "SYNTHETIC PEPTIDES IN THE DIAGNOSIS OF HIV INFECTION," Curr Protein Pept Sci. 4(4):285-290; Baillou, A. et al. (1991) "FINE SEROTYPING OF HUMAN IMMUNODEFICIENCY VIRUS SEROTYPE 1 (HIV-1) AND HIV-2 INFECTIONS BY USING SYNTHETIC OLIGOPEPTIDES REPRESENTING AN IMMUNODOMINANT DOMAIN OF HIV-1 AND HIV-2/SIMIAN IMMUNODEFICIENCY VIRUS," J Clin Microbiol. 29(7):1387-1391; Gnann, J. W. Jr. et al. (1989) "CUSTOM-DESIGNED SYNTHETIC PEPTIDE IMMUNOASSAYS FOR DISTINGUISHING HIV TYPE 1 AND TYPE 2 INFECTIONS," Methods Enzymol. 178:693-714; Beristain, C. N. et al. (1995) "EVALUATION OF A DIPSTICK METHOD FOR THE DETECTION OF HUMAN IMMUNODEFICIENCY VIRUS INFECTION," J Clin Lab Anal. 1995; 9(6):347-350; Modrow, S. et al. (1989) "CARRIER BOUND SYNTHETIC OLIGOPEPTIDES IN ELISA TEST SYSTEMS FOR DISTINCTION BETWEEN HIV-1 AND HIV-2 INFECTION," J Acquir Immune Defic Syndr. 2(2):141-148; Smith, R. S. et al. (1990) "SYNTHETIC PEPTIDE ASSAYS TO DETECT HUMAN IMMUNODEFICIENCY VIRUS TYPES 1 AND 2 IN SEROPOSITIVE INDIVIDUALS," Arch Pathol Lab Med. 114(3):254-258).

Synthetic peptide antigens coupled with ELISA offers several potential advantages over other types of assays, potentially increasing the sensitivity and specificity of the assay, decreasing its cost, and providing a relatively simple format that would be suitable for testing sizeable number of samples in any laboratory (Manocha, M. et al. (2003) "COMPARING MODIFIED AND PLAIN PEPTIDE LINKED ENZYME IMMUNOSORBENT Assay (ELISA) For Detection Of Human Immunodeficiency Virus Type-1 (HIV-1) And Type-2 (HIV-2) Antibodies," Immunol Lett. 85(3):275-278). Additionally, such peptides, if they elicit antibody formation, could be used as an anti-HIV vaccine (Petrov, R. V. et al. (1990) "The Use Of Synthetic Peptides In The Diagnosis Of HIV Infections," Biomed Sci. 1(3):239-244).

Suitable synthetic peptides comprise short protein sequences that can be recognized by antibodies that have been elicited through an individual's exposure to the intact viral protein (Alcaro, M. C. et al. (2003) "Synthetic Peptides In The Diagnosis Of HIV Infection," Curr Protein Pept Sci. 4(4):285-290). In particular, it has been proposed that such peptides must possess the following characteristics: (1) an ability to detect an antibody response in all HIV-infected individuals; (2) an ability to detect an antibody response as early as possible after infection; and (3) an ability to maintain detection of antibody response over all stages of the disease (Döpel, S. H. et al. (1991) "Comparison Of Four Anti-HIV Screening Assays Which Belong To Different Test Generations," Eur. J. Clin. Chem. Clin. Biochem. 29:331-337; Döpel, S. H. et al. (1990) "Fine Mapping Of An Immunodominant Region Of The Transmembrane Protein Of The Human Immunodeficiency Virus (HIV-1)," J. Virol. Meth. 25:167-178; Alcaro, M. C. et al. (2003) "Synthetic Peptides In The Diagnosis Of HIV Infection," Curr Protein Pept Sci. 4(4):285-290). In particular, the HIV-1 p24 (gag) protein, gp160/120 (env) protein and gp41 (env envelope transmembrane protein) have been proposed as having serodiagnostic importance, and as being a potential source of suitable peptides (Alcaro, M. C. et al. (2003) "Synthetic Peptides In The Diagnosis OF HIV Infection," Curr Protein Pept Sci. 4(4):285-290).

Additionally, it is important to be able to distinguish between the HIV-1 and HIV-2 variants of HIV (Smith, R. S. et al. (1990) "Synthetic Peptide Assays To Detect HUMAN Immunodeficiency Virus Types 1 And 2 In Seropositive Individuals," Arch Pathol Lab Med. 114(3):254-258; Baillou, A. et al. (1991) "Fine Serotyping Of Human Immunodeficiency Virus Serotype 1 (HIV-1) And HIV-2 Infections By Using Synthetic Oligopeptides Representing An Immunodominant Domain Of HIV-1 And HIV-2/Simian Immunodeficiency Virus," J Clin Microbiol. 29(7):1387-1391; Modrow, S. et al. (1989) "Carrier Bound Synthetic Oligopeptides In ELISA Test Systems for Distinction Between HIV-1 And HIV-2 Infection," J Acquir Immune Defic Syndr. 2(2):141-148). These variants share 40-60% homology at the amino acid level (Alcaro, M. C. et al. (2003) "Synthetic Peptides In The Diagnosis Of HIV Infection," Curr Protein Pept Sci. 4(4):285-290; Gueye-Ndiaye, A. et al. (1993) "Cost-Effective Diagnosis Of HIV-1 And HIV-2 By Recombinant-Expressed Env Peptide (566/996) Dot-Blot Analysis," AIDS. 7(4):475-481).

Methods for detecting HIV or other viral pathogens are disclosed in WO9008162A1, and in U.S. Pat. Nos: 6,689,879; 6,649,749; 6,623,920; 6,589,734; 6,586,177; 6,582,920; 6,541,609; 6,534,285; 6,531,276; 6,492,104; 6,458,527; 6,399,307; 6,352,826; 6,270,959; 6,252,059; 6,245,737; 6,048,685; 6,008,044; 5,928,642; 5,925,513; 5,891,623; 5,856,088; 5,849,494; 5,830,641; 5,721,095; 5,712,385; 5,705,331; 5,695,930; 5,681,696; 5,660,979; 5,637,453; 5,599,662; 5,476,765; 5,462,852; 5,459,060; 5,260,189; and in European Patent Documents EP0439077B1, EP0439077A2.

Substantial progress has been made in the management and treatment of HIV-1 infection. However, available antiretroviral therapies can cause metabolic toxicity (Sommerfelt, M. A. et al. (2004) "Novel Peptide-Based HIV-1 Immunotherapy," Expert Opin Biol Ther. 4(3):349-61), and thus alternative strategies to control HIV-1 infection are needed (McGaughey, G. B. et al. (2004) "Progress Towards The Development Of A HIV-1 GP41-Directed Vaccine," Curr HIV Res. 2(2):193-204). The use of peptide immunogens has been proposed as the basis for an anti-HIV-1 vaccine (Sommerfelt, M. A. et al. (2004) "Novel Peptide-Based HIV-1 Immunotherapy," Expert Opin Biol Ther. 4(3):349-61; Berzofsky, J. A. et al. (1995) "Novel Approaches To Peptide And Engineered Protein Vaccine S For HIV Using Defined Epitopes: Advances In 1994-1995," AIDS 9 Suppl A:S143-157; Choppin, J. et al. (2001) "Characteristics Of HIV-1 Nef Regions Containing Multiple CD8+ T Cell Epitopes: Wealth Of HLA-Binding Motifs And Sensitivity To Proteasome Degradation," J. Immunol. 166 (10):6164-6169; Berzofsky, J A. et al. (1999) "Approaches To Improve Engineered Vaccine S For Human Immunodeficiency Virus And Other Viruses That Cause Chronic Infections," Immunol Rev. 170:151-172; Cho, M. W. (2003) "Subunit Protein Vaccine S: Theoretical And Practical Considerations For HIV-1," Curr Mol. Med. 3(3):243-263; Sabatier, J. M. et al. (1989) "Use Of Synthetic Peptides For The Detection Of Antibodies Against The NEF Regulating Protein In Sera Of HIV-Infected Patients," AIDS. 3(4):215-220; van der Ryst, E. (2002) "Progress In HIV Vaccine Research," Oral Dis. 8 Suppl 2:21-26; Zolla-Pazner, S. (2004) "Identifying Epitopes Of HIV-1 That Induce Protective Antibodies," Nat Rev Immunol. 4(3):199-210.

Unfortunately, the identification of suitable peptides is encumbered by the rapid mutation and recombination exhibited by retroviruses, extreme variability is found in HIV proteins. Although conserved regions in HIV-1 gp120 (residues 495-516), gp41 (residues 67-83 and 584-618), and gp36 (residues 574-602) have been investigated as potential sequences for candidate peptides (Alcaro, M. C. et al. (2003) "Synthetic Peptides In The Diagnosis Of HIV Infection," Curr Protein Pept Sci. 4(4):285-290), prior efforts to define suitable peptides have not been fully satisfactory. Petrov, R. V. et al. disclose that many candidate peptides failed to identify HIV infection in HIV-infected individuals, necessitating the use of multiple peptides in order to detect HIV infection (Petrov, R. V. et al. (1990) "The Use Of Synthetic Peptides In The Diagnosis Of HIV Infections," Biomed Sci. 1(3):239-244). Thus, an important problem facing the field of HIV diagnostics is the identification of a suitable peptide that would be recognized broadly, or universally, by the full range of clinically identified HIV variants. Likewise, at present no identified peptide has resulted in an HIV-1 immunotherapy that could be used as the basis for a vaccine that would provide substantial or full immunoprotection to infection by such variants (Sommerfelt, M. A. et al. (2004) "Novel Peptide-Based HIV-1 Immunotherapy," Expert Opin Biol Ther. 4(3):349-61). In addition, suitable diagnostic tests should be able to distinguish between individuals whose sera contain anti-HIV antibodies as a result of their receipt of an anti-HIV vaccine and individuals whose sera contain anti-HIV antibodies as a result of HIV infection. The present invention is directed to this and other needs.

SUMMARY OF THE INVENTION

This invention relates to compositions and methods for the detection of immunodeficiency virus infection, especially human immunodeficiency virus-1 (HIV-1) and human immunodeficiency virus-2 (HIV-2) infection. The invention particularly concerns compositions and methods that may be used in HIV vaccine recipients whose sera may contain vaccine-generated anti-HIV antibodies. The invention also concerns peptide antigens that may be used in anti-HIV vaccine compositions.

Most of the HIV-1 prophylactic vaccines currently under development are complex products containing multiple viral genes or proteins. As a result, vaccine recipients' sera are expected to be identified as reactive in HIV-1 or HIV-2 or both HIV 1 & 2 seroconversion detection assays and thus to produce patterns indistinguishable form sera obtained from infected individuals. This will have a negative impact on future clinical trials of prophylactic HIV vaccines that require early detection of breakthrough infections. It will also exclude all vaccines from the pool of potential blood donors, and may contribute to other social harms. The present invention is directed, in part, to the identification of new HIV-1 and HIV-2 epitopes which are: (a) broadly reactive with early serum samples from individuals infected with HIV virus strains from all clades; (b) do not contain protective antibody or cytotoxic epitopes; and (c) can be easily removed from current and future HIV-1 candidates. In a preferred embodiment, Gene-Fragment Phage Display libraries constructed from whole HIV-1 genome are used to identify such epitopes and to construct differential enzyme-immunoassays that are capable of distinguishing reactivities from infection-induced anti-HIV antibodies from vaccine-induced anti-HIV reactivities.

In one aspect, the invention relates to a method for detecting the presence, or measuring the concentration, of an anti-HIV-1 antibody in a biological sample of a human, wherein said method comprises conducting an immunoassay comprising the steps of: (a) contacting said biological sample with a peptide having an epitope that is recognized by said anti-HIV-1 antibody, said contacting being under conditions sufficient to permit said anti-HIV-1 antibody if present in said sample to bind to said epitope and form a peptide-anti-HIV-1 antibody complex; (b) contacting said formed peptide-anti-HIV-1 antibody complex with an anti-HIV-1 antibody binding molecule, said contacting being under conditions sufficient to permit said anti-HIV-1 antibody binding molecule to bind to anti-HIV-1 antibody of said formed peptide-anti-HIV-1 antibody complex and form an extended complex; and (c) determining the presence or concentration of said anti-111V-1 antibody in said biological sample by determining the presence or concentration of said formed extended complex; wherein said epitope is present on a peptide having an amino acid sequence selected from the group consisting of SEQ ID NOs:1-11, 49-56, 90 and 141.

In another aspect, the invention relates to a a peptide or protein comprising an epitope that is recognized by an anti-HIV-1 antibody, wherein said epitope is present on a peptide having the amino acid sequence of SEQ ID NO:3, SEQ ID NO:50, SEQ ID NO:55 or SEQ ID NO:141.

In another aspect, the invention relates to a peptide or protein having the amino acid sequence of SEQ ID NO:3, SEQ ID NO:50, SEQ ID NO:55 or SEQ ID NO:141.

In another aspect, the invention relates to an immunological complex comprising a peptide bound to an anti-HIV-1 antibody, wherein said anti-HIV-1 antibody is additionally bound to an anti-HIV antibody binding molecule, wherein said peptide or protein comprises an epitope that is recognized by an anti-HIV-1 antibody, said epitope being present on a peptide or protein having an amino acid sequence selected from the group consisting of SEQ ID NOs:1-11, 49-56, 90 and 141.

In a further aspect, the invention relates to a kit for detecting the presence, or measuring the concentration, of an anti-HIV-1 antibody in a biological sample of a human, wherein said kit comprises a hollow casing comprising a multilayer filter system, and first and second porous carriers, wherein said second porous carrier is in communication with said first porous carrier, and said first porous carrier is in communication with said multilayer filter system, a portion of which is accessible from said casing; wherein said first porous carrier contains a non-immobilized, labeled peptide or protein; and said second porous carrier contains an immobilized, unlabeled antibody that binds to human IgG; wherein said peptide or protein comprises an epitope that is present on a peptide having an amino acid sequence selected from the group consisting of SEQ ID NOs:1-11, 49-56, 90 and 141.

In a further aspect, the invention relates to a method for detecting the presence, or measuring the concentration, of an anti-HIV-2 antibody in a biological sample of a human, wherein said method comprises conducting an immunoassay comprising the steps of: (a) contacting said biological sample with a peptide having an epitope that is recognized by said anti-HIV-2 antibody, said contacting being under conditions sufficient to permit said anti-HIV-2 antibody if present in said sample to bind to said epitope and form a peptide-anti-HIV-2 antibody complex; (b) contacting said formed peptide-anti-HIV-2 antibody complex with an anti-HIV-2 antibody binding molecule, said contacting being under conditions sufficient to permit said anti-HIV-2 antibody binding molecule to bind to anti-HIV-2 antibody of said formed peptide-anti-HIV-2 antibody complex and form an extended complex; and (c) determining the presence or concentration of said anti-HIV-2 antibody in said biological sample by determining the presence or concentration of said formed extended complex; wherein said epitope is present on a peptide having an amino acid sequence selected from the group consisting of SEQ ID NOs:101-102.

In another aspect, the invention relates to a method for detecting the presence, or measuring the concentration, of an anti-HIV-1 antibody in a biological sample of a human, wherein said method comprises conducting an immunoassay comprising the steps of: (a) contacting said biological sample with an epitope set comprising at least one epitope that is recognized by said anti-HIV-1 antibody, wherein said epitope set consists essentially of an HIV-1 GAG p6 epitope or epitopes, an HIV-1 gp41 terminal region epitope or epitopes, or a combination of an HIV-1 GAG p6 epitope or epitopes and an HIV-1 gp41 terminal region epitope or epitopes, said contacting being under conditions sufficient to permit said anti-HIV-1 antibody if present in said sample to bind to epitopes in said epitope set and form an epitope-anti-HIV-1 antibody complex; (b) contacting said formed epitope-anti-HIV-1 antibody complex with an anti-HIV-1 antibody binding molecule, said contacting being under conditions sufficient to permit said anti-HIV-1 antibody binding molecule to bind to anti-HIV-1 antibody of said formed epitope-anti-HIV-1 antibody complex and form an extended complex; and (c) determining the presence or concentration of said anti-HIV-1 antibody in said biological sample by determining the presence or concentration of said formed extended complex.

In a further aspect, the invention relates to a method for detecting the presence, or measuring the concentration, of an anti-HIV-2 antibody in a biological sample of a human, wherein said method comprises conducting an immunoassay comprising the steps of: (a) contacting said biological sample with an epitope set comprising at least one epitope that is recognized by said anti-HIV-2 antibody, wherein said epitope set consists essentially of an HIV-2 GAG p6 epitope or epitopes, an HIV-2 Env-gp36 epitope or epitopes, or a combination of an HIV-2 GAG p6 epitope or epitopes and an HIV-2 Env-gp36 epitope or epitopes, said contacting being under conditions sufficient to permit said anti-HIV-2 antibody if present in said sample to bind to epitopes in said epitope set and form an epitope-anti-HIV-2 antibody complex; (b) contacting said formed epitope-anti-HIV-2 antibody complex with an anti-HIV-2 antibody binding molecule, said contacting being under conditions sufficient to permit said anti-HIV-2 antibody binding molecule to bind to anti-HIV-1 antibody of said formed epitope-anti-HIV-1 antibody complex and form an extended complex; and (c) determining the presence or concentration of said anti-HIV-2 antibody in said biological sample by determining the presence or concentration of said formed extended complex.

DESCRIPTION OF THE PREFERRED EMBODIMENTS

Figure 1:
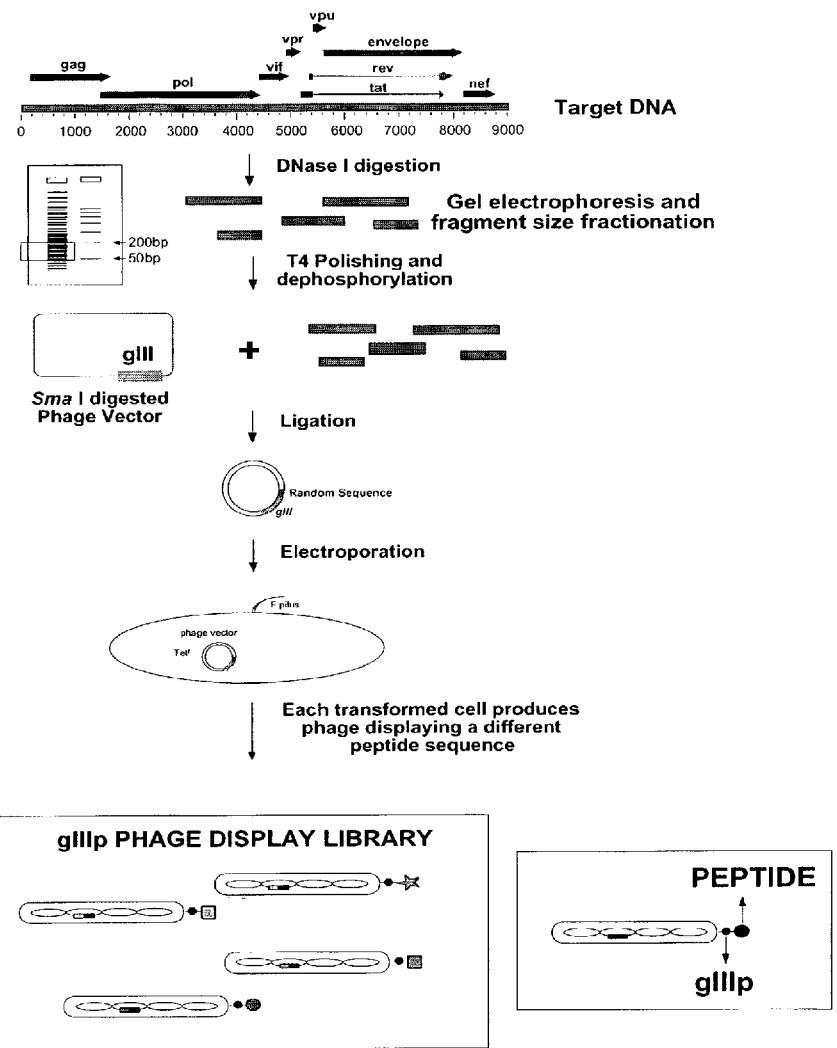
FIG. 1 shows a general scheme for constructing the gene fragment phage display libraries used in a preferred embodiment of the invention to obtain novel HIV epitopes.
Figure 2:
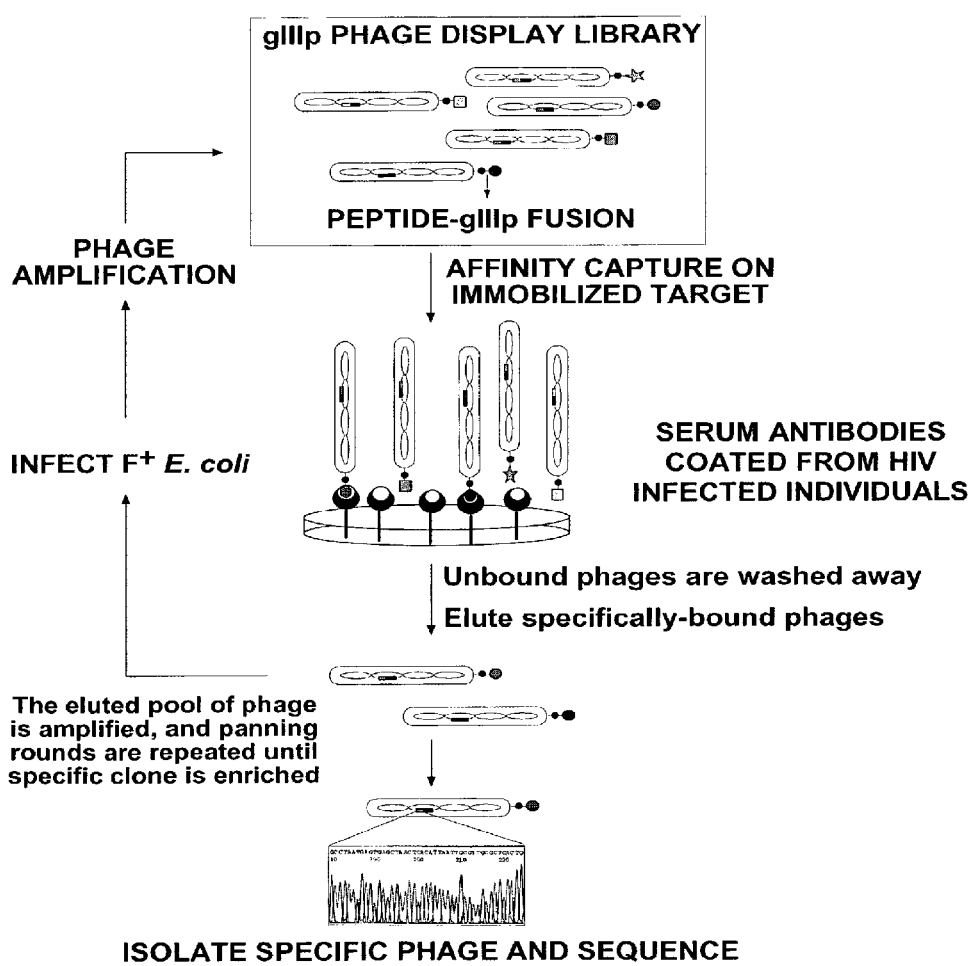
FIG. 2 shows a general scheme for panning gene fragment phage display libraries.
Figure 3:
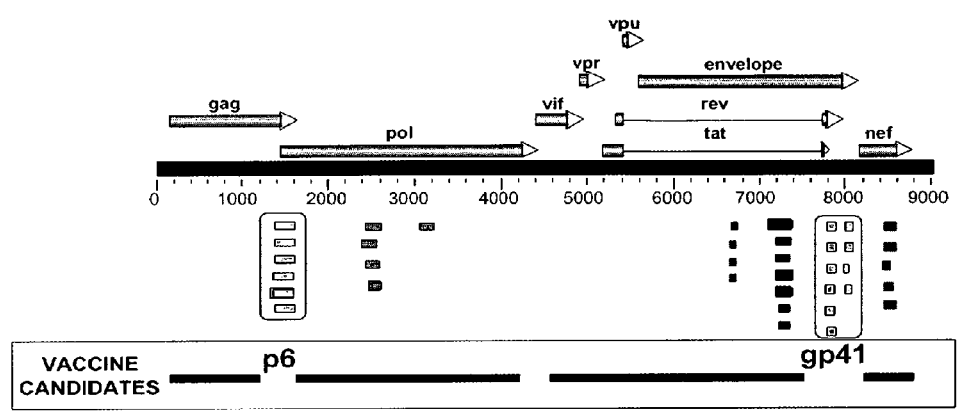
FIG. 3 illustrates the relationship between the epitopes employed in HIV vaccines and those identified in the preferred embodiments of the present invention.
Figure 4:
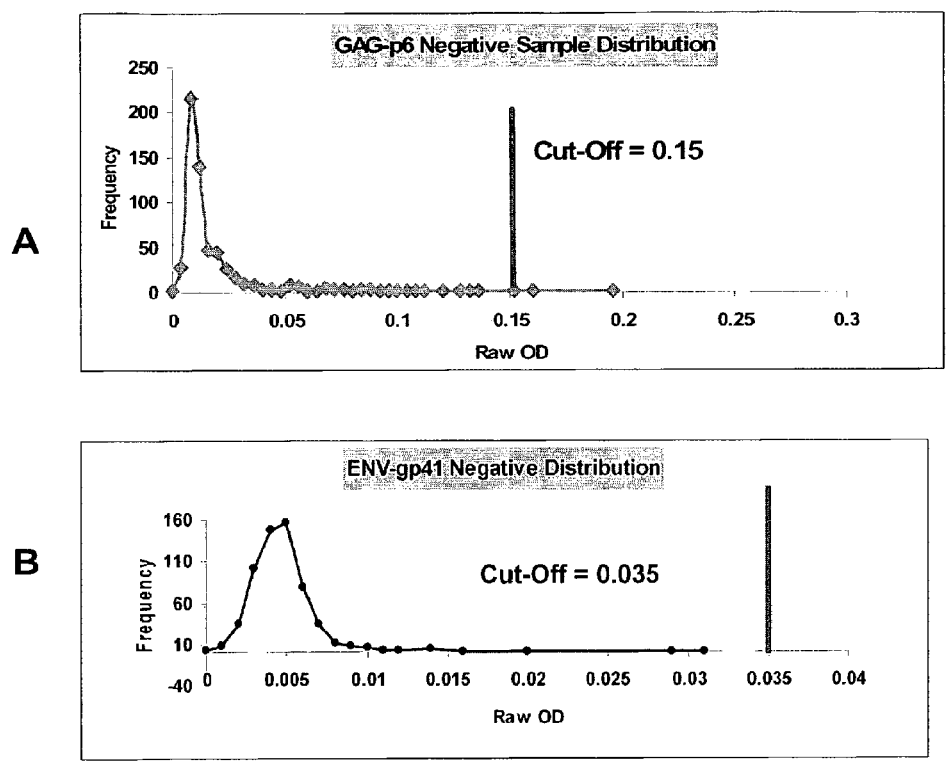
FIG. 4 shows the frequency of negative samples (n=600) obtained in ELISAs employing the GAG-p6 (SEQ ID NO:3; Panel A) and gp41 (SEQ ID NO:50; Panel B) peptides.
Figure 5:
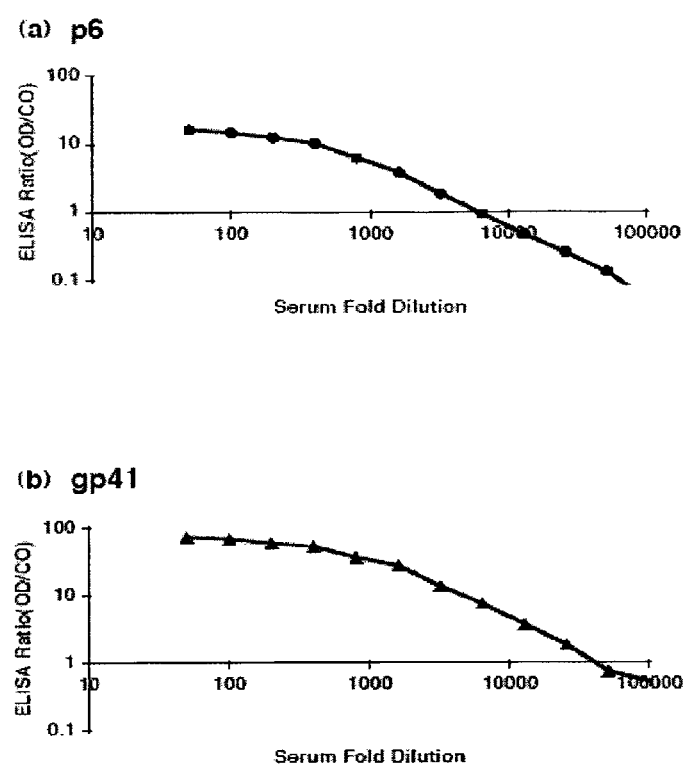
FIG. 5, Panels a-d, shows the dynamic range of serum reactivity and reproducibility of the p6 (SEQ ID NO:3) and gp41 (SEQ ID NO:50 and SEQ ID NO:55) peptide-based HIV-SELECTEST. ELISA conditions were described in Example 9, METHODS. A well characterized panel of nine HIV seropositive and three HIV seronegative human plasma (SeraCare BioServices) were subjected to serial two-fold dilutions starting at 1:50. Reactivity of one of the seropositive samples, PRB-204-06, with p6 (Panel a) and gp41 (Panel b) peptides is shown. Quality assurance data obtained with p6 (Panel c) and gp41 (SEQ ID NO:50 and SEQ ID NO:55) (Panel d) demonstrate the reproducibility of the new assay. In these panels, the same plasma was tested on nine dates at a 1:100 dilution. All data are represented as ratios between test specimen optical density (OD) to cut-off absorbance (CO) on the Y-axis. The Cut-off value for each peptide was determined as the mean absorbance+5 standard deviations (SD) obtained with 1000 HIV seronegative samples. The upper and lower limits (Panels c, d) are the average OD/CO values±2SD of the plasma sample upon repeated testing, representing the 95% confidence intervals for the given control sample. Data shown represents similar results with all nine plasma samples in the control panel.
Figure 5:
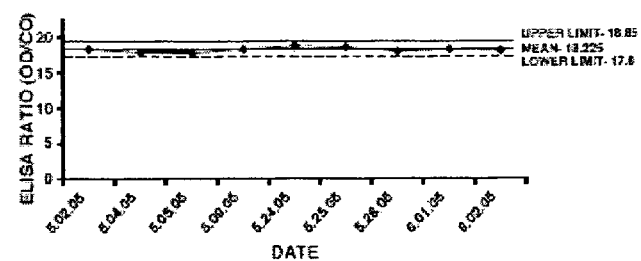
Figure 5:
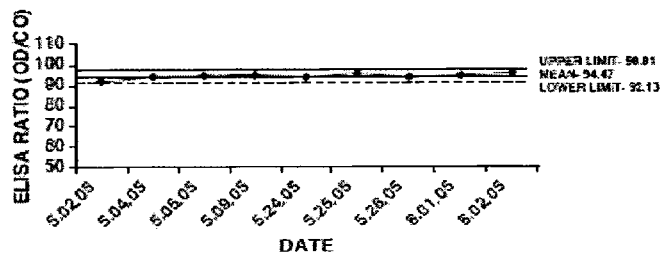

This invention relates to compositions and methods for the detection of immunodeficiency virus infection, especially immunodeficiency virus-1 (HIV-1) infection. The invention particularly concerns compositions and methods that may be used in HIV vaccine recipients whose sera may contain vaccine-generated anti-HIV-1 antibodies.

Since 1987, more than 10,000 individuals have received immunizations with human immunodeficiency virus (HIV) preventive vaccine constructs. Two large phase III trials are close to completion in the U.S. and Thailand (8,000 vaccinees) and a new phase III trial is ongoing in Thailand (16,000 vaccinees). Earlier vaccine candidates were simple and usually included a single gene product, such as the viral glycoprotein gp120 or gp160. Most of the HIV-1 prophylactic vaccines currently under development are complex products containing multiple viral genes or proteins.

Unfortunately, despite such efforts, the HIV pandemic continues to take its toll globally, with more than 16,000 reported infections and 8,500 deaths occurring daily. Concerted efforts are underway to develop preventative HIV vaccines that will be both efficacious and economical. In the wake of the unsuccessful efficacy trials conducted with vaccines containing gp120 envelope alone (Francis, D. P. et al. (2003) "CANDIDATE HIV/AIDS VACCINE S: LESSONS LEARNED FROM THE WORLD'S FIRST PHASE III EFFICACY TRIALS," Aids 17:147-56; Graham, B. S. et al. (2005) "LESSONS FROM FAILURE—PREPARING FOR FUTURE HIV-1 VACCINE EFFICACY TRIALS," J Infect Dis 191, 647-649), the new generation of vaccine candidates are complex products, containing multiple HIV genes or proteins, using diverse delivery systems and new adjuvants. It is anticipated that within few years several vaccine candidates will progress into large scale efficacy trials, particularly in countries with high infection rates. It is hoped that the new generation vaccines will offer at least partial protection against new infections and possibly reduce viral loads and delay disease progression in infected vaccinated individuals. In order to achieve the statistical power needed to demonstrate partial efficacy, it will be necessary to recruit thousands of volunteers into future phase III HIV vaccine trials. Many of these volunteers will react positively in licensed HIV detection tests. Hence, further improvements in HIV diagnosis are urgently required.

One of the critical determinations during ongoing trials in high-risk populations is the HIV infection status of trial participants. Intercurrent infections must be detected as soon as possible in order to stop vaccination and monitor infected individuals for viral load, immune status, and disease progression. Treatment and public health measures depend on a timely diagnostic information. Currently, vaccine trials are using an algorithm of HIV detection that incorporates antibody or antigen-based kits, followed by Western Blots and finally, confirmatory PCR based assays. Unfortunately, many of the vaccine trial participants, irrespective of their HIV infection status, seroconvert in all licensed antibody detection kits, including the recently licensed rapid tests ((Ackers, M. L. et al. (2003) "HUMAN IMMUNODEFICIENCY VIRUS (HIV) SEROPOSITIVITY AMONG UNINFECTED HIV VACCINE RECIPIENTS," J Infect Dis 187:879-986; Pitisuttithum, P. et al. (2003) "SAFETY AND IMMUNOGENICITY OF COMBINATIONS OF RECOMBINANT SUBTYPE E AND B HUMAN IMMUNODEFICIENCY VIRUS TYPE 1 ENVELOPE GLYCOPROTEIN 120 VACCINE S IN HEALTHY THAI ADULTS," J Infect Dis 188:219-227; Chuenchitra, T. et al. (2003) "LONGITUDINAL STUDY OF HUMORAL IMMUNE RESPONSES IN HIV TYPE 1 SUBTYPE CRF01_AE (E)-INFECTED THAI PATIENTS WITH DIFFERENT RATES OF DISEASE PROGRESSION," AIDS Res Hum Retroviruses 19:293-305; Schwartz, D. H. et al. (1995) "UTILITY OF VARIOUS COMMERCIALLY AVAILABLE HUMAN IMMUNODEFICIENCY VIRUS (HIV) ANTIBODY DIAGNOSTIC KITS FOR USE IN CONJUNCTION WITH EFFICACY TRIALS OF HIV-1 VACCINE S," Clin Diagn Lab Immunol 2, 268-271). This is due to the fact that vaccine components are very similar to the diagnostic kits in composition. Therefore, recruitment of volunteers into future trials may be impeded if the informed consent forms state that volunteers are likely to seroconvert in licensed detection kits and may remain seropositive for a long time. In published surveys, it has been shown that positive HIV serodiagnosis is the most important concern for volunteers willing to participate in HIV clinical trials (Gross, M. et al. (1996) "INTEREST AMONG GAY/BISEXUAL MEN IN GREATER BOSTON IN PARTICIPATING IN CLINICAL TRIALS OF PREVENTIVE HIV VACCINE S," J Acquir Immune Defic Syndr Hum Retrovirol 12:406-412). Thus, there is an immediate need to develop a simple and inexpensive assay that does not score uninfected vaccine recipients as positive, but provides the necessary specificity and sensitivity to detect true HIV infections in the presence of vaccine-induced antibodies.

The systems used to deliver such vaccines span the gamut from plasmid DNA to viral and bacterial vectors. Prime-boost strategies have been employed in order to optimize the cellular and humoral immune responses and reach meaningful (protective) titers and breadth of neutralizing antibodies and high frequency of cytotoxic T cells. Unfortunately, many of these constructs elicit antibodies detected by standard serologic tests for HIV-1 seroconversion. In a recent publication from the United States' Center for Disease control and Prevention, it was reported that 90% of vaccinees receiving a Canarypox construct expressing multiple HIV genes (env, gag, pol, protease, net) followed by an envelope protein boost, exhibited positive results in an enzyme immunoassay (EIA), rapid test, and Western blot (Marta-Louise Ackers et al. J. Infect. Dis. 2003, 187:879).

Due to increasing complexity of HIV-1 vaccine candidates, most vaccinees are expected to react positive in the licensed HIV-1 detection assays (EIA, rapid test, Western blots). There are several negative outcomes to the anticipated high prevalence of false-positives in the vaccinated individuals. These outcomes reflect the criticality of distinguishing between HIV infected recipients and individuals who have merely become seroconverted due to the administration of the vaccine:

(a) Phase III trials of prophylactic HIV-1 vaccines are typically and desirably conducted in high risk populations. As such, it is essential to diagnose break-through infections at the earliest possible times. This is necessary since infected individuals must stop vaccinations and get re-assigned to a follow-up group that are analyzed separately. Additionally, such individuals may be entitled to anti-viral therapies;

(b) Since HIV-1 infected individuals are excluded from the pool of potential blood donors, it is important to ensure both that infected individuals do not donate blood, and that individuals who have merely become seroconverted due to the administration of the vaccine are not erroneously precluded from serving as blood donors.

(c) Since HIV-1 infected individuals face exclusions from health insurance, immigration and travel across countries, employment limitations, and preclusion from military service, it is important to be able to ensure that healthy vaccine recipients are not erroneously scored as HIV-infected individuals.

(d) Informing potential participants about the strong possibility of having reactive serologic HIV-1 tests, could deter potential volunteers from participating because of anticipated social harms. Therefore, it is important to design new testing strategies for vaccine participants that will clearly discriminate between vaccine-induced reactivity and HIV-1 infection.

The present invention addresses these concerns by providing new HIV-1 epitopes that will fulfill some, and more preferably all, of the following criteria:

(1) Do not contain important neutralizing or CTL epitopes;

(2) Are not present in HIV vaccine constructs;

(3) Arc highly immunogenic in infected individuals;

(4) Are recognized by antibodies from HIV infected individuals at early times post-infection; and (5) Are highly conserved among clades and subtypes.

Identification of the Novel Epitopes of the Present Invention

In order to identify epitopes that conform to the above criteria, it is desirable to evaluate a large pool of potential epitopes. Advantageously, a gene-fragment phage display library may be employed for this purpose. Preferably, such a library is produced using limited DNase I digestion of HIV-1 or HIV-2 DNA (FIG. 1). Thus, target DNA, containing HIV-1 or HIV-2, is subjected to DNAse I digestion, and the digestion products are fractionated, for example using gel electrophoresis. The termini of the fractionated samples are preferably polished using T4 polymerase (see, e.g., Costa, G. L. et al. (1994) "Polishing With T4 Or Pfu Polymerase Increases The Efficiency Of Cloning Of PCR Fragments," Nucleic Acids Res. 22(12):2423) and dephosphorylated. The treated fragments are then preferably introduced into a phagemid or phage vectors (based on filamentous phages including M13, f1, etc.) operably linked to a displayed phage protein and are then amplified to produce a phage display library, each of whose members displays an HIV peptide sequence on its surface. Alternatively, other libraries can be used including Ribosomal display, other viruses, and phages or bacterial cells or Yeast or other eukaryotic display systems for the same purpose.

Desired peptides are then identified, preferably by panning the library on immobilized serum antibodies from HIV-1-infected individual (early seroconversion) under conditions that permit the recovery of library members that bind strongly to the immobilized antibodies (FIG. 2). Preferably, this is accomplished by capturing library members whose arrayed HIV peptide binds to an immobilized anti-HIV antibody. After discarding unbound phagemids, the bound phagemids are eluted and recovered (eluted phagemids may be amplified to enhance their recovery).

Suitable members mapping to the HIV-1 GAG-p6, RT, IN, Vif, gp120, gp41, and Nef genes, for example, can be identified in this manner. Of particular interest are members mapping to the gag, pol, Envelope and nef encoding regions of HIV. Further screenings are preferably conducted using panels of sequential sera from HIV-1 seroconvertors. FIG. 3 illustrates the relationship between the desired epitopes of the present invention, and those of vaccine candidates.

Epitopes mapping to the HIV-1 GAG-p6, gp41, Vif and Nef genes are believed to possess significant utility as diagnostic agents for the detection of anti-HIV antibodies, since, for gp41 and p6, there is >90% sequence conservation among HIV-1 clades. Moreover, gp41 and Gag-p6 peptides were recognized at high frequency (combined sensitivity of 99.1%) by serum/plasma of 1200 samples from seropositive individuals including early seroconvertors. The specificity is currently at 98.2% for p6 and 100% for gp41 (1000 negative samples). The Gag-p6 and gp41 peptides do not contain important known neutralizing antibody or CTL epitopes and they are not present in most HIV vaccines. Identified peptides are suitable for use in HIV diagnostic kits.

In particular, the following HIV-1 peptide Gag-p6 sequences were identified as comprising desired epitopes:

Each of these sequences was attached individually to a carboxy-terminal (SEQ ID NO: 138) GGGC peptide linker.

Identified GAG Epitopes

The identified GAG epitopes (SEQ ID NOs:1-11) differ in sequence from the sequences of previously identified GAG peptides. For example, aligning SEQ ID NO:1 and SEQ ID NO:2 against the HIV-1 GAG sequence (SEQ ID NO:12; NC_001802) yields the following comparison (sites of SEQ ID NO:12 that are not conserved are shown in single-underline (if conserved in either SEQ ID NO:1 or SEQ ID NO:2) or in double-underline (if not conserved in either SEQ ID NO:1 or SEQ ID NO:2)) (Table 1):

```
C-GAG-p6
                                                          (SEQ ID NO: 1)
SRPEPTAPPA ESFRFGEEIT PTPSQKQEPK DKELYPPLAS LRSLFGNDPS SN
1         10         20         30         40         50 52

GAG-p6
                                                          (SEQ ID NO: 2)
SRPEPTAPPE ESFRFGEETT TPSQKQEPID KELYPLASLR SLFGSDPSSQ
1         10         20         30         40         50

CON-GAG-p6
                                                          (SEQ ID NO: 3)
SRPEPTAPPA ESFRFGEEIT PTPSQKQEPK DKELYPPLAS LRSLFGNDPS SQ
1         10         20         30         40         50 52

CON-M-p6
                                                          (SEQ ID NO: 4)
SRPEPTAPPA ESFRFGEETT PSPKQEPKDK ELYPLTSLKS LFGNDPLSQ
1         10         20         30         40         49

P6-CON-of-CON
                                                          (SEQ ID NO: 5)
SRPEPTAPPA ESFGFGEEIT PSPKQEPKDK ELYPLASLKS LFGNDPLSQ
1         10         20         30         40         49

CON-p6 A > E
                                                          (SEQ ID NO: 6)
SRPEPTAPPE ESFRFGEEIT PTPSQKQEPK DKELYPPLAS LRSLFGNDPS SQ
1         10         20         30         40         50 52

New -GAG-p6
                                                          (SEQ ID NO: 7)
SRPEPTAPPE ESFRFGEEIT PTPSQKQEPK DKELYPLASL RSLFGNDPSS  Q
1         10         20         30         40         50 51 p6-S-S
                                                          (SEQ ID NO: 8)
SRPEPTAPPA ESFRFGEEIT TSPSQKQEPK DKELYPLASL KSLFGND
1         10         20         30         40      47 p6-S-E
                                                          (SEQ ID NO: 9)
SRPEPTAPPA ESFRFGEEIT TSPSQKQEPK DKE
1         10         20         30  33 p6-T-S
                                                         (SEQ ID NO: 10)
TPTPSQKQEP KDKELYPPLA SLRSLFGNDP  S
1         10         20         30 31 p6-S-Q
                                                         (SEQ ID NO: 11)
SFRFGEEITP TPSQKQEPKD KELYPPLASL  RSLFGNDPSS Q
1         10         20         30 31
```

TABLE 1

| SEQ ID NO | Description | Sequence |
|---|---|---|
| 1 | Isolated Epitope | SRPEPTAPPAESFRFGEEITPTPSQKQEPKDKELYPPLASLRSLFGNDPSSN |
| 2 | Isolated Epitope | SRPEPTAPPEESFRFGEETT•TPSQKQEPIDKELYP•LASLRSLFGSDPSSQ |
| 12 | Gag | SRPEPTAPP<u>E</u>ESFR<u>S</u>G<u>V</u>ETT•TP<u>P</u>QKQEP<u>I</u>DKELYP•L<u>T</u>SLRSLEG<u>N</u>DPSS<u>Q</u> |

Thus, both SEQ ID NO:1 and SEQ ID NO:2 differ in sequence from the sequence of the corresponding native HIV-1 gag gene product (SEQ ID NO:12). An alignment of these sequences with a series of gag consensus sequences (Table 2) indicates that SEQ ID NO:1 and SEQ ID NO:2 differ in sequence from the consensus sequences. The "$" symbol in Table 2 indicates a stop codon.

TABLE 2

| SEQ ID NO | Description | Sequence |
|---|---|---|
| 12 | Gag | SRPEPTAPPEESFRSGVET•T•TPPQKQEPIDKE•LYP•LTSLRSLFGNDPSSQ |
| 1 | Isolated Epitope | SRPEPTAPP<u>A</u>ESFRF<u>G</u>•<u>EI</u>•T<u>P</u>TP<u>S</u>QKQEP<u>K</u>DKE•LYP<u>P</u><u>L</u>ASLRSLFGNDPSS<u>N</u> |
| 2 | Isolated Epitope | SRPEPTAPPEESFRF<u>G</u>•<u>E</u>••<u>TTT</u>P<u>S</u>QKQEPIDKE•LYP•L<u>A</u>SLRSLFG<u>S</u>DPSSQ |
| 13 | Consensus_B (33) | SRPEPTAPPEESFRF<u>G</u>•<u>EE</u>•<u>TTT</u>P<u>S</u>QKQEPIDKE•LYP•L<u>A</u>SLRSLFGNDPSSQ |
| 14 | Consensus_02(8) | SRPEPTAPP<u>A</u>ESF<u>GMG</u>•<u>EEIT</u>••<u>SS</u>PKQEP<u>R</u>DKG•LYPP<u>L</u><u>A</u>SL<u>K</u>SLFGNDP<u>$</u>SQ |
| 15 | Consensus_D(8) | SRPEPTAPP<u>A</u>ESF<u>GFG</u>•<u>EEIT</u>••P<u>S</u>QKQE<u>Q</u><u>K</u>DKE•LYP•LTSL<u>K</u>SLFGNDP<u>L</u>SQ |
| 16 | Consensus F1-F2(9) | <u>N</u>RPEPTAPP<u>A</u>ESF<u>GFR</u>•<u>EEIT</u>••P<u>S</u>PKQE<u>Q</u><u>K</u>D•EGLYPP<u>L</u><u>A</u>SL<u>K</u>SLFGNDP••• |
| 17 | Consensus_G(5) | <u>N</u>RPEPTAPP<u>A</u>ESF<u>GFG</u>•<u>EEIA</u>••P<u>S</u>PKQE<u>Q</u><u>K</u>E<u>K</u>E•LYP•L<u>A</u>SL<u>K</u>SLFG<u>S</u>DP<u>$</u>SQ |
| 18 | Consensus_K (3) | SRPEPTAPP<u>A</u>ESF<u>GFG</u>•<u>EEIT</u>P••<u>S</u>P<u>R</u>QE<u>T</u><u>K</u>DKE•<u>Q</u>GPPLTSL<u>K</u>SLFGNDP<u>L</u>SQ |
| 19 | Consensus_A-A1-A2(15) | SRPEPTAPP<u>AEI</u>F<u>GMG</u>•<u>EEITS</u>••<u>P</u>PKQE<u>Q</u><u>K</u>DRE•<u>Q</u>NPP<u>SV</u>L<u>K</u>SLFGNDP<u>L</u>SQ |
| 20 | Consensus_H (3) | SRPEPTAPP<u>A</u>ESF<u>GFG</u>•<u>EEMT</u>••P<u>S</u>PKQE<u>L</u><u>K</u>DKE•••PPL<u>A</u>SLRSLFGNDP<u>L</u>SQ |
| 21 | Consensus_01 (11) | SRPEPTAPP<u>AENGMGE</u>•<u>E</u>•<u>ITSLP</u>••<u>K</u>QE<u>Q</u><u>K</u>DKE•HPPP<u>L</u><u>V</u>SL<u>K</u>SLFGNDP<u>L</u>SQ |
| 22 | Consensus_c (41) | SRPEPTAPP<u>A</u>ESFRF•••<u>EE</u>•T•TP<u>A</u>PKQEP<u>K</u>DRE••••PLTSL<u>K</u>SLFG<u>S</u>DP<u>L</u>SQ |

The invention also relates to the following HIV 1 Gag p6 consensus epitopes shown in Table 3 below:

TABLE 3

| SEQ ID NO | Description | Sequence |
|---|---|---|
| 23 | Con of Cons | SRPEPTAPPA ESFGFGEEIT PSPKQEPKDK ELYPLASLKS LFGNDPLSQ |
| 24 | M.group.anc | SRPEPTAPPA ESFGFGEEIT PSPKQEPKDK ELYPLASLKS LFGSDPLSQ |
| 25 | consensus A1 | SRPEPTAPPA EIFGMGEEIT SPPKQEQKDR EQDPPLVSLK SLFGNDPLSQ |
| 26 | A1.anc | SRPEPTAPPA ENFGMGEEMI SSPKQEQKDR EQYPPLVSLK SLFGNDPLSQ |
| 27 | consensus A2 | SRTEPTAPPA ENLRMGEEIT SSLKQELKTR EPYNPAISLK SLFGNDPLSQ |
| 28 | consensus B | SRPEPTAPPE ESFRFGEETT TPSQKQEPID KELYPLASLR SLFGNDPSSQ |

TABLE 3-continued

| SEQ ID NO | Description | Sequence |
|---|---|---|
| 29 | B.anc | SRPEPTAPPE ESFRFGEETT TPSQKQEPID KELYPLASLK SLFGNDPSSQ |
| 30 | consensus C | NRPEPTAPPA ESFRFEETTP APKQEPKDRE PLTSLKSLFG SDPLSQ |
| 31 | C.anc | SRPEPTAPPA ESFRFEETTP APKQEPKDRE PLTSLKSLFG SDPLSQ |
| 32 | consensus D | SRPEPTAPPA ESFGFGEEIT PSQKQEQKDK ELYPLTSLKS LFGNDPLSQ |
| 33 | consensus F1 | SRPEPTAPPA ESFGFREEIT PSPKQEQKDE GLYPPLASLK SLFGNDP |
| 34 | consensus G | NRPEPTAPPA ESFGFGEEIA PSPKQEQKEK ELYPLASLKS LFGSDP |
| 35 | consensus H | SRPEPTAPPA ESFGFGEEMT PSPKQELKDK EPPLASLRSL FGNDPLSQ |
| 36 | consensus K | SRPEPTAPPA ESFGFGEEIT PSPRQETKDK EQGPPLTSLK SLFGNDPLSQ |
| 37 | consensus_01_AE | SRPEPTAPPA ENWGMGEEIT SLPKQEQKDK EHPPPLVSLK SLFGNDPLSQ |
| 38 | consensus_02_AG | SRPEPTAPPA ESFGMGEEIT SSPKQEPRDK GLYPPLTSLK SLFGNDP |
| 39 | consensus_03_AB | SRPEPSAPPA ENFGMGEEIT PSLKQEQKDR EQHPPSISLK SLFGNDPLSQ |
| 40 | consensus_04_CPX | SRPEPTAPPA ESLEMKEETT SSPKQEPRDK ELYPLTSLKS LFGSDPLSQ |
| 41 | consensus_06_CPX | NRPEPTAPPA ESFGFGEETA PSPKQEPKEK ELYPLASLKS LFGNDP |
| 42 | consensus_07_BC | SRPEPTAPPE ESFRFGEETT TPSQKQEPID KELYPLTSLK SLFGNDPSSQ |
| 43 | consensus_08_BC | SRPEPTAPPA ESFRFEETTP APKQEPKDRE PLTSLRSLFG SDPLSQ |
| 44 | consensus_10_CD | SRPEPTAPPA ESFGFGEEIT PSQKQEQKDK ELHPLASLKS LFGNDPLSQ |
| 45 | consensus_11_CPX | SRPEPTAPPA ESFGFGEEIA PSPKQEPKEK ELYPLTSLKS LFGSDPLSQ |
| 46 | consensus_12_BF | NRPEPTAPPA ESFGFGEEIT PSPKQEQKDE GLYPPLASLK SLFGNDP |
| 47 | consensus_14_BG | NRPEPTAPPA ESFGFGEEIA PSPKQEPKEK EIYPLASLKS LFGSDP$SQ |

A blast search of SEQ ID NO:1 failed to identify any identical gene sequences. A blast search of SEQ ID NO:2 identified three sequences that were 100% identical to SEQ ID NO:2 (Sequence AAC28445 (Fang, H. et al., (1995) J. Virol. 69(1):75-81; Sequence P12493 (Buckler, C. E. et al. Direct Submission); Sequence AAB04036 (Willey, R. L. et al. (1986) Proc. Natl. Acad. Sci. U.S.A. 83 (14), 5038-5042).

U.S. Pat. No. 6,458,527 relates to an immunoassay to detect the presence of a human immunodeficiency virus using a GAG antigen that comprises at least seven contiguous amino acids from a GAG open reading frame that includes SEQ ID NO:48:

```
SRPEPTAPPE ESFRFGEEKT TTPSQKQEPI DKELYPLT S LRSLFGNDPS SN
2149       2179       2209       2239     2269         2299
```

A comparison of this sequence to SEQ ID NO:1 and SEQ ID NO:2 indicates that these sequences share more than seven contiguous residues with SEQ ID NO:48) (Table 4):

TABLE 4

| SEQ ID NO | Description | Sequence |
|---|---|---|
| 48 | GAG | SRPEPTAPPEESFRFGEEKTTTPSQKQEPIDKELYPLT·SLRSLFGNDPSSN |
| 1 | Isolated Epitope | SRPEPTAPPAESFRFGEEITPTPSQKQEPKDKELYPPLASLRSLFGNDPSSN |
| 2 | Isolated Epitope | SRPEPTAPPEESFRFGEET··TPSQKQEPIDKELYPL·ASLRSLFGSDPSSQEF |

The identified Gag epitope sequences (SEQ ID NO:1 or SEQ ID NO:2), or any of SEQ ID NOS:3-47 are useful as diagnostic agents in accordance with the principles of the present invention. SEQ ID NOs:1-7 are preferred as a gag epitope sequences, and SEQ ID NO:3 is particularly preferred as a gag epitope sequence.

Identified gp41 Epitopes

```
HIV-1 Env-gp41 (SEQ ID NO: 49):
LIAARTVELL GHSSLKGLRL GWEGLRYLWN LLLYWGRELK ISAINLVDTI AIAVAGWTDR
1          10         20         30         40         50         60

VIEIGQRIGR AILHIPRRIR QGLERALL
           70         80       88

CON-ENV-2-gp41 (SEQ ID NO: 50):
LIAARIVELL GHSSLKGLRR GWEALKYLWN LLQYWGQELK NSAISL
1          10         20         30         40     46

ENV-gp41 (SEQ ID NO: 51):
LIVTRIVELL GRRGWEALKY WWNLLNYWSQ ELKNSAVNL
1          10         20         30        39

Env2-gp41-A-Q
                                                            (SEQ ID NO: 52)
ARIVELLGHS SLKGLRRGWE ALKYLWNLLQ YWGQ
1          10         20         30  34

Env3-gp41-seq
                                                            (SEQ ID NO: 53)
CRAILNIPRR IRQGLERALL
1          10         20

Env4-gp41 seq
                                                            (SEQ ID NO: 54)
AVAEGTDRVI EVVQRV
1          10    16

Env34-gp41 seq
                                                            (SEQ ID NO: 55)
AVAEGTDRVI EVVQRVCRAI LNIPRRIRQG FERALL
1          10         20         30     36
```

The identified gp41 epitopes (SEQ ID NO:50 and SEQ ID NO:51) differ in sequence from the sequences of previously identified gp41 peptides. Aligning SEQ ID NO:50 and SEQ ID NO:51 against the HIV-1 gp41 sequence (SEQ ID NO:56; NC_001802) yields the following comparison (sites of SEQ ID NO:56 that are not conserved are shown in single-underline (if conserved in either SEQ ID NO:50 or SEQ ID NO:51) or in double-underline (if not conserved in either SEQ ID NO:50 or SEQ ID NO:51)) (Table 5):

TABLE 5

| SEQ ID NO | Description | Sequence |
|---|---|---|
| 50 | Isolated Epitope | LIAARIVELLGHSSLKGLRRGWEALKYLWNLLQYWGQELKNSAISL |
| 51 | Isolated Epitope | LIVTRIVELLG••••••RRGWEALKYWWNLLQYWSQELKNSAVNL |
| 56 | Gp41 | LIVTRIVELLG••••••RRGWEALKYWWNLLQYWSQELKNSAVSL |

Thus, both SEQ ID NO:50 and SEQ ID NO:51 differ in sequence from the sequence of the corresponding native HIV-1 gp41 gene product (SEQ ID NO:56). An alignment of these sequences with a series of gp41 consensus sequences (Table 6) indicates that SEQ ID NO:50 and SEQ ID NO:51 differ in sequence from the consensus sequences.

TABLE 6

| SEQ ID NO | Description | Sequence |
|---|---|---|
| 56 | GP41 | LIVTRIVELLG••••••RRGWEALKYWWNLLQYWSQELKNSAVSL |
| 50 | Isolated Epitope | LIAARIVELLGHSSLKGLRRGWEALKYLWNLLQYWGQELKNSAISL |
| 51 | Isolated Epitope | LIVTRIVELLG••••••RRGWEALKYWWNLLQYWSQELKNSAVNL |
| 57 | Consensus_B (128) | LIVTRIVELLG••••••RRGWEALKYWWNLLQYWSQELKNSAVNL |
| 58 | Consensus_D (17) | LIAARIVELLG••••••RRGWEALKYLWNLLQYWIQELKNSAISL |
| 59 | Consensus_F1-F2 (10) | LIAARTVDRGL••••••KRGWEALKYLWNLTQYWGQELKNSAISL |
| 60 | Consensus_H (3) | LIVVRTVELLG••••••RRGREALKYLWNLLQYWGQELKNSAINL |
| 61 | Consensus_A-A1-A2 (24) | LIAARTVELLGHSSLKGLRLGWEGLKYLWNLLLYWGRELKISAINL |
| 62 | Consensus_C (50) | LIAARAVELLGRSSLRGLQRGWEALKYLGSLVQYWGLELKKSAISL |
| 63 | Consensus_G (9) | LIAARTVELLGRSSLKGLRLGWEGLKYLWNLLLYWGQELKNSAINL |
| 64 | Consensus_01 (32) | LIAARTVELLGHSSLKGLRRGWEGLKYLGNLLLYWGQELKISAISL |
| 65 | Consensus_02 (16) | LIAARTVELLGHSSLKGLRLGWEALKYLGNLLSYWGQELKNSAINL |

A blast search of SEQ ID NO:50 failed to identify any identical gene sequences. A blast search of SEQ ID NO:51 identified two sequences that were 100% identical to SEQ ID NO:51 (Sequence AAC28452 (Fang, H. et al. (1995) J. Virol. 69 (1), 75-81; Sequence PO4582 (Ratner, L. et al. (1985) Nature 313:277-284 (1985). Of the sequences that differed from SEQ ID NO:51 by one amino acid residue, a substitution of L38→N38 was common (see, e.g., Sequence CAD10927 (Zheng, N. N. et al., Direct Submission). SEQ ID NOs:50, 53 and 55 are particularly preferred as gp41 epitope sequences.

The invention also relates to the following HIV 1 gp41 consensus epitopes shown in Table 7 below:

TABLE 7

| SEQ ID No. | Description | Sequence |
|---|---|---|
| 66 | CON_OF_CONS | LIAARTVELLGRRGWEALKYLWNLLQYWGQELKNSAISLLDTTAIAVAEGT DRVIEVVQRVCRAILNIPRRIRQGFERALL |
| 67 | Mgroup.anc | LIAARTVELLGRRGWEALKYLWNLLQYWGQELKNSAISLLDTTAIAVAEGT DRVIEVVQRACRAILHIPRRIRQGFERALL |
| 68 | CONSENSUS_A1 | LIAARTVELLGHSSLEGLRLGWEGLKYLWNLLLYWGRELKISAINLVDTIA IAVAGW TDRVIEIGQRIGRAILHIPRRIRQGLERALL |
| 69 | A1.anc | LIAARTVELLGRSSLEGLRLGWEGLKYLWNLLLYWGRELKISAINLIDTIA IAVAGWTDRVIEIGQRICRAILNIPRRIRQGLERALL |
| 70 | CONSENSUS_A2 | LIAARTVELLGHSSLKGLRLGWEGLKYLWNLLLYWGRELKNSAISLLDTIA VAVAEWTDRVIEIGQRACRAILNIPRRIRQGFERALL |
| 71 | CONSENSUS_B | LIVTRIVELLGRRGWEVLKYWWNLLQYWSQELKNSAVSLLNATAIAVAEGT DRVIEVVQRACRAILHIPRRIRQGLERALL |
| 72 | B.anc | LIVARIVELLGRRGWEALKYWWNLLQYWSQELKNSAVSLLNATAIAVAEGT DRVIEVVQRACRAILHIPRRIRQGLERALL |
| 73 | CONSENSUS_C | LIAARAVELLGRSSLRGLQRGWEALKYLGSLVQYWGLELERSAISLLDTIA IAVAEGTDRIIELIQRICRAIRNIPRRIRQGFEAALQ |
| 74 | C.anc | LIAARAVELLGRSSLRGLQRGWEALKYLGSLVQYWGLELKKSAISLLDTIA IAVAEGTDRIIELIQRICRAIRNIPRRIRQGFEAALL |
| 75 | CONSENSUS_D | LIAARIVELLGRRGWEALKYLWNLLQWYIQELKNSAISLFDTTAIAVAEGT DRVIEIVQRACRAILNIPTRIRQGLERALL |
| 76 | CONSENSUS_F1 | LIAARIVDRGLRRGWEALKYLGNLTQYWSQELKNSAISLLNTTAIVVAEGT DRVIEALQRAGRAVLNIPRRIRQGLERALL |
| 77 | CONSENSUS_F2 | LIAARTVDMGLKRGWEALKYLWNLPQYWGQELKNSAISLLDTTAIAVAEGT DRIIEVLQRAGRAVLHIPRRIRQGFERALL |

TABLE 7-continued

| SEQ ID No. | Description | Sequence |
|---|---|---|
| 78 | CONSENSUS_G | LIAARTVELLGRSSLKGLRLGWEGLKYLWNLLLYWGQELKNSAINLLDTIA IAVANWTDRVIEVAQRACRAILNIPRRIRQGLERALL |
| 79 | CONSENSUS_H | LIVVRTVELLGRRGREALKYLWNLLQYWGQELKNSAINLLNTTAIAVAEGT DRIIEIVQRAWRAILHIPRRIRQGFERTLL |
| 80 | CONSENSUS_01_AE | LIAARTVELLGHSSLKGLRRGWEGLKYLGNLLLYWGQELKISAISLLDATA IAVAGWTDRVIEVAQGAWRAILHIPRRIRQGLERALL |
| 81 | CONSENSUS_02_AG | LIAARTVELLGHSSLKGLRLGWEALKYLGNLLSYWGQELKNSAINLLDTIA IAVANWTDRVIEIGQRAGRAILNIPRRIRQGLERALL |
| 82 | CONSENSUS_03_AB | LIAARIVELLGRRGWEALKYWWNLLQYWIQELKSSAINLIDTIAIAVAGWT DRVIEIGQRFCRAIRNIPRRIRQGAEKALQ |
| 83 | CONSENSUS_04_CPX | LIVARTVELLGIRGWEALKYLWNLLLYWGQELRNSAINLLDTTAIAVAEGT DRIIEAVQRACRAIRNIPRRIRQGLERALL |
| 84 | CONSENSUS_06_CPX | LIAARTVETLGHRGWEILKYLGNLVCYWGQELKNSAISLLDTTAIAVANWT DRVIEVVQRVFRAFLNIPRRIRQGFERALL |
| 85 | CONSENSUS_08_BC | LTARGVELLGRNSLRGLQRGWEALKYLGSLVQYWGLELKKSTISLVDTIAI AVAEGTDRIINIVQGICRAIHNIPRRIRQGFEAALQ |
| 86 | CONSENSUS_10_CD | LIATRIVELLGRRGWEAIKYLWNLLQYWIQELKNSAISLLDTTAIAVAEGT DRAIEIVQRAVRAVLNIPTRIRQGLERALL |
| 87 | CONSENSUS_11_CPX | LIAARIVETLGRRGWEILKYLGNLAQYWGQELKNSAISLLNATAIAVAEGT DRIIEVVHRVLRAILHIPRRIRQGFERALL |
| 88 | CONSENSUS_12_BF | LIVTRIVELLGRRGWEVLKYWWNLLQYWSQELKNSAISLLNTTAIVVAEGT DRVIEALQRVGRAILNIPRRIRQGLERALL |
| 89 | CONSENSUS_14_BG | LIAARTVELLGRSSLKGLRLGWEGLKYLWNLLLYWGRELKNSAINLLDTVA IAVANWTDRAIEVVQRVGRAVLNIPVRIRQGLERALL |

The identified HIV-1 gp41 epitope sequences (SEQ ID NO:50 or SEQ ID NO:55), or any of SEQ ID NOS:49-89 are useful as diagnostic agents in accordance with the principles of the present invention.

As one embodiment of the invention, diagnostic assays are contemplated wherein an HIV-1 epitope sets are employed wherein the peptide epitope sets consist essentially of HIV-1 gp41 terminal region epitopes or HIV-1 GAG p6 epitopes or a combination of gp41 and GAG p6 epitopes. As used herein, "HIV-1 gp41 terminal region epitopes" refers to epitopes contained on amino acids 784-871 of Consensus aligned seq in Los Alamos database, or mutants or derivatives thereof. As used herein HIV-1 GAG-p6 epitopes refers to to epitopes on amino acids 452-502 of Consensus aligned sequence in Los Alamos database, or mutants or derivatives thereof. As used herein, an epitope set will consist essentially of gp41 and GAG p6 epitopes when the peptide epitope set does not contain other epitopes that show significant reactivity (i.e. preferably less than 130% of background level, more preferably less than 120% of background level, and most preferably less than 110% of background level) with anti-HIV 1 antibodies.

Identified Nef Epitope

```
NEF Peptide (SEQ ID NO: 90):
GLIHSQRRQD ILDLWIYHTQ GYFPDWQNYT PGPGVRYPL
1         10         20         30        39
```

The identified Nef epitope (SEQ ID NO:90) is identical in sequence with the HIV-1 Nef sequence (NC_001802) (SEQ ID NO:91). An alignment of these sequences with a series of Nef consensus sequences (Table 8) indicates that SEQ ID NO:90 is highly conserved.

TABLE 8

| SEQ ID NO | Description | Sequence |
|---|---|---|
| 91 | nef | GLIHSQRRQDILDLWIYHTQGYFPDWQNYTPGPGVRYPL |
| 90 | Isolated Epitope | GLIHSQRRQDILDLWIYHTQGYFPDWQNYTPGPGVRYPL |
| 92 | Consensus_B (266) | GLIYSQKRQDILDLWVYHTQGYFPDWQNYTPGPGIRYPL |
| 93 | Consensus_D (4) | GLIWSQKRQEILDLWVYHTQGFFPDWQNYTPGPGIRYPL |
| 94 | Consensus_A-A1-A2 (14) | GLIYSKKRQEILDLWVYHTQGYFPDWQNYTPGPGIRYPL |

TABLE 8-continued

| SEQ ID NO | Description | Sequence |
|---|---|---|
| 95 | Consensus_C (44) | GLIYSKKRQEILDLWVYHTQGYFPDWQNYTPGPGVRYPL |
| 96 | Consensus_F1-F2 (7) | GLIYSKKRQDILDLWVYHTQGYFPDWQNYTPGPGIRYPL |
| 97 | Consensus_01 (31) | GLIYSKKRQEILDLWVYNTQGFFPDWQNYTPGPGIRYPL |
| 98 | Consensus_02 (12) | GLIYSKKRQEILDLWVYHTQGFFPDWQNYTPGPGTRFPL |
| 99 | Consensus_G (7) | GLIYSKKRQEILDLWVYNTQGFFPDWQNYTPGPGTRFPL |
| 100 | Consensus_H (5) | GLIYSKKRQEILDLWVYNTQGYFPDWQNYTPGPGERYPL |

The identified nef epitope sequence (SEQ ID NO:90), or any of SEQ ID NOS:92-100 are useful as diagnostic agents in accordance with the principles of the present invention.

Identified HIV-2 Epitopes

As one aspect of the invention, it is contemplated that peptides comprising epitopes that are contained on HIV-2 Env-gp36 (e.g. amino acids 817-927 of MAC.US.-0.239_M33262 ENV aligned seq in Los Alamos database, or mutants or derivatives thereof) or epitopes that are contained on HIV-2 GAG-p6 (amino acids 461-555 of MAC.US.-0.239_M33262 GAGPRO aligned seq in Los Alamos database, or mutants or derivatives thereof) will be useful in the diagnosis of HIV-2 infection. In particular, it is contemplated as an aspect of the invention that a combination of at least one epitope contained on HIV-2 gp36 and at least one epitope contained on HIV-2 GAG-p6 will be useful in the diagnosis of breakthrough HIV-2 infections in individuals that have been vaccinated against the HIV-1 or HIV-2 virus, or viral genes or gene products of these viruses.

```
HIV-2 GAG-p6
                                                          (SEQ ID NO: 101)
APQGLIPTAP PMNPAFGMTP QGAIPSAPPA DPAADLLEKY LQQGRKQREQ RERPYKEVTE
1        10         20         30         40         50         60

DLLHLEQGET PRREATEDLL HLNSLFGKDQ
         70         80         90

HIV-2 Env-gp36
                                                          (SEQ ID NO: 102)
FLIRLLIRLL IGLYNICRTL ISKSFQTLQP ISQGLQRALT AIRDWLRPGA AYLQYGCEWI
1        10         20         30         40         50         60

QEALQAFARA TRETLTSVWR NFCGTMGQIG RGILAIPRRI RQGAELALL
         70         80         90        100       109
```

The invention also relates to HIV-2 GAG p6 and HIV-2 Env-gp36 epitopes shown below in Table 9 and Table 10, respectively.

TABLE 9

| SEQ ID NO | Description | Sequence |
|---|---|---|
| 103 | MAC.US.-.239 _M33262 | VHQGLMPTAPPEDPAVDLLKNYMQLGKQQREKQRESREKPYKEVTEDLLHLN SLFGGDQ |
| 104 | H2A.CI.88.UC2 _U38293 | APQGLIPTAPPADPAADLLEKYLQQGRKQREQRERPYKEVTEDLLHLEQGET PRRE-ATEDLLHLNSLFGKDQ |
| 105 | MAC.US.-.MM142 _M16403 | VHQGLTPTAPPEEPAVDLLKNYMHLGKQQRESRGKPYKEVTEDLLHLNSLFG GDQ |
| 106 | MNE.US.-.MNE027 _U79412 | MEQGLTPTAPPEDPAVDLLKNYMQLGKQQRESKRKPYKEVAEDLLELNSLFG EDQ |
| 107 | SMM.US.-.H9 _M80194 | MPQGLTPTAPPEDPAVDLLKNYMKVGRRQRENRERPYKEVTEDLLHLNSLFG EDQ |
| 108 | H2B.CI.-.EHO _U27200 | APQGIVPSAPPMNPAFGMTPQGAIPSAPPADPAEEMLKNYMQLGKKQKENRE RPYKEVTEDLLHLNSLFGEDQ |

TABLE 9-continued

| SEQ ID NO | Description | Sequence |
|---|---|---|
| 109 | H2B.CI.88.UC1_L07625 | VPQGVTPSAPPMDPAEGMTPRGATPSAPPADPAVEMLKSYMRMGRQQRESRERPYKEVTEDLLHLNSLFGEDQ |
| 110 | H2B.GH.86.D205_X61240 | VPQGVTPSAPPMNPAEGMTPRGATPSAPPADPAVEMLKSYMQMGRQQRESRERPYKEVTEDLLHLNSLFGEDQ |
| 111 | H2B.JP.01.KR020_AB100245 | APQGILPSAPPMNPAENMTPQGAMPSAPPADPAVEMLKDYMQLGRKQGGREKPYKEVTEDLLHLNSLFGEDQ |
| 112 | H2G.CI-.ABT96_AF208027 | VPQGLTPSAPPMDPAVDLLKNYMQLGRKQEQRNKPYKEVTEXLLHLSSLFGDDQ |
| 113 | H2U.FR.96.12034_AY530889 | VPQGLTPTAPPAEPAVDLLTPTAPPADPAVDLLKSYMQQGKKQKENRERPYKEVTEDLLHLNSLFGNDQ |
| 114 | H2AB.CI.-.7312A_L36874 | VPQEIVPSAPPMNTAEGKTHQGAIPSAPPADPAVEMLKSYMQLGKQQREKQGRPYKEVTEDLLHLNSLFGEDQ |
| 115 | SMM.SL.92.SL92B_AF334679 | TTSLTPSAPPDPAARIVKEYLEKAQREKTRRSRPYKEVTEDLLHLNSLFGEDQ |

TABLE 10

| SEQ ID NO | Description | Sequence |
|---|---|---|
| 116 | MAC.US.-.239_M33262 | FLIRQLIRLLTWLFSNCRTLLSRVYQILQPILQRLSATLQRIREVLRTELTYLQYGWSYFHEAVQAVWRSATETLAGAWGDLWETLRRGGRWILAIPRRIRQGLELTLL |
| 117 | H2A.-.-.CBL21_U05350 | FLIRLLIRLLIGLYNICRTLISKSFQTLQPISQGLQRALTAIRDWLRPGAAYLQYGCEWIQEALQAFARATRETLTSVWRNFCGTMGQIGRGILAIPRRIRQGAELALL |
| 118 | H2A.CI.88.UC2_U38293 | LLIHLLTRLLTGLYSICRDLLSANSPTRRLISQNLTAIRDWLRLKAAYLQYGCEWIQEAFQAIARTARETLAGAWRGLCKAVQRIGRGILAVPRRIRQGAEIALL |
| 119 | H2A.DE.-.BEN_M30502 | FLIHHLLTRLLIGLYNICRDLLSKNSPTRRLISQSLTAIRDWLRLKAAQLQYGCEWIQEAFQAFARTTRETLAGAWGWLWEAARRIGRGILAVPRRIRQGAELALL |
| 120 | H2A.GH.-.GH1_M30895 | FLIHHLLTRLLTGLYKICRDLLSTNSPTHRLISQNLTAIRDWLRLKAAYLQYGGEWIQEAFQAFAKTTRETLASAWGGLCAAVQRVGRGILAVPRRIRQGAEIALL |
| 121 | H2A.GM.87.D194_J04542 | FLIHLLTRLLTGLYNSCRGLLSKNSPTRRLISQSLTAIRDWLRLKAAYLQYGCEWIQEAFRAFARTARETIAGAWRGLCEAAQRIGRGILAVPRRIRQGAEIALL |
| 122 | H2A.GM.90.CBL24_U05353 | FLIRLLIRLLIGLYNICRDLLSRSSLILQPILQSLQRALTAIRDWLRLEAAYLQYGCEWIQEALQALTRATRETLAGAWRNLWGALQRIGRGILAVPRRIRQGAELALL |
| 123 | H2A.GW.-.CAM3_U05355 | FLIRLLIRLLTRLYNSCRDLLSRSFLTLQPIFQNLRDWLRLRTAFLQYGRQWIQEAFQAFARATRETLTSACRGLWRTLDNFGRGILSIPRRIRQGAEIALL |
| 124 | H2A.SN.-.ST_M31113 | FLIRQLIRLLNRLYNICRDLLSRSFQTLQLISQSLRRALTAVRDWLRFNTAYLQYGGEWIQEAFRAFARATGETLTNAWRGFWGTLGQIGRGILAVPRRIRQGAEIALL |
| 125 | H2A.SN.85.ROD_M15390 | FLIRQLIRLLTRLYSICRDLLSRSFLTLQLIYQNLRDWLRLRTAFLQYGCEWIQEAFQAAARATRETLAGACRGLWRVLERIGRGILAVPRRIRQGAEIALL |
| 126 | H2A.GM.-.ISY_J04498 | FLIRLLIRLLTRLYNSCRDLLSRLYLILQPLRDWLRLKAAYLQYGCEWIQEAFQALARVTRETLTSAGRSLWGALGRIGRGILAVPRRIRQGAEIALL |
| 127 | H2B.CI.-.EHO_U27200 | FPIRQLRDLLIWLYSGCRTLLSKTFQTLQPVLQPLRLPPAYLRYGISWFQEAIQAAARAAGETLASAARTSWGVLRRAAGEIIAIPRRIRQGAELALL |
| 128 | H2B.GH.86.D205_X16109 | FLLRQLRNLLIWLYNGCRTLLLKTFQILHQISTNLQPLRLPVAYLQYGISWFQEALRAAAARATGETLASAGETLWEALRRAARAIIAIPRRIRQGLELTLL |
| 129 | H2G.CI.-.ABT96_AF208027 | FLXRQLGNLLTWLYSNCRALLSRIXQTLQPLFQRISRTLQAIREHLRLEAAYFSYGFRWLQEACTAATRAAQETLTSTWRALWKTLGRVGRGILAIPRRIRQGLELTLL |
| 130 | H2U.FR.96.12034_AY530889 | FLIHQLIRLLTWLYSSCRDLLSRICQSLQPLFQSIRERLHLEIAYLQYGWQYFKEAFQAFGKAARETLSRTGRELWETLGRVGRWLRAIPRRIRQGFELALL |

TABLE 10-continued

| SEQ ID NO | Description | Sequence |
|---|---|---|
| 131 | H2AB.CI.-.7312A_L36874 | FLIRQLRNLLIWLYDGCRTLLLKTFQTLQPALQPLRLLFAYLQYGIGWFQEAVQAAA GATGETLASTGRTLWEALRRTARGIIAVPRRIRQGLELALL |
| 132 | MAC.US.-.BR5_AY290716 | FLIRQLIRLLTWLFSNCRTLLSRVYQILQPIFQRLSATLQRIREVLRTELTYLQYGW SYFHEAVQAVWRSATETLAGAWGDLWETLARGGRW |
| 133 | MAC.US.-.BR5_AY290710 | FLIRQLIRLLTWLFSNCRTLLSRVYQILQPMFQGLSATLQRIREVLRTELTYLQYGW SYFHEAVQAVWRAATETLAGAWGDLWETLRRGGRW |
| 134 | MAC.US.-.BR5_AY290709 | FLIRQLIRLLTWLFSNCRTLLSRVYQILQPIFQGLSATLQRIREVLATELTYLQYGW SYFHEAVQAVWRAATETLAGAWGDLWETLRRGGRW |
| 135 | MNE.US.-.MNE027_U79412 | FLIRQLIRLLTWLFSNCRTLLSRAYQILQPIFQRFSTTLQRVREVLRTELTYLQYGW SYFQEAVQVAWRSATETLAGAWGDLWETLGRVGRWILAIPRRIRQELELTLL |
| 136 | SMM.SL.92.SL92B_AF334679 | FLIRQLIRILTWLYNNLTRLASRAYQNLQQLCQRLSEISQPIRELVRREAGYIRYGW NYFIEACQEAWRSAQEAIVGAWGLIWETLGRVGRGIAAIPRRIRQGLELMLN |
| 137 | SMM.US.-.PT583_AY221512 | FLIRQLIRLLTWLFSSCRDWLLRIYQILQPVLQGLSRTLQRVREVIRIEITYLQYGW SYFQEAAQAWWKFARETLASAWRDIWETLGRVGRGILAIPRRVRQGLELALL |

The identified HIV-2 GAG-p6 epitope sequence (SEQ ID NO:101), or any of SEQ ID NOS:103-115 are useful as diagnostic agents in accordance with the principles of the present invention. Likewise, the identified HIV-2 Env-gp36 epitope sequence (SEQ ID NO:102), or any of SEQ ID NOS:116-137 are useful as diagnostic agents in accordance with the principles of the present invention.

As one embodiment of the invention, diagnostic assays are contemplated wherein HIV-2 epitope sets are employed, wherein the epitope sets consist essentially of HIV-2 GAG-p6 epitopes or HIV-2 Env-gp36 epitopes. As used herein, an epitope set will consist essentially of HIV-2 GAG-p6 epitopes and HIV-2 Env-gp36 epitopes when the peptide epitope set does not contain other epitopes that show significant reactivity (i.e. preferably less than 130% of background level, more preferably less than 120% of background level, and most preferably less than 110% of background level) with anti-HIV 2 antibodies.

Peptide molecules containing the epitopes of the invention may be prepared using virtually any art-known technique for the preparation of peptides. For example, the peptides may be prepared using conventional step-wise solution or solid phase peptide syntheses, or recombinant DNA techniques or proteolysis or modifications of purified viral proteins/peptides or recombinant proteins. Peptides may be prepared using conventional step-wise solution or solid phase synthesis (see, e.g., Merrifield, R B. (1969) "SOLID-PHASE PEPTIDE SYNTHESIS," Adv. Enzymol. Relat Areas Mol. Biol. 32:221-296; Fairwell, T. et al. (1987) "HUMAN PLASMA APOLIPOPROTEIN C-II: TOTAL SOLID-PHASE SYNTHESIS AND CHEMICAL AND BIOLOGICAL CHARACTERIZATION," Proc. Natl. Acad. Sci. U.S.A 84:4796-4800; Kent, S. B. H. "CHEMICAL SYNTHESIS OF PEPTIDES AND PROTEINS," (1988) Ann. Rev. Biochem. 57, 957-984, CHEMICAL APPROACHES TO THE SYNTHESIS OF PEPTIDES AND PROTEINS, Williams et al., Eds., 1997, CRC Press, Boca Raton Fla., and references cited therein; SOLID PHASE PEPTIDE SYNTHESIS: A PRACTICAL APPROACH, Atherton & Sheppard, Eds., 1989, IRL Press, Oxford, England, and references cited therein).

Alternatively, such peptides of the invention may be prepared by way of segment condensation, as described, for example, in Schnölzer, M. et al., "CONSTRUCTING PROTEINS BY DOVETAILING UNPROTECTED SYNTHETIC PEPTIDES: BACKBONE-ENGINEERED HIV PROTEASE," Science. 1992 Apr. 10; 256(5054): 221-5; Schnölzer, M., "IN SITU NEUTRALIZATION IN BOC-CHEMISTRY SOLID PHASE PEPTIDE SYNTHESIS. RAPID, HIGH YIELD ASSEMBLY OF DIFFICULT SEQUENCES," Int Pept Protein Res. 1992 September-October; 40 (3-4):180-193; Rose et al., "STEPWISE SOLID-PHASE SYNTHESIS OF POLYAMIDES AS LINKERS," J. Am. Chem. Soc. 1999 August 4, 121:7034-7038. Methods for preparing peptides are disclosed in U.S. Pat. Nos. 6,004,925 and 6,429,289.

Assays for the Detection of HIV-1 and HIV-2

The present invention is directed in part to the use of novel epitopes in diagnostic assays for the detection of HIV-1 or HIV-2. In a preferred embodiment, such assays of HIV will comprise enzyme immunosorbent assays (EIAs) that employ one or more of the above-described gp41, GAG and/or nef peptides, or fragments or variants thereof, or one or more of the above described HIV-2 GAG or Env-gp36 peptides, or fragments or variants thereof. In a preferred embodiment, 1, 2 or 3 such peptides are employed in such assays. The selected peptides, alone or in combination, can be used to differentiate between vaccine directed antibodies and breakthrough infection generated antibodies to assess the efficacy of vaccine clinical trials, or to monitor potential infections.

Fragments or variants of the peptides preferably comprise at least 10, 20 or 30 contiguous amino acids of the peptides and are at least 70%, preferably at least 75%, 80%, or 85%, more preferably at least 90%, and most preferably at least 95% homologous to the indicated peptides.

A preferred method for determining the best overall match between a query sequence (a sequence of the present invention) and a subject sequence (i.e. homology), also referred to as a global sequence alignment, can be determined using the FASTDB computer program based on the algorithm of Brutlag et al., 1990, Comp. App. Biosci. 6:237-245. In a sequence alignment the query and subject sequences are both amino acid sequences. The result of said global sequence alignment is in percent identity. Preferred parameters used in a FASTDB amino acid alignment are: Matrix=PAM 0, k-tuple=2, Mismatch Penalty=1, Joining Penalty=20, Randomization Group Length=0, Cutoff Score=1, Window Size=sequence length, Gap Penalty=5, Gap Size Penalty=0.05, Window Size=500 or the length of the subject amino acid sequence, whichever is shorter.

If the subject sequence is shorter than the query sequence due to N- or C-terminal deletions, not because of internal deletions, a manual correction must be made to the results. This is because the FASTDB program does not account for N- and C-terminal truncations of the subject sequence when calculating global percent identity. For subject sequences truncated at the N- and C-termini, relative to the query sequence, the percent identity is corrected by calculating the number of residues of the query sequence that are N- and C-terminal of the subject sequence, which are not matched/aligned with a corresponding subject residue, as a percent of the total residues of the query sequence. Whether a residue is matched/aligned is determined by results of the FASTDB sequence alignment. This percentage is then subtracted from the percent identity, calculated by the above FASTDB program using the specified parameters, to arrive at a final percent identity score. This final percent identity score is what is used for the purposes of the present invention. Only residues to the N- and C-termini of the subject sequence, which are not matched/aligned with the query sequence, are considered for the purposes of manually adjusting the percent identity score. That is, only query residue positions outside the farthest N- and C-terminal residues of the subject sequence.

For example, a 90 amino acid residue subject sequence is aligned with a 100 residue query sequence to determine percent identity. The deletion occurs at the N-terminus of the subject sequence and therefore, the FASTDB alignment does not show a matching/alignment of the first 10 residues at the N-terminus. The 10 unpaired residues represent 10% of the sequence (number of residues at the N- and C-termini not matched/total number of residues in the query sequence) so 10% is subtracted from the percent identity score calculated by the FASTDB program. If the remaining 90 residues were perfectly matched the final percent identity would be 90%. In another example, a 90 residue subject sequence is compared with a 100 residue query sequence. This time the deletions are internal deletions so there are no residues at the N- or C-termini of the subject sequence which are not matched/aligned with the query. In this case the percent identity calculated by FASTDB is not manually corrected. Once again, only residue positions outside the N- and C-terminal ends of the subject sequence, as displayed in the FASTDB alignment, which are not matched/aligned with the query sequence are manually corrected for. No other manual corrections are to be made for the purposes of the present invention.

The present invention concerns the binding of peptide epitopes and antibodies. As used herein, an "epitope" is a 2- or 3-dimensional region of an antigen that is recognized by and that specifically binds to an antibody. As used herein, an epitope and an antibody are said to be "specific" for one another, or to "recognize" one another, or to "bind" to one another if they are capable of immunospecific binding to one another.

Any of a wide variety of assay formats may be used in accordance with the methods of the present invention. Such formats may be heterogeneous or homogeneous, sequential or simultaneous, competitive or noncompetitive. U.S. Pat. Nos. 5,563,036; 5,627,080; 5,633,141; 5,679,525; 5,691,147; 5,698,411; 5,747,352; 5,811,526; 5,851,778; and 5,976,822 illustrate several different assay formats and applications. Such assays can be formatted to be quantitative, to measure the concentration or amount of an anti-HIV antibody, or they may be formatted to be qualitative, to measure the presence or absence of an anti-HIV antibody. Additional descriptions of immunoassays that may be adapted for use in accordance with the principles of the present invention are available in the scientific literature (Gnann, J. W. Jr et al. "CUSTOM-DESIGNED SYNTHETIC PEPTIDE IMMUNOASSAYS FOR DISTINGUISHING HIV TYPE 1 AND TYPE 2 INFECTIONS," Methods Enzymol. 1989; 178:693-714; Dopel, S. H. et al. "COMPARISON OF FOUR ANTI-HIV SCREENING ASSAYS WHICH BELONG TO DIFFERENT TEST GENERATIONS," Eur J Clin Chem Clin Biochem. 1991 May; 29(5):331-7; Manocha, M. et al. "COMPARING MODIFIED AND PLAIN PEPTIDE LINKED ENZYME IMMUNOSORBENT ASSAY (ELISA) FOR DETECTION OF HUMAN IMMUNODEFICIENCY VIRUS TYPE-1 (HIV-1) AND TYPE-2 (HIV-2) ANTIBODIES," Immunol Lett. 2003 Feb. 3; 85(3):275-8); Brattegaard, K. et al. "INSENSITIVITY OF A SYNTHETIC PEPTIDE-BASED TEST (PEPTI-LAV 1-2) FOR THE DIAGNOSIS OF HIV INFECTION IN AFRICAN CHILDREN," AIDS. 1995 June; 9(6):656-7; Beristain, C. N. et al. "EVALUATION OF A DIPSTICK METHOD FOR THE DETECTION OF HUMAN IMMUNODEFICIENCY VIRUS INFECTION," J Clin Lab Anal. 1995; 9(6):347-50; Modrow, S. et al. "CARRIER BOUND SYNTHETIC OLIGOPEPTIDES IN ELISA TEST SYSTEMS FOR DISTINCTION BETWEEN HIV-1 AND HIV-2 INFECTION," J Acquir Immune Defic Syndr. 1989; 2(2):141-8; Gueye-Ndiaye, A. et al. "COST-EFFECTIVE DIAGNOSIS OF HIV-1 AND HIV-2 BY RECOMBINANT-EXPRESSED ENV PEPTIDE (566/996) DOT-BLOT ANALYSIS," AIDS. 1993 April; 7(4):475-81; Sabatier, J. M. et al. "USE OF SYNTHETIC PEPTIDES FOR THE DETECTION OF ANTIBODIES AGAINST THE NEF REGULATING PROTEIN IN SERA OF HIV-INFECTED PATIENTS," AIDS. 1989 April; 3(4):215-20; Sommerfelt, M. A. et al. "NOVEL PEPTIDE-BASED HIV-1 IMMUNOTHERAPY," Expert Opin Biol Ther. 2004 March; 4(3):349-361; Alcaro, M. C. et al. "SYNTHETIC PEPTIDES IN THE DIAGNOSIS OF HIV INFECTION," Curr Protein Pept Sci. 2003 August; 4(4):285-90; Smith, R. S. et al. "SYNTHETIC PEPTIDE ASSAYS TO DETECT HUMAN IMMUNODEFICIENCY VIRUS TYPES 1 AND 2 IN SEROPOSITIVE INDIVIDUALS," Arch Pathol Lab Med. 1990 March; 114(3):254-8; Petrov, R. V. et al. "THE USE OF SYNTHETIC PEPTIDES IN THE DIAGNOSIS OF HIV INFECTIONS," Biomed Sci. 1990 March; 1(3):239-44; Zolla-Pazner S. "IDENTIFYING EPITOPES OF HIV-1 THAT INDUCE PROTECTIVE ANTIBODIES," Nat Rev Immunol. 2004 March; 4(3):199-210; Baillou, A. et al. "FINE SEROTYPING OF HUMAN IMMUNODEFICIENCY VIRUS SEROTYPE 1 (HIV-1) AND HIV-2 INFECTIONS BY USING SYNTHETIC OLIGOPEPTIDES REPRESENTING AN IMMUNODOMINANT DOMAIN OF HIV-1 AND HIV-2/SIMIAN IMMUNODEFICIENCY VIRUS," J Clin Microbiol. 1991 July; 29(7):1387-91; McGaughey, G. B. et al. "PROGRESS TOWARDS THE DEVELOPMENT OF A HIV-1 GP41-DIRECTED VACCINE," Curr HIV Res. 2004 April; 2(2):193-204).

Heterogeneous immunoassay techniques typically involve the use of a solid phase material to which the reaction product becomes bound, but may be adapted to involve the binding of non-immobilized antigens and antibodies (i.e., a solution-phase immunoassay). The reaction product is separated from excess sample, assay reagents, and other substances by removing the solid phase from the reaction mixture (e.g., by washing). One type of solid phase immunoassay that may be used in accordance with the present invention is a sandwich immunoassay. In the sandwich assay, the more analyte present in the sample, the greater the amount of label present on the solid phase. This type of assay format is generally preferred, especially for the visualization of low analyte concentrations, because the appearance of label on the solid phase is more readily detected.

In accordance with a preferred embodiment of the present invention, a peptide of the present invention that is specifically reactive with an anti-HIV antibody is bound to a solid support (i.e., immobilized) and incubated in contact with the biological sample being tested for the presence of an anti-HIV antibody. A blocking agent may be added to reduce non-specific binding.

As will be appreciated, the peptide may be incubated with the biological sample in an unbound state and then subsequently bound to the solid support (i.e., immobilizable). The supports are then preferably extensively treated (e.g., by washing, etc.) to substantially remove non-HIV antibodies that may be present but that failed to bind to the bound peptide. In consequence of such treatment, an immune complex forms between the peptide and anti-HIV antibody.

A detectably labeled second antibody (capable of binding to the initial antibody (e.g., an anti-human IgG antibody)) is then preferably added and the support is incubated under conditions sufficient to permit the second antibody to bind to any anti-HIV antibody that may be present. The support is then preferably extensively treated (e.g., by washing, etc.) to substantially remove any unbound second antibody. If anti-HIV antibody is present in the test sample, then the two antibodies will form an immune complex with the immobilized peptide (i.e., a second antibody/anti-HIV antibody/immobilized peptide sandwich). In such an assay, the detection of second antibody bound to the support is indicative of anti-HIV antibody in the sample being tested. Sandwich assay formats are described by Schuurs et al. U.S. Pat. Nos. 3,791,932 and 4,016,043, and by Pankratz, et al., U.S. Pat. No. 5,876,935. The second antibody may be a natural immunoglobulin isolated from nonhuman species (e.g., anti-human IgG murine antibody, anti-human IgG goat antibody, anti-human IgM goat antibody, etc.), or it can be produced recombinantly or synthetically. It may be an intact immunoglobulin, or an immunoglobulin fragment (e.g., FAb, F[Ab]$_2$, etc.). As desired, other binding molecules (capable of binding to anti-HIV antibodies) may be employed in concert with or in lieu of such second antibodies. For example, the anti-HIV antibodies can be biotinylated and the second antibody can be replaced with labeled avidin or streptavidin.

To eliminate the bound-free separation step and reduce the time and equipment needed for a chemical binding assay, a homogeneous assay format may alternatively be employed. In such assays, one component of the binding pair may still be immobilized; however, the presence of the second component of the binding pair is detected without a bound-free separation. Examples of homogeneous optical methods are the EMIT method of Syva, Inc. (Sunnyvale, Calif.), which operates through detection of fluorescence quenching; the laser nephelometry latex particle agglutination method of Behringwerke (Marburg, Germany), which operates by detecting changes in light scatter; the LPIA latex particle agglutination method of Mitsubishi Chemical Industries (Tokyo, Japan); the TDX fluorescence depolarization method of Abbott Laboratories (Abbott Park, Ill.); and the fluorescence energy transfer method of Cis Bio International (Paris, France). Any of such assays may be adapted for use in accordance with the objectives of the present invention.

The binding assay of the present invention may be configured as a competitive assay. In a competitive assay, the more anti-HIV antibody present in the test sample, the lower the amount of label present on the solid phase.

In a manner similar to the sandwich assay, the competitive assay can be conducted by providing a defined amount of a labeled anti-HIV antibody and determining whether the fluid being tested contains anti-HIV antibody that would compete with the labeled antibody for binding to the support. In such a competitive assay, the amount of captured labeled antibody is inversely proportional to the amount of analyte present in the test sample. Smith (U.S. Pat. No. 4,401,764) describes an alternative competitive assay format using a mixed binding complex that can bind analyte or labeled analyte but in which the analyte and labeled analyte cannot simultaneously bind the complex. Clagett (U.S. Pat. No. 4,746,631) describes an immunoassay method using a reaction chamber in which an analyte/ligand/marker conjugate is displaced from the reaction surface in the presence of test sample analyte and in which the displaced analyte/ligand/marker conjugate is immobilized at a second reaction site. The conjugate includes biotin, bovine serum albumin, and synthetic peptides as the ligand component of the conjugate, and enzymes, chemiluminescent materials, enzyme inhibitors, and radionucleotides as the marker component of the conjugate. Li (U.S. Pat. No. 4,661,444) describes a competitive immunoassay using a conjugate of an anti-idiotype antibody and a second antibody, specific for a detectable label, in which the detectable response is inversely related to the presence of analyte in the sample. Allen (European Patent Appln. No. 177,191) describes a binding assay involving a conjugate of a ligand analog and a second reagent, such as fluorescein, in which the conjugate competes with the analyte (ligand) in binding to a labeled binding partner specific for the ligand, and in which the resultant labeled conjugate is then separated from the reaction mixture by means of solid phase carrying a binding partner for the second reagent. This binding assay format combines the use of a competitive binding technique and a reverse sandwich assay configuration; i.e., the binding of conjugate to the labeled binding member prior to separating conjugate from the mixture by the binding of the conjugate to the solid phase. The assay result, however, is determined as in a conventional competitive assay in which the amount of label bound to the solid phase is inversely proportional to the amount of analyte in the test sample. Chieregatt et al. (GB Patent No. 2,084,317) describe a similar assay format using an indirectly labeled binding partner specific for the analyte. Mochida et al. (U.S. Pat. No. 4,185,084) also describe the use of a double-antigen conjugate that competes with an antigen analyte for binding to an immobilized antibody and that is then labeled. This method also results in the detection of label on a solid phase in which the amount of label is inversely proportional to the amount of analyte in the test sample. Sadeh et al. (U.S. Pat. No. 4,243,749) describe a similar enzyme immunoassay in which a hapten conjugate competes with analyte for binding to an antibody immobilized on a solid phase. Any of such variant assays may be used in accordance with the present invention.

In all such assay formats, at least one component of the assay reagents will preferably be labeled or otherwise detectable by the evolution or quenching of light. Such component may be a second antibody, anti-HIV antibody, or the peptide that binds to the anti-HIV antibody, depending on the immunoassay format employed. Radioisotopic-binding assay formats (e.g., a radioimmunoassay, etc.) employ a radioisotope as such label; the signal is detectable by the evolution of light in the presence of a fluorescent or fluorogenic moiety (see Lucas et al., U.S. Pat. No. 5,698,411 and Landrum et al., U.S. Pat. No. 5,976,822). Enzymatic-binding assay formats (e.g., an ELISA, etc.) employ an enzyme as a label; the signal is detectable by the evolution of color or light in the presence of a chromogenic or fluorogenic moiety. Other labels, such as paramagnetic labels, materials used as colored particles, latex particles, colloidal metals such as selenium and gold, and dye particles (see U.S. Pat. Nos. 4,313,734; 4,373,932, and 5,501, 985) may also be employed. The use of enzymes (especially alkaline phosphatase, β-galactosidase, horse radish peroxidase, or urease) as the detectable label (i.e., an enzyme immunoassay or EIA) is preferred.

The presence of enzymatic labels may be detected through the use of chromogenic substrates (including those that evolve or adsorb fluorescent, UV, visible light, etc.) in response to catalysis by the enzyme label. More preferably, chemical labels may be employed (e.g., colloidal gold, latex bead labels, etc.). Detection of label can be accomplished using multiple detectors, multipass filters, gratings, or spectrally distinct fluors (see e.g., U.S. Pat. No. 5,759,781), etc. It is particularly preferred to employ peroxidase as an enzyme label, especially in concert with the chromogenic substrate 3, 3',5, 5'-tetramethylbenzidine (TMB), OPD, or ABTS. In the case of labeling of the antibodies with peroxidase as enzyme, it is possible to use the periodate technique (Nakane, P. K. et al. (1974) "PEROXIDASE-LABELED ANTIBODY. A NEW METHOD OF CONJUGATION," J Histochem Cytochem. 22:1084-90) or a method reported in which the partners are linked with a heterobifunctional reagent (Ishikawa, E. et al. (1983) "ENZYME-LABELING OF ANTIBODIES AND THEIR FRAGMENTS FOR ENZYME IMMUNOASSAY AND IMMUNOHISTOCHEMICAL STAINING," J. Immunoassay. 49(3):209-327).

Any of a wide variety of solid supports may be employed in the immunoassays of the present invention. Suitable materials for the solid support are synthetics such as polystyrene, polyvinyl chloride, polyamide, or other synthetic polymers, natural polymers such as cellulose, as well as derivatized natural polymers such as cellulose acetate or nitrocellulose, and glass, especially glass fibers. The support can take the form of spheres, rods, tubes, and microassay or microtiter plates. Sheet-like structures such as paper strips, small plates, and membranes are likewise suitable. The surface of the carriers can be permeable and impermeable for aqueous solutions.

Although the foregoing description pertains to assaying for the presence of anti-HIV antibodies in biological samples that are fluids (e.g., sera, blood, urine, saliva, pancreatic juice, cerebrospinal fluid, semen, etc.), it will be appreciated that any fluidic biological sample (e.g., tissue or biopsy extracts, extracts of feces, sputum, etc.) may likewise be employed in the assays of the present invention. Most preferably, the biological sample being assayed will be serum or plasma. Table 11 illustrates the variables that may be employed in an ELISA (BSA—bovine serum albumin; FBS—fetal bovine serum; HRP—horsradish peroxidase; AP—alkaline phosphatase; TMB—3, 3',5, 5'-tetramethylbenzidine; OPD—o-phenylenediamine dihydrochloride).

carrier means being compartmentalized to receive in close confinement; one or more containers means vials, tubes and the like; each of the containers means comprising one of the separate elements to be used in the method. For example, one of the containers means may comprise a peptide of the present invention (for example, any of SEQ ID NOS: 1-11 or 49-55 or 141, with or without the a peptide linker, e.g. a carboxy-terminal GGGC (SEQ ID NO:138) peptide linker) bound to a solid support A second container may comprise soluble, detectably labeled second antibody, preferably in lyophilized form, or in solution. In addition, the kit may also contain one or more containers, each of which comprises a (different) predetermined amount of an anti-HIV antibody. These latter containers can be used to prepare a standard curve into which can be interpolated the results obtained from the sample containing the unknown amount of anti-HIV antibodies.

In using the kit, all the user need do is add to a container a premeasured amount of a sample suspected of containing a measurable yet unknown amount of anti-HIV antibody, a premeasured amount of support-hound peptide present in the first container, and a premeasured amount of the detectably labeled second antibody present in the second container. After an appropriate time for incubation, an immune complex is formed (if the sample contained anti-HIV antibody) and is separated from the supernatant fluid, and the immune complex or the supernatant fluid are detected, as by radioactive counting, addition of an enzyme substrate, and color development, or by inclusion of a chemical label (e.g., colloidal gold, latex beads, etc.).

The present invention particularly relates to the use of immuno-chromatographic assay formats to detect anti-HIV antibodies. In a preferred immunochromatographic assay format, two contacting, but spatially distinct, porous carriers are employed. The first such carrier will contain a non-immobilized, labeled peptide of the present invention and the second such carrier will contain an immobilized, but unlabeled antibody that binds to IgG (e.g., where human anti-HIV antibodies are being assayed, the unlabeled antibody may be an anti-human IgG antibody). Preferably, the device will comprise a hollow casing constructed of, for example, a plastic

TABLE 11

| Epitope Presentation | Coating Amount | Blocking Agent | Serum/Plasma Dilution | $2^{nd}$ Antibody | $2^{nd}$ Antibody Dilution | Substrate |
|---|---|---|---|---|---|---|
| GST Protein | 1,000 ng | BSA (Sigma) | 1:50 | HRP-Anti-Human IgG | 1:1,000 | Slow TMB |
| Peptide | 500 ng | BSA (ICN) | 1:100 | HRP-Anti-Human IgG + IgM | 1:2,000 | Turbo TMB |
| Biotin-Peptide | 400 ng | Gelatin | | HRP-Anti-Human IgG + IgM-Fc | 1:5,000 | Ultra TMB |
| | 250 ng | FBS | | AP-Anti-Human IgG + IgM | 1:10,000 | OPD (Pierce) |
| | 100 ng | Milk | | AP-Anti-Human IgG + IgM-Fc | 1:20,000 | OPD (NEN) |
| | 33 ng | | | HRP-Anti-Human IgG-Fc | | ABTS |

In a preferred embodiment of the present invention, the ELISA employs a peptide for epitope presentation, a 33 ng (for GAG-p6) or 250 ng (for Env-gp41) coating, blocking by milk, a HRP-Anti-Human IgG+IgG-Fc as the $2^{nd}$ antibody (at a 10,000 fold dilution), and OPD as a substrate. Buffers that may be employed include commonly used buffers such as PBS or Tris buffers, with or without Tween-20 or other detergents commonly used for immunoassays.

Materials for use in the assay of the invention are ideally suited for the preparation of a kit. Such a kit may comprise a material, etc., in which the first carrier will communicate indirectly with the interior of the casing via a multilayer filter system that is accessible from the device (e.g., by protruding therefrom or by being incompletely covered by the device), such that a serum, plasma, or whole blood test sample can be applied directly to the filter system and will permeate therefrom into the first porous carrier. In such a device, the permeation of fluid containing anti-HIV antibodies will cause the non-immobilized labeled peptide of the first carrier to become bound to the migrating antibodies, and will then permeate into the second carrier. Because the second carrier contains immobilized antibody that binds human IgG, any labeled peptide entering the second carrier will be entrapped therein. Detection of labeled peptide in the carrier containing the immobilized unlabeled antibody thus indicates that anti-HIV antibodies were present in the sample being evaluated. The assay can be made quantitative by measuring the quantity of labeled peptide that becomes bound within the second porous carrier.

Having now generally described the invention, the same will be more readily understood through reference to the following examples, which are provided by way of illustration, and are not intended to be limiting of the present invention, unless specified.

EXAMPLE 1

Identification of New Serologic Epitopes

In order to identify new serologic epitopes that conform to the above discussed criteria, gene-fragment phage display libraries are constructed by limited DNase 1 digestion of HIV-1 DNA (NL4-3 clone) to generate random DNA fragments, 50-300 bp long. The fragments are purified and polished with T4 DNA polymerase and cloned at the N-termini of the coat protein of phage display vectors (FIG. 1). This procedure results in the formation of a phage library that contains every possible encoded peptide in any of the reading frames.

The library is subjected to panning on immobilized serum antibodies from HIV-1-infected individual (early seroconversion). Phages that bind to the immobilized antibodies are retained, while non-binding, or weakly binding, phages are washed-off (FIG. 2).

DNA sequencing of the captured phages (after amplification in and individual separation in *E. coli*) allows the mapping of the selected peptides to known HIV proteins. Initially, 11 "phagotopes" were selected and sequenced. They map to GAG-p6, RT, IN, Vif, gp120, gp41, and Nef. These sequences are produced as synthetic peptides.

Further screenings were conducted with 5 panels of sequential sera from HIV-1 seroconvertors (provided by Boston Biomedica Inc.). Four of the initial 11 epitopes are found to interact with early post-infection sera, demonstrating medium to high binding affinity. They map to GAG-p6, gp120, gp41, and Nef. Furthermore, in extended screens of random HIV seropositive plasma samples, these peptides are found to be reactive with 80-99% of all seropositive plasma tested. No false reactivity is detected with 100 sera from seronegative individuals.

Based on the above-described results, it is concluded that a combination of 1, 2, or more of the selected peptides are useful in the detection of breakthrough infections in the context of HIV vaccine trials. Sequence alignment of 3 selected peptides (from GAG-p6, gp41, and Nef) with consensus sequences for all clades in the Los Alamos database, reveals a high degree of conservation (FIG. 3).

EXAMPLE 2

Production and Use of New Serologic Epitopes

Large quantities of highly purified synthetic peptides expressing the identified sequences from HIV-1 GAG-p6, gp41, and Nef, or HIV-2 Gag-p6 and gp36, are produced under GLP conditions. The synthetic peptides are used to coat ELISA plates.

The reactivities of the synthetic peptides are tested with early seroconversion samples from different countries and different clades (under standardized conditions). Pre-clinical and clinical samples of immune sera from recent HIV vaccine candidates, likely to proceed to phase I/II/III trials, are screened in order to confirm and expand the above-described demonstration of the ability of the newly discovered HIV-1 epitopes, either alone or in combination, to react with high percentage of plasma from early seroconversion-patients. Currently licensed EIA kits may be used for side-by-side analysis.

The reactivity of immune sera from recipients of complex HIV vaccine candidates (as well as from pre-clinical studies of these vaccines) should be negative.

If plasma from Africa or Asia are not uniformly reactive with the Glade B epitopes, they should score positive on consensus peptides. In addition, new Gene-fragment phage-display libraries can be constructed using HIV genomes from other clades.

The selected peptides in combination can be used to differentiate between vaccine directed antibodies and breakthrough infection generated antibodies during HIV vaccine clinical trials.

EXAMPLE 3

HIV ELISA

In order to determine preferred conditions for conducting an ELISA using the peptides of the present invention, various combinations of peptides, coating amounts, blocking agents, serum/plasma dilutions, second antibodies, second antibody dilutions and substrates are tested (a few are summarized in Table 11). ELISAs are characterized for the following sample types: normal (non-HIV infected) serum samples (for cut-off determination); confirmed HIV infected serum samples; seroconversion samples, serum samples from patients infected with different HIV-1 subtypes, randomly collected serum samples-blinded panel, vaccinated individual serum samples. ELISAs are also characterized for cross-reactivity with other pathogens including reteroviruses.

From such characterizations preferred assay conditions are found to employ a peptide for epitope presentation, a coating of 33 ng (for GAG-p6) or 250 ng (for ENV-gp-41), blocking by 2% milk, a 1:100 serum/plasma dilution, a HRP-Anti-Human IgG-Fc as the $2^{nd}$ antibody (at 1:10,000 fold dilution), and OPD as substrate. Buffers employed may be common buffers such as PBS or Tris buffer, with or without Tween-20 or other detergents commonly used for immunoassays. All incubations are done at room temperature for 1 hr each, except for blocking by milk, which is done for 2-3 hrs. The peptides employed are the GAG-p6 (SEQ ID NO:3) and gp41 (SEQ ID NO:50 and SEQ ID NO:55)), alone and in combination. These assay conditions are employed in the ELISAs described in the examples provided below, unless otherwise indicated.

FIG. 4 shows the frequency of negative samples (n=600) obtained in ELISAs employing the GAG-p6 (SEQ ID NO:3; Panel A) and gp41 (SEQ ID NO:50 and SEQ ID NO:55); Panel B) peptides, alone and in combination (Panel C). For the GAG-p6 ELISA results shown in FIG. 4, panel A, the average optical density (OD) was 0.018, the standard deviation (SD) was 0.024, and the calculated cut-off was the average optical density+3×SD (=0.137). The actual cut-off used was 0.15. For the gp41 ELISA results reported in FIG. 4, Panel B, the average optical density (OD) was 0.005, the standard deviation (SD) was 0.0025, and the calculated cutoff was the average optical density+3×SD (=0.0173). The actual cut-off used was 0.035. For these ELISAs, the Specimen/Cut-Off Ratio is defined as the Absorbance of the Test Sample divided by the actual Cut-Off Value. If the Specimen/Cut-Off Ratio is greater than or equal to 1, the sample is scored as positive for the presence of anti-HIV antibodies, and is termed "HIV positive." If the Specimen/Cut-Off Ratio is less than 1, the sample is scored as negative for the presence of anti-HIV antibodies, and is termed "HIV negative."

Using the above-described preferred assay conditions, the Specimen/Cut-Off Ratio was determined for an HIV+ serum sample at times ranging from 0 to 40 days. The results of this experiment are shown in Table 12. In Table 12, Abbott HIV 1/2 is a licensed HIV serodetection kit. HIV Ag is a licensed kit to detect p24. Data relating to FDA licensed EIA Kits was generated by Boston Biomedica Inc (Gaithersburg, USA).

TABLE 12

| Sample I.D. | Day Collected | CBER P6 | CBER gp41 | Abbott HIV 1/2 | Abbott HIV Ag | FDA LIC. EIA KITS |
|---|---|---|---|---|---|---|
| PRB-929-01 | 0 | 0.56 | 0.43 | 0.2 | 0.5 | 0/5 |
| PRB-929-02 | 4 | 0.48 | 0.4 | 0.2 | 0.5 | 0/5 |
| PRB-929-03 | 14 | 0.9 | 0.56 | 0.2 | 0.9 | 0/5 |
| PRB-929-04 | 18 | 0.94 | 0.52 | 0.2 | 13.4 | 0/5 |
| PRB-929-05 | 21 | 0.8 | 0.5 | 0.9 | >22.7 | 0/5 |
| PRB-929-06 | 25 | 1.2 | 0.74 | >16.3 | >22.7 | 1/5 |
| PRB-929-07 | 28 | 8.4 | 1.02 | >16.3 | >22.7 | 3/5 |

The seroreactivity of the peptides during acute infection was evaluated. The results of these ELISAs are shown in Table 13.

TABLE 13

| Sample I.D. | Day Collected | CBER p6 | CBER Gp41 | Abbott HIV 1/2 | Abbott HIV Ag | FDA LIC. EIA KITS |
|---|---|---|---|---|---|---|
| PRB910-1 | 0 | 0.45 | 0.32 | 0.2 | 0.4 | 0/5 |
| PRB910-2 | 14 | 0.88 | 0.57 | 0.2 | 5.7 | 0/5 |
| PRB910-3 | 26 | 2.8 | 0.69 | 10.4 | 0.6 | 5/5 |
| PRB910-4 | 28 | 2.87 | 0.89 | 7.4 | 0.5 | 5/5 |
| PRB910-5 | 32 | 4.66 | 0.97 | 7.6 | 0.4 | 5/5 |
| PRB910-6 | 35 | 4.25 | 1.04 | 7.1 | 0.4 | 5/5 |
| PRB910-7 | 40 | 3.84 | 2.01 | 7.8 | 0.4 | 5/5 |

The analysis of five different seroconversion panels shows that HIV-1 infection can be detected using the peptides of the present invention within 2-3 weeks following HIV-1 RNA detection by the polymerase chain reaction (PCR).

EXAMPLE 4

Early Detection of HIV-1 Infection by Peptides in Seroconversion Panels

The peptides and assays of the present invention are employed using the above-described ELISA conditions to detect HIV-1 infection in serum from seroconverted individuals. The data from such assays is shown in Table 14.

TABLE 14

| Sample ID | ID Number | Day Collected | Specimen/Cut-Off Ratio p6 | Specimen/Cut-Off Ratio gp41 |
|---|---|---|---|---|
| AUS-105 | PS04017 | 0 | 0.51 | 3.97 |
|  |  | 8 | 0.56 | 5.41 |
|  |  | 29 | 0.7 | 12.33 |
|  |  | 56 | 0.87 | 16.24 |
|  |  | 168 | 0.88 | 25.93 |
|  |  | 259 | 2.69 | 29.32 |
| AUS-107 | PS01019 | 0 | 0.93 | 3.52 |
|  |  | 28 | 1.07 | 4.95 |
|  |  | 61 | 0.71 | 4.97 |
|  |  | 168 | 0.78 | 11.95 |
| AUS-108 | PS02016 | 0 | 1.73 | 0.42 |
|  |  | 12 | 2.64 | 0.45 |
|  |  | 31 | 1.24 | 0.99 |
|  |  | 66 | 3.06 | 4.82 |
|  |  | 192 | 0.73 | 7.89 |
|  |  | 269 | 0.77 | 19.35 |
| AUS-113 | PS01026 | 0 | 0.41 | 12.56 |
|  |  | 27 | 0.56 | 14.91 |
|  |  | 56 | 0.73 | 20.15 |
|  |  | 166 | 0.75 | 21.22 |
| AUS-114 | PS01029 | 0 | 2.77 | 7.4 |
|  |  | 7 | 2.12 | 7.22 |
|  |  | 28 | 2.86 | 7.41 |
|  |  | 56 | 7.63 | 8.18 |
|  |  | 147 | 16.19 | 19.21 |
| AUS-115 | PM01002 | 0 | 0.84 | 11.49 |
|  |  | 159 | 1.37 | 14.14 |
| AUS-116 | PM01003 | 0 | 1.11 | 0.61 |
|  |  | 7 | 1.65 | 1.32 |
|  |  | 20 | 1.32 | 2.68 |
|  |  | 55 | 2.11 | 11.92 |
|  |  | 168 | 1.28 | 20.92 |
| AUS-117 | PM02001 | 0 | 1.48 | 7.87 |
|  |  | 7 | 1.24 | 7.43 |
|  |  | 28 | 1.48 | 13.61 |
|  |  | 61 | 0.8 | 19.22 |
|  |  | 169 | 1.03 | 23.07 |
|  |  | 252 | 0.82 | 21.89 |
|  |  | 364 | 0.8 | 26.58 |
| AUS-118 | PM02002 | 0 | 16.07 | 0.81 |
|  |  | 10 | 14.17 | 0.9 |
|  |  | 25 | 12.9 | 4.82 |
|  |  | 50 | 15.8 | 12.66 |
|  |  | 170 | 18.21 | 27.58 |
|  |  | 252 | 15.47 | 27.33 |
|  |  | 374 | 7.9 | 30.96 |
| AUS-120 | PM02004 | 0 | 1.27 | 0.71 |
|  |  | 7 | 1.21 | 0.78 |
|  |  | 36 | 2.28 | 1.58 |
|  |  | 70 | 5.34 | 1.98 |
|  |  | 182 | 5.47 | 3.51 |
|  |  | 259 | 5.48 | 7.38 |
| AUS-121 | PM02006 | 0 | 0.57 | 5.85 |
|  |  | 9 | 0.52 | 4.65 |
|  |  | 28 | 0.53 | 3.74 |
|  |  | 56 | 0.69 | 4.39 |
|  |  | 168 | 0.51 | 1.76 |
|  |  | 252 | 0.54 | 1.17 |
| AUS-123 | PM03001 | 0 | 1.93 | 6.14 |
|  |  | 18 | 1.18 | 4.53 |
|  |  | 57 | 0.76 | 2.89 |
|  |  | 87 | 0.71 | 2.63 |

The data demonstrate that the peptides and assays of the present invention can be employed to detect HIV-1 infection in serum from seroconverted individuals.

EXAMPLE 5

Cross Clade Reactivity of Peptides for HIV-1 Diagnosis

The peptides and assays of the present invention are evaluated using the above-described ELISA conditions for cross-clade reactivity in their detection of HIV-1 infection. The data from such assays is shown in Table 15.

TABLE 15

| Sample I.D. | HIV-1 Genotype | p6 | gp41 | Origin of Sample | Abbott HIV 1/2 | FDA LIC. EIA KITS |
|---|---|---|---|---|---|---|
| WWRB303-01 | A | 6.26 | 29.17 | Ghana | >15.9 | 4/4 |
| WWRB303-02 | A | 18.44 | 0.53 | Ghana | >15.9 | 4/4 |
| WWRB303-03 | C | 3.24 | 4.53 | S. Africa | >15.9 | 4/4 |
| WWRB303-04 | C | 5.12 | 1.09 | S. Africa | >15.9 | 4/4 |
| WWRB303-05 | D | 2.90 | 62.43 | Uganda | >15.9 | 4/4 |
| WWRB303-06 | D | 15.90 | 2.50 | Uganda | >15.9 | 4/4 |
| WWRB303-07 | G | 3.02 | 0.52 | Ghana | >15.9 | 4/4 |
| WWRB303-08 | G | 1.10 | 0.23 | Ivory Coast | >15.9 | 4/4 |
| WWRB303-09 | O | 0.53 | 0.31 | Spain | 2.4 | 4/4 |
| WWRB303-10 | F | 2.44 | 0.38 | Argentina | >15.9 | 4/4 |
| WWRB303-11 | HIV-2 | 0.03 | 0.05 | Ivory Coast | 0.3 | 2/4 |
| WWRB303-12 | NEG | 0.03 | 0.07 | Argentina | 0.4 | 0/4 |
| WWRB303-13 | A | 13.60 | 50.17 | Uganda | >15.9 | 4/4 |
| WWRB303-14 | C | 5.37 | 1.63 | Zimbabwe | >15.9 | 4/4 |
| WWRB303-15 | B | 0.73 | 55.40 | U.S.A | >15.9 | 4/4 |

The data demonstrates that the peptides and assays of the present invention exhibit broad cross-clade reactivity in their detection of HIV-1 infection.

EXAMPLE 6

Reactivity of Peptides with Random Serum Samples from individuals Infected with Diverse HIV-1 Clades The peptides and assays of the present invention are evaluated using the above-described ELISA conditions for their ability to detect HIV-1 infection using random serum samples from individuals infected with diverse HIV-1 clades. The data from such assays is shown in Table 16.

TABLE 16

| Sample I.D. | Subtype | p6 | gp41 |
|---|---|---|---|
| NYU-01 | $AG^{pro}$ $AG^{gag}$ $A^{env}$ | 3.8 | 91.63 |
| NYU-02 | $AG^{pro}$ | 17.79 | 36.96 |
| NYU-03 | $AG^{pro}$ $AG^{gag}$ $AG^{env}$ | 0.75 | 1.53 |
| NYU-04 | $AG^{pro}$ $G^{gag}$ $G^{env}$ | 9.24 | 87.7 |
| NYU-05 | $AG^{pro}$ $AG^{gag}$ $A^{env}$ | 5.64 | 53.8 |
| NYU-06 | $AG^{pro}$ $A^{gag}$ $A^{env}$ | 19.15 | 91.6 |
| NYU-07 | $J^{pro}$ | 11.76 | 0.1 |
| NYU-08 | $A^{pro}$ | 1.84 | 86.8 |
| NYU-09 | $AG^{pro}$ $AG^{gag}$ $A^{env}$ | 1.6 | 45.43 |
| NYU-10 | $AG^{pro}$ | 1.86 | 0.47 |
| NYU-11 | $AG^{pro}$ | 7.52 | 96.57 |
| NYU-12 | $AG^{pro}$ | 14.78 | 6.07 |
| NYU-13 | $AG^{pro}$ | 0.26 | 95.87 |
| NYU-14 | $AG^{pro}$ | 0.45 | 6.83 |
| NYU-15 | $AG^{pro}$ | 1.3 | 0.33 |
| NYU-16 | $AG^{pro}$ $AG^{gag}$ $AG^{env}$ | 0.9 | 88.03 |
| NYU-17 | $AG^{pro}$ $AG^{gag}$ $AG^{env}$ | 1.56 | 73.07 |
| NYU-18 | $A^{pro}$ | 0.4 | 3.73 |
| NYU-19 | $A^{pro}$ $A^{gag}$ $AG^{env}$ | 5.67 | 79.27 |
| NYU-20 | $A^{pro}$ $A^{gag}$ $A^{env}$ | 18.56 | 16.17 |
| NYU-21 | $AG^{pro}$ | 18.33 | 91.97 |
| NYU-22 | $A^{pro}$ $A^{gag}$ $A^{env}$ | 1.63 | 93.43 |
| NYU-23 | $AG^{pro}$ | 15.05 | 70.27 |
| NYU-24 | $AG^{pro}$ | 3.86 | 1.63 |
| NYU-25 | $AG^{pro}$ | 16.14 | 73.97 |
| NYU-26 | $AG^{pro}$ $AG^{gag}$ $A^{env}$ | 20.48 | 87.27 |
| NYU-27 | $AG^{pro}$ | 4.68 | 0.8 |
| NYU-28 | $AG^{pro}$ | 15.66 | 87 |
| NYU-29 | $AG^{pro}$ | 7 | 0.47 |
| NYU-30 | $AG^{pro}$ | 8.78 | 84.3 |
| NYU-31 | $AG^{pro}$ | 2.33 | 87.17 |
| NYU-32 | $A^{pro}$ | 0.39 | 1.7 |
| NYU-33 | $AG^{pro}$ $F2^{gag}$ $F2^{env}$ | 13.67 | 97.67 |
| NYU-34 | $AG^{pro}$ $AG^{gag}$ $AG^{env}$ | 1.48 | 72.5 |
| NYU-35 | $AG^{pro}$ | 4.96 | 15.37 |
| NYU-36 | $J^{pro}$ | 0.04 | 56.26 |
| NYU-37 | $G^{pro}$ $G^{gag}$ $G^{env}$ | 0.58 | 92.37 |
| NYU-38 | $AG^{pro}$ | 1.23 | 1.93 |
| NYU-39 | $AG^{pro}$ | 0.59 | 0.33 |
| NYU-40 | $AG^{pro}$ | 18.07 | 89.9 |
| NYU-41 | $AG^{pro}$ | 10.41 | 93.43 |
| NYU-42 | $AG^{pro}$ | 0.67 | 77.73 |
| NYU-43 | $C^{pro}$ | 1.15 | 0.57 |
| NYU-44 | $AG^{pro}$ $AG^{gag}$ $AG^{env}$ | 1.31 | 1.03 |
| NYU-45 | $AG^{pro}$ | 10.73 | 5.23 |
| NYU-46 | $A^{pro}$ $AE^{gag}$ $A^{env}$ | 9.65 | 72.7 |
| NYU-47 | $AG^{pro}$ | 1.71 | 44.7 |
| NYU-48 | $AG^{pro}$ | 8.06 | 90.97 |
| NYU-49 | $AG^{pro}$ | 1.04 | 86.23 |
| NYU-50 | $AG^{pro}$ | 2.27 | 92.6 |
| NYU-51 | $A^{pro}$ | 4.65 | 0.67 |
| NYU-52 | $D^{pro}$ | 1.84 | 94.5 |
| NYU-53 | $D^{pro}$ $D^{gag}$ $D^{env}$ | 2.3 | 35.8 |
| NYU-54 | $J^{pro}$ $G^{gag}$ $A^{env}$ | 18.24 | 93.03 |
| NYU-55 | $AG^{pro}$ | 3.05 | 92.83 |
| NYU-56 | $G^{pro}$ $G^{gag}$ $A^{env}$ | 1.96 | 2 |
| NYU-57 | $AG^{pro}$ | 15.89 | 84.8 |
| NYU-58 | $G^{pro}$ | 1.57 | 8.83 |
| NYU-59 | $U^{pro}$ | 1.5 | 68.7 |
| NYU-60 | $A^{pro}$ | 3.18 | 95.5 |
| NYU-61 | $A^{pro}$ | 0.58 | 93 |
| NYU-62 | $AG^{pro}$ | 6.22 | 77.97 |
| NYU-63 | $A^{pro}$ | 1.31 | 96.1 |
| NYU-64 | $AG^{pro}$ | 11.61 | 30.3 |
| NYU-65 | $A^{pro}$ | 0.92 | 77.53 |
| NYU-66 | $AG^{pro}$ $AG^{gag}$ $A^{env}$ | 2.24 | 6.3 |
| NYU-67 | $AG^{pro}$ | 20.34 | 7.07 |
| NYU-68 | $AG^{pro}$ | 7.93 | 49.17 |
| NYU-69 | $AG^{pro}$ | 2.01 | 96.2 |
| NYU-70 | $AG^{pro}$ $AG^{gag}$ $AG^{env}$ | 1.29 | 53.17 |
| NYU-71 | $AG^{pro}$ | 20.66 | 9.56 |
| NYU-72 | $AG^{pro}$ | 3 | 12.14 |
| NYU-73 | $AG^{pro}$ | 6.27 | 54.16 |
| NYU-74 | $A^{pro}$ | 19.21 | 4.68 |
| NYU-75 | $AG^{pro}$ | 16.09 | 15.82 |
| NYU-76 | $AG^{pro}$ | 6.79 | 54.58 |
| NYU-77 | $J^{pro}$ $11cpx^{gag}$ $11cpx^{env}$ | 1.63 | 11.84 |
| NYU-78 | $AG^{pro}$ | 6.13 | 0.1 |
| NYU-79 | $AG^{pro}$ | 6.12 | 92.07 |
| NYU-80 | $AG^{pro}$ | 0.37 | 91.97 |
| NYU-81 | $G^{pro}$ | 3.87 | 25.6 |
| NYU-82 | $D^{pro}$ | 0.38 | 7.23 |
| NYU-83 | $AG^{pro}$ | 10.1 | 30.7 |
| NYU-84 | $H^{pro}$ | 0.87 | 97.6 |
| NYU-85 | $AG^{pro}$ $AG^{gag}$ $A^{env}$ | 1.39 | 2.1 |
| NYU-86 | $D^{pro}$ | 7.4 | 1.43 |
| NYU-87 | $F2^{pro}$ | 0.49 | 86.1 |
| NYU-88 | $A^{pro}$ $AG^{gag}$ $AG^{env}$ | 16.62 | 97.47 |
| NYU-89 | $AG^{pro}$ | 15.99 | 79.2 |
| NYU-90 | $G^{pro}$ $G^{gag}$ $G^{env}$ | 6.96 | 95.83 |
| NYU-91 | $AG^{pro}$ $C^{gag}$ $AG^{env}$ | 1.03 | 1.03 |
| NYU-92 | $J^{pro}$ $11cpx^{gag}$ $A^{env}$ | 1.21 | 0.77 |
| NYU-93 | $AG^{pro}$ $AG^{gag}$ $AG^{env}$ | 1 | 97.9 |
| NYU-94 | $C^{pro}$ $C^{gag}$ $C^{env}$ | 5.24 | 0.33 |
| NYU-95 | $C^{pro}$ | 6.54 | 1.17 |
| NYU-96 | $AG^{pro}$ | 0.97 | 0.06 |
| NYU-97 | $U^{pro}$ $AG^{gag}$ $A^{env}$ | 1.03 | 1.22 |
| NYU-98 | $AG^{pro}$ | 20.6 | 2.08 |
| NYU-99 | $AG^{pro}$ $AG^{gag}$ $AG^{env}$ | 3.63 | 56.8 |
| NYU-100 | $F2^{pro}$ $F2^{gag}$ $F2^{env}$ | 4.89 | 40.8 |

The data shown in Table 16 indicates that the gag p6 epitope had an individual sensitivity of 83%, compared with 67% for the gp41 epitope. The use of both epitopes had an individual sensitivity of 82%. The overall sensitivity was 100%.

EXAMPLE 7

Reactivity of Peptides Designed Based on HIV-1 Subtype Consensus Sequences with False Negative Serum Samples The reactivity of peptides designed based on HIV-1 subtype consensus sequences with false negative serum samples (using the HIV subtype-B based peptides) is evaluated using the above-described ELISA conditions. The data is shown in Table 17 below.

TABLE 17

| Sample ID | Specimen/Cut-Off Ratio | | | |
|---|---|---|---|---|
| | p6 | gp41 | Consensus p6 | Consensus gp41 |
| NYU-02 | 18.67 | 12.86 | 19.28 | 22.28 |
| NYU-03 | 0.96 | 0.2 | 3.06 | 0.31 |
| NYU-14 | 0.64 | 0.19 | 3.31 | 0.21 |
| NYU-18 | 0.83 | 0.38 | 1.37 | 0.18 |
| NYU-32 | 0.66 | 0.23 | 2.15 | 0.26 |
| NYU-36 | 18.14 | 11.19 | 17.01 | 10.04 |
| NYU-39 | 1.11 | 0.72 | 1.31 | 0.53 |
| NYU-82 | 0.65 | 0.22 | 0.8 | 0.32 |
| NYU-96 | 2.22 | 0.2 | 3.94 | 0.47 |
| CBER Negative | 0.49 | 0.1 | 0.36 | 0.12 |
| CBER Positive | 0.09 | 29.4 | 0.19 | 26.28 |
| HIV Ig | 7.28 | 42.53 | 6.18 | 36.49 |

The data shows that peptides designed based on HIV-1 subtype consensus sequences with false negative serum could detect HIV infection.

In summary, the data shows that HIV-1 specific peptides individually or in combination are able to detect anti-HIV-1 antibodies in serum or plasma early after acute infection. The assay specificity for the 1200 samples obtained from individuals infected with diverse HIV clades is found to be 98.2% (For Consensus peptide GAG-p6) and 100% (For Consensus peptide CON-Env2-gp41). The cross Glade combined reactivity is found to be 94.4% sensitivity (B-subtype) and 99.1% (for Consensus peptides). The peptides and assays of the present invention are able to detect HIV epitopes in serum samples infected with diverse HIV-1 subtypes.

EXAMPLE 8

Reactivity of Peptides with Random Serum Samples

The reactivity of the CBER p6 and CBER gp41 with a wide variety of diverse serum samples are shown in Table 18 below.

TABLE 18

| SAMPLE ID | CBER p6 | CBER Gp41 | Subtype and Infection Status |
|---|---|---|---|
| NHLBI-1 | 17.57 | 0.23 | Brazil; clade B; LSI |
| NHLBI-2 | 0.98 | 6.22 | Brazil; clade B; LSI |
| NHLBI-3 | 0.69 | 13.55 | Brazil; clade B; LSI |
| NHLBI-4 | 1.44 | 27.58 | Brazil; clade B; LSI |
| NHLBI-5 | 7.86 | 35.23 | Brazil; clade B; LSI |
| NHLBI-6 | 3.18 | 0.43 | Brazil; clade B; LSI |
| NHLBI-7 | 7.21 | 33.97 | Brazil; clade B; LSI |
| NHLBI-8 | 4.77 | 1.75 | Brazil; clade B; LSI |
| NHLBI-9 | 15.90 | 0.18 | Brazil; clade B; LSI |
| NHLBI-10 | 6.34 | 0.35 | Brazil; clade B; LSI |

TABLE 18-continued

| SAMPLE ID | CBER p6 | CBER Gp41 | Subtype and Infection Status |
|---|---|---|---|
| NHLBI-11 | 10.56 | 24.45 | Brazil; clade B; LSI |
| NHLBI-12 | 2.63 | 7.94 | Brazil; clade B; LSI |
| NHLBI-13 | 1.13 | 14.96 | Brazil; clade B; LSI |
| NHLBI-14 | 2.03 | 7.58 | Brazil; clade B; LSI |
| NHLBI-15 | 3.18 | 0.51 | Brazil; clade B; LSI |
| NHLBI-16 | 15.74 | 6.25 | Brazil; clade B; LSI |
| NHLBI-17 | 2.01 | 0.30 | Brazil; clade B; LSI |
| NHLBI-18 | 13.14 | 32.63 | Brazil; clade B; LSI |
| NHLBI-19 | 5.52 | 4.30 | Brazil; clade B; LSI |
| NHLBI-20 | 1.14 | 0.93 | Brazil; clade B; LSI |
| NHLBI-21 | 3.52 | 12.28 | Brazil; clade B; LSI |
| NHLBI-22 | 10.25 | 26.03 | Brazil; clade B; LSI |
| NHLBI-23 | 2.91 | 0.36 | Brazil; clade B; LSI |
| NHLBI-24 | 6.88 | 0.20 | Brazil; clade B; LSI |
| NHLBI-25 | 3.03 | 8.89 | Brazil; clade B; LSI |
| NHLBI-26 | 0.95 | 2.89 | Brazil; clade B; recent |
| NHLBI-27 | 7.90 | 1.94 | Brazil; clade B; recent |
| NHLBI-28 | 2.45 | 0.35 | Brazil; clade B; recent |
| NHLBI-29 | 4.73 | 0.57 | Brazil; clade B; recent |
| NHLBI-30 | 5.21 | 1.64 | Brazil; clade B; recent |
| NHLBI-31 | 2.60 | 0.55 | Brazil; clade B; recent |
| NHLBI-32 | 0.73 | 2.1 | Brazil; clade B; recent |
| NHLBI-33 | 1.63 | 0.25 | Brazil; clade B; recent |
| NHLBI-34 | 1.67 | 1.78 | Brazil; clade B; recent |
| NHLBI-35 | 1.20 | 1.16 | Brazil; clade B; recent |
| NHLBI-36 | 3.72 | 0.12 | Brazil; clade B; recent |
| NHLBI-37 | 6.59 | 0.43 | Brazil; clade B; recent |
| NHLBI-38 | 0.63 | 1.40 | Brazil; clade B; recent |
| NHLBI-39 | 4.32 | 15.82 | Brazil; clade B; recent |
| NHLBI-40 | 1.57 | 0.31 | Brazil; clade B; recent |
| NHLBI-41 | 3.19 | 0.43 | Brazil; clade B; recent |
| NHLBI-42 | 15.65 | 0.77 | Brazil; clade B; recent |
| NHLBI-43 | 5.44 | 1.91 | Brazil; clade B; recent |
| NHLBI-44 | 1.13 | 0.39 | Brazil; clade B; recent |
| NHLBI-45 | 0.89 | 1.39 | Brazil; clade B; recent |
| NHLBI-46 | 2.86 | 0.93 | Brazil; clade B; recent |
| NHLBI-47 | 1.13 | 3.13 | Brazil; clade B; recent |
| NHLBI-48 | 6.11 | 0.37 | Brazil; clade B; recent |
| NHLBI-49 | 0.65 | 7.13 | Brazil; clade B; recent |
| NHLBI-50 | 1.97 | 0.50 | Brazil; clade B; recent |
| NHLBI-51 | 0.42 | 0.23 | US false positive: EIA R; WB ind |
| NHLBI-52 | 0.31 | 0.09 | US false positive: EIA R; WB ind |
| NHLBI-53 | 0.04 | 0.10 | US false positive: EIA R; WB ind |
| NHLBI-54 | 0.62 | 0.20 | US false positive: EIA R; WB ind |
| NHLBI-55 | 0.06 | 0.13 | US false positive: EIA R; WB ind |
| NHLBI-56 | 0.18 | 0.13 | US false positive: EIA R; WB ind |
| NHLBI-57 | 0.10 | 0.08 | US false positive: EIA R; WB ind |
| NHLBI-58 | 0.44 | 0.29 | US false positive: EIA R; WB ind |
| NHLBI-59 | 0.23 | 0.18 | US false positive: EIA R; WB ind |
| NHLBI-60 | 0.59 | 0.24 | US false positive: EIA R; WB ind |
| NHLBI-61 | 0.18 | 0.18 | US false positive: EIA R; WB ind |
| NHLBI-62 | 0.77 | 0.23 | US false positive: EIA R; WB ind |
| NHLBI-63 | 0.30 | 0.18 | US false positive: EIA R; WB ind |
| NHLBI-64 | 0.04 | 0.08 | US false positive: EIA R; WB ind |
| NHLBI-65 | 0.10 | 0.10 | US false positive: EIA R; WB ind |
| NHLBI-66 | 0.06 | 0.07 | US false positive: EIA R; WB ind |
| NHLBI-67 | 0.13 | 0.21 | US false positive: EIA R; WB ind |
| NHLBI-68 | 0.09 | 0.18 | US false positive: EIA R; WB ind |
| NHLBI-69 | 0.16 | 0.20 | US false positive: EIA R; WB ind |
| NHLBI-70 | 0.11 | 0.23 | US false positive: EIA R; WB ind |
| NHLBI-71 | 0.10 | 0.14 | US false positive: EIA R; WB ind |
| NHLBI-72 | 0.13 | 0.39 | US false positive: EIA R; WB ind |
| NHLBI-73 | 0.80 | 0.10 | US false positive: EIA R; WB ind |
| NHLBI-74 | 0.53 | 0.19 | US false positive: EIA R; WB ind |
| NHLBI-75 | 0.16 | 0.41 | US false positive: EIA R; WB ind |
| NHLBI-76 | 0.04 | 0.18 | US false positive: EIA R; WB neg |
| NHLBI-77 | 0.13 | 0.13 | US false positive: EIA R; WB neg |
| NHLBI-78 | 0.09 | 0.16 | US false positive: EIA R; WB neg |
| NHLBI-79 | 0.34 | 0.26 | US false positive: EIA R; WB neg |
| NHLBI-80 | 0.10 | 0.20 | US false positive: EIA R; WB neg |
| NHLBI-81 | 0.37 | 0.18 | US false positive: EIA R; WB neg |
| NHLBI-82 | 0.40 | 0.28 | US false positive: EIA R; WB neg |
| NHLBI-83 | 0.28 | 0.23 | US false positive: EIA R; WB neg |
| NHLBI-84 | 0.36 | 0.10 | US false positive: EIA R; WB neg |
| NHLBI-85 | 0.12 | 0.55 | US false positive: EIA R; WB neg |
| NHLBI-86 | 0.71 | 0.65 | US false positive: EIA R; WB neg |
| NHLBI-87 | 0.81 | 0.21 | US false positive: EIA R; WB neg |

TABLE 18-continued

| SAMPLE ID | CBER p6 | CBER Gp41 | Subtype and Infection Status |
|---|---|---|---|
| NHLBI-88 | 0.28 | 0.31 | US false positive: EIA R; WB neg |
| NHLBI-89 | 0.12 | 0.20 | US false positive: EIA R; WB neg |
| NHLBI-90 | 0.06 | 0.37 | US false positive: EIA R; WB neg |
| NHLBI-91 | 0.39 | 0.23 | US false positive: EIA R; WB neg |
| NHLBI-92 | 0.38 | 0.63 | US false positive: EIA R; WB neg |
| NHLBI-93 | 0.36 | 0.53 | US false positive: EIA R; WB neg |
| NHLBI-94 | 0.41 | 0.28 | US false positive: EIA R; WB neg |
| NHLBI-95 | 0.16 | 0.23 | US false positive: EIA R; WB neg |
| NHLBI-96 | 0.74 | 0.50 | US false positive: EIA R; WB neg |
| NHLBI-97 | 0.09 | 0.40 | US false positive: EIA R; WB neg |
| NHLBI-98 | 0.15 | 0.20 | US false positive: EIA R; WB neg |
| NHLBI-99 | 0.16 | 0.20 | US false positive: EIA R; WB neg |
| NHLBI-100 | 0.09 | 0.26 | US false positive: EIA R; WB neg |
| NHLBI-101 | 0.17 | 0.11 | US HIV uninfected: EIA NR; WB NT |
| NHLBI-102 | 0.19 | 0.49 | US HIV uninfected: EIA NR; WB NT |
| NHLBI-103 | 0.45 | 0.56 | US HIV uninfected: EIA NR; WB NT |
| NHLBI-104 | 0.11 | 0.13 | US HIV uninfected: EIA NR; WB NT |
| NHLBI-105 | 0.11 | 0.17 | US HIV uninfected: EIA NR; WB NT |
| NHLBI-106 | 0.22 | 0.17 | US HIV uninfected: EIA NR; WB NT |
| NHLBI-107 | 0.35 | 0.28 | US HIV uninfected: EIA NR; WB NT |
| NHLBI-108 | 0.32 | 0.43 | US HIV uninfected: EIA NR; WB NT |
| NHLBI-109 | 0.61 | 0.1 | US HIV uninfected: EIA NR; WB NT |
| NHLBI-110 | 0.26 | 0.44 | US HIV uninfected: EIA NR; WB NT |
| NHLBI-111 | 0.19 | 0.12 | US HIV uninfected: EIA NR; WB NT |
| NHLBI-112 | 0.41 | 0.13 | US HIV uninfected: EIA NR; WB NT |
| NHLBI-113 | 0.14 | 0.33 | US HIV uninfected: EIA NR; WB NT |
| NHLBI-114 | 0.20 | 0.36 | US HIV uninfected: EIA NR; WB NT |
| NHLBI-115 | 0.13 | 0.31 | US HIV uninfected: EIA NR; WB NT |
| NHLBI-116 | 0.50 | 0.44 | US HIV uninfected: EIA NR; WB NT |
| NHLBI-117 | 0.26 | 0.43 | US HIV uninfected: EIA NR; WB NT |
| NHLBI-118 | 0.19 | 0.30 | US HIV uninfected: EIA NR; WB NT |
| NHLBI-119 | 0.21 | 0.34 | US HIV uninfected: EIA NR; WB NT |
| NHLBI-120 | 0.17 | 0.36 | US HIV uninfected: EIA NR; WB NT |
| NHLBI-121 | 0.20 | 0.42 | US HIV uninfected: EIA NR; WB NT |
| NHLBI-122 | 0.20 | 0.26 | US HIV uninfected: EIA NR; WB NT |
| NHLBI-123 | 0.29 | 0.41 | US HIV uninfected: EIA NR; WB NT |
| NHLBI-124 | 0.15 | 0.30 | US HIV uninfected: EIA NR; WB NT |
| NHLBI-125 | 0.48 | 0.84 | US HIV uninfected: EIA NR; WB NT |
| NHLBI-126 | 0.27 | 0.62 | US HIV uninfected: EIA NR; WB NT |
| NHLBI-127 | 0.57 | 0.11 | US HIV uninfected: EIA NR; WB NT |
| NHLBI-128 | 0.17 | 0.66 | US HIV uninfected: EIA NR; WB NT |
| NHLBI-129 | 0.37 | 0.56 | US HIV uninfected: EIA NR; WB NT |
| NHLBI-130 | 0.20 | 0.34 | US HIV uninfected: EIA NR; WB NT |
| NHLBI-131 | 0.23 | 0.35 | US HIV uninfected: EIA NR; WB NT |
| NHLBI-132 | 0.19 | 0.39 | US HIV uninfected: EIA NR; WB NT |
| NHLBI-133 | 0.25 | 0.46 | US HIV uninfected: EIA NR; WB NT |
| NHLBI-134 | 0.19 | 0.34 | US HIV uninfected: EIA NR; WB NT |
| NHLBI-135 | 0.28 | 0.33 | US HIV uninfected: EIA NR; WB NT |
| NHLBI-136 | 0.08 | 0.14 | US HIV uninfected: EIA NR; WB NT |
| NHLBI-137 | 0.50 | 0.36 | US HIV uninfected: EIA NR; WB NT |
| NHLBI-138 | 0.21 | 0.43 | US HIV uninfected: EIA NR; WB NT |
| NHLBI-139 | 0.19 | 0.29 | US HIV uninfected: EIA NR; WB NT |
| NHLBI-140 | 0.52 | 0.68 | US HIV uninfected: EIA NR; WB NT |
| NHLBI-141 | 0.23 | 0.49 | US HIV uninfected: EIA NR; WB NT |
| NHLBI-142 | 0.23 | 0.19 | US HIV uninfected: EIA NR; WB NT |
| NHLBI-143 | 0.24 | 0.38 | US HIV uninfected: EIA NR; WB NT |
| NHLBI-144 | 0.19 | 0.42 | US HIV uninfected: EIA NR; WB NT |
| NHLBI-145 | 0.26 | 0.41 | US HIV uninfected: EIA NR; WB NT |
| NHLBI-146 | 0.15 | 0.45 | US HIV uninfected: EIA NR; WB NT |
| NHLBI-147 | 11.20 | 0.33 | US HIV uninfected: EIA NR; WB NT |
| NHLBI-148 | 0.37 | 0.34 | US HIV uninfected: EIA NR; WB NT |
| NHLBI-149 | 0.19 | 0.30 | US HIV uninfected: EIA NR; WB NT |
| NHLBI-150 | 0.22 | 0.35 | US HIV uninfected: EIA NR; WB NT |
| NHLBI-151 | 0.67 | 3.34 | US; clade B; presumed LSI |
| NHLBI-152 | 0.47 | 1.90 | US; clade B; presumed LSI |
| NHLBI-153 | 0.86 | 13.98 | US; clade B; presumed LSI |
| NHLBI-154 | 0.96 | 21.23 | US; clade B; presumed LSI |
| NHLBI-155 | 0.25 | 9.07 | US; clade B; presumed LSI |
| NHLBI-156 | 0.25 | 10.32 | US; clade B; presumed LSI |
| NHLBI-157 | 0.20 | 5.31 | US; clade B; presumed LSI |
| NHLBI-158 | 6.81 | 0.37 | US; clade B; presumed LSI |
| NHLBI-159 | 0.24 | 0.28 | US; clade B; presumed LSI |
| NHLBI-160 | 0.83 | 10.63 | US; clade B; presumed LSI |
| NHLBI-161 | 1.28 | 13.47 | US; clade B; presumed LSI |
| NHLBI-162 | 0.23 | 3.57 | US; clade B; presumed LSI |
| NHLBI-163 | 7.04 | 0.13 | US; clade B; presumed LSI |
| NHLBI-164 | 0.10 | 6.87 | US; clade B; presumed LSI |
| NHLBI-165 | 0.24 | 4.44 | US; clade B; presumed LSI |
| NHLBI-166 | 0.20 | 9.78 | US; clade B; presumed LSI |
| NHLBI-167 | 0.74 | 3.60 | US; clade B; presumed LSI |
| NHLBI-168 | 1.66 | 0.40 | US; clade B; presumed LSI |
| NHLBI-169 | 0.62 | 23.03 | US; clade B; presumed LSI |
| NHLBI-170 | 8.35 | 0.09 | US; clade B; presumed LSI |
| NHLBI-171 | 0.10 | 36.57 | US; clade B; presumed LSI |
| NHLBI-172 | 0.41 | 1.3 | US; clade B; presumed LSI |
| NHLBI-173 | 0.97 | 34.2 | US; clade B; presumed LSI |
| NHLBI-174 | 2.25 | 2.48 | US; clade B; presumed LSI |
| NHLBI-175 | 0.93 | 13.76 | US; clade B; presumed LSI |
| NHLBI-176 | 1 | 0.46 | US; clade B; presumed LSI |
| NHLBI-177 | 0.38 | 0.64 | US; clade B; presumed LSI |
| NHLBI-178 | 8.93 | 14.48 | US; clade B; presumed LSI |
| NHLBI-179 | 0.63 | 15.94 | US; clade B; presumed LSI |
| NHLBI-180 | 0.40 | 15.36 | US; clade B; presumed LSI |
| NHLBI-181 | 18.17 | 3.13 | US; clade B; presumed LSI |
| NHLBI-182 | 0.47 | 1.36 | US; clade B; presumed LSI |
| NHLBI-183 | 0.34 | 12.5 | US; clade B; presumed LSI |
| NHLBI-184 | 0.37 | 1.42 | US; clade B; presumed LSI |
| NHLBI-185 | 0.07 | 2.00 | US; clade B; presumed LSI |
| NHLBI-186 | 0.07 | 11.24 | US; clade B; presumed LSI |
| NHLBI-187 | 0.17 | 24.03 | US; clade B; presumed LSI |
| NHLBI-188 | 0.27 | 10.29 | US; clade B; presumed LSI |
| NHLBI-189 | 1.55 | 17.98 | US; clade B; presumed LSI |
| NHLBI-190 | 0.21 | 9.35 | US; clade B; presumed LSI |
| NHLBI-191 | 0.14 | 1.31 | US; clade B; presumed LSI |
| NHLBI-192 | 0.16 | 2.73 | US; clade B; presumed LSI |
| NHLBI-193 | 0.10 | 24.76 | US; clade B; presumed LSI |
| NHLBI-194 | 11.37 | 0.24 | US; clade B; presumed LSI |
| NHLBI-195 | 9.84 | 9.46 | US; clade B; presumed LSI |
| NHLBI-196 | 0.60 | 5.82 | US; clade B; presumed LSI |
| NHLBI-197 | 3.44 | 1.90 | US; clade B; presumed LSI |
| NHLBI-198 | 18.01 | 9.06 | US; clade B; presumed LSI |
| NHLBI-199 | 0.27 | 1.49 | US; clade B; presumed LSI |
| NHLBI-200 | 4.10 | 0.72 | US; clade B; presumed LSI |
| NHLBI-201 | 0.97 | 1.18 | SA (black); clade C; recent |
| NHLBI-202 | 0.54 | 1.40 | SA (black); clade C; recent |
| NHLBI-203 | 0.48 | 2.47 | SA (black); clade C; recent |
| NHLBI-204 | 0.67 | 1.62 | SA (black); clade C; recent |
| NHLBI-205 | 0.81 | 5.62 | SA (black); clade C; recent |
| NHLBI-206 | 0.55 | 1.02 | SA (black); clade C; recent |
| NHLBI-207 | 2.37 | 1.48 | SA (black); clade C; recent |
| NHLBI-208 | 9.02 | 0.46 | SA (black); clade C; recent |
| NHLBI-209 | 2.73 | 0.58 | SA (black); clade C; recent |
| NHLBI-210 | 4.04 | 0.62 | SA (black); clade C; recent |
| NHLBI-211 | 0.30 | 1.70 | SA (black); clade C; recent |
| NHLBI-212 | 2.41 | 0.44 | SA (black); clade C; recent |
| NHLBI-213 | 2.49 | 3.89 | SA (black); clade C; recent |
| NHLBI-214 | 0.73 | 3.24 | SA (black); clade C; recent |
| NHLBI-215 | 0.88 | 2.96 | SA (black); clade C; recent |
| NHLBI-216 | 1.07 | 0.68 | SA (black); clade C; recent |
| NHLBI-217 | 1.57 | 4.78 | SA (black); clade C; recent |
| NHLBI-218 | 0.35 | 1.38 | SA (black); clade C; recent |
| NHLBI-219 | 0.31 | 4.53 | SA (black); clade C; recent |
| NHLBI-220 | 4.71 | 2.11 | SA (black); clade C; recent |
| NHLBI-221 | 0.40 | 2.36 | SA (black); clade C; recent |
| NHLBI-222 | 3.97 | 0.60 | SA (black); clade C; recent |
| NHLBI-223 | 3.34 | 2.34 | SA (black); clade C; recent |
| NHLBI-224 | 0.90 | 1.12 | SA (black); clade C; recent |
| NHLBI-225 | 1.94 | 0.50 | SA (black); clade C; recent |
| NHLBI-226 | 2.57 | 59.11 | SA (black); clade C; LSI |
| NHLBI-227 | 3.18 | 0.40 | SA (black); clade C; LSI |
| NHLBI-228 | 0.75 | 55.56 | SA (black); clade C; LSI |
| NHLBI-229 | 1.03 | 31.31 | SA (black); clade C; LSI |
| NHLBI-230 | 2.13 | 0.58 | SA (black); clade C; LSI |
| NHLBI-231 | 0.40 | 16.64 | SA (black); clade C; LSI |
| NHLBI-232 | 0.37 | 51.67 | SA (black); clade C; LSI |
| NHLBI-233 | 2.87 | 0.90 | SA (black); clade C; LSI |
| NHLBI-234 | 0.17 | 54.16 | SA (black); clade C; LSI |
| NHLBI-235 | 0.43 | 1.60 | SA (black); clade C; LSI |
| NHLBI-236 | 1.04 | 0.86 | SA (black); clade C; LSI |
| NHLBI-237 | 2.59 | 46.40 | SA (black); clade C; LSI |
| NHLBI-238 | 1.09 | 3.51 | SA (black); clade C; LSI |
| NHLBI-239 | 2.26 | 10.00 | SA (black); clade C; LSI |
| NHLBI-240 | 0.75 | 21.18 | SA (black); clade C; LSI |
| NHLBI-241 | 1.44 | 1.02 | SA (black); clade C; LSI |

TABLE 18-continued

| SAMPLE ID | CBER p6 | CBER Gp41 | Subtype and Infection Status |
|---|---|---|---|
| NHLBI-242 | 0.79 | 1.06 | SA (black); clade C; LSI |
| NHLBI-243 | 1.40 | 3.22 | SA (black); clade C; LSI |
| NHLBI-244 | 0.53 | 9.87 | SA (black); clade C; LSI |
| NHLBI-245 | 0.58 | 3.11 | SA (black); clade C; LSI |
| NHLBI-246 | 15.40 | 1.84 | SA (black); clade C; LSI |
| NHLBI-247 | 1.33 | 9.62 | SA (black); clade C; LSI |
| NHLBI-248 | 0.31 | 9.36 | SA (black); clade C; LSI |
| NHLBI-249 | 1.86 | 47.27 | SA (black); clade C; LSI |
| NHLBI-250 | 0.57 | 20.16 | SA (black); clade C; LSI |
| NHLBI-251 | 2.14 | 5.42 | US (ARC); clade B; recent |
| NHLBI-252 | 0.66 | 1.50 | US (ARC); clade B; recent |
| NHLBI-253 | 10.06 | 1.00 | US (ARC); clade B; recent |
| NHLBI-254 | 1.13 | 0.58 | US (ARC); clade B; recent |
| NHLBI-255 | 0.60 | 1.02 | US (ARC); clade B; recent |
| NHLBI-256 | 1.49 | 5.47 | US (ARC); clade B; recent |
| NHLBI-257 | 3.25 | 12.07 | US (ARC); clade B; recent |
| NHLBI-258 | 3.86 | 1.62 | US (ARC); clade B; recent |
| NHLBI-259 | 1.78 | 25.64 | US (ARC); clade B; recent |
| NHLBI-260 | 1.09 | 1.58 | US (ARC); clade B; recent |
| NHLBI-261 | 0.18 | 5.36 | US (ARC); clade B; recent |
| NHLBI-262 | 1.99 | 15.73 | US (ARC); clade B; recent |
| NHLBI-263 | 6.14 | 2.02 | US (ARC); clade B; recent |
| NHLBI-264 | 9.39 | 1.06 | US (ARC); clade B; recent |
| NHLBI-265 | 0.55 | 0.64 | US (ARC); clade B; recent |
| NHLBI-266 | 1.68 | 30.49 | US (ARC); clade B; recent |
| NHLBI-267 | 1.09 | 0.56 | US (ARC); clade B; recent |
| NHLBI-268 | 1.50 | 0.48 | US (ARC); clade B; recent |
| NHLBI-269 | 3.43 | 7.08 | US (ARC); clade B; recent |
| NHLBI-270 | 0.43 | 4.11 | US (ARC); clade B; recent |
| NHLBI-271 | 0.50 | 3.56 | US (ARC); clade B; recent |
| NHLBI-272 | 0.27 | 1.12 | US (ARC); clade B; recent |
| NHLBI-273 | 1.03 | 0.74 | US (ARC); clade B; recent |
| NHLBI-274 | 5.41 | 13.78 | US (ARC); clade B; recent |
| NHLBI-275 | 1.06 | 2.20 | US (ARC); clade B; recent |
| NHLBI-276 | 3.55 | 2.64 | US (ARC); clade B; recent |
| NHLBI-277 | 18.51 | 55.93 | US (ARC); clade B; recent |
| NHLBI-278 | 0.56 | 0.30 | US (ARC); clade B; recent |
| NHLBI-279 | 1.82 | 17.11 | US (ARC); clade B; recent |
| NHLBI-280 | 0.64 | 4.96 | US (ARC); clade B; recent |
| NHLBI-281 | 1.20 | 1.62 | US (ARC); clade B; recent |
| NHLBI-282 | 9.25 | 0.42 | US (ARC); clade B; recent |
| NHLBI-283 | 0.39 | 1.20 | US (ARC); clade B; recent |
| NHLBI-284 | 1.85 | 0.47 | US (ARC); clade B; recent |
| NHLBI-285 | 0.29 | 5.87 | US (ARC); clade B; recent |
| NHLBI-286 | 0.52 | 4.00 | US (ARC); clade B; recent |
| NHLBI-287 | 0.83 | 1.16 | US (ARC); clade B; recent |
| NHLBI-288 | 2.60 | 2.70 | US (ARC); clade B; recent |
| NHLBI-289 | 2.54 | 0.44 | US (ARC); clade B; recent |
| NHLBI-290 | 1.90 | 1.36 | US (ARC); clade B; recent |
| NHLBI-291 | 4.04 | 22.56 | US (ARC); clade B; recent |
| NHLBI-292 | 0.41 | 1.50 | US (ARC); clade B; recent |
| NHLBI-293 | 3.22 | 3.18 | US (ARC); clade B; recent |
| NHLBI-294 | 0.80 | 1.64 | US (ARC); clade B; recent |
| NHLBI-295 | 1.28 | 0.37 | US (ARC); clade B; recent |
| NHLBI-296 | 1.04 | 1.22 | US (ARC); clade B; recent |
| NHLBI-297 | 7.88 | 0.76 | US (ARC); clade B; recent |
| NHLBI-298 | 1.55 | 8.62 | US (ARC); clade B; recent |
| NHLBI-299 | 2.15 | 0.64 | US (ARC); clade B; recent |
| NHLBI-300 | 1.36 | 0.47 | US (ARC); clade B; recent |

Table 19 summarizes the ability of the HIV-SELECTEST to detect HIV-infected serum with diverse clades.

TABLE 19

Summary of HIV-SELECTEST with HIV-Infected Serum Samples with Diverse Clades

| Subtype | Number of Samples | HIV-SELECTEST Reactive | % Combined Sensitivity |
|---|---|---|---|
| A | 25 | 25 | 100 |
| B | 263 | 259 | 98.48 |
| C | 50 | 50 | 100 |
| D | 20 | 19 | 95 |
| E | 104 | 103 | 99.04 |
| G | 11 | 11 | 100 |
| J | 4 | 4 | 100 |
| AG | 150 | 150 | 100 |
| AJ | 7 | 7 | 100 |
| F2, U, H, J/G Recombinants | 9 | 9 | 100 |
| CRF | 21 | 21 | 100 |
| Unknown Genotypes | 589 | 585 | 99.32 |
| Total No. Samples | 1253 | 1243 | 99.2 |

EXAMPLE 8

Reactivity of Peptides with RV124 Vaccine Trial Samples: a Comparison with the BioRad Kit The reactivity of CBER p6 and CBER p41 with RV124 vaccine trial samples were compared with the reactivity of the BioRad Kit with RV124 vaccine trial samples at 0 and 182 days post-vaccination. The vaccination given in the RV124 vaccine trials was as follows: ALVAC-HIV (vCP205; gag-LAI+pro-LAI+gp120MN/gp41TM-LAI) with HIV-1 gp160 protein boost (gp120MN, gp41 LAI-2) (with Gag-p6). The results for individual samples are shown in Table 20 below. The results show substantially more false positive reactions using the BioRad kit versus the use of CBER p6 or CBER p41.

TABLE 20

Reactivity Of RV-124 Clinical Trial Samples In The 'HIV-Selectest'

| SERUM SAMPLE | Day 0 New HIV ELISA' | | Day 182 New HIV ELISA' | | HIV INFECTION STATUS | Day 0 BioRad HIV-1/2 plus O | Day 182 BioRad HIV-1/2 plus O |
|---|---|---|---|---|---|---|---|
| | p6 | gp41 | p6 | gp41 | | | |
| RV124-1 | 0.09 | 0.15 | 0.36 | 0.21 | NEGATIVE | 0.14 | 11.42 |
| RV124-2 | 0.08 | 0.10 | 0.18 | 0.19 | NEGATIVE | 0.12 | 11.14 |
| RV124-3 | 0.32 | 0.15 | 0.61 | 0.28 | NEGATIVE | 0.15 | 11.45 |
| RV124-4 | 0.16 | 0.15 | 0.35 | 0.18 | NEGATIVE | 0.14 | 11.40 |
| RV124-5 | 0.11 | 0.16 | 0.17 | 0.13 | NEGATIVE | 0.16 | 11.08 |
| RV124-6 | 0.10 | 0.14 | 0.14 | 0.15 | NEGATIVE | 0.16 | 11.78 |
| RV124-7 | 0.11 | 0.18 | 0.12 | 0.20 | NEGATIVE | 0.24 | 11.96 |

TABLE 20-continued

Reactivity Of RV-124 Clinical Trial Samples In The 'HIV-Selectest'

| SERUM SAMPLE | Day 0 New HIV ELISA' | | Day 182 New HIV ELISA' | | HIV INFECTION STATUS | Day 0 BioRad HIV-1/2 plus O | Day 182 BioRad HIV-1/2 plus O |
|---|---|---|---|---|---|---|---|
| | p6 | gp41 | p6 | gp41 | | | |
| RV124-8  | 0.39 | 0.22 | 0.33 | 0.14 | NEGATIVE | 0.23 | 12.01 |
| RV124-9  | 0.13 | 0.13 | 0.16 | 0.13 | NEGATIVE | 0.27 | 11.72 |
| RV124-10 | 0.10 | 0.12 | 0.13 | 0.13 | NEGATIVE | 0.13 | 11.69 |
| RV124-11 | 0.15 | 0.18 | 0.25 | 0.28 | NEGATIVE | 0.46 | 10.93 |
| RV124-12 | 0.09 | 0.08 | 0.22 | 0.19 | NEGATIVE | 0.47 | 11.38 |
| RV124-13 | 0.37 | 0.09 | 0.59 | 0.22 | NEGATIVE | 0.14 | 11.54 |
| RV124-14 | 0.16 | 0.19 | 0.26 | 0.18 | NEGATIVE | 0.11 | 11.19 |
| RV124-15 | 0.19 | 0.10 | 0.25 | 0.16 | NEGATIVE | 0.10 | 11.51 |
| RV124-16 | 0.16 | 0.16 | 0.20 | 0.19 | NEGATIVE | 0.13 | 1.97 |
| RV124-17 | 0.09 | 0.05 | 0.17 | 0.10 | NEGATIVE | 0.17 | 11.38 |
| RV124-18 | 0.30 | 0.08 | 0.43 | 0.16 | NEGATIVE | 0.13 | 11.65 |
| RV124-19 | 0.26 | 0.13 | 0.04 | 0.09 | NEGATIVE | 0.20 | 12.17 |
| RV124-20 | 0.21 | 0.10 | 0.19 | 0.10 | NEGATIVE | 0.20 | 11.96 |
| RV124-21 | 0.16 | 0.07 | 0.18 | 0.10 | NEGATIVE | 0.22 | 11.31 |
| RV124-22 | 0.30 | 0.23 | 0.67 | 0.43 | NEGATIVE | 0.27 | 11.13 |
| RV124-23 | 0.94 | 0.15 | 0.41 | 0.22 | NEGATIVE | 0.37 | 0.24 |
| RV124-24 | 0.15 | 0.11 | 0.51 | 0.42 | NEGATIVE | 0.48 | 11.04 |
| RV124-25 | 0.44 | 0.09 | 0.48 | 0.21 | NEGATIVE | 0.15 | 11.53 |
| RV124-26 | 0.09 | 0.08 | 0.41 | 0.22 | NEGATIVE | 0.14 | 11.26 |
| RV124-27 | 0.24 | 0.42 | 0.34 | 0.47 | NEGATIVE | 0.14 | 11.71 |
| RV124-28 | 0.14 | 0.11 | 0.32 | 0.20 | NEGATIVE | 0.15 | 11.96 |
| RV124-29 | 0.16 | 0.79 | 13.53 | 0.50 | NEGATIVE | 0.19 | 11.68 |
| RV124-30 | 0.80 | 0.15 | 0.22 | 0.17 | NEGATIVE | 0.15 | 11.56 |
| RV124-31 | 0.17 | 0.14 | 0.24 | 0.17 | NEGATIVE | 0.27 | 12.00 |
| RV124-32 | 0.20 | 0.15 | 0.28 | 0.14 | NEGATIVE | 0.21 | 11.89 |
| RV124-33 | 0.43 | 0.29 | 0.37 | 0.18 | NEGATIVE | 0.30 | 11.59 |
| RV124-34 | 0.05 | 0.06 | 0.43 | 0.17 | NEGATIVE | 0.31 | 11.40 |
| RV124-35 | 0.04 | 0.03 | 1.56 | 0.27 | NEGATIVE | 0.59 | 0.11 |
| RV124-36 | 0.13 | 0.10 | 0.77 | 0.37 | NEGATIVE | 0.52 | 11.55 |
| RV124-37 | 0.23 | 0.28 | 0.26 | 0.29 | NEGATIVE | 0.13 | 0.13 |
| RV124-38 | 0.31 | 0.38 | 0.45 | 0.33 | NEGATIVE | 0.12 | 11.12 |
| RV124-39 | 0.31 | 0.20 | 0.47 | 0.19 | NEGATIVE | 0.11 | 11.64 |
| RV124-40 | 0.27 | 0.16 | 0.54 | 0.22 | NEGATIVE | 0.15 | 11.42 |
| RV124-41 | 0.30 | 0.18 | 0.43 | 0.19 | NEGATIVE | 0.38 | 10.64 |
| RV124-42 | 0.37 | 0.23 | 0.96 | 0.20 | NEGATIVE | 0.21 | 10.65 |
| RV124-43 | 0.53 | 0.21 | 0.50 | 0.24 | NEGATIVE | 0.26 | 0.14 |
| RV124-44 | 0.18 | 0.37 | 0.13 | 0.23 | NEGATIVE | 0.24 | 10.95 |
| RV124-45 | 0.10 | 0.36 | 0.08 | 0.22 | NEGATIVE | 0.31 | 10.99 |
| RV124-46 | 0.20 | 0.18 | 0.15 | 0.10 | NEGATIVE | 0.41 | 10.13 |
| RV124-47 | 0.41 | 0.20 | 0.99 | 0.17 | NEGATIVE | 0.35 | 10.81 |
| RV124-48 | 0.32 | 0.19 | 0.75 | 0.17 | NEGATIVE | 0.33 | 10.40 |
| RV124-49 | 0.67 | 0.30 | 0.47 | 0.16 | NEGATIVE | 0.35 | 0.14 |
| RV124-50 | 0.63 | 0.18 | 0.43 | 0.11 | NEGATIVE | 0.35 | 10.55 |
| RV124-51 | 0.22 | 0.09 | 0.99 | 0.09 | NEGATIVE | 0.46 | 10.43 |
| RV124-52 | 0.87 | 0.33 | 0.23 | 0.27 | NEGATIVE | 0.32 | 10.68 |
| RV124-53 | 0.63 | 0.18 | 0.52 | 0.25 | NEGATIVE | 0.20 | 11.07 |
| RV124-54 | 0.26 | 0.13 | 0.53 | 0.13 | NEGATIVE | 0.15 | 1.17 |
| RV124-55 | 0.27 | 0.14 | 0.27 | 0.12 | NEGATIVE | 0.16 | 0.19 |
| RV124-56 | 0.85 | 0.11 | 0.98 | 0.20 | NEGATIVE | 0.15 | 10.89 |
| RV124-57 | 0.36 | 0.29 | 0.74 | 0.25 | NEGATIVE | 0.17 | 0.48 |
| RV124-58 | 0.23 | 0.20 | 0.73 | 0.20 | NEGATIVE | 0.22 | 10.90 |
| RV124-59 | 0.40 | 0.37 | 0.45 | 0.20 | NEGATIVE | 0.22 | 0.53 |
| RV124-60 | 0.71 | 0.25 | 0.12 | 0.36 | NEGATIVE | 0.20 | 10.66 |
| RV124-61 | 0.67 | 0.18 | 0.66 | 0.11 | NEGATIVE | 0.19 | 0.36 |
| RV124-62 | 0.52 | 0.47 | 0.43 | 0.37 | NEGATIVE | 0.16 | 0.15 |
| RV124-63 | 0.01 | 0.07 | 0.64 | 0.35 | NEGATIVE | 0.21 | 10.30 |
| RV124-64 | 0.16 | 0.08 | 0.10 | 0.12 | NEGATIVE | 0.26 | 0.17 |
| RV124-65 | 0.13 | 0.30 | 0.21 | 0.18 | NEGATIVE | 0.23 | 0.19 |
| RV124-66 | 0.26 | 0.23 | 0.24 | 0.24 | NEGATIVE | 0.19 | 0.18 |
| RV124-67 | 0.64 | 0.20 | 0.41 | 0.10 | NEGATIVE | 0.19 | 10.52 |
| RV124-68 | 0.48 | 0.29 | 0.44 | 0.21 | NEGATIVE | 0.26 | 0.27 |
| RV124-69 | 0.30 | 0.17 | 0.17 | 0.11 | NEGATIVE | 0.18 | 0.39 |
| RV124-70 | 0.31 | 0.25 | 0.30 | 0.11 | NEGATIVE | 0.16 | 10.86 |
| RV124-71 | 0.37 | 0.18 | 0.45 | 0.18 | NEGATIVE | 0.21 | 10.45 |
| RV124-72 | 0.32 | 0.19 | 0.84 | 0.15 | NEGATIVE | 0.23 | 9.66 |
| RV124-73 | 0.41 | 0.23 | 0.63 | 0.11 | NEGATIVE | 0.22 | 9.97 |
| RV124-74 | 0.32 | 0.23 | 0.28 | 0.31 | NEGATIVE | 0.21 | 10.45 |
| RV124-75 | 0.27 | 0.08 | 0.44 | 0.12 | NEGATIVE | 0.22 | 9.37 |

TABLE 20-continued

Reactivity Of RV-124 Clinical Trial Samples In The 'HIV-Selectest'

| SERUM SAMPLE | Day 0 New HIV ELISA' | | Day 182 New HIV ELISA' | | HIV INFECTION STATUS | Day 0 BioRad HIV-1/2 plus O | Day 182 BioRad HIV-1/2 plus O |
|---|---|---|---|---|---|---|---|
| | p6 | gp41 | p6 | gp41 | | | |
| RV124-76 | 0.47 | 0.16 | 0.47 | 0.20 | NEGATIVE | 0.31 | 10.95 |
| RV124-77 | 0.49 | 0.10 | 0.37 | 0.29 | NEGATIVE | 0.17 | 10.67 |
| RV124-78 | 0.04 | 0.24 | 0.07 | 0.20 | NEGATIVE | 0.15 | 5.88 |
| RV124-79 | 0.32 | 0.20 | 0.25 | 0.18 | NEGATIVE | 0.15 | 0.14 |

EXAMPLE 8

Reactivity of Peptides with VRC-004 & VRC-006 Vaccine Trial Samples: A Comparison with the BioRad Kit The reactivity of CBER p6 and CBER p41 with VRC-004 and VRC-006 vaccine trial samples are compared with the reactivity of the BioRad Kit with VRC-004 and VRC-006 vaccine trial samples. The results are shown in Table 21 below. The results show substantially more false positive reactions using the BioRad kit versus the use of CBER p6 or CBER p41.

TABLE 21

| SAMPLE ID | p6 | gp41 | HIV INFECTION STATUS | FDA LICENSED EIA |
|---|---|---|---|---|
| VRC-004 trial-4 PLASMIDS-pGag-Pol-Nef + pEnv A, pEnv B + pEnv C | | | | |
| 004-001-05 | 0.07 | 0.1 | Negative (−) | Negative (−) |
| 004-002-05 | 0.03 | 0.1 | Negative (−) | Negative (−) |
| 004-003-08 | 0.01 | 15.73 | Positive (+) | Negative (−) |
| 004-004-05 | 0.05 | 0.07 | Negative (−) | Negative (−) |
| 004-005-05 | 0.02 | 0.1 | Negative (−) | Negative (−) |
| 004-006-05 | 0.02 | 0.07 | Negative (−) | Negative (−) |
| 004-007-05 | 0.03 | 0.07 | Negative (−) | Negative (−) |
| 004-008-05 | 0.07 | 0.1 | Negative (−) | Negative (−) |
| 004-009-05 | 0.03 | 0.07 | Negative (−) | Positive (+) |
| 004-010-05 | 0.04 | 0.1 | Negative (−) | Positive (+) |
| 004-011-05 | 0.05 | 0.13 | Negative (−) | Negative (−) |
| 004-012-05 | 0.03 | 0.03 | Negative (−) | Positive (+) |
| 004-013-05 | 0.03 | 0.07 | Negative (−) | Negative (−) |
| 004-014-05 | 0.03 | 0.13 | Negative (−) | Negative (−) |
| 004-015-05 | 0.04 | 0.1 | Negative (−) | Negative (−) |
| 004-016-05 | 0.04 | 0.1 | Negative (−) | Negative (−) |
| 004-017-05 | 0.05 | 0.1 | Negative (−) | Negative (−) |
| 004-018-05 | 0.03 | 0.1 | Negative (−) | Negative (−) |
| 004-019-05 | 0.04 | 0.2 | Negative (−) | Negative (−) |
| 004-020-05 | 2.51 | 1.13 | Positive (+) | Positive (+) |
| 004-021-05 | 0.01 | 0.03 | Negative (−) | Negative (−) |
| 004-022-05 | 0.02 | 0.13 | Negative (−) | Negative (−) |
| 004-023-05 | 0.01 | 0.03 | Negative (−) | Negative (−) |
| 004-024-05 | 0.03 | 0.2 | Negative (−) | Positive (+) |
| 004-025-05 | 0.03 | 0 | Negative (−) | Positive (+) |
| 004-026-05 | 0.1 | 0.23 | Negative (−) | Negative (−) |
| 004-027-05 | 0.02 | 0.13 | Negative (−) | Negative (−) |
| 004-028-05 | 0.02 | 0.1 | Negative (−) | Negative (−) |
| 004-029-05 | 0.05 | 0.1 | Negative (−) | Negative (−) |
| 004-030-05 | 0.03 | 0.07 | Negative (−) | Negative (−) |
| 004-031-05 | 0.21 | 0.13 | Negative (−) | Negative (−) |
| 004-032-05 | 0.01 | 0.07 | Negative (−) | Negative (−) |
| 004-033-05 | 0.03 | 0.1 | Negative (−) | Negative (−) |
| 004-034-05 | 0.01 | 0.07 | Negative (−) | Negative (−) |
| 004-035-05 | 0.03 | 0.13 | Negative (−) | Positive (+) |
| 004-036-05 | 0.04 | 0.1 | Negative (−) | Positive (+) |
| 004-037-05 | 0.05 | 0.07 | Negative (−) | Positive (+) |
| 004-038-05 | 0.05 | 0.03 | Negative (−) | Positive (+) |
| 004-039-05 | 0.19 | 0.03 | Negative (−) | Negative (−) |

TABLE 21-continued

| SAMPLE ID | p6 | gp41 | HIV INFECTION STATUS | FDA LICENSED EIA |
|---|---|---|---|---|
| 004-040-05 | 0.05 | 0.13 | Negative (−) | Positive (+) |
| 004-041-05 | 0.02 | 0.07 | Negative (−) | Negative (−) |
| 004-042-05 | 0.61 | 0.07 | Negative (−) | Negative (−) |
| 004-043-05 | 0.11 | 0.03 | Negative (−) | Negative (−) |
| 004-044-05 | 0.06 | 0.03 | Negative (−) | Negative (−) |
| 004-045-05 | 0.04 | 0.03 | Negative (−) | Negative (−) |
| 004-046-05 | 0.12 | 0.13 | Negative (−) | Negative (−) |
| 004-047-05 | 0.05 | 0.03 | Negative (−) | Negative (−) |
| 004-048-05 | 0.06 | 0.1 | Negative (−) | Negative (−) |
| 004-049-05 | 0.13 | 0.13 | Negative (−) | Negative (−) |
| 004-050-05 | 0.03 | 0.03 | Negative (−) | Negative (−) |
| VRC-006 trial-4 Ad5-Ad5-Gag-Pol + Ad5-Env A, Ad5-Env B + Ad5-Env C | | | | |
| 006-001-03 | 0.19 | 0.2 | Negative (−) | Negative (−) |
| 006-002-03 | 0.01 | −0.07 | Negative (−) | Negative (−) |
| 006-003-03 | 0.44 | 0.1 | Negative (−) | Negative (−) |
| 006-004-03 | 0.03 | 0.13 | Negative (−) | Positive (+) |
| 006-005-03 | 0.01 | 0.07 | Negative (−) | Negative (−) |
| 006-006-03 | 0.04 | 0.07 | Negative (−) | Negative (−) |
| 006-007-03 | 0.05 | 0.17 | Negative (−) | Negative (−) |
| 006-008-03 | 0.01 | 0.1 | Negative (−) | Negative (−) |
| 006-009-03 | 0.02 | 0.1 | Negative (−) | Negative (−) |
| 006-010-03 | 0.04 | 0.07 | Negative (−) | Positive (+) |
| 006-011-03 | 0.04 | 0.07 | Negative (−) | Positive (+) |
| 006-012-03 | 0.02 | 0.03 | Negative (−) | Negative (−) |
| 006-013-03 | 0.03 | 0.07 | Negative (−) | Negative (−) |
| 006-014-03 | 0.01 | 0.03 | Negative (−) | Positive (+) |
| 006-015-03 | 0.28 | 0.1 | Negative (−) | Positive (+) |
| 006-016-03 | 0.07 | 0.07 | Negative (−) | Positive (+) |
| 006-017-03 | 0.03 | 0.07 | Negative (−) | Negative (−) |
| 006-018-03 | 0.01 | 0.03 | Negative (−) | Positive (+) |
| 006-019-03 | 0.03 | 0.03 | Negative (−) | Positive (+) |
| 006-020-03 | 0.05 | 0.1 | Negative (−) | Positive (+) |
| 006-021-03 | 0.01 | 0.03 | Negative (−) | Negative (−) |
| 006-022-03 | 0.03 | 0.07 | Negative (−) | Negative (−) |
| 006-023-03 | 0.04 | 0.1 | Negative (−) | Negative (−) |
| 006-024-03 | 0.1 | 0.07 | Negative (−) | Negative (−) |
| 006-025-03 | 0.05 | 0.1 | Negative (−) | Negative (−) |
| 006-026-03 | 0.03 | 0.13 | Negative (−) | Positive (+) |
| 006-027-03 | 0.01 | 0.07 | Negative (−) | Positive (+) |
| 006-028-03 | 0.07 | 0.2 | Negative (−) | Positive (+) |
| 006-029-03 | 0.03 | 0.1 | Negative (−) | Positive (+) |
| 006-030-03 | 0.05 | 0.13 | Negative (−) | Negative (−) |
| 006-031-03 | 0.03 | 0.13 | Negative (−) | Positive (+) |
| 006-032-03 | 0.03 | 0.1 | Negative (−) | Positive (+) |
| 006-033-03 | 0.02 | 0.07 | Negative (−) | Positive (+) |
| 006-034-03 | 0.03 | 0.1 | Negative (−) | Positive (+) |
| 006-035-03 | 0.03 | 0.13 | Negative (−) | Negative (−) |
| 006-036-03 | 0.02 | 0.13 | Negative (−) | Positive (+) |
| SUMMARY | 1/86 | 2/86 | 2/86 | 29/86 |

EXAMPLE 9

The "HIV-SELECTEST"

A New HIV-1 Detection Assay

The present invention provides a new HIV-1 detection assay, in which vaccine-generated antibodies will not cross-react, while seroconversion can be detected early post-infection. The selection criteria for HIV sequences to be used in such an assay included epitopes that are: 1) not included in HIV vaccines, 2) recognized by antibodies early after HIV infection, and 3) highly conserved among HIV clades and subtypes.

To identify such sequences, a Gene-Fragment Phage Display Library was constructed from the entire HIV-1 genome and used for screening of sera from HIV-infected individuals around the time of seroconversion. As discussed above, this strategy led to the discovery of three novel epitopes, one in Gag p6 and two in the gp41 cytoplasmic tail. The development of a new HIV enzyme-linked immunosorbent assay, termed HIV-SELECTEST, which distinguishes between HIV infected individuals and uninfected vaccine recipients is described below. HIV-SELECTEST is a low cost, high throughput assay that could be implemented in clinical sites and blood collection centers worldwide, and serve as an important diagnostic tool in HIV vaccine trials.

Methods

Construction of a Complete HIV Genome Gene-Fragment Phage Display Library

Plasmid pNL4-3, containing the complete HIV-1 NL4-3 proviral DNA was obtained from the NIH AIDS Research and Reference Reagent Program (McKesson BioServices Corp., Rockville, Md.). Full length HIV-1 genome was PCR amplified from pNL4-3 DNA with the Expand long template polymerase preparation (Roche Diagnostics, Indianapolis, Ind.) and primers spanning the Lys t-RNA primer binding site (MSF12, (SEQ ID NO:139) 5'-AAAAATCTCTAGCAGTG-GCGCCCGAACAG-3') and the poly-A signal region of 3'-LTR (MSR5, (SEQ ID NO:140) 5'-AAGCACTCAAG-GCAAGCTTTATTGAGGCT-3'), which amplifies the entire HIV-1 genome except for 75 bp in the unique-5' (U5) region of the LTR. The purified amplified DNA product was digested with DNase I using DNase shotgun cleavage kit (Novagen, Madison, Wis.), and fragments between 50 and 300 bp were isolated by preparative gel electrophoresis, treated with T4 DNA polymerase to generate blunt ends, and dephosphorylated using calf intestinal alkaline phosphatase (CIP) (Roche Diagnostics, Indianapolis, Ind.). DNA was again purified using nucleotide removal kit (Qiagen Inc, Valencia, Calif.) and was ligated in the presence of Srf I enzyme into the Sma I site of the M13 derived phage vector for expression as gIIIp fusion protein, followed by electroporation into E. coli TGI cells. Tet-resistant transformants were harvested and expanded in liquid culture (2X-YT) at 37° C. The cell-free phage supernatant was isolated by centrifugation and phage titer was determined as Tee transduction units. Ninety six individual clones were isolated and DNA inserts were amplified by standard PCR and sequenced to determine the insert size distribution and library diversity.

Selection of Phages Reactive with HIV Antibodies from Early Infected Individuals Seven plasma samples constituting the HIV-1 seroconversion panel PRB-910 from SeraCare BioServices (Gaithersburg, Md.) were used for panning of the HIV-1 gene-fragment phage display library (GFPDL). For removal of plasma components, which could non-specifically interact with phage proteins, 5-fold diluted plasma was pre-adsorbed three times on sterile polystyrene Petri dishes (35 mm diameter) coated with $10^{13}$ UV-killed VCSM13. For biopanning, the microtiter strips (NUNC Inc, Naperville, Ill.) were coated with a mixture of 500 ng each of goat anti-human IgG-Fc and goat anti-human IgM-Fc specific antibodies in PBS, pH 7.4. After three washings with PBST (20 mM PBS containing 0.1% Tween 20), DMEM containing 5% FBS (blocking solution) was added to wells to block the unoccupied reactive sites. VCSM13 pre-adsorbed HIV-1 human plasma was added to the wells and incubated for 1 h at room temperature (RT). Wells were washed thrice with PBST and $10^{10}$ phages per well of the HIV-1 GFPDL, diluted in blocking solution, were added for 2 h at RT. The unbound phages were removed in twelve washes with PBST followed by three washes with PBS. Bound phages were eluted by addition of 0.1 N HCl containing BSA (1 mg/ml), for 10 min at RT, and neutralized by adding 8 µl of 2 M Tris solution per 100 µA eluate. Four rounds of affinity selection were carried out with each individual serum sample comprising the HIV seroconversion panel PRB-910.

Analysis of Affinity Selected Phage Clones

Twenty two phage clones enriched after four rounds of biopanning on each PRB-910 plasma sample were further screened for specific recognition by HIV seropositive sera and absence of reactivity with seronegative sera in affinity-capture phage ELISA. The wells of ELISA plates (Immulon 2HB, Thermo Labsystems, Franklin, Mass.) were coated with 100 ng/well of anti-phage antibody (GE Healthcare, Piscataway, N.J.), and blocked with DMEM/5% FBS. Subsequently, $10^{10}$ phages of the selected clones were added per well and incubated for 1 h at RT. Serially diluted sera (in DMEM/5% FBS) were added to the 96-well plates in duplicate and incubated at RT for 1 h. The bound antibodies were probed with HRP-conjugated goat anti-human IgG-IgM antibodies and the reactions were developed with OPD substrate solution (Pierce Biotechnology, Rockford, Ill.). The clones demonstrating the best differential reactivity with HIV-1 seropositive sera were expanded and the inserts were sequenced and mapped to individual HIV-1 genes. Several inserts were selected for synthetic peptide synthesis and development of the HIV-SELECTEST.

Peptides Used in New HIV-SELECTEST

Peptide sequences from Gag-p6 (SEQ ID NO:3; 452-SRPEPTAPPAESFRFGEE-ITPTPSQKQEPKDKELYPPLASLRSLFGNDPSSQ-502) and gp41 cytoplasmic region (SK1; SEQ ID NO:50; 784-LIAARIVELLGHSSLKGLRRGWEALKYL-WNLLQYWGQELKNSAISL-829 and SK2; SEQ ID NO:55; 836-AVAEGTDRVIEVVQRVCRAILNIPRR-IRQGFERALL-871) were chemically synthesized (amino acid residues are numbered based on the CON—OF—CONS alignment sequence in the Los Alamos database). All peptides were synthesized at the Facility for Biotechnology Resources, CBER, FDA, on Applied Biosystems peptide synthesizer models 431 and 433 (Foster City, Calif.) by standard 9-fluorenyl methoxycarbonyl chemistry (Fmoc). Peptides were purified by reverse-phase high performance liquid chromatography (RP-HPLC) and characterized by mass spectrometry (MALDI-TOF MS).

HIV-SELECTEST

Based on preliminary screening of HIV seronegative and seropositive sera, the optimal conditions for the p6 and gp41 ELISA were determined. The p6 peptide was coated at 30 ng/100 µl/well while the gp41 peptides (SEQ ID NO:50 and SEQ ID NO:55) were coated at 150 ng/100 µl/well each (total 300 ng/well) on Immulon-2HB plates. After three washes with PBST (20 mM PBS, 0.1% Tween-20), the unoccupied reactive sites were blocked by PBST containing 2% whole milk (2% WMPBST). All specimens (serum or plasma) were diluted 1:100 in 2% WMPBST, added to peptide-coated wells, and incubated for 1 h at RT. The plates were then washed six times with PBST and 100 Owen of HRP-conjugated goat anti-Human IgG Fc-specific antibody (Jackson ImmunoResearch, West Grove, Pa.), diluted 1:10,000 in 2% WMPBST was added. The reactions were quantified using O-Phenylenediamine (OPD) substrate.

Based on the results with 1000 seronegative samples, cut-off values were determined for p6 and gp41 peptides individually. The cut-off values used are the average absorbance of Negative sera+5 Standard Deviations (for each peptide). Specimens with an Absorbance/Cut-off ratios of ≥1 are considered HIV-1 seropositive and those with ratios<1 are considered HIV-1 seronegative.

HIV Seroconversion Panels and Vaccine Trial Samples

HIV-1 seroconversion panels PRB-910, PRB-924, PRB-927, PRB-928, PRB-929, PRB-931 and mixed titer panel PRB-204 were purchased from SeraCare BioServices, (Gaithersburg, Md.). A seroconversion panel consists of plasma samples collected serially early after HIV-1 infection, and the virological and immunological profiles as assessed by commercial diagnostic kits for these plasma samples were provided by SeraCare BioServices. Additionally, twenty eight seroconversion panels were provided by the University of New South Wales (PHAEDRA Inventory, Sydney, Australia). HIV negative serum samples were obtained from National Institutes of Health Blood Bank and the Vaccine Research Center (VRC, NIAID, NIH, Bethesda, Md.).

Serum/Plasma samples from the following HIV vaccine trials were tested: HVTN 203 (246 vaccinees and 78 placebos; conducted by the HIV Vaccine Trial Network), RV124 (conducted by the Walter Reed Army Institute of Research), VRC 004 (40 vaccinees and 10 placebos), VRC 006 (30 vaccinees and 6 placebos), VRC 009 (9 vaccinees and no placebos) and VRC 010 were conducted by the Vaccine Research Center (NIAID, NIH), VAX 003 and VAX 004 were conducted by VaxGen Inc. The HIV infection status of a given sample was provided by the collaborating groups and also determined by in house testing using the BioRad HIV-1/2 plus 0 kit (Bio Rad laboratories, Woodinwille, Wash.). Samples obtained from VRC 009 and VRC 010 trials were also tested with the Capillus HIV-1/HIV-2 and Uni-Gold HIV rapid tests (Trinity Biotech, N.Y.).

Identification of HIV Sequences Recognized by Early Seroconversion Sera Using Gene-Fragment Phage Display Library In order to identify all the HIV sequences recognized by antibodies generated soon after HIV infection, a gene-fragment phage display library (GFPDL) was constructed spanning the entire HIV-1 open reading frame of NL4-3. The HIV-1 GFPDL, contained more than $10^7$ independent transformants. PCR-based analysis and sequencing of the inserts confirmed that the library consisted of 100% recombinants, with an insert size of 50-300 bp, and random distribution across the HIV genome.

Seven plasma samples constituting a seroconversion panel PRB-910 (obtained from acutely HIV-1 infected individual; SeraCare BioServices, Gaithersburg, Md.) were used as bait for affinity selection of phages displaying HIV-1 peptides. After four rounds of biopanning, 22 clones (for each plasma sample) were selected for insert sequencing, and were analyzed by phage ELISA with HIV positive and negative sera, to confirm the specificity of reactivity. Alignment of inserts with the HIV-1 genome led to identification of twelve immunodominant epitopes, mapping to Gag-p24 & p6, Pol, Env-gp120 & gp41, and Nef. Interestingly, phages displaying sequences from the intracytoplasmic tail of gp41 (amino acids 784-871) were repeatedly recognized by antibodies from both early (1-6 months) and chronically infected individuals. The cytoplasmic tail of gp41 was selected as the primary candidate for the differential assay as it is unlikely to be targeted by HIV-neutralizing antibodies, and it is not included in most HIV vaccines currently under development. In addition, a p6 sequence was also selected, even though it was included in early generation HIV vaccines, it contains very few HLA restricted CTL epitopes (Frahm, N. et al. (2004) "CONSISTENT CYTOTOXIC-T-LYMPHOCYTE TARGETING OF IMMUNODOMINANT REGIONS IN HUMAN IMMUNODEFICIENCY VIRUS ACROSS MULTIPLE ETHNICITIES. J Virol 78:2187-2200) (Los Alamos database; http://hiv-web.lanl.gov). Importantly, the selected gp41 [spanning amino acids 784-829 (SK1) and 836-871 (SK2)], and the p6 (amino acids 452-502) sequences are highly conserved among all HIV-1 M subtypes.

Establishment of the 'HIV-SELECTEST'

Figure 7:
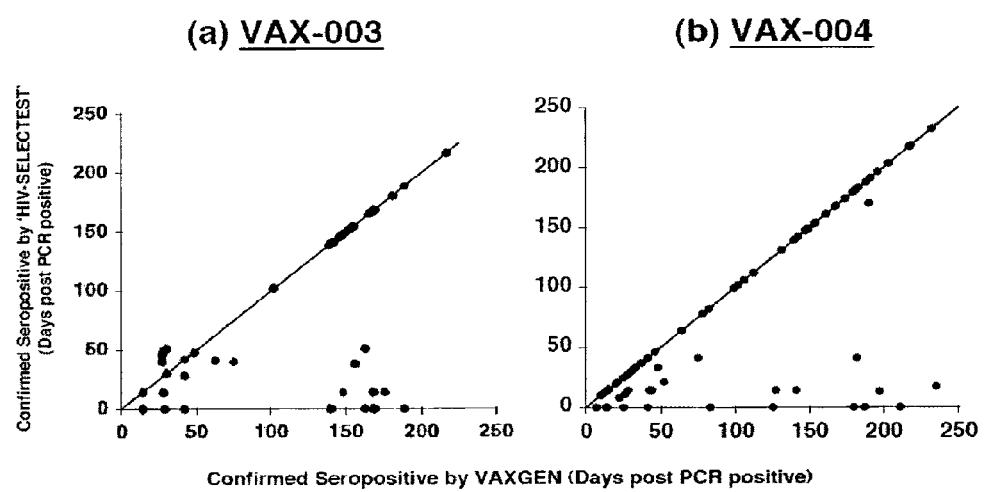
FIG. 7, Panels a and b shows comparative reactivity of early samples from HIV infections during the VAX 003 (Thailand) and VAX 004 (United States and the Netherlands) clinical trials in the HIV-SELECTEST and licensed HIV detection kits used in the VaxGen trials. Early sequential samples obtained from HIV infected vaccine trial participants in VAX 003 (30 vaccinees and 35 placebos; Panel a) and VAX 004 (53 vaccinees and 28 placebos; Panel b) were tested in the HIV-SELECTEST as described in METHODS, and by VaxGen using licensed HIV diagnostic tests. Day 0 represents the day of confirmed infection by qualitative PCR. Each dot in the figures represent the earliest bleed (post infection) on which a given infected individual scored positive by the licensed HIV diagnostic kits (X-axis) compared with the HIV-SELECTEST (Y-axis).

The p6 and two gp41-derived peptides were chemically synthesized and used for the development of the new assay. Based on the Los Alamos HIV sequence database, consensus peptides were designed to encompass the genetic variability among HIV-1 clades. Initially, each peptide was evaluated individually to determine specificity and establish cut-off values. Since both gp41 peptides (SK1 and SK2) displayed similar very low reactivity with HIV seronegative samples, the two were combined. Multiple ELISA conditions were tested and after screening of 1000 seronegative samples, cut-off (CO) values for the gp41 (CO=0.03) and p6 (CO=0.15) peptides were determined. Each CO value represents the average absorbance of negative sera+5 standard deviations. Additional panels containing high, intermediate, and low HIV-specific antibody titers were used to determine the dynamic range of the assay. FIG. 7, Panels (a) and (b) demonstrate the binding of serially diluted representative plasma, PRB-204-06 (from SeraCare BioServices), in the p6 and gp41 ELISA, respectively. Multiple titrations with different samples demonstrated higher maximum reactivity with the gp41 peptides and a broader dynamic range when compared with the p6 peptide. Based on these analyses, all subsequent ELISA testing was conducted with 1:100 dilution of sera or plasma. The HIV infection status of a given sample was determined by licensed detection kits conducted either in-house or by an outside laboratory. An assay specificity of 100% for the gp41 peptides and 99.4% for the p6 peptide was established after screening of >2500 samples from uninfected or from individuals infected with diverse HIV-1 clades. The combined sensitivity of the gp41 and p6 peptides is 99.3% for detection of early and chronic infections in multiple geographical sites with clades A, B, C, D, E, F, J and multiple circulating recombinant forms.

Assay Robustness and Statistical Analysis

The reproducibility of the assay was determined by repeatedly testing nine HIV seropositive and three HIV seronegative samples from SeraCare BioServices. The distributions of the results obtained on multiple dates were evaluated for normality and the appropriate p-values were calculated using SigmaPlot. Representative plots are shown for one individual on the p6 and gp41 peptides (FIG. 7, Panels (c) and (d), respectively. The upper and lower limits (±2SD) represent the 95% confidence intervals. Inter-assay variability was ≤10% and intra-assay variability was ≤5% for all the samples tested.

Acute Infections are Detected with HIV-SELECTEST

To determine how soon post-infection HIV-specific antibodies are detected with the HIV-SELECTEST, several well-characterized seroconversion panels were obtained from SeraCare BioServices containing sequential bleeds within 30-40 days of estimated exposure dates. As shown in Table 12 top panel, the p6 peptide reacted positively with PBR-910 on collection day 26, in agreement with results obtained using licensed HIV antibody detection kits. The gp41 peptides were reactive with the day 32 sample from the same individual. For PRB-929, day 25 and day 28 samples reacted with p6 and gp41 peptides, respectively (Table 13). In that individual, infection was confirmed by PCR on day 14 and the Abbott HIV Ag test was positive on day 18. In Tables 12 and 13, ELISA data for P6 and GP41 are shown as the ratio of test specimen absorbance to cut-off value. Ratios of 1.00 or greater are considered HIV seropositive and a sample ratio of less than 1 is considered HIV negative; for Abbott assays, PCR, and FDA licensed EIA kits, HIV early seroconversion panels (within 6 weeks after HIV infection) and data for HIV RNA PCR quantification and FDA licensed serodiagnostic kits were provided by SeraCare BioServices, (Gaithersburg, Md.).

the midpoint between the last seronegative and first seropositive results obtained with licensed HIV diagnostic kits.

Evaluation of Samples from HIV Vaccine Trials

The main proof-of-concept in support of the HIV-SELECTEST should come from evaluating the reactivity of vaccine induced antibodies in the course of prophylactic vaccine trials. To that end, six blinded panels from completed vaccine trials (502 vaccinees) were tested including HVTN 203 (conducted by the HIV Vaccine Trial Network), RV124 (conducted by the Walter Reed Army Institute of Research) and VRC 004, VRC 006, VRC 009, and VRC 010 (conducted by the Vaccine Research Center, NIAID, NIH). The description of the vaccine constructs used in the various trials and summary of the results obtained with the HIV-SELECTEST appear in Table 22. Canarypox vaccine constructs used in the RV124 and HVTN 203 contained the p6 epitope used in the new assay. Additionally, the protein boost in RV124 was gp 160. In contrast, the vaccine constructs used in VRC 004 and VRC 006 lacked the peptide sequences used in the HIV-SELECTEST.

TABLE 22

Summary of HIV-SELECTEST Reactivity with Vaccine Trial Samples

| Sponsor & Vaccine Trial | Vaccine Composition | | Total No. of Samples | No. of HIV Infected | No. of Samples Positive by FDA | HIV-SELECTEST Reactivity | |
|---|---|---|---|---|---|---|---|
| Number | Prime | Booster | Tested | Samples | Licensed Kits (%) | p6 (%) | gp41 (%) |
| RV124[1] | vCP205 (gag + pro + env) | gp160 protein | 79 | 0 | 63 (80%) | 2 (2.5%) | 0 |
| HVTN 203[2] | vCP1452 (gag-pro-gp140 + Pol & Nef-CTL epitopes | gp140 protein | 324 | 2 | 97 (30%) | 38 (12%) | 2 (0.6%)[5] |
| VRC 004[3] | pGag-Pol-Nef + pEnvA + pEnvB + pEnvC | SAME AS PRIME | 50[6] | 2 | 15 (38%) | 1 (2%)[5] | 2 (4%)[5] |
| VRC 006[3] | Ad5-Gag-Pol + Ad5-EnvA + Ad5-EnvB + Ad5-EnvC | — | 36[6] | 0 | 18 (60%) | 0 | 0 |
| VRC 009[3] | pGag-Pol-Nef + pEnvA + pEnvB + pEnvC | Ad5-Gag-Pol + Ad5-EnvA + Ad5-EnvB + Ad5-EnvC | 9[6] | 0 | 9 (100%) | 0 | 0 |
| VRC 010[3] | pGag + pPol + pNef + pEnvA + pEnvB + pEnvC | Ad5-Gag-Pol + Ad5-EnvA + Ad5-EnvB + Ad5-EnvC | 4[6] | 0 | 4 (100%) | 0 | 0 |

[1]The RV124 vaccine immunogens contained both the p6 & gp41 peptides used in the HIV-SELECTEST.
[2]The HVTN 203 vaccine immunogen contained the p6 but not the gp41 sequences used in HIV-SELECTEST.
[3]The VRC 004, 006, 009 vaccines did not contain either p6 or gp41 epitopes used in the HIV-SELECTEST, but participants in VRC 010 received p6-containing DNA (pGag) prime during VRC 007 phase I trial.
[4]Bio-Rad HIV-1/2 + O EIA kit was used for sample screening. Seroconversion in VRC 009 and VRC 010 was determined by rapid tests, Capillus HIV-1/HIV-2 and Uni-Gold HIV.
[5]Upon unblinding, these seropositive samples were confirmed as true HIV infections.
[6]VRC 004 had 10 placebo subjects and VRC 006 had 6 placebos, while VRC 009 and VRC 010 had no placebo subjects.

Similar results were obtained with additional seroconversion panels from SeraCare BioServices, and demonstrated that HIV infection could be detected by the HIV-SELECTEST within 2-4 weeks following HIV-1 RNA detection by PCR, concurrent with the sensitivity limits of licensed HIV diagnostic tests. In addition, we evaluated 28 seroconversion panels spanning 6-18 months post-infection from Australia (Table 14). With these panels, p6 showed variable reactivity at later times post-infection, whereas anti-gp41 reactivity increased over time and was maintained at high levels in most individuals, indicating that the kinetics and avidity of the antibody responses against the p6 and gp41 epitopes were not linked. In Table 23, the date of infection was estimated to be The RV124 trial represents the worst case scenario, wherein all the peptide sequences used in the HIV-SELECTEST were part of either the priming or boosting immunogens. After the last boost (day 182), 80% of vaccinees strongly seroconverted in commercial HIV-1 detection kits even though none were HIV infected (Table 22 and Table 20). However, only two individuals scored positive in the p6-ELISA, and none reacted in the gp41-ELISA. These findings suggested that the epitopes used in the HIV-SELECTEST were not very immunogenic in the context of the RV124 vaccine constructs.

The HVTN 203 blinded specimens included samples from pre-vaccination and four & six months post-vaccination obtained from 324 trial participants. In this panel, 30% of vaccinees seroconverted in the licensed HIV detection assays, while only 12% reacted with the p6 peptide in the HIV-SELECTEST (Table 22). This finding was not surprising since the Canarypox/HIV prime (vCP1452) contained p6. Unexpectedly, two specimens were repeatedly reactive with gp41 even though these sequences were not in the vaccine constructs. However, after unblinding, it was confirmed that both samples were obtained from trial participants who got infected during this phase II trial.

The VRC phase I trials VRC 004, VRC 006, VRC 009, and VRC 010 were conducted in 2002-2005. The DNA plasmids (VRC 004) and non-replicating recombinant Adenovirus serotype 5 vector (rAd5) (VRC 006) express Gag-Pol-Nef (in VRC 004) or Gag-Pol (in VRC 006) and multi-clade (A, B, C) envelope genes (gp145 in the DNA vaccine and gp140 in the rAd5 vaccine). Among the 50 participants in VRC 004, 38% (15/40) of vaccinated individuals seroconverted by licensed HIV diagnostic kits (Table 22). Unexpectedly, two samples reacted positive in the gp41 ELISA, of which one sample also reacted with p6 in the HIV-SELECTEST (Table 22). Upon unblinding, it was determined that both individuals (both in the placebo arm) became infected during the VRC 004 trial. In the VRC 006 (Ad5/HIV), no intercurrent HIV infections were identified, yet 60% of vaccine recipients (18/30) tested positive in licensed HIV detection tests. In contrast, none of the vaccinees reacted with either the p6 or gp41 in the HIV-SELECTEST (Table 22). In VRC 009 and VRC 010, a subset of DNA vaccinated individuals (from VRC 004 and VRC 007 trials, respectively) was boosted with the rAd5/HIV vaccine. The 4 weeks post-boost samples demonstrated a very significant increase in total HIV-specific antibodies (data not shown), and 100% seroconversion using two licensed rapid tests (Capillus HIV-1/HIV-2 and Uni-Gold HIV, Trinity Biotech, N.Y.). Importantly, all vaccinees in these trials tested negative in the HIV-SELECTEST (Table 22).

Detection of Intercurrent HIV Infections During Vaccine Trials

Data obtained with the blinded panels from HIV vaccine trials tested to date indicates that vaccine-generated antibodies are most likely to give negative reactivity in the HIV-SELECTEST, especially if the vaccines do not contain the p6 sequence. Importantly, the new test detected all intercurrent infections in the blinded samples. To further determine the sensitivity of new assay in detecting acute HIV infections in the course of vaccine trials, sequential samples were tested from HIV infections in completed Phase I, Phase II, and Phase III trials conducted by HVTN (Lee, D. et al. (2004) "BREAKTHROUGH INFECTIONS DURING PHASE 1 AND 2 PRIME-BOOST HIV-1 VACCINE TRIALS WITH CANARYPDX VECTORS (ALVAC) AND BOOSTER DOSE OF RECOMBINANT GP120 OR GP160," J Infect Dis 190:903-907) VRC, and VaxGen (VAX 003/VAX 004 efficacy trials) (Gilbert, P. B. et al. (2005) "CORRELATION BETWEEN IMMUNOLOGIC RESPONSES TO A RECOMBINANT GLYCOPROTEIN 120 VACCINE AND INCIDENCE OF HIV-1 INFECTION IN A PHASE 3 HIV-1 PREVENTIVE VACCINE TRIAL," J Infect Dis 191:666-677 (2005).

Figure 6:
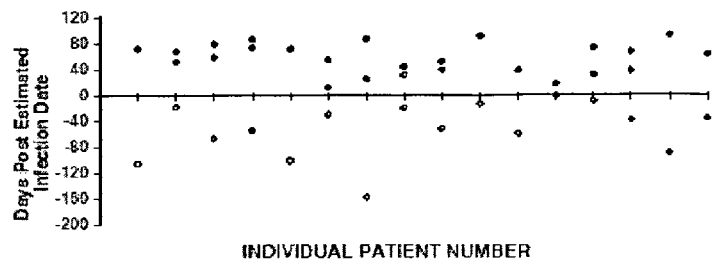
FIG. 6 shows the seroreactivity of intercurrent HIV infections during HIV vaccine trials. Reactivity in the HIV-SELECTEST of sequential plasma samples obtained from intercurrent infections in the course of: (a) multiple phase I/II HIV vaccine trials conducted by the HVTN (15 vaccinees and 4 placebos) and VRC 004 (2 placebos); (b) VAX 003 phase III trial in Thailand (30 vaccinees and 35 placebos); (c) VAX 004 phase III trial in the United States and the Netherlands (53 vaccinees and 28 placebos). For each infected subject, multiple time points within 3 months of estimated infection date (panel a) or confirmed infection by PCR (depicted as day 0 on Y-axis, panels b and c) are shown vertically. Open circles (○) represent negative reactivity in the HIV-SELECTEST (OD/CO<1), and filled circles (●) represent positive reactivity in the HIV-SELECTEST (OD/CO≥1). Detailed reactivity data for all the samples tested are shown in Table 27, Table 29 and Table 30.
Figure 6:
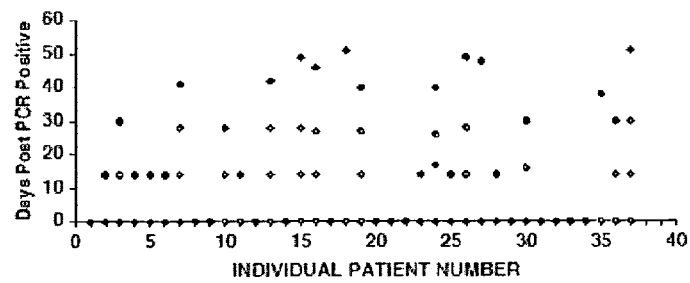
Figure 6:
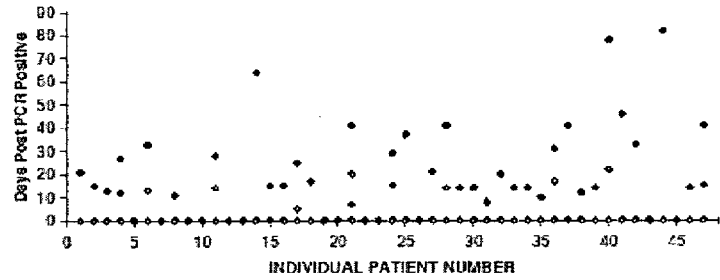

As can be seen in Table 23, FIG. 6, Panel (a), and Table 24, sequential samples obtained from 22 vaccinees infected with HIV during the HVTN trials and the VRC 004 trial reacted positive in the HIV-SELECTEST at early time points after the estimated infection dates. Importantly, no reactivity in the HIV-SELECTEST was observed prior to HIV infections in trial participants, even though they were immunized with complex vaccine products.

TABLE 23

HIV-SELECTEST Specifically Detects Intercurrent HIV Infections During Multiple HIV Vaccine Trials

| Serum Sample | Days After Estimated Date of HIV Infection[1] | HIV-SELECTEST p6 | gp41 | Vaccine Immunogen |
|---|---|---|---|---|
| HIVNET-1-1 | −102.00 | 0.52 | 0.13 | vCP205 + SF-2 rgp120 |
| HIVNET-1-2 | 71 | 0.71 | 83.33 | vCP205 + SF-2 rgp120 |
| HIVNET-1-3 | 99 | 6.41 | 80.77 | vCP205 + SF-2 rgp120 |
| HIVNET-2-1 | −158.00 | 0.22 | 0.30 | vCP205 + Saline placebo |
| HIVNET-2-2 | 24 | 11.19 | 0.13 | vCP205 + Saline placebo |
| HIVNET-2-3 | 87 | 11.74 | 88.83 | vCP205 + Saline placebo |
| HVTN 203-1-1 | −22 | 0.32 | 0.13 | vCP1452 mo (0, 1, 3, 6) + AIDSVAX B/B mo (3, 6) |
| HVTN 203-1-2 | 16 | 15.78 | 0.10 | vCP1452 mo (0, 1, 3, 6) + AIDSVAX B/B mo (3, 6) |
| HVTN 203-1-3 | 712 | 1.01 | 16.83 | vCP1452 mo (0, 1, 3, 6) + AIDSVAX B/B mo (3, 6) |
| AVEG-1-1 | −9 | 0.67 | 0.10 | vCP205 (mo 0, 1) + SF-2 rpg120 (mo 6, 9, 12) |
| AVEG-1-2 | 31 | 15.25 | 1.13 | vCP205 (mo 0, 1) + SF-2 rpg120 (mo 6, 9, 12) |
| AVEG-1-3 | 72 | 16.51 | 46.33 | vCP205 (mo 0, 1) + SF-2 rpg120 (mo 6, 9, 12) |
| VRC 004-1-1 | −9 | 0.06 | 0.07 | Placebo |
| VRC 004-1-2 | 19 | 1.15 | 0.17 | Placebo |
| VRC 004-1-3 | 47 | 2.95 | 0.33 | Placebo |
| VRC 004-1-4 | 130 | 9.97 | 23.07 | Placebo |

[1]Sequential samples from HIV infections during VRC 004 and multiple HVTN clinical trials and the estimated dates of infection were provided by the clinical oversight boards.

TABLE 24

Reactivity Of Intercurrent Hiv Infection Samples During HVTN & VRC-004 Clinical Trials In The 'HIV-SELECTEST'

| Serum Sample | Days Post Infection | New HIV ELISA' p6 | gp41 | Vaccine Type |
|---|---|---|---|---|
| HVTN-1-1 | −106.00 | 0.27 | 0.07 | vCP205 + rgp120 |
| HVTN-1-2 | 71 | 1.92 | 8.10 | |
| HVTN-1-3 | 105.00 | 1.31 | 59.27 | |
| HVTN-2-1 | −19.00 | 0.08 | 0.13 | Placebo-Saline |
| HVTN-2-2 | 51 | 0.22 | 3.13 | |
| HVTN-2-3 | 67 | 0.17 | 33.00 | |
| HVTN-3-1 | −67.00 | 0.04 | 0.13 | Placebo-Saline |
| HVTN-3-2 | 58 | 0.40 | 46.70 | |
| HVTN-3-3 | 79 | 0.28 | 50.77 | |
| HVTN-4-1 | −55.00 | 0.03 | 0.13 | vCP205 + Saline |
| HVTN-4-2 | 72 | 1.09 | 0.13 | |
| HVTN-4-3 | 85 | 1.15 | 0.17 | |
| HVTN-5-1 | −102.00 | 0.52 | 0.13 | vCP205 + rgp120 |
| HVTN-5-2 | 71 | 0.71 | 83.33 | |
| HVTN-5-3 | 99 | 6.41 | 80.77 | |
| HVTN-6-1 | −30.00 | 0.07 | 0.17 | vCP205 + rgp120 |
| HVTN-6-2 | 11 | 0.04 | 0.07 | |
| HVTN-6-3 | 53 | 0.78 | 28.37 | |
| HVTN-7-1 | −158.00 | 0.22 | 0.30 | vCP205 + Saline |
| HVTN-7-2 | 24 | 11.19 | 0.13 | |
| HVTN-7-3 | 87 | 11.74 | 88.83 | |
| HVTN-8-1 | −20.00 | 0.08 | 0.30 | vCP205 + rgp120 |
| HVTN-8-2 | 30 | 0.35 | 0.23 | |
| HVTN-8-3 | 44 | 0.25 | 5.07 | |
| HVTN-9-1 | −91.00 | 0.78 | 0.17 | vCP205 + Saline |
| HVTN-9-2 | 106 | 4.22 | 14.33 | |
| HVTN-9-3 | 169.00 | 0.87 | 4.37 | |
| HVTN-10-1 | −52 | 0.49 | 0.10 | vCP1452 |
| HVTN-10-2 | 39 | 6.29 | 0.17 | |
| HVTN-10-3 | 52 | 5.16 | 2.33 | |
| HVTN-11-1 | −14 | 0.09 | 0.10 | vCP1452 + AIDSVAX B/B |
| HVTN-11-2 | 91 | 0.64 | 78.07 | |

TABLE 24-continued

Reactivity Of Intercurrent Hiv Infection Samples During HVTN & VRC-004 Clinical Trials In The 'HIV-SELECTEST'

| Serum Sample | Days Post Infection | New HIV ELISA' p6 | gp41 | Vaccine Type |
|---|---|---|---|---|
| HVTN-12-1 | −60 | 0.09 | 0.07 | vCP1452 |
| HVTN-12-2 | 38 | 0.45 | 6.03 | |
| HVTN-13-1 | −22 | 0.32 | 0.13 | vCP1452 + AIDSVAX B/B |
| HVTN-13-2 | 16 | 15.78 | 0.10 | |
| HVTN-13-3 | 712 | 1.01 | 16.83 | |
| HVTN-14-1 | −9 | 0.03 | 0.10 | Placebo-Saline |
| HVTN-14-2 | 5 | 0.05 | 0.20 | |
| HVTN-14-3 | 95 | 0.13 | 23.30 | |
| HVTN-15-1 | −9 | 0.67 | 0.10 | vCP205 + rgp120 |
| HVTN-15-2 | 31 | 15.25 | 1.13 | |
| HVTN-15-3 | 72 | 16.51 | 46.33 | |
| HVTN-16-1 | −1030 | 0.39 | 0.13 | vCP205 + gp160 |
| HVTN-16-2 | 211 | 0.17 | 87.17 | |
| HVTN-16-3 | 307 | 0.13 | 92.33 | |
| HVTN-17-1 | −39.00 | 0.02 | 0.10 | Placebo-Saline |
| HVTN-17-2 | 37 | 0.11 | 23.67 | |
| HVTN-17-3 | 66 | 0.15 | 44.70 | |
| HVTN-18-1 | −408.00 | 0.05 | 0.10 | vCP65 + rgp120 |
| HVTN-18-2 | 242.00 | 0.13 | 82.20 | |
| HVTN-18-3 | 272.00 | 0.16 | 85.63 | |
| HVTN-19-1 | −90.00 | 0.37 | 0.13 | vCP205 + rgp120 |
| HVTN-19-2 | 92 | 3.97 | 31.10 | |
| HVTN-19-3 | 191.00 | 3.70 | 77.33 | |
| HVTN-20-1 | −37.00 | 0.03 | 0.07 | Placebo-Saline |
| HVTN-20-2 | 63 | 0.77 | 42.83 | |
| VRC-004-1-1 | −136 | 0.09 | 0.47 | Placebo-Saline |
| VRC-004-1-2 | −40 | 0.28 | 0.37 | |
| VRC-004-1-3 | 44 | 0.61 | 42.43 | |
| VRC-004-2-1 | −13 | 0.05 | 0.07 | Placebo-Saline |
| VRC-004-2-2 | 14 | 1.15 | 0.17 | |
| VRC-004-2-3 | 69 | 2.95 | 0.33 | |
| VRC-004-2-4 | 145 | 9.97 | 23.07 | |

Sequential samples soon after the first confirmed PCR positive visit were also obtained from 65 HIV infections during VAX 003 (AIDSVAX gp120 B/E) and 81 HIV infections during VAX 004 (AIDS VAX gp120 B/B') trials conducted by VaxGen. The dates of PCR positively and seroconversion by licensed HIV tests were provided by VaxGen. Table 25 contains analysis of two representative HIV infections in VAX 003 and VAX 004 trials that developed strong reactivity to p6 and gp41 peptides. Furthermore, the HIV-SELECTEST identified all intercurrent HIV infections within 90 days of PCR confirmation (FIG. 6, Panels (b) and (c); Table 26 and Table 27, for VAX 003 and VAX 004, respectively).

TABLE 25

Early Diagnosis Of Intercurrent HIV Infections by HIV-SELECTEST During VaxGen Clinical Trials VAX 003 & VAX 004

| Serum Sample | Draw Date | HIV PCR Analysis[1] | HIV Seroconversion (EIA and WB) | HIV-SELECTEST p6 | gp41 |
|---|---|---|---|---|---|
| VAX-003-9-1 | 02/02/00 | + | − | 0.69 | 0.23 |
| VAX-003-9-2 | 16/02/00 | + | + | 7.49 | 2.13 |
| VAX-003-9-3 | 09/03/00 | + | + | 12.17 | 15.57 |
| VAX-003-9-4 | 20/03/00 | + | + | 14.42 | 70.4 |
| VAX-003-9-5 | 18/04/00 | + | + | 7.18 | 45.53 |
| VAX-003-14-1 | 01/02/01 | + | − | 4.05 | 0.23 |
| VAX-003-14-2 | 15/02/01 | + | − | 12.83 | 0.9 |
| VAX-003-14-3 | 15/03/01 | + | + | 8.21 | 12.33 |
| VAX-003-14-4 | 12/04/01 | + | + | 7.32 | 12.3 |
| VAX-003-14-5 | 10/05/01 | + | + | 6.56 | 13.17 |
| VAX-004-9-1 | 17/02/99 | + | − | 0.03 | 0.11 |
| VAX-004-9-2 | 02/03/99 | + | − | 0.31 | 0.15 |
| VAX-004-9-3 | 22/03/99 | + | − | 4.73 | 1.04 |
| VAX-004-9-4 | 06/04/99 | + | + | 2.73 | 5.15 |
| VAX-004-51-1 | 14/12/98 | + | − | 0.51 | 0.19 |
| VAX-004-51-2 | 28/12/98 | + | − | 3.15 | 0.3 |
| VAX-004-51-3 | 12/01/99 | + | − | 5.69 | 14.22 |
| VAX-004-51-4 | 27/01/99 | + | + | 3.87 | 51.33 |

[1]Sequential samples from HIV infections during VAX 003 and VAX 004 clinical trials and the results of PCR and licensed HIV serodiagnostic assays were provided by the VaxGen clinical lab

TABLE 26

Reactivity of Intercurrent HIV Infections During VAX-003 Clinical Trials in the HIV-SELECTEST

| Serum Sample | Draw Date | HIV PCR Analysis[1] | HIV Seroconversion (EIA and WB) | HIV-SELECTEST p6 | gp41 |
|---|---|---|---|---|---|
| VAX-003-1-1 | Jul. 15, 1999 | + | − | 0.09 | 0.00 |
| VAX-003-1-2 | Jul. 29, 1999 | + | − | 0.06 | 0.17 |
| VAX-003-1-3 | Dec. 9, 1999 | + | + | 1.47 | 59.60 |
| VAX-003-1-4 | Dec. 28, 1999 | + | + | 1.14 | 53.37 |
| VAX-003-1-5 | Jan. 4, 2000 | + | + | 1.01 | 50.20 |
| VAX-003-2-1 | Oct. 1, 2001 | + | − | 0.07 | 2.20 |
| VAX-003-2-2 | Oct. 15, 2001 | + | + | 0.13 | 21.20 |
| VAX-003-2-3 | Nov. 7, 2001 | + | + | 0.38 | 80.23 |
| VAX-003-2-4 | Dec. 4, 2001 | + | + | 0.23 | 87.30 |
| VAX-003-3-1 | Oct. 1, 2001 | + | − | 0.58 | 0.20 |
| VAX-003-3-2 | Oct. 15, 2001 | + | − | 1.77 | 0.80 |
| VAX-003-3-3 | Mar. 26, 2002 | + | + | 0.47 | 41.53 |
| VAX-003-3-4 | Apr. 9, 2002 | + | + | 4.31 | 81.17 |
| VAX-003-3-5 | May 17, 2002 | + | + | 3.77 | 83.60 |
| VAX-003-4-1 | Jan. 13, 2000 | + | − | 0.04 | 0.27 |
| VAX-003-4-2 | Jan. 27, 2000 | + | − | 0.05 | 0.23 |
| VAX-003-4-3 | Jun. 26, 2000 | + | + | 1.17 | 76.80 |
| VAX-003-4-4 | Jul. 14, 2000 | + | + | 0.79 | 63.17 |
| VAX-003-4-5 | Jul. 24, 2000 | + | + | 0.59 | 69.27 |
| VAX-003-5-1 | Apr. 24, 2002 | + | − | 0.07 | 0.20 |
| VAX-003-5-2 | May 8, 2002 | + | − | 0.08 | 0.73 |
| VAX-003-5-3 | Aug. 28, 2002 | + | + | 0.07 | 86.47 |
| VAX-003-5-4 | Dec. 11, 2002 | + | + | 0.08 | 82.63 |
| VAX-003-6-1 | Jun. 22, 1999 | + | − | 0.10 | 0.23 |
| VAX-003-6-2 | Jul. 6, 1999 | + | − | 0.03 | 0.13 |
| VAX-003-6-3 | Jul. 22, 1999 | + | + | 0.21 | 23.50 |
| VAX-003-6-4 | Aug. 9, 1999 | + | + | 0.11 | 89.90 |
| VAX-003-6-5 | Aug. 19, 1999 | + | + | 0.18 | 93.50 |
| VAX-003-7-1 | Jan. 9, 2001 | + | − | 0.33 | 0.20 |
| VAX-003-7-2 | Jan. 23, 2001 | + | − | 1.28 | 0.73 |
| VAX-003-7-3 | Jun. 26, 2001 | + | + | 0.25 | 39.43 |
| VAX-003-7-4 | Jul. 17, 2001 | + | + | 0.33 | 42.17 |
| VAX-003-7-5 | Jul. 27, 2001 | + | + | 0.27 | 39.83 |
| VAX-003-8-1 | Aug. 25, 1999 | + | − | 0.19 | 0.10 |
| VAX-003-8-2 | Sep. 8, 1999 | + | − | 12.41 | 0.43 |
| VAX-003-8-3 | Jan. 20, 2000 | + | + | 0.53 | 83.40 |
| VAX-003-8-4 | Jun. 13, 2000 | + | + | 0.19 | 83.97 |
| VAX-003-8-5 | Aug. 29, 2000 | + | + | 0.32 | 89.20 |
| VAX-003-9-1 | Feb. 2, 2000 | + | − | 0.69 | 0.23 |
| VAX-003-9-2 | Feb. 16, 2000 | + | + | 7.49 | 2.13 |
| VAX-003-9-3 | Mar. 9, 2000 | + | + | 12.17 | 15.57 |
| VAX-003-9-4 | Mar. 20, 2000 | + | + | 14.42 | 70.40 |
| VAX-003-9-5 | Apr. 18, 2000 | + | + | 7.18 | 45.53 |
| VAX-003-10-1 | Jun. 6, 2000 | + | − | 0.07 | 0.23 |
| VAX-003-10-2 | Jun. 20, 2000 | + | − | 0.11 | 0.13 |
| VAX-003-10-3 | Nov. 20, 2000 | + | + | 0.20 | 83.60 |

TABLE 26-continued

Reactivity of Intercurrent HIV Infections During VAX-003 Clinical Trials in the HIV-SELECTEST

| Serum Sample | Draw Date | HIV PCR Analysis[1] | HIV Seroconversion (EIA and WB) | HIV-SELECTEST p6 | HIV-SELECTEST gp41 |
|---|---|---|---|---|---|
| VAX-003-10-4 | Dec. 18, 2000 | + | + | 0.11 | 77.57 |
| VAX-003-10-5 | Jan. 5, 2001 | + | + | 0.11 | 84.07 |
| VAX-003-11-1 | Aug. 1, 2001 | + | − | 0.26 | 0.20 |
| VAX-003-11-2 | Aug. 15, 2001 | + | − | 0.33 | 0.17 |
| VAX-003-11-3 | Jan. 16, 2002 | + | + | 0.48 | 2.87 |
| VAX-003-11-4 | Feb. 1, 2002 | + | + | 1.90 | 14.10 |
| VAX-003-11-5 | Feb. 15, 2002 | + | + | 1.57 | 11.93 |
| VAX-003-12-1 | Mar. 15, 2000 | + | − | 0.07 | 0.13 |
| VAX-003-12-2 | Mar. 28, 2000 | + | − | 0.22 | 0.10 |
| VAX-003-12-3 | Aug. 30, 2000 | + | + | 0.55 | 81.40 |
| VAX-003-12-4 | Sep. 11, 2000 | + | + | 0.25 | 70.73 |
| VAX-003-12-5 | Sep. 25, 2000 | + | + | 0.41 | 80.20 |
| VAX-003-13-1 | Aug. 5, 1999 | + | − | 0.06 | 0.17 |
| VAX-003-13-2 | Aug. 19, 1999 | + | − | 0.07 | 0.17 |
| VAX-003-13-3 | Sep. 2, 1999 | + | − | 0.08 | 0.03 |
| VAX-003-13-4 | Sep. 15, 1999 | + | − | 0.33 | 1.80 |
| VAX-003-13-5 | Oct. 6, 1999 | + | + | 0.61 | 18.77 |
| VAX-003-13-6 | Nov. 16, 1999 | + | + | 2.01 | 36.57 |
| VAX-003-13-7 | Nov. 30, 1999 | + | + | 0.91 | 35.37 |
| VAX-003-14-1 | Feb. 1, 2001 | + | − | 4.05 | 0.23 |
| VAX-003-14-2 | Feb. 15, 2001 | + | − | 12.83 | 0.90 |
| VAX-003-14-3 | Mar. 15, 2001 | + | + | 8.21 | 12.33 |
| VAX-003-14-4 | Apr. 12, 2001 | + | + | 7.32 | 12.30 |
| VAX-003-14-5 | May 10, 2001 | + | + | 6.56 | 13.17 |
| VAX-003-15-1 | Feb. 21, 2001 | + | − | 1.25 | 0.17 |
| VAX-003-15-2 | Mar. 8, 2001 | + | − | 1.39 | 0.20 |
| VAX-003-15-3 | Aug. 29, 2001 | + | + | 0.79 | 88.90 |
| VAX-003-15-4 | Sep. 27, 2001 | + | + | 0.71 | 81.17 |
| VAX-003-15-5 | Oct. 24, 2001 | + | + | 0.68 | 80.80 |
| VAX-003-16-1 | Oct. 20, 1999 | + | − | 0.23 | 0.13 |
| VAX-003-16-2 | Nov. 3, 1999 | + | − | 0.37 | 0.27 |
| VAX-003-16-3 | Nov. 17, 1999 | + | − | 0.29 | 4.67 |
| VAX-003-16-4 | Dec. 1, 1999 | + | + | 0.22 | 30.80 |
| VAX-003-16-5 | Dec. 15, 1999 | + | + | 0.16 | 66.13 |
| VAX-003-16-6 | Jan. 6, 2000 | + | + | 0.22 | 82.23 |
| VAX-003-17-1 | Sep. 22, 2000 | + | − | 0.09 | 0.27 |
| VAX-003-17-2 | Oct. 6, 2000 | + | − | 0.09 | 0.30 |
| VAX-003-17-3 | Mar. 9, 2001 | + | + | 0.36 | 83.40 |
| VAX-003-17-4 | Mar. 23, 2001 | + | + | 0.19 | 84.27 |
| VAX-003-17-5 | Apr. 9, 2001 | + | + | 0.23 | 85.80 |
| VAX-003-18-1 | Aug. 9, 1999 | + | − | 0.20 | 0.17 |
| VAX-003-18-2 | Aug. 23, 1999 | + | − | 1.47 | 0.63 |
| VAX-003-18-3 | Sep. 6, 1999 | + | + | 5.07 | 25.90 |
| VAX-003-18-4 | Sep. 17, 1999 | + | + | 2.89 | 39.00 |
| VAX-003-18-5 | Oct. 1, 1999 | + | + | 2.39 | 69.73 |
| VAX-003-19-1 | Aug. 14, 2001 | + | − | 0.16 | 0.13 |
| VAX-003-19-2 | Sep. 3, 2001 | + | − | 0.11 | 0.47 |
| VAX-003-19-3 | Jan. 29, 2002 | + | + | 0.27 | 14.53 |
| VAX-003-19-4 | Feb. 20, 2002 | + | + | 1.17 | 51.33 |
| VAX-003-19-5 | Mar. 6, 2002 | + | + | 0.83 | 42.07 |
| VAX-003-20-1 | Jan. 8, 2001 | + | − | 1.37 | 25.63 |
| VAX-003-20-2 | Jan. 22, 2001 | + | + | 1.53 | 34.60 |
| VAX-003-20-3 | Feb. 5, 2001 | + | + | 0.83 | 28.33 |
| VAX-003-20-4 | Feb. 21, 2001 | + | + | 0.79 | 40.83 |
| VAX-003-21-1 | Nov. 16, 1999 | + | − | 0.21 | 0.20 |
| VAX-003-21-2 | Nov. 30, 1999 | + | − | 0.16 | 0.13 |
| VAX-003-21-3 | Dec. 14, 1999 | + | − | 0.19 | 0.17 |
| VAX-003-21-4 | Dec. 28, 1999 | + | + | 0.24 | 1.13 |
| VAX-003-21-5 | Jan. 11, 2000 | + | + | 0.21 | 11.53 |
| VAX-003-21-6 | Jan. 28, 2000 | + | + | 0.50 | 38.43 |
| VAX-003-22-1 | Nov. 10, 1999 | + | − | 1.91 | 0.10 |
| VAX-003-22-2 | Nov. 24, 1999 | + | − | 1.24 | 0.10 |
| VAX-003-22-3 | Apr. 21, 2000 | + | + | 2.28 | 85.60 |
| VAX-003-22-4 | May 11, 2000 | + | + | 2.37 | 86.97 |
| VAX-003-22-5 | Nov. 2, 2000 | + | + | 1.25 | 85.40 |
| VAX-003-23-1 | Mar. 7, 2002 | + | − | 0.31 | 0.10 |
| VAX-003-23-2 | Mar. 21, 2002 | + | − | 0.36 | 0.10 |
| VAX-003-23-3 | Aug. 21, 2002 | + | + | 0.41 | 92.23 |
| VAX-003-23-4 | Sep. 11, 2002 | + | + | 1.97 | 93.60 |
| VAX-003-23-5 | Oct. 17, 2002 | + | + | 2.98 | 94.47 |
| VAX-003-24-1 | Jan. 19, 2000 | + | − | 0.04 | 0.17 |
| VAX-003-24-2 | Feb. 2, 2000 | + | − | 0.05 | 0.07 |
| VAX-003-24-3 | Feb. 16, 2000 | + | + | 0.15 | 0.47 |
| VAX-003-24-4 | Mar. 8, 2000 | + | + | 0.30 | 35.87 |
| VAX-003-24-5 | Mar. 15, 2000 | + | + | 0.41 | 65.67 |
| VAX-003-25-1 | Jan. 27, 2000 | + | − | 0.12 | 0.17 |
| VAX-003-25-2 | Feb. 10, 2000 | + | − | 0.09 | 0.07 |
| VAX-003-25-3 | Feb. 23, 2000 | + | + | 0.05 | 0.33 |
| VAX-003-25-4 | Mar. 13, 2000 | + | + | 0.13 | 13.23 |
| VAX-003-25-5 | Mar. 24, 2000 | + | + | 0.12 | 17.23 |
| VAX-003-26-1 | Feb. 1, 2000 | + | − | 0.03 | 0.13 |
| VAX-003-26-2 | Feb. 17, 2000 | + | − | 0.37 | 0.10 |
| VAX-003-26-3 | Jun. 22, 2000 | + | + | 1.33 | 80.00 |
| VAX-003-26-4 | Sep. 13, 2000 | + | + | 0.45 | 69.80 |
| VAX-003-26-5 | Nov. 6, 2000 | + | + | 0.55 | 85.30 |
| VAX-003-27-1 | Jan. 4, 2000 | + | − | 1.99 | 0.27 |
| VAX-003-27-2 | Jan. 17, 2000 | + | − | 7.77 | 0.10 |
| VAX-003-27-3 | May 23, 2000 | + | + | 6.41 | 71.83 |
| VAX-003-27-4 | Jun. 12, 2000 | + | + | 3.79 | 57.77 |
| VAX-003-27-5 | Jun. 19, 2000 | + | + | 4.27 | 63.70 |
| VAX-003-28-1 | May 11, 2000 | + | − | 0.18 | 0.20 |
| VAX-003-28-2 | May 25, 2000 | + | − | 0.23 | 0.10 |
| VAX-003-28-3 | Oct. 25, 2000 | + | + | 1.76 | 91.73 |
| VAX-003-28-4 | Nov. 28, 2000 | + | + | 0.95 | 90.67 |
| VAX-003-28-5 | Dec. 20, 2000 | + | + | 1.42 | 94.77 |
| VAX-003-29-1 | Jun. 13, 2000 | + | − | 0.05 | 0.10 |
| VAX-003-29-2 | Aug. 3, 2000 | + | + | 0.30 | 87.20 |
| VAX-003-29-3 | Nov. 23, 2000 | + | + | 0.20 | 92.07 |
| VAX-003-29-4 | Dec. 22, 2000 | + | + | 0.16 | 97.23 |
| VAX-003-29-5 | Jan. 8, 2001 | + | + | 0.05 | 95.70 |
| VAX-003-30-1 | Dec. 22, 1999 | + | − | 0.04 | 0.10 |
| VAX-003-30-2 | Jan. 5, 2000 | + | − | 0.04 | 0.17 |
| VAX-003-30-3 | Jan. 18, 2000 | + | + | 0.11 | 0.50 |
| VAX-003-30-4 | Jan. 31, 2000 | + | + | 0.13 | 16.50 |
| VAX-003-30-5 | Feb. 29, 2000 | + | + | 0.09 | 36.33 |
| VAX-003-31-1 | Dec. 29, 1999 | + | − | 2.77 | 0.33 |
| VAX-003-31-2 | Jan. 12, 2000 | + | − | 3.89 | 0.50 |
| VAX-003-31-3 | Mar. 29, 2000 | + | + | 7.35 | 8.90 |
| VAX-003-31-4 | May 12, 2000 | + | + | 4.45 | 12.83 |
| VAX-003-32-1 | Mar. 7, 2000 | + | − | 1.83 | 0.10 |
| VAX-003-32-2 | Mar. 21, 2000 | + | − | 2.19 | 0.07 |
| VAX-003-32-3 | Jul. 25, 2000 | + | + | 2.17 | 85.57 |
| VAX-003-32-4 | Aug. 11, 2000 | + | + | 0.72 | 81.80 |
| VAX-003-32-5 | Aug. 30, 2000 | + | + | 0.95 | 81.17 |
| VAX-003-33-1 | Jul. 25, 2000 | + | − | 0.19 | 6.70 |
| VAX-003-33-2 | Aug. 8, 2000 | + | + | 0.23 | 12.43 |
| VAX-003-33-3 | Aug. 18, 2000 | + | + | 0.09 | 5.17 |
| VAX-003-33-4 | Sep. 8, 2000 | + | + | 0.10 | 3.93 |
| VAX-003-34-1 | Oct. 16, 2001 | + | − | 0.05 | 0.17 |
| VAX-003-34-2 | Oct. 30, 2001 | + | − | 0.04 | 0.17 |
| VAX-003-34-3 | Apr. 23, 2002 | + | + | 0.04 | 77.67 |
| VAX-003-34-4 | May 14, 2002 | + | + | 0.15 | 91.90 |
| VAX-003-34-5 | May 23, 2002 | + | + | 0.18 | 91.90 |
| VAX-003-35-1 | Jan. 17, 2000 | + | − | 0.80 | −0.03 |
| VAX-003-35-2 | Jan. 31, 2000 | + | − | 3.61 | 0.70 |
| VAX-003-35-3 | Feb. 14, 2000 | + | + | 6.53 | 17.03 |
| VAX-003-35-4 | Mar. 3, 2000 | + | + | 2.87 | 49.10 |
| VAX-003-35-5 | Mar. 20, 2000 | + | + | 2.45 | 77.63 |
| VAX-003-36-1 | Jan. 21, 2000 | + | − | 0.83 | 0.13 |
| VAX-003-36-2 | Feb. 7, 2000 | + | − | 0.75 | 0.20 |
| VAX-003-36-3 | Feb. 16, 2000 | + | − | 0.56 | 0.17 |
| VAX-003-36-4 | Mar. 1, 2000 | + | − | 0.78 | 12.83 |
| VAX-003-36-5 | Apr. 5, 2000 | + | + | 0.74 | 18.40 |
| VAX-003-36-6 | Apr. 24, 2000 | + | + | 0.67 | 29.90 |
| VAX-003-36-7 | May 12, 2000 | + | + | 0.50 | 27.30 |
| VAX-003-37-1 | Jan. 24, 2001 | + | − | 0.08 | 0.10 |
| VAX-003-37-2 | Feb. 7, 2001 | + | − | 0.63 | 1.13 |
| VAX-003-37-3 | Jul. 11, 2001 | + | + | 0.61 | 1.63 |
| VAX-003-37-4 | Aug. 3, 2001 | + | + | 0.75 | 2.10 |
| VAX-003-37-5 | Aug. 17, 2001 | + | + | 0.67 | 4.47 |

TABLE 26-continued

Reactivity of Intercurrent HIV Infections During VAX-003 Clinical Trials in the HIV-SELECTEST

| Serum Sample | Draw Date | HIV PCR Analysis[1] | HIV Seroconversion (EIA and WB) | HIV-SELECTEST p6 | HIV-SELECTEST gp41 |
|---|---|---|---|---|---|
| VAX-003-38-1 | Dec. 15, 2000 | + | − | 0.06 | 0.13 |
| VAX-003-38-2 | Dec. 28, 2000 | + | − | 0.07 | 0.17 |
| VAX-003-38-3 | May 18, 2001 | + | + | 0.03 | 31.40 |
| VAX-003-38-4 | Jun. 1, 2001 | + | + | 0.05 | 45.17 |
| VAX-003-38-5 | Jun. 13, 2001 | + | + | 0.05 | 54.13 |
| VAX-003-39-1 | Jan. 17, 2000 | + | − | 0.49 | 0.27 |
| VAX-003-39-2 | Jan. 31, 2000 | + | − | 0.64 | 0.10 |
| VAX-003-39-3 | Feb. 14, 2000 | + | + | 0.89 | 0.17 |
| VAX-003-39-4 | Mar. 6, 2000 | + | + | 0.55 | 9.70 |
| VAX-003-39-5 | Mar. 16, 2000 | + | + | 0.52 | 20.07 |
| VAX-003-40-1 | Jun. 19, 2001 | + | − | 0.07 | 0.47 |
| VAX-003-40-2 | Aug. 6, 2001 | + | + | 0.09 | 9.77 |
| VAX-003-40-3 | Aug. 27, 2001 | + | + | 0.11 | 30.83 |
| VAX-003-40-4 | Sep. 14, 2001 | + | + | 0.05 | 40.50 |
| VAX-003-41-1 | Nov. 29, 2001 | + | − | 0.07 | 0.13 |
| VAX-003-41-2 | Dec. 13, 2001 | + | − | 0.09 | 0.13 |
| VAX-003-41-3 | Mar. 11, 2002 | + | + | 6.83 | 79.80 |
| VAX-003-41-4 | Mar. 26, 2002 | + | + | 9.95 | 90.63 |
| VAX-003-41-5 | Apr. 9, 2002 | + | + | 8.75 | 92.20 |
| VAX-003-42-1 | Jan. 19, 2000 | + | − | 0.09 | 0.20 |
| VAX-003-42-2 | Feb. 2, 2000 | + | + | 1.38 | 0.77 |
| VAX-003-42-3 | Feb. 17, 2000 | + | + | 0.69 | 13.77 |
| VAX-003-42-4 | Mar. 23, 2000 | + | + | 0.87 | 22.23 |
| VAX-003-43-1 | Jan. 15, 2002 | + | − | 0.05 | 0.13 |
| VAX-003-43-2 | Jan. 31, 2002 | + | − | 0.06 | 0.20 |
| VAX-003-43-3 | Jul. 15, 2002 | + | + | 0.09 | 63.87 |
| VAX-003-43-4 | Aug. 7, 2002 | + | + | 0.17 | 76.53 |
| VAX-003-43-5 | Aug. 21, 2002 | + | + | 0.15 | 81.37 |
| VAX-003-44-1 | Apr. 5, 2000 | + | − | 0.05 | 0.17 |
| VAX-003-44-2 | Apr. 19, 2000 | + | − | 0.07 | 0.17 |
| VAX-003-44-3 | Sep. 7, 2000 | + | + | 2.33 | 58.07 |
| VAX-003-44-4 | Oct. 16, 2000 | + | + | 1.18 | 39.40 |
| VAX-003-44-5 | Nov. 2, 2000 | + | + | 0.73 | 34.37 |
| VAX-003-45-1 | Mar. 7, 2002 | + | − | 0.28 | 0.37 |
| VAX-003-45-2 | Mar. 20, 2002 | + | − | 0.22 | 0.23 |
| VAX-003-45-3 | Aug. 6, 2002 | + | + | 0.21 | 78.80 |
| VAX-003-45-4 | Aug. 30, 2002 | + | + | 0.35 | 86.13 |
| VAX-003-45-5 | Sep. 10, 2002 | + | + | 0.28 | 79.07 |
| VAX-003-46-1 | Aug. 23, 2001 | + | − | 2.05 | 49.57 |
| VAX-003-46-2 | Sep. 6, 2001 | + | − | 1.01 | 48.90 |
| VAX-003-46-3 | Feb. 7, 2002 | + | + | 0.71 | 16.03 |
| VAX-003-46-4 | Mar. 14, 2002 | + | + | 1.06 | 76.90 |
| VAX-003-46-5 | May 30, 2002 | + | + | 0.83 | 78.97 |
| VAX-003-47-1 | May 9, 2000 | + | − | 0.99 | 0.33 |
| VAX-003-47-2 | May 25, 2000 | + | − | 0.79 | 0.07 |
| VAX-003-47-3 | Jun. 8, 2000 | + | + | 1.01 | 1.43 |
| VAX-003-47-4 | Aug. 2, 2000 | + | + | 0.29 | 63.67 |
| VAX-003-47-5 | Sep. 29, 2000 | + | + | 0.26 | 72.13 |
| VAX-003-48-1 | Apr. 26, 2000 | + | − | 1.33 | 0.63 |
| VAX-003-48-2 | May 10, 2000 | + | + | 1.07 | 11.27 |
| VAX-003-48-3 | May 25, 2000 | + | + | 0.40 | 52.40 |
| VAX-003-48-4 | Jun. 23, 2000 | + | + | 0.33 | 61.27 |
| VAX-003-49-1 | Apr. 24, 2001 | + | − | 0.06 | 0.10 |
| VAX-003-49-2 | May 9, 2001 | + | − | 0.05 | 0.07 |
| VAX-003-49-3 | Sep. 20, 2001 | + | + | 0.95 | 89.80 |
| VAX-003-49-4 | Oct. 4, 2001 | + | + | 0.99 | 86.63 |
| VAX-003-49-5 | Oct. 26, 2001 | + | + | 1.30 | 89.77 |
| VAX-003-50-1 | Apr. 1, 2002 | + | − | 0.07 | 0.10 |
| VAX-003-50-2 | Apr. 17, 2002 | + | − | 0.08 | 0.23 |
| VAX-003-50-3 | Aug. 30, 2002 | + | + | 0.09 | 78.00 |
| VAX-003-50-4 | Sep. 20, 2002 | + | + | 0.13 | 81.07 |
| VAX-003-50-5 | Nov. 4, 2002 | + | + | 0.14 | 82.93 |
| VAX-003-51-1 | Mar. 4, 2002 | + | − | 2.40 | 0.13 |
| VAX-003-51-2 | Mar. 21, 2002 | + | − | 1.99 | 0.10 |
| VAX-003-51-3 | Aug. 20, 2002 | + | + | 0.27 | 71.43 |
| VAX-003-52-1 | Sep. 12, 2000 | + | − | 0.27 | 1.07 |
| VAX-003-52-2 | Sep. 26, 2000 | + | + | 0.31 | 6.53 |
| VAX-003-52-3 | Oct. 11, 2000 | + | + | 0.07 | 20.03 |
| VAX-003-52-4 | Oct. 26, 2000 | + | + | 0.13 | 10.07 |
| VAX-003-53-1 | Jun. 15, 2000 | + | − | 0.10 | 0.13 |
| VAX-003-53-2 | Jun. 28, 2000 | + | − | 0.17 | 0.07 |
| VAX-003-53-3 | Nov. 1, 2000 | + | + | 0.41 | 10.53 |
| VAX-003-53-4 | Nov. 15, 2000 | + | + | 0.23 | 7.20 |
| VAX-003-53-5 | Nov. 28, 2000 | + | + | 0.17 | 6.00 |
| VAX-003-54-1 | Jun. 12, 2000 | + | − | 1.93 | 0.07 |
| VAX-003-54-2 | Jun. 26, 2000 | + | − | 3.84 | 0.10 |
| VAX-003-54-3 | Jul. 11, 2000 | + | + | 3.41 | 2.20 |
| VAX-003-54-4 | Jul. 26, 2000 | + | + | 0.99 | 3.87 |
| VAX-003-54-5 | Aug. 8, 2000 | + | + | 2.02 | 20.30 |
| VAX-003-55-1 | Oct. 3, 2001 | + | − | 0.09 | 0.17 |
| VAX-003-55-2 | Oct. 17, 2001 | + | − | 0.09 | 0.03 |
| VAX-003-55-3 | Mar. 18, 2002 | + | + | 0.37 | 27.47 |
| VAX-003-55-4 | Apr. 10, 2002 | + | + | 0.84 | 64.53 |
| VAX-003-55-5 | Apr. 24, 2002 | + | + | 0.61 | 57.60 |
| VAX-003-56-1 | Jun. 12, 2000 | + | − | 0.08 | 0.27 |
| VAX-003-56-2 | Jul. 20, 2000 | + | − | 0.24 | 10.27 |
| VAX-003-56-3 | Nov. 15, 2000 | + | + | 0.11 | 78.27 |
| VAX-003-56-4 | Dec. 19, 2000 | + | + | 0.07 | 71.00 |
| VAX-003-56-5 | Jan. 12, 2001 | + | + | 0.05 | 76.80 |
| VAX-003-57-1 | Jun. 29, 2000 | + | − | 0.05 | 0.30 |
| VAX-003-57-2 | Jul. 13, 2000 | + | − | 0.07 | 0.20 |
| VAX-003-57-3 | Nov. 16, 2000 | + | + | 0.69 | 53.63 |
| VAX-003-57-4 | Dec. 14, 2000 | + | + | 0.32 | 22.80 |
| VAX-003-57-5 | Dec. 21, 2000 | + | + | 0.36 | 22.37 |
| VAX-003-58-1 | May 24, 2000 | + | − | 0.13 | 0.17 |
| VAX-003-58-2 | Jun. 7, 2000 | + | − | 0.32 | 0.23 |
| VAX-003-58-3 | Jun. 23, 2000 | + | + | 0.43 | 9.57 |
| VAX-003-58-4 | Jul. 7, 2000 | + | + | 1.70 | 37.17 |
| VAX-003-58-5 | Jul. 20, 2000 | + | + | 4.71 | 73.57 |
| VAX-003-59-1 | Apr. 17, 2002 | + | − | 0.05 | 0.17 |
| VAX-003-59-2 | May 1, 2002 | + | − | 0.06 | 0.13 |
| VAX-003-59-3 | Oct. 1, 2002 | + | + | 0.26 | 49.53 |
| VAX-003-59-4 | Oct. 18, 2002 | + | + | 0.85 | 81.63 |
| VAX-003-60-1 | Aug. 30, 2002 | + | − | 0.05 | 0.20 |
| VAX-003-60-2 | Sep. 13, 2002 | + | − | 0.07 | 0.27 |
| VAX-003-60-3 | Apr. 4, 2003 | + | + | 0.68 | 50.27 |
| VAX-003-61-1 | May 15, 2001 | + | − | 0.07 | 0.27 |
| VAX-003-61-2 | May 30, 2001 | + | − | 0.07 | 0.27 |
| VAX-003-61-3 | Oct. 31, 2001 | + | + | 0.12 | 57.97 |
| VAX-003-61-4 | Nov. 14, 2001 | + | + | 0.21 | 82.40 |
| VAX-003-61-5 | Nov. 29, 2001 | + | + | 0.29 | 84.47 |
| VAX-003-62-1 | Nov. 21, 2002 | + | − | 0.05 | 0.17 |
| VAX-003-62-2 | Dec. 3, 2002 | + | − | 0.07 | 0.20 |
| VAX-003-62-3 | May 7, 2003 | + | + | 0.37 | 89.37 |
| VAX-003-63-1 | Sep. 20, 2000 | + | − | 0.33 | 0.13 |
| VAX-003-63-2 | Oct. 4, 2000 | + | − | 0.43 | 0.13 |
| VAX-003-63-3 | Feb. 13, 2001 | + | + | 3.66 | 86.27 |
| VAX-003-63-4 | Feb. 28, 2001 | + | + | 2.82 | 83.40 |
| VAX-003-63-5 | Mar. 21, 2001 | + | + | 3.07 | 86.03 |
| VAX-003-64-1 | Jul. 5, 2000 | + | − | 0.06 | 0.10 |
| VAX-003-64-2 | Jul. 19, 2000 | + | − | 0.10 | 0.17 |
| VAX-003-64-3 | Aug. 4, 2000 | + | + | 0.13 | 0.87 |
| VAX-003-64-4 | Aug. 25, 2000 | + | + | 0.11 | 64.30 |
| VAX-003-64-5 | Sep. 6, 2000 | + | + | 0.06 | 66.97 |
| VAX-003-65-1 | Sep. 21, 2000 | + | − | 0.16 | 0.10 |
| VAX-003-65-2 | Oct. 5, 2000 | + | − | 0.15 | 0.10 |
| VAX-003-65-3 | Feb. 21, 2001 | + | + | 0.49 | 26.87 |
| VAX-003-65-4 | Mar. 15, 2001 | + | + | 1.53 | 38.03 |
| VAX-003-65-5 | Mar. 28, 2001 | + | + | 1.43 | 50.53 |

TABLE 27

Reactivity of Intercurrent HIV Infections During VAX-004 Clinical Trials in the HIV-SELECTEST

| Serum Sample | Draw Date | HIV PCR Analysis[1] | HIV Seroconversion (EIA and WB) | HIV-SELECTEST p6 | HIV-SELECTEST gp41 |
|---|---|---|---|---|---|
| VAX-004-1-1 | Feb. 11, 2000 | + | − | 0.03 | 0.15 |
| VAX-004-1-2 | Mar. 3, 2000 | + | − | 0.46 | 1.16 |
| VAX-004-1-3 | Apr. 3, 2000 | + | + | 0.48 | 60.36 |
| VAX-004-2-1 | Feb. 14, 2001 | + | − | 0.50 | 0.37 |
| VAX-004-2-2 | Mar. 1, 2001 | + | + | 0.82 | 1.84 |
| VAX-004-3-1 | May 10, 2000 | + | − | 0.07 | 0.11 |
| VAX-004-3-2 | May 25, 2000 | + | − | 0.05 | 0.20 |
| VAX-004-3-3 | Nov. 8, 2000 | + | + | 0.25 | 103.48 |
| VAX-004-4-1 | Mar. 20, 2001 | + | − | 0.03 | 0.30 |
| VAX-004-4-2 | Apr. 2, 2001 | + | − | 0.07 | 1.15 |
| VAX-004-4-3 | Oct. 3, 2001 | + | + | 0.05 | 99.60 |
| VAX-004-5-1 | Feb. 17, 1999 | + | − | 0.07 | 0.19 |
| VAX-004-5-2 | Mar. 3, 1999 | + | − | 0.09 | 0.37 |
| VAX-004-5-3 | Mar. 17, 1999 | + | − | 0.09 | 0.11 |
| VAX-004-5-4 | Mar. 31, 1999 | + | − | 0.13 | 0.30 |
| VAX-004-5-5 | Aug. 4, 1999 | + | + | 0.25 | 76.67 |
| VAX-004-6-1 | Sep. 21, 2000 | + | − | 0.03 | 0.20 |
| VAX-004-6-2 | Oct. 3, 2000 | + | − | 0.33 | 0.15 |
| VAX-004-6-3 | Oct. 18, 2000 | + | + | 0.92 | 3.48 |
| VAX-004-7-1 | Jun. 14, 2000 | + | − | 0.31 | 39.44 |
| VAX-004-7-2 | Dec. 18, 2000 | + | + | 0.44 | 74.07 |
| VAX-004-8-1 | May 1, 2001 | + | − | 0.12 | 0.15 |
| VAX-004-8-2 | Aug. 8, 2001 | + | + | 0.63 | 99.37 |
| VAX-004-9-1 | Feb. 17, 1999 | + | − | 0.03 | 0.11 |
| VAX-004-9-2 | Mar. 2, 1999 | + | − | 0.31 | 0.15 |
| VAX-004-9-3 | Mar. 22, 1999 | + | − | 4.73 | 1.04 |
| VAX-004-9-4 | Apr. 6, 1999 | + | + | 2.73 | 5.15 |
| VAX-004-10-1 | Oct. 13, 2000 | + | − | 0.17 | 12.56 |
| VAX-004-10-2 | Apr. 11, 2001 | + | + | 0.07 | 16.56 |
| VAX-004-11-1 | Oct. 23, 1998 | + | − | 0.19 | 0.44 |
| VAX-004-11-2 | Nov. 3, 1998 | + | − | 0.23 | 1.33 |
| VAX-004-11-3 | Nov. 18, 1998 | + | + | 0.18 | 4.37 |
| VAX-004-12-1 | Nov. 2, 2000 | + | + | 0.09 | 1.37 |
| VAX-004-13-1 | Feb. 11, 2000 | + | − | 0.06 | 0.11 |
| VAX-004-13-2 | Aug. 10, 2000 | + | + | 0.05 | 87.08 |
| VAX-004-14-1 | Sep. 13, 2000 | + | − | 1.97 | 1.63 |
| VAX-004-14-2 | Sep. 27, 2000 | + | + | 1.81 | 38.40 |
| VAX-004-15-1 | Jan. 25, 2001 | + | − | 0.03 | 0.11 |
| VAX-004-15-2 | Feb. 8, 2001 | + | − | 0.12 | 0.22 |
| VAX-004-15-3 | Jul. 11, 2001 | + | + | 0.02 | 8.72 |
| VAX-004-16-1 | Feb. 22, 2001 | + | − | 0.59 | 0.19 |
| VAX-004-16-2 | Mar. 8, 2001 | + | − | 0.45 | 0.19 |
| VAX-004-16-3 | Aug. 29, 2001 | + | + | 1.00 | 82.28 |
| VAX-004-17-1 | Jul. 23, 1999 | + | − | 0.15 | 0.19 |
| VAX-004-17-2 | Aug. 6, 1999 | + | − | 0.11 | 0.26 |
| VAX-004-17-3 | Aug. 20, 1999 | + | + | 0.27 | 2.19 |
| VAX-004-18-1 | Feb. 10, 2000 | + | − | 0.06 | 0.26 |
| VAX-004-18-2 | Jul. 27, 2000 | + | + | 0.09 | 58.72 |
| VAX-004-19-1 | Dec. 5, 2000 | + | + | 0.16 | 8.33 |
| VAX-004-19-2 | Apr. 9, 2001 | + | + | 0.65 | 59.85 |
| VAX-004-20-1 | Mar. 6, 2000 | + | − | 2.13 | 0.11 |
| VAX-004-20-2 | Mar. 22, 2000 | + | − | 2.56 | 0.33 |
| VAX-004-20-3 | Oct. 3, 2000 | + | + | 1.43 | 106.70 |
| VAX-004-21-1 | Apr. 11, 2001 | + | − | 0.01 | 0.04 |
| VAX-004-21-2 | Jun. 14, 2001 | + | + | 0.14 | 21.93 |
| VAX-004-22-1 | May 4, 2000 | + | − | 0.37 | 0.22 |
| VAX-004-22-2 | Sep. 12, 2000 | + | + | 1.15 | 96.70 |
| VAX-004-23-1 | Oct. 31, 2000 | + | − | 0.20 | 0.96 |
| VAX-004-23-2 | Nov. 15, 2000 | + | + | 0.20 | 13.12 |
| VAX-004-24-1 | Oct. 6, 1999 | + | − | 0.03 | 0.11 |
| VAX-004-24-2 | Oct. 21, 1999 | + | + | 3.92 | 0.60 |
| VAX-004-25-1 | Sep. 21, 2000 | + | − | 0.14 | 0.22 |
| VAX-004-25-2 | Sep. 26, 2000 | + | − | 0.13 | 0.37 |
| VAX-004-25-3 | Oct. 16, 2000 | + | + | 1.05 | 21.56 |
| VAX-004-26-1 | Jan. 6, 1999 | + | − | 0.02 | 0.15 |
| VAX-004-26-2 | Jan. 22, 1999 | + | − | 0.13 | 0.22 |
| VAX-004-26-3 | May 28, 1999 | + | + | 0.63 | 18.44 |
| VAX-004-27-1 | Sep. 21, 1999 | + | − | 0.23 | 0.15 |
| VAX-004-27-2 | Oct. 14, 1999 | + | − | 0.85 | 0.96 |
| VAX-004-27-3 | Mar. 30, 2000 | + | + | 1.39 | 35.00 |
| VAX-004-28-1 | Jan. 14, 2000 | + | − | 0.07 | 0.11 |
| VAX-004-28-2 | Jan. 28, 2000 | + | − | 0.07 | 0.11 |
| VAX-004-28-3 | Jul. 11, 2000 | + | + | 0.31 | 87.04 |
| VAX-004-29-1 | Nov. 26, 2001 | + | − | 0.19 | 0.20 |
| VAX-004-29-2 | Mar. 18, 2002 | + | + | 2.09 | 95.56 |
| VAX-004-29-3 | Apr. 8, 2002 | + | + | 1.54 | 101.07 |
| VAX-004-30-1 | Feb. 28, 2001 | + | − | 0.05 | 0.26 |
| VAX-004-30-2 | Oct. 3, 2001 | + | + | 0.08 | 79.24 |
| VAX-004-31-1 | Oct. 20, 2000 | + | − | 0.11 | 0.22 |
| VAX-004-31-2 | Nov. 6, 2000 | + | − | 0.11 | 2.33 |
| VAX-004-31-3 | Jun. 12, 2001 | + | + | 0.21 | 111.12 |
| VAX-004-32-1 | Oct. 11, 1999 | + | − | 0.10 | 0.19 |
| VAX-004-32-2 | Oct. 25, 1999 | + | − | 0.11 | 0.11 |
| VAX-004-32-3 | Mar. 27, 2000 | + | + | 0.81 | 52.40 |
| VAX-004-33-1 | Jun. 15, 2000 | + | − | 0.21 | 0.11 |
| VAX-004-33-2 | Sep. 29, 2000 | + | + | 4.34 | 106.40 |
| VAX-004-34-1 | Jan. 23, 2001 | + | − | 0.40 | 3.04 |
| VAX-004-34-2 | Jan. 30, 2001 | + | + | 0.49 | 5.89 |
| VAX-004-35-1 | Oct. 27, 2000 | + | − | 0.05 | 0.07 |
| VAX-004-35-2 | Nov. 3, 2000 | + | − | 0.12 | 0.15 |
| VAX-004-35-3 | Nov. 16, 2000 | + | − | 0.13 | 0.52 |
| VAX-004-35-4 | Dec. 7, 2000 | + | + | 0.05 | 2.19 |
| VAX-004-36-1 | Jul. 24, 2000 | + | − | 1.91 | 0.00 |
| VAX-004-36-2 | Jul. 31, 2000 | + | + | 4.55 | 0.24 |
| VAX-004-37-1 | Apr. 14, 1999 | − | − | 0.17 | 0.04 |
| VAX-004-37-2 | Jul. 14, 1999 | + | − | 5.73 | 0.07 |
| VAX-004-37-3 | Jul. 21, 1999 | + | + | 8.76 | 0.74 |
| VAX-004-38-1 | Oct. 4, 2000 | + | − | 0.03 | 0.11 |
| VAX-004-38-2 | Oct. 19, 2000 | + | − | 0.11 | 0.22 |
| VAX-004-38-3 | May 10, 2001 | + | + | 1.52 | 88.93 |
| VAX-004-39-1 | May 19, 1999 | + | − | 0.04 | 0.15 |
| VAX-004-39-2 | Jun. 3, 1999 | + | − | 0.13 | 0.19 |
| VAX-004-39-3 | Jun. 17, 1999 | + | + | 0.15 | 1.10 |
| VAX-004-40-1 | Jul. 30, 1999 | + | − | 0.06 | 0.11 |
| VAX-004-40-2 | Aug. 12, 1999 | + | − | 0.07 | 0.22 |
| VAX-004-40-3 | Dec. 30, 1999 | + | + | 0.77 | 16.96 |
| VAX-004-41-1 | Jun. 11, 2001 | + | − | 0.05 | 0.26 |
| VAX-004-41-2 | Jun. 25, 2001 | + | + | 1.24 | 0.28 |
| VAX-004-42-1 | Jun. 13, 2000 | + | − | 0.04 | 0.11 |
| VAX-004-42-2 | Jul. 20, 2000 | + | + | 0.24 | 41.00 |
| VAX-004-43-1 | Aug. 27, 1999 | + | − | 0.21 | 0.22 |
| VAX-004-43-2 | Sep. 10, 1999 | + | − | 0.50 | 0.26 |
| VAX-004-43-3 | Mar. 10, 2000 | + | + | 0.18 | 30.44 |
| VAX-004-44-1 | May 14, 2001 | + | − | 0.15 | 0.33 |
| VAX-004-44-2 | Aug. 24, 2001 | + | + | 0.84 | 27.78 |
| VAX-004-44-3 | Sep. 7, 2001 | + | + | 0.61 | 24.04 |
| VAX-004-45-1 | Jul. 31, 2000 | + | − | 0.04 | 0.22 |
| VAX-004-45-2 | Aug. 10, 2000 | + | − | 0.07 | 0.22 |
| VAX-004-45-3 | Feb. 19, 2001 | + | + | 0.07 | 10.16 |
| VAX-004-46-1 | Oct. 4, 1999 | + | − | 1.63 | 0.11 |
| VAX-004-46-2 | Oct. 18, 1999 | + | + | 1.60 | 2.04 |
| VAX-004-46-3 | Oct. 27, 1999 | + | + | 1.49 | 4.56 |
| VAX-004-47-1 | Aug. 2, 2000 | + | − | 0.97 | 0.19 |
| VAX-004-47-2 | Jan. 19, 2001 | + | + | 5.58 | 18.04 |
| VAX-004-47-3 | Feb. 8, 2001 | + | + | 5.55 | 14.80 |
| VAX-004-48-1 | Sep. 7, 1999 | + | − | 0.15 | 0.15 |
| VAX-004-48-2 | Sep. 27, 1999 | + | − | 0.14 | 0.48 |
| VAX-004-48-3 | Feb. 8, 2000 | + | + | 0.16 | 37.04 |
| VAX-004-49-1 | Nov. 14, 2000 | + | − | 0.09 | 0.20 |
| VAX-004-49-2 | Dec. 5, 2000 | + | + | 3.11 | 0.78 |
| VAX-004-50-1 | Nov. 7, 2001 | + | − | 0.08 | 0.22 |
| VAX-004-50-2 | Nov. 21, 2001 | + | − | 0.73 | 0.52 |
| VAX-004-50-3 | Dec. 18, 2001 | + | + | 1.67 | 88.28 |
| VAX-004-51-1 | Dec. 14, 1998 | + | − | 0.51 | 0.19 |
| VAX-004-51-2 | Dec. 28, 1998 | + | − | 3.15 | 0.30 |
| VAX-004-51-3 | Jan. 12, 1999 | + | − | 5.69 | 14.22 |
| VAX-004-51-4 | Jan. 27, 1999 | + | + | 3.87 | 51.33 |
| VAX-004-52-1 | Apr. 2, 1999 | + | − | 0.26 | 2.04 |
| VAX-004-52-2 | Apr. 16, 1999 | + | − | 0.23 | 5.41 |
| VAX-004-52-3 | Apr. 30, 1999 | + | + | 0.55 | 15.15 |

TABLE 27-continued

Reactivity of Intercurrent HIV Infections During VAX-004 Clinical Trials in the HIV-SELECTEST

| Serum Sample | Draw Date | HIV PCR Analysis[1] | HIV Seroconversion (EIA and WB) | HIV-SELECTEST p6 | gp41 |
|---|---|---|---|---|---|
| VAX-004-53-1 | Nov. 30, 2000 | + | − | 0.06 | 0.19 |
| VAX-004-53-2 | Dec. 14, 2000 | + | − | 0.07 | 0.15 |
| VAX-004-53-3 | May 23, 2001 | + | + | 0.16 | 102.52 |
| VAX-004-54-1 | Mar. 30, 1999 | + | − | 0.44 | 0.22 |
| VAX-004-54-2 | Apr. 7, 1999 | + | − | 1.36 | 0.48 |
| VAX-004-54-3 | Apr. 21, 1999 | + | + | 2.35 | 6.24 |
| VAX-004-55-1 | Sep. 14, 1999 | + | − | 0.65 | 0.74 |
| VAX-004-55-2 | Oct. 4, 1999 | + | + | 2.07 | 4.44 |
| VAX-004-56-1 | Mar. 19, 2001 | + | − | 0.05 | 0.19 |
| VAX-004-56-2 | Aug. 15, 2001 | + | + | 8.01 | 0.40 |
| VAX-004-57-1 | Jan. 24, 2002 | + | − | 0.09 | 0.30 |
| VAX-004-57-2 | Feb. 7, 2002 | + | + | 0.19 | 3.44 |
| VAX-004-57-3 | Feb. 11, 2002 | + | + | 0.19 | 3.93 |
| VAX-004-58-1 | Feb. 9, 2000 | + | − | 0.15 | 0.32 |
| VAX-004-58-2 | Aug. 8, 2000 | + | + | 0.19 | 38.12 |
| VAX-004-59-1 | Oct. 17, 2001 | + | − | 0.04 | 0.15 |
| VAX-004-59-2 | Nov. 9, 2001 | + | − | 0.13 | 0.07 |
| VAX-004-59-3 | Mar. 14, 2002 | + | + | 0.24 | 84.33 |
| VAX-004-60-1 | Jul. 5, 2001 | + | − | 0.07 | 0.30 |
| VAX-004-60-2 | Jul. 19, 2001 | + | − | 0.04 | 2.33 |
| VAX-004-60-3 | Nov. 9, 2001 | + | + | 0.05 | 9.67 |
| VAX-004-61-1 | Jun. 28, 1999 | + | − | 0.47 | 0.59 |
| VAX-004-61-2 | Jul. 8, 1999 | + | + | 0.35 | 1.20 |
| VAX-004-62-1 | Feb. 23, 2000 | + | − | 0.90 | 0.11 |
| VAX-004-62-2 | Mar. 7, 2000 | + | − | 0.55 | 0.19 |
| VAX-004-62-3 | Aug. 24, 2000 | + | + | 0.81 | 1.08 |
| VAX-004-63-1 | Sep. 20, 1999 | + | − | 0.07 | 0.19 |
| VAX-004-63-2 | Oct. 7, 1999 | + | − | 0.17 | 0.56 |
| VAX-004-63-3 | Oct. 21, 1999 | + | + | 0.26 | 3.84 |
| VAX-004-64-1 | Jun. 5, 2001 | + | − | 0.03 | 0.11 |
| VAX-004-64-2 | Oct. 23, 2001 | + | + | 0.25 | 101.26 |
| VAX-004-65-1 | Oct. 8, 1999 | + | − | 0.05 | 0.22 |
| VAX-004-65-2 | Oct. 26, 1999 | + | − | 0.03 | 0.11 |
| VAX-004-65-3 | Feb. 25, 2000 | + | + | 0.11 | 1.48 |
| VAX-004-66-1 | Sep. 3, 1999 | + | − | 0.05 | 0.22 |
| VAX-004-66-2 | Oct. 14, 1999 | + | − | 0.04 | 1.22 |
| VAX-004-66-3 | Nov. 17, 1999 | + | + | 0.16 | 9.00 |
| VAX-004-67-1 | Jul. 8, 1999 | + | − | 0.65 | 0.30 |
| VAX-004-67-2 | Jul. 20, 1999 | + | + | 0.51 | 1.03 |
| VAX-004-67-3 | Aug. 10, 1999 | + | + | 1.10 | 21.59 |
| VAX-004-68-1 | Sep. 4, 2001 | + | − | 0.04 | 0.22 |
| VAX-004-68-2 | Jan. 29, 2002 | + | + | 0.09 | 79.80 |
| VAX-004-69-1 | Apr. 7, 1999 | + | − | 0.20 | 0.11 |
| VAX-004-69-2 | Apr. 21, 1999 | + | + | 5.29 | 10.22 |
| VAX-004-69-3 | May 5, 1999 | + | + | 4.98 | 48.76 |
| VAX-004-70-1 | Dec. 13, 1999 | + | − | 0.06 | 0.22 |
| VAX-004-70-2 | Jan. 4, 2000 | + | − | 0.11 | 0.22 |
| VAX-004-70-3 | Feb. 29, 2000 | + | + | 0.15 | 14.92 |
| VAX-004-71-1 | Oct. 10, 2001 | + | − | 0.41 | 0.19 |
| VAX-004-71-2 | Oct. 25, 2001 | + | − | 0.41 | 0.15 |
| VAX-004-71-3 | Mar. 20, 2002 | + | + | 1.13 | 94.68 |
| VAX-004-72-1 | Nov. 6, 2001 | + | − | 0.05 | 0.30 |
| VAX-004-72-2 | Apr. 4, 2002 | + | + | 0.09 | 103.44 |
| VAX-004-73-1 | Feb. 23, 2001 | + | − | 0.03 | 0.15 |
| VAX-004-73-2 | Apr. 10, 2001 | + | + | 0.49 | 20.00 |
| VAX-004-74-1 | Dec. 9, 1999 | + | − | 0.05 | 0.15 |
| VAX-004-74-2 | Jan. 11, 2000 | + | + | 0.07 | 4.84 |
| VAX-004-75-1 | Aug. 2, 2000 | + | − | 0.04 | 0.59 |
| VAX-004-75-2 | Mar. 22, 2001 | + | + | 0.05 | 26.48 |
| VAX-004-76-1 | Feb. 26, 2002 | + | − | 1.28 | 0.44 |
| VAX-004-76-2 | May 20, 2002 | + | + | 2.04 | 80.84 |
| VAX-004-77-1 | May 10, 2001 | + | − | 0.07 | 0.07 |
| VAX-004-77-2 | Jul. 31, 2001 | + | + | 0.23 | 116.12 |
| VAX-004-78-1 | Oct. 14, 1999 | + | − | 0.11 | 1.00 |
| VAX-004-78-2 | Nov. 24, 1999 | + | + | 1.43 | 2.12 |
| VAX-004-79-1 | Nov. 3, 1999 | + | − | 0.27 | 0.19 |
| VAX-004-79-2 | Nov. 17, 1999 | + | − | 0.36 | 4.85 |
| VAX-004-79-3 | Mar. 23, 2000 | + | + | 0.16 | 1.08 |
| VAX-004-80-1 | Dec. 5, 2000 | + | − | 0.07 | 0.26 |
| VAX-004-80-2 | Apr. 23, 2001 | + | + | 1.85 | 48.00 |
| VAX-004-81-1 | Feb. 24, 1999 | + | − | 0.23 | 0.19 |
| VAX-004-81-2 | Mar. 11, 1999 | + | − | 0.25 | 0.22 |
| VAX-004-81-3 | Mar. 23, 1999 | + | − | 0.17 | 0.41 |
| VAX-004-81-4 | Apr. 6, 1999 | + | − | 0.65 | 4.15 |
| VAX-004-81-5 | Aug. 25, 1999 | + | + | 0.24 | 94.26 |

It was also possible to compare the performance of the HIV-SELECTEST with results obtained with the FDA-licensed kits provided by VaxGen (FIG. 7). In most cases, the earliest positive results were observed with the same samples using the licensed diagnostics and the HIV-SELECTEST (dots falling on the diagonal lines). Surprisingly, 24 intercurrent HIV infections in VAX 003, and 25 infections in VAX 004 were detected earlier in the HIV-SELECTEST compared with the licensed kits [dots under the diagonal lines in FIG. 7, Panels (a) and (b)], displaying the efficacy of HIV-SELECTEST in early diagnosis of HIV infection. Therefore, the new assay could be part of an algorithm that will provide an important differential diagnostic tool during future phase III prophylactic vaccine trials and for testing of blood and tissue donors.

The use of a phage display library to clone and express the entire open reading frames of HIV afforded the opportunity to identify all the epitopes that are recognized by seroconversion antibodies during acute HIV infection. Affinity selection of the phage display library using seroconversion panels led to the discovery of new epitopes in gp41 and p6, which were selected to develop a new differential diagnostic test.

The results described above demonstrate that vaccine generated antibodies scored either negative or weakly positive in the HIV-SELECTEST even when the p6 or gp41 sequences were part of the vaccine constructs (i.e., RV124 and HVTN 203). Furthermore, the HIV-SELECTEST detected all intercurrent HIV infections. It should be noted that while all intercurrent infections in the VAX 004 trial (conducted in the United States and the Netherlands) were with Glade B viruses, all the HIV infections in the VAX 003 trial (conducted in Thailand), were with Glade E variants, demonstrating the feasibility of using the HIV-SELECTEST outside the United States in a multiclade scenario, which is a prerequisite for global vaccine trials. Together, these data provide strong proof of the specificity and sensitivity of the new p6 and gp41 peptide-based ELISA. They further suggest that if future vaccine candidates do not contain these epitopes all uninfected vaccinees are expected to score negative in the new assay. In contrast, antibodies generated following intercurrent infections in the course of HIV vaccine trials, or at later times, should be detected by the HIV-SELECTEST soon after infection.

This inexpensive and high-throughput assay could be added to the algorithm of detection tests used in clinical sites and in blood and plasma collection centers. As such, this assay will be highly relevant for early diagnosis of intercurrent HIV infections in future vaccine trials, particularly in the setting of HIV vaccines that, while not able to prevent infection, may reduce viral loads after acquisition. Importantly, the HIV-SELECTEST should help to alleviate the concerns regarding social and economic harms due to long-term seroconversion of uninfected participants in preventive HIV vaccine trials.

EXAMPLE 10

Improved Gag-p6 Peptide for HIV-1 Detection Assay

During the above-described testing, it was observed that some of the sera from individuals infected with Glade C viruses (mainly from Southern Africa) did not react strongly with the consensus Gag-p6 employed (SEQ ID NO:3). The employed peptide was therefore altered to produce a peptide denoted "Gag-p6-C-sub" that is better recognized by all plasma and serum samples from HIV-1 Glade C infected individuals. The sequence of the Gag-p6-C-sub peptide is provided below:

```
GAG-p6-C-sub
                                                        (SEQ ID NO: 141)
SRPEPTAPPA ESFRFEETTP APKQEPKDRE PLTSLKSLFG SDPLSQ
1          10         20         30         40     46
```

While HIV detection assays may be conducted using the Gag-p6-C-sub (SEQ ID NO:141) peptide alone, or in conjunction with any other peptide(s), etc., it is particularly preferred to combine the Gag p6-C-sub peptide (SEQ ID NO:141) with peptides having the sequence of the consensus Gag-p6 (SEQ ID NO:3) in the same ELISA plate.

All publications and patents mentioned in this specification are herein incorporated by reference to the same extent as if each individual publication or patent application was specifically and individually indicated to be incorporated by reference. While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth.

---

What is claimed is:

1. A method for detecting the presence, or measuring the concentration, of an anti-HIV-1 antibody in a biological sample of a human, wherein said method comprises conducting an immunoassay comprising the steps of: (a) contacting said biological sample with at least one epitope that is recognized by said anti-HIV-1 antibody, wherein said contacting being under conditions sufficient to permit said anti-HIV-1 antibody if present in said sample to bind to said epitope and form an epitope-anti-HIV-1 antibody complex; (b) contacting said formed epitope-anti-HIV-1 antibody complex with an anti-HIV-1 antibody binding molecule, said contacting being under conditions sufficient to permit said anti-HIV-1antibody binding molecule to bind to anti-HIV-1 antibody of said formed epitope-anti-HIV-1antibody complex and form an extended complex; and (c) determining the presence or concentration of said anti-HIV-1 antibody in said biological sample by determining the presence or concentration of said formed extended complex; said epitope being present on a peptide consisting essentially of SEQ ID No. 55.

2. The method of claim 1, wherein said immunoassay is an ELISA.

3. The method of claim 2, wherein said ELISA comprises incubating said biological sample in the presence of a solid support, wherein said peptide is immobilized to said support, wherein said support is coated with milk, and wherein said anti-HIV-1antibody binding molecule is selected from the group consisting of anti-human IgG+IgM -Fc, anti-human IgG-Fc, anti-human-IgG+IgM, and anti-human IgG; said anti-HIV-1 antibody binding molecule being conjugated to an enzyme.

4. The method of claim 1, wherein said immunoassay is an immunochromatographic assay.

5. The immunoassay of claim 4, wherein in said immunochromatographic immunoassay: in said step (a), said biological sample is placed in contact with a first porous carrier, said first porous carrier containing said peptide, said peptide being non-immobilized and detectably labeled; in said step (b), said formed peptide-anti-HIV-1antibody complex is placed in contact with a second porous carrier, said second porous carrier being in communication with said first porous carrier, and containing an immobilized anti-HIV-1antibody binding molecule; and in said step (c), the presence or concentration of said anti-HIV antibody in said biological sample is determined by detecting the presence of said labeled peptide in said second porous carrier.

6. A method for detecting the presence, or measuring the concentration, of an anti-HIV-1 antibody in a biological sample of a human, wherein said method comprises conducting an immunoassay comprising the steps of: (a) contacting said biological sample with at least one epitope that is recognized by said anti-HIV-1 antibody, wherein said contacting being under conditions sufficient to permit said anti-HIV-1 antibody if present in said sample to bind to said epitope and form an epitope-anti-HIV-1 antibody complex; (b) contacting said formed epitope-anti-HIV-1 antibody complex with an anti-HIV-1 antibody binding molecule, said contacting being under conditions sufficient to permit said anti-HIV-1 antibody binding molecule to bind to anti-HIV-1 antibody of said formed epitope-anti-HIV-1 antibody complex and form an extended complex; and (c) determining the presence or concentration of said anti- HIV-1antibody in said biological sample by determining the presence or concentration of said formed extended complex; said epitope being present on a peptide consisting of SEQ ID No. 55.

7. The method of claim 6, wherein said immunoassay is an ELISA.

8. The method of claim 6, wherein said ELISA comprises incubating said biological sample in the presence of a solid support, wherein said peptide is immobilized to said support, wherein said support is coated with milk, and wherein said anti-HIV-1 antibody binding molecule is selected from the group consisting of anti-human IgG+IgM-Fc, anti-human IgG-Fc, anti-human-IgG+IgM, and anti-human IgG; said anti-HIV-1 antibody binding molecule being conjugated to an enzyme.

9. The method of claim 6, wherein said immunoassay is an immunochromatographic assay.

10. The immunoassay of claim 9, wherein in said immunochromatographic immunoassay: in said step (a), said biological sample is placed in contact with a first porous carrier, said first porous carrier containing said peptide, said peptide being non-immobilized and detectably labeled; in said step (b), said formed peptide-anti-HIV-1 antibody complex is placed in contact with a second porous carrier, said second porous carrier being in communication with said first porous carrier, and containing an immobilized anti-HIV-1 antibody binding molecule; and in said step (c), the presence or concentration of said anti-HIV antibody in said biological sample is determined by detecting the presence of said labeled peptide in said second porous carrier.

* * * * *

SEQUENCE LISTING

```
<160> NUMBER OF SEQ ID NOS: 141

<210> SEQ ID NO 1
<211> LENGTH: 52
<212> TYPE: PRT
<213> ORGANISM: Human immunodeficiency virus type 1

<400> SEQUENCE: 1

Ser Arg Pro Glu Pro Thr Ala Pro Pro Ala Glu Ser Phe Arg Phe Gly
1               5                   10                  15

Glu Glu Ile Thr Pro Thr Pro Ser Gln Lys Gln Glu Pro Lys Asp Lys
            20                  25                  30

Glu Leu Tyr Pro Pro Leu Ala Ser Leu Arg Ser Leu Phe Gly Asn Asp
        35                  40                  45

Pro Ser Ser Asn
    50

<210> SEQ ID NO 2
<211> LENGTH: 50
<212> TYPE: PRT
<213> ORGANISM: Human immunodeficiency virus type 1

<400> SEQUENCE: 2

Ser Arg Pro Glu Pro Thr Ala Pro Pro Glu Glu Ser Phe Arg Phe Gly
1               5                   10                  15

Glu Glu Thr Thr Thr Pro Ser Gln Lys Gln Glu Pro Ile Asp Lys Glu
            20                  25                  30

Leu Tyr Pro Leu Ala Ser Leu Arg Ser Leu Phe Gly Ser Asp Pro Ser
        35                  40                  45
```

```
Ser Gln
    50

<210> SEQ ID NO 3
<211> LENGTH: 52
<212> TYPE: PRT
<213> ORGANISM: Human immunodeficiency virus type 1

<400> SEQUENCE: 3

Ser Arg Pro Glu Pro Thr Ala Pro Ala Glu Ser Phe Arg Phe Gly
1               5                   10                  15

Glu Glu Ile Thr Pro Thr Pro Ser Gln Lys Gln Glu Pro Lys Asp Lys
                20                  25                  30

Glu Leu Tyr Pro Pro Leu Ala Ser Leu Arg Ser Leu Phe Gly Asn Asp
        35                  40                  45

Pro Ser Ser Gln
    50

<210> SEQ ID NO 4
<211> LENGTH: 49
<212> TYPE: PRT
<213> ORGANISM: Human immunodeficiency virus type 1

<400> SEQUENCE: 4

Ser Arg Pro Glu Pro Thr Ala Pro Ala Glu Ser Phe Arg Phe Gly
1               5                   10                  15

Glu Glu Thr Thr Pro Ser Pro Lys Gln Glu Pro Lys Asp Lys Glu Leu
                20                  25                  30

Tyr Pro Leu Thr Ser Leu Lys Ser Leu Phe Gly Asn Asp Pro Leu Ser
        35                  40                  45

Gln

<210> SEQ ID NO 5
<211> LENGTH: 49
<212> TYPE: PRT
<213> ORGANISM: Human immunodeficiency virus type 1

<400> SEQUENCE: 5

Ser Arg Pro Glu Pro Thr Ala Pro Ala Glu Ser Phe Gly Phe Gly
1               5                   10                  15

Glu Glu Ile Thr Pro Ser Pro Lys Gln Glu Pro Lys Asp Lys Glu Leu
                20                  25                  30

Tyr Pro Leu Ala Ser Leu Lys Ser Leu Phe Gly Asn Asp Pro Leu Ser
        35                  40                  45

Gln

<210> SEQ ID NO 6
<211> LENGTH: 52
<212> TYPE: PRT
<213> ORGANISM: Human immunodeficiency virus type 1

<400> SEQUENCE: 6

Ser Arg Pro Glu Pro Thr Ala Pro Pro Glu Glu Ser Phe Arg Phe Gly
1               5                   10                  15

Glu Glu Ile Thr Pro Thr Pro Ser Gln Lys Gln Glu Pro Lys Asp Lys
                20                  25                  30

Glu Leu Tyr Pro Pro Leu Ala Ser Leu Arg Ser Leu Phe Gly Asn Asp
        35                  40                  45

Pro Ser Ser Gln
```

<210> SEQ ID NO 7
<211> LENGTH: 51
<212> TYPE: PRT
<213> ORGANISM: Human immunodeficiency virus type 1

<400> SEQUENCE: 7

Ser Arg Pro Glu Pro Thr Ala Pro Pro Glu Glu Ser Phe Arg Phe Gly
1               5                   10                  15

Glu Glu Ile Thr Pro Thr Pro Ser Gln Lys Gln Glu Pro Lys Asp Lys
            20                  25                  30

Glu Leu Tyr Pro Leu Ala Ser Leu Arg Ser Leu Phe Gly Asn Asp Pro
        35                  40                  45

Ser Ser Gln
    50

<210> SEQ ID NO 8
<211> LENGTH: 47
<212> TYPE: PRT
<213> ORGANISM: Human immunodeficiency virus type 1

<400> SEQUENCE: 8

Ser Arg Pro Glu Pro Thr Ala Pro Ala Glu Ser Phe Arg Phe Gly
1               5                   10                  15

Glu Glu Ile Thr Thr Ser Pro Ser Gln Lys Gln Glu Pro Lys Asp Lys
            20                  25                  30

Glu Leu Tyr Pro Leu Ala Ser Leu Lys Ser Leu Phe Gly Asn Asp
        35                  40                  45

<210> SEQ ID NO 9
<211> LENGTH: 33
<212> TYPE: PRT
<213> ORGANISM: Human immunodeficiency virus type 1

<400> SEQUENCE: 9

Ser Arg Pro Glu Pro Thr Ala Pro Ala Glu Ser Phe Arg Phe Gly
1               5                   10                  15

Glu Glu Ile Thr Thr Ser Pro Ser Gln Lys Gln Glu Pro Lys Asp Lys
            20                  25                  30

Glu

<210> SEQ ID NO 10
<211> LENGTH: 31
<212> TYPE: PRT
<213> ORGANISM: Human immunodeficiency virus type 1

<400> SEQUENCE: 10

Thr Pro Thr Pro Ser Gln Lys Gln Glu Pro Lys Asp Lys Glu Leu Tyr
1               5                   10                  15

Pro Pro Leu Ala Ser Leu Arg Ser Leu Phe Gly Asn Asp Pro Ser
            20                  25                  30

<210> SEQ ID NO 11
<211> LENGTH: 41
<212> TYPE: PRT
<213> ORGANISM: Human immunodeficiency virus type 1

<400> SEQUENCE: 11

Ser Phe Arg Phe Gly Glu Glu Ile Thr Pro Thr Pro Ser Gln Lys Gln
1               5                   10                  15

```
Glu Pro Lys Asp Lys Glu Leu Tyr Pro Pro Leu Ala Ser Leu Arg Ser
            20                  25                  30

Leu Phe Gly Asn Asp Pro Ser Ser Gln
        35                  40
```

<210> SEQ ID NO 12
<211> LENGTH: 50
<212> TYPE: PRT
<213> ORGANISM: Human immunodeficiency virus type 1

<400> SEQUENCE: 12

```
Ser Arg Pro Glu Pro Thr Ala Pro Pro Glu Glu Ser Phe Arg Ser Gly
1               5                   10                  15

Val Glu Thr Thr Thr Pro Pro Gln Lys Gln Glu Pro Ile Asp Lys Glu
            20                  25                  30

Leu Tyr Pro Leu Thr Ser Leu Arg Ser Leu Phe Gly Asn Asp Pro Ser
        35                  40                  45

Ser Gln
    50
```

<210> SEQ ID NO 13
<211> LENGTH: 50
<212> TYPE: PRT
<213> ORGANISM: Human immunodeficiency virus type 1

<400> SEQUENCE: 13

```
Ser Arg Pro Glu Pro Thr Ala Pro Pro Glu Glu Ser Phe Arg Phe Gly
1               5                   10                  15

Glu Glu Thr Thr Thr Pro Ser Gln Lys Gln Glu Pro Ile Asp Lys Glu
            20                  25                  30

Leu Tyr Pro Leu Ala Ser Leu Arg Ser Leu Phe Gly Asn Asp Pro Ser
        35                  40                  45

Ser Gln
    50
```

<210> SEQ ID NO 14
<211> LENGTH: 49
<212> TYPE: PRT
<213> ORGANISM: Human immunodeficiency virus type 1

<400> SEQUENCE: 14

```
Ser Arg Pro Glu Pro Thr Ala Pro Pro Ala Glu Ser Phe Gly Met Gly
1               5                   10                  15

Glu Glu Ile Thr Ser Ser Pro Lys Gln Glu Pro Arg Asp Lys Gly Leu
            20                  25                  30

Tyr Pro Pro Leu Ala Ser Leu Lys Ser Leu Phe Gly Asn Asp Pro Ser
        35                  40                  45

Gln
```

<210> SEQ ID NO 15
<211> LENGTH: 49
<212> TYPE: PRT
<213> ORGANISM: Human immunodeficiency virus type 1

<400> SEQUENCE: 15

```
Ser Arg Pro Glu Pro Thr Ala Pro Pro Ala Glu Ser Phe Gly Phe Gly
1               5                   10                  15

Glu Glu Ile Thr Pro Ser Gln Lys Gln Glu Gln Lys Asp Lys Glu Leu
            20                  25                  30
```

```
Tyr Pro Leu Thr Ser Leu Lys Ser Leu Phe Gly Asn Asp Pro Leu Ser
         35                  40                  45

Gln

<210> SEQ ID NO 16
<211> LENGTH: 47
<212> TYPE: PRT
<213> ORGANISM: Human immunodeficiency virus type 1

<400> SEQUENCE: 16

Asn Arg Pro Glu Pro Thr Ala Pro Pro Ala Glu Ser Phe Gly Phe Arg
1               5                   10                  15

Glu Glu Ile Thr Pro Ser Pro Lys Gln Glu Gln Lys Asp Glu Gly Leu
            20                  25                  30

Tyr Pro Pro Leu Ala Ser Leu Lys Ser Leu Phe Gly Asn Asp Pro
         35                  40                  45

<210> SEQ ID NO 17
<211> LENGTH: 48
<212> TYPE: PRT
<213> ORGANISM: Human immunodeficiency virus type 1

<400> SEQUENCE: 17

Asn Arg Pro Glu Pro Thr Ala Pro Pro Ala Glu Ser Phe Gly Phe Gly
1               5                   10                  15

Glu Glu Ile Ala Pro Ser Pro Lys Gln Glu Gln Lys Glu Lys Glu Leu
            20                  25                  30

Tyr Pro Leu Ala Ser Leu Lys Ser Leu Phe Gly Ser Asp Pro Ser Gln
         35                  40                  45

<210> SEQ ID NO 18
<211> LENGTH: 50
<212> TYPE: PRT
<213> ORGANISM: Human immunodeficiency virus type 1

<400> SEQUENCE: 18

Ser Arg Pro Glu Pro Thr Ala Pro Pro Ala Glu Ser Phe Gly Phe Gly
1               5                   10                  15

Glu Glu Ile Thr Pro Ser Pro Arg Gln Glu Thr Lys Asp Lys Glu Gln
            20                  25                  30

Gly Pro Pro Leu Thr Ser Leu Lys Ser Leu Phe Gly Asn Asp Pro Leu
         35                  40                  45

Ser Gln
    50

<210> SEQ ID NO 19
<211> LENGTH: 50
<212> TYPE: PRT
<213> ORGANISM: Human immunodeficiency virus type 1

<400> SEQUENCE: 19

Ser Arg Pro Glu Pro Thr Ala Pro Pro Ala Glu Ile Phe Gly Met Gly
1               5                   10                  15

Glu Glu Ile Thr Ser Pro Lys Gln Glu Gln Lys Asp Arg Glu Gln
            20                  25                  30

Asn Pro Pro Ser Val Ser Leu Lys Ser Leu Phe Gly Asn Asp Pro Leu
         35                  40                  45

Ser Gln
    50
```

<210> SEQ ID NO 20
<211> LENGTH: 48
<212> TYPE: PRT
<213> ORGANISM: Human immunodeficiency virus type 1

<400> SEQUENCE: 20

Ser Arg Pro Glu Pro Thr Ala Pro Pro Ala Glu Ser Phe Gly Phe Gly
1               5                   10                  15

Glu Glu Met Thr Pro Ser Pro Lys Gln Glu Leu Lys Asp Lys Glu Pro
            20                  25                  30

Pro Leu Ala Ser Leu Arg Ser Leu Phe Gly Asn Asp Pro Leu Ser Gln
        35                  40                  45

<210> SEQ ID NO 21
<211> LENGTH: 49
<212> TYPE: PRT
<213> ORGANISM: Human immunodeficiency virus type 1

<400> SEQUENCE: 21

Ser Arg Pro Glu Pro Thr Ala Pro Pro Ala Glu Asn Gly Met Gly Glu
1               5                   10                  15

Glu Ile Thr Ser Leu Pro Lys Gln Glu Gln Lys Asp Lys Glu His Pro
            20                  25                  30

Pro Pro Leu Val Ser Leu Lys Ser Leu Phe Gly Asn Asp Pro Leu Ser
        35                  40                  45

Gln

<210> SEQ ID NO 22
<211> LENGTH: 46
<212> TYPE: PRT
<213> ORGANISM: Human immunodeficiency virus type 1

<400> SEQUENCE: 22

Ser Arg Pro Glu Pro Thr Ala Pro Pro Ala Glu Ser Phe Arg Phe Glu
1               5                   10                  15

Glu Thr Thr Pro Ala Pro Lys Gln Glu Pro Lys Asp Arg Glu Pro Leu
            20                  25                  30

Thr Ser Leu Lys Ser Leu Phe Gly Ser Asp Pro Leu Ser Gln
        35                  40                  45

<210> SEQ ID NO 23
<211> LENGTH: 49
<212> TYPE: PRT
<213> ORGANISM: Human immunodeficiency virus type 1

<400> SEQUENCE: 23

Ser Arg Pro Glu Pro Thr Ala Pro Pro Ala Glu Ser Phe Gly Phe Gly
1               5                   10                  15

Glu Glu Ile Thr Pro Ser Pro Lys Gln Glu Pro Lys Asp Lys Glu Leu
            20                  25                  30

Tyr Pro Leu Ala Ser Leu Lys Ser Leu Phe Gly Asn Asp Pro Leu Ser
        35                  40                  45

Gln

<210> SEQ ID NO 24
<211> LENGTH: 49
<212> TYPE: PRT
<213> ORGANISM: Human immunodeficiency virus type 1

```
<400> SEQUENCE: 24

Ser Arg Pro Glu Pro Thr Ala Pro Pro Ala Glu Ser Phe Gly Phe Gly
1               5                   10                  15

Glu Glu Ile Thr Pro Ser Pro Lys Gln Glu Pro Lys Asp Lys Glu Leu
                20                  25                  30

Tyr Pro Leu Ala Ser Leu Lys Ser Leu Phe Gly Ser Asp Pro Leu Ser
            35                  40                  45

Gln

<210> SEQ ID NO 25
<211> LENGTH: 50
<212> TYPE: PRT
<213> ORGANISM: Human immunodeficiency virus type 1

<400> SEQUENCE: 25

Ser Arg Pro Glu Pro Thr Ala Pro Pro Ala Glu Ile Phe Gly Met Gly
1               5                   10                  15

Glu Glu Ile Thr Ser Pro Pro Lys Gln Glu Gln Lys Asp Arg Glu Gln
                20                  25                  30

Asp Pro Pro Leu Val Ser Leu Lys Ser Leu Phe Gly Asn Asp Pro Leu
            35                  40                  45

Ser Gln
    50

<210> SEQ ID NO 26
<211> LENGTH: 50
<212> TYPE: PRT
<213> ORGANISM: Human immunodeficiency virus type 1

<400> SEQUENCE: 26

Ser Arg Pro Glu Pro Thr Ala Pro Pro Ala Glu Asn Phe Gly Met Gly
1               5                   10                  15

Glu Glu Met Ile Ser Ser Pro Lys Gln Glu Gln Lys Asp Arg Glu Gln
                20                  25                  30

Tyr Pro Pro Leu Val Ser Leu Lys Ser Leu Phe Gly Asn Asp Pro Leu
            35                  40                  45

Ser Gln
    50

<210> SEQ ID NO 27
<211> LENGTH: 50
<212> TYPE: PRT
<213> ORGANISM: Human immunodeficiency virus type 1

<400> SEQUENCE: 27

Ser Arg Thr Glu Pro Thr Ala Pro Pro Ala Glu Asn Leu Arg Met Gly
1               5                   10                  15

Glu Glu Ile Thr Ser Ser Leu Lys Gln Glu Leu Lys Thr Arg Glu Pro
                20                  25                  30

Tyr Asn Pro Ala Ile Ser Leu Lys Ser Leu Phe Gly Asn Asp Pro Leu
            35                  40                  45

Ser Gln
    50

<210> SEQ ID NO 28
<211> LENGTH: 50
<212> TYPE: PRT
<213> ORGANISM: Human immunodeficiency virus type 1
```

<400> SEQUENCE: 28

Ser Arg Pro Glu Pro Thr Ala Pro Pro Glu Glu Ser Phe Arg Phe Gly
1               5                   10                  15

Glu Glu Thr Thr Thr Pro Ser Gln Lys Gln Glu Pro Ile Asp Lys Glu
            20                  25                  30

Leu Tyr Pro Leu Ala Ser Leu Arg Ser Leu Phe Gly Asn Asp Pro Ser
        35                  40                  45

Ser Gln
    50

<210> SEQ ID NO 29
<211> LENGTH: 50
<212> TYPE: PRT
<213> ORGANISM: Human immunodeficiency virus type 1

<400> SEQUENCE: 29

Ser Arg Pro Glu Pro Thr Ala Pro Pro Glu Glu Ser Phe Arg Phe Gly
1               5                   10                  15

Glu Glu Thr Thr Thr Pro Ser Gln Lys Gln Glu Pro Ile Asp Lys Glu
            20                  25                  30

Leu Tyr Pro Leu Ala Ser Leu Lys Ser Leu Phe Gly Asn Asp Pro Ser
        35                  40                  45

Ser Gln
    50

<210> SEQ ID NO 30
<211> LENGTH: 46
<212> TYPE: PRT
<213> ORGANISM: Human immunodeficiency virus type 1

<400> SEQUENCE: 30

Asn Arg Pro Glu Pro Thr Ala Pro Pro Ala Glu Ser Phe Arg Phe Glu
1               5                   10                  15

Glu Thr Thr Pro Ala Pro Lys Gln Glu Pro Lys Asp Arg Glu Pro Leu
            20                  25                  30

Thr Ser Leu Lys Ser Leu Phe Gly Ser Asp Pro Leu Ser Gln
        35                  40                  45

<210> SEQ ID NO 31
<211> LENGTH: 46
<212> TYPE: PRT
<213> ORGANISM: Human immunodeficiency virus type 1

<400> SEQUENCE: 31

Ser Arg Pro Glu Pro Thr Ala Pro Pro Ala Glu Ser Phe Arg Phe Glu
1               5                   10                  15

Glu Thr Thr Pro Ala Pro Lys Gln Glu Pro Lys Asp Arg Glu Pro Leu
            20                  25                  30

Thr Ser Leu Lys Ser Leu Phe Gly Ser Asp Pro Leu Ser Gln
        35                  40                  45

<210> SEQ ID NO 32
<211> LENGTH: 49
<212> TYPE: PRT
<213> ORGANISM: Human immunodeficiency virus type 1

<400> SEQUENCE: 32

Ser Arg Pro Glu Pro Thr Ala Pro Pro Ala Glu Ser Phe Gly Phe Gly
1               5                   10                  15

-continued

Glu Glu Ile Thr Pro Ser Gln Lys Gln Gln Lys Asp Lys Glu Leu
             20                  25                  30

Tyr Pro Leu Thr Ser Leu Lys Ser Leu Phe Gly Asn Asp Pro Leu Ser
         35                  40                  45

Gln

<210> SEQ ID NO 33
<211> LENGTH: 47
<212> TYPE: PRT
<213> ORGANISM: Human immunodeficiency virus type 1

<400> SEQUENCE: 33

Ser Arg Pro Glu Pro Thr Ala Pro Ala Glu Ser Phe Gly Phe Arg
1               5                   10                  15

Glu Glu Ile Thr Pro Ser Pro Lys Gln Glu Gln Lys Asp Glu Gly Leu
             20                  25                  30

Tyr Pro Pro Leu Ala Ser Leu Lys Ser Leu Phe Gly Asn Asp Pro
         35                  40                  45

<210> SEQ ID NO 34
<211> LENGTH: 46
<212> TYPE: PRT
<213> ORGANISM: Human immunodeficiency virus type 1

<400> SEQUENCE: 34

Asn Arg Pro Glu Pro Thr Ala Pro Ala Glu Ser Phe Gly Phe Gly
1               5                   10                  15

Glu Glu Ile Ala Pro Ser Pro Lys Gln Glu Gln Lys Glu Lys Glu Leu
             20                  25                  30

Tyr Pro Leu Ala Ser Leu Lys Ser Leu Phe Gly Ser Asp Pro
         35                  40                  45

<210> SEQ ID NO 35
<211> LENGTH: 48
<212> TYPE: PRT
<213> ORGANISM: Human immunodeficiency virus type 1

<400> SEQUENCE: 35

Ser Arg Pro Glu Pro Thr Ala Pro Ala Glu Ser Phe Gly Phe Gly
1               5                   10                  15

Glu Glu Met Thr Pro Ser Pro Lys Gln Glu Leu Lys Asp Lys Glu Pro
             20                  25                  30

Pro Leu Ala Ser Leu Arg Ser Leu Phe Gly Asn Asp Pro Leu Ser Gln
         35                  40                  45

<210> SEQ ID NO 36
<211> LENGTH: 50
<212> TYPE: PRT
<213> ORGANISM: Human immunodeficiency virus type 1

<400> SEQUENCE: 36

Ser Arg Pro Glu Pro Thr Ala Pro Ala Glu Ser Phe Gly Phe Gly
1               5                   10                  15

Glu Glu Ile Thr Pro Ser Pro Arg Gln Glu Thr Lys Asp Lys Glu Gln
             20                  25                  30

Gly Pro Pro Leu Thr Ser Leu Lys Ser Leu Phe Gly Asn Asp Pro Leu
         35                  40                  45

Ser Gln
    50

<210> SEQ ID NO 37
<211> LENGTH: 50
<212> TYPE: PRT
<213> ORGANISM: Human immunodeficiency virus type 1

<400> SEQUENCE: 37

Ser Arg Pro Glu Pro Thr Ala Pro Pro Ala Glu Asn Trp Gly Met Gly
1               5                   10                  15

Glu Glu Ile Thr Ser Leu Pro Lys Gln Glu Gln Lys Asp Lys Glu His
            20                  25                  30

Pro Pro Pro Leu Val Ser Leu Lys Ser Leu Phe Gly Asn Asp Pro Leu
        35                  40                  45

Ser Gln
    50

<210> SEQ ID NO 38
<211> LENGTH: 47
<212> TYPE: PRT
<213> ORGANISM: Human immunodeficiency virus type 1

<400> SEQUENCE: 38

Ser Arg Pro Glu Pro Thr Ala Pro Pro Ala Glu Ser Phe Gly Met Gly
1               5                   10                  15

Glu Glu Ile Thr Ser Ser Pro Lys Gln Glu Pro Arg Asp Lys Gly Leu
            20                  25                  30

Tyr Pro Pro Leu Thr Ser Leu Lys Ser Leu Phe Gly Asn Asp Pro
        35                  40                  45

<210> SEQ ID NO 39
<211> LENGTH: 50
<212> TYPE: PRT
<213> ORGANISM: Human immunodeficiency virus type 1

<400> SEQUENCE: 39

Ser Arg Pro Glu Pro Ser Ala Pro Ala Glu Asn Phe Gly Met Gly
1               5                   10                  15

Glu Glu Ile Thr Pro Ser Leu Lys Gln Glu Gln Lys Asp Arg Glu Gln
            20                  25                  30

His Pro Pro Ser Ile Ser Leu Lys Ser Leu Phe Gly Asn Asp Pro Leu
        35                  40                  45

Ser Gln
    50

<210> SEQ ID NO 40
<211> LENGTH: 49
<212> TYPE: PRT
<213> ORGANISM: Human immunodeficiency virus type 1

<400> SEQUENCE: 40

Ser Arg Pro Glu Pro Thr Ala Pro Pro Ala Glu Ser Leu Glu Met Lys
1               5                   10                  15

Glu Glu Thr Thr Ser Ser Pro Lys Gln Glu Pro Arg Asp Lys Glu Leu
            20                  25                  30

Tyr Pro Leu Thr Ser Leu Lys Ser Leu Phe Gly Ser Asp Pro Leu Ser
        35                  40                  45

Gln

<210> SEQ ID NO 41
<211> LENGTH: 46

<212> TYPE: PRT
<213> ORGANISM: Human immunodeficiency virus type 1

<400> SEQUENCE: 41

Asn Arg Pro Glu Pro Thr Ala Pro Ala Glu Ser Phe Gly Phe Gly
1               5                   10                  15

Glu Glu Thr Ala Pro Ser Pro Lys Gln Glu Pro Lys Glu Lys Glu Leu
                20                  25                  30

Tyr Pro Leu Ala Ser Leu Lys Ser Leu Phe Gly Asn Asp Pro
        35                  40                  45

<210> SEQ ID NO 42
<211> LENGTH: 50
<212> TYPE: PRT
<213> ORGANISM: Human immunodeficiency virus type 1

<400> SEQUENCE: 42

Ser Arg Pro Glu Pro Thr Ala Pro Pro Glu Glu Ser Phe Arg Phe Gly
1               5                   10                  15

Glu Glu Thr Thr Thr Pro Ser Gln Lys Gln Glu Pro Ile Asp Lys Glu
                20                  25                  30

Leu Tyr Pro Leu Thr Ser Leu Lys Ser Leu Phe Gly Asn Asp Pro Ser
        35                  40                  45

Ser Gln
    50

<210> SEQ ID NO 43
<211> LENGTH: 46
<212> TYPE: PRT
<213> ORGANISM: Human immunodeficiency virus type 1

<400> SEQUENCE: 43

Ser Arg Pro Glu Pro Thr Ala Pro Pro Ala Glu Ser Phe Arg Phe Glu
1               5                   10                  15

Glu Thr Thr Pro Ala Pro Lys Gln Glu Pro Lys Asp Arg Glu Pro Leu
                20                  25                  30

Thr Ser Leu Arg Ser Leu Phe Gly Ser Asp Pro Leu Ser Gln
        35                  40                  45

<210> SEQ ID NO 44
<211> LENGTH: 49
<212> TYPE: PRT
<213> ORGANISM: Human immunodeficiency virus type 1

<400> SEQUENCE: 44

Ser Arg Pro Glu Pro Thr Ala Pro Pro Ala Glu Ser Phe Gly Phe Gly
1               5                   10                  15

Glu Glu Ile Thr Pro Ser Gln Lys Gln Glu Gln Lys Asp Lys Glu Leu
                20                  25                  30

His Pro Leu Ala Ser Leu Lys Ser Leu Phe Gly Asn Asp Pro Leu Ser
        35                  40                  45

Gln

<210> SEQ ID NO 45
<211> LENGTH: 49
<212> TYPE: PRT
<213> ORGANISM: Human immunodeficiency virus type 1

<400> SEQUENCE: 45

Ser Arg Pro Glu Pro Thr Ala Pro Pro Ala Glu Ser Phe Gly Phe Gly

```
                1               5                   10                  15
            Glu Glu Ile Ala Pro Ser Pro Lys Gln Glu Pro Lys Glu Lys Glu Leu
                            20                  25                  30

Tyr Pro Leu Thr Ser Leu Lys Ser Leu Phe Gly Ser Asp Pro Leu Ser
                        35                  40                  45

Gln

<210> SEQ ID NO 46
<211> LENGTH: 47
<212> TYPE: PRT
<213> ORGANISM: Human immunodeficiency virus type 1

<400> SEQUENCE: 46

Asn Arg Pro Glu Pro Thr Ala Pro Pro Ala Glu Ser Phe Gly Phe Gly
1               5                   10                  15

Glu Glu Ile Thr Pro Ser Pro Lys Gln Glu Gln Lys Asp Glu Gly Leu
                20                  25                  30

Tyr Pro Pro Leu Ala Ser Leu Lys Ser Leu Phe Gly Asn Asp Pro
            35                  40                  45

<210> SEQ ID NO 47
<211> LENGTH: 48
<212> TYPE: PRT
<213> ORGANISM: Human immunodeficiency virus type 1

<400> SEQUENCE: 47

Asn Arg Pro Glu Pro Thr Ala Pro Pro Ala Glu Ser Phe Gly Phe Gly
1               5                   10                  15

Glu Glu Ile Ala Pro Ser Pro Lys Gln Glu Pro Lys Glu Lys Glu Ile
                20                  25                  30

Tyr Pro Leu Ala Ser Leu Lys Ser Leu Phe Gly Ser Asp Pro Ser Gln
            35                  40                  45

<210> SEQ ID NO 48
<211> LENGTH: 51
<212> TYPE: PRT
<213> ORGANISM: Human immunodeficiency virus type 1

<400> SEQUENCE: 48

Ser Arg Pro Glu Pro Thr Ala Pro Pro Glu Glu Ser Phe Arg Phe Gly
1               5                   10                  15

Glu Glu Lys Thr Thr Thr Pro Ser Gln Lys Gln Glu Pro Ile Asp Lys
                20                  25                  30

Glu Leu Tyr Pro Leu Thr Ser Leu Arg Ser Leu Phe Gly Asn Asp Pro
            35                  40                  45

Ser Ser Asn
    50

<210> SEQ ID NO 49
<211> LENGTH: 88
<212> TYPE: PRT
<213> ORGANISM: Human immunodeficiency virus type 1

<400> SEQUENCE: 49

Leu Ile Ala Ala Arg Thr Val Glu Leu Leu Gly His Ser Ser Leu Lys
1               5                   10                  15

Gly Leu Arg Leu Gly Trp Glu Gly Leu Lys Tyr Leu Trp Asn Leu Leu
                20                  25                  30

Leu Tyr Trp Gly Arg Glu Leu Lys Ile Ser Ala Ile Asn Leu Val Asp
```

```
                35                  40                  45
Thr Ile Ala Ile Ala Val Ala Gly Trp Thr Asp Arg Val Ile Glu Ile
            50                  55                  60
Gly Gln Arg Ile Gly Arg Ala Ile Leu His Ile Pro Arg Arg Ile Arg
65                  70                  75                  80
Gln Gly Leu Glu Arg Ala Leu Leu
                85

<210> SEQ ID NO 50
<211> LENGTH: 46
<212> TYPE: PRT
<213> ORGANISM: Human immunodeficiency virus type 1

<400> SEQUENCE: 50

Leu Ile Ala Ala Arg Ile Val Glu Leu Leu Gly His Ser Ser Leu Lys
1               5                   10                  15
Gly Leu Arg Arg Gly Trp Glu Ala Leu Lys Tyr Leu Trp Asn Leu Leu
                20                  25                  30
Gln Tyr Trp Gly Gln Glu Leu Lys Asn Ser Ala Ile Ser Leu
            35                  40                  45

<210> SEQ ID NO 51
<211> LENGTH: 39
<212> TYPE: PRT
<213> ORGANISM: Human immunodeficiency virus type 1

<400> SEQUENCE: 51

Leu Ile Val Thr Arg Ile Val Glu Leu Leu Gly Arg Arg Gly Trp Glu
1               5                   10                  15
Ala Leu Lys Tyr Trp Trp Asn Leu Leu Asn Tyr Trp Ser Gln Glu Leu
                20                  25                  30
Lys Asn Ser Ala Val Asn Leu
            35

<210> SEQ ID NO 52
<211> LENGTH: 34
<212> TYPE: PRT
<213> ORGANISM: Human immunodeficiency virus type 1

<400> SEQUENCE: 52

Ala Arg Ile Val Glu Leu Leu Gly His Ser Ser Leu Lys Gly Leu Arg
1               5                   10                  15
Arg Gly Trp Glu Ala Leu Lys Tyr Leu Trp Asn Leu Leu Gln Tyr Trp
                20                  25                  30
Gly Gln

<210> SEQ ID NO 53
<211> LENGTH: 20
<212> TYPE: PRT
<213> ORGANISM: Human immunodeficiency virus type 1

<400> SEQUENCE: 53

Cys Arg Ala Ile Leu Asn Ile Pro Arg Arg Ile Arg Gln Gly Leu Glu
1               5                   10                  15
Arg Ala Leu Leu
            20

<210> SEQ ID NO 54
<211> LENGTH: 16
<212> TYPE: PRT
```

-continued

```
<213> ORGANISM: Human immunodeficiency virus type 1

<400> SEQUENCE: 54

Ala Val Ala Glu Gly Thr Asp Arg Val Ile Glu Val Val Gln Arg Val
1               5                   10                  15

<210> SEQ ID NO 55
<211> LENGTH: 36
<212> TYPE: PRT
<213> ORGANISM: Human immunodeficiency virus type 1

<400> SEQUENCE: 55

Ala Val Ala Glu Gly Thr Asp Arg Val Ile Glu Val Val Gln Arg Val
1               5                   10                  15

Cys Arg Ala Ile Leu Asn Ile Pro Arg Arg Ile Arg Gln Gly Phe Glu
            20                  25                  30

Arg Ala Leu Leu
        35

<210> SEQ ID NO 56
<211> LENGTH: 39
<212> TYPE: PRT
<213> ORGANISM: Human immunodeficiency virus type 1

<400> SEQUENCE: 56

Leu Ile Val Thr Arg Ile Val Glu Leu Leu Gly Arg Arg Gly Trp Glu
1               5                   10                  15

Ala Leu Lys Tyr Trp Trp Asn Leu Leu Gln Tyr Trp Ser Gln Glu Leu
            20                  25                  30

Lys Asn Ser Ala Val Ser Leu
        35

<210> SEQ ID NO 57
<211> LENGTH: 39
<212> TYPE: PRT
<213> ORGANISM: Human immunodeficiency virus type 1

<400> SEQUENCE: 57

Leu Ile Val Thr Arg Ile Val Glu Leu Leu Gly Arg Arg Gly Trp Glu
1               5                   10                  15

Ala Leu Lys Tyr Trp Trp Asn Leu Leu Gln Tyr Trp Ser Gln Glu Leu
            20                  25                  30

Lys Asn Ser Ala Val Asn Leu
        35

<210> SEQ ID NO 58
<211> LENGTH: 39
<212> TYPE: PRT
<213> ORGANISM: Human immunodeficiency virus type 1

<400> SEQUENCE: 58

Leu Ile Ala Ala Arg Ile Val Glu Leu Leu Gly Arg Arg Gly Trp Glu
1               5                   10                  15

Ala Leu Lys Tyr Leu Trp Asn Leu Leu Gln Tyr Trp Ile Gln Glu Leu
            20                  25                  30

Lys Asn Ser Ala Ile Ser Leu
        35

<210> SEQ ID NO 59
<211> LENGTH: 39
<212> TYPE: PRT
```

<213> ORGANISM: Human immunodeficiency virus type 1

<400> SEQUENCE: 59

Leu Ile Ala Ala Arg Thr Val Asp Arg Gly Leu Lys Arg G

<210> SEQ ID NO 64
<211> LENGTH: 46
<212> TYPE: PRT
<213> ORGANISM: Human immunodeficiency virus type 1

<400> SEQUENCE: 64

Leu Ile Ala Ala Arg Thr Val Glu Leu Leu Gly His Ser Ser Leu Lys
1               5                   10                  15

Gly Leu Arg Arg Gly Trp Glu Gly Leu Lys Tyr Leu Gly Asn Leu Leu
            20                  25                  30

Leu Tyr Trp Gly Gln Glu Leu Lys Ile Ser Ala Ile Ser Leu
        35                  40                  45

<210> SEQ ID NO 65
<211> LENGTH: 46
<212> TYPE: PRT
<213> ORGANISM: Human immunodeficiency virus type 1

<400> SEQUENCE: 65

Leu Ile Ala Ala Arg Thr Val Glu Leu Leu Gly His Ser Ser Leu Lys
1               5                   10                  15

Gly Leu Arg Leu Gly Trp Glu Ala Leu Lys Tyr Leu Gly Asn Leu Leu
            20                  25                  30

Ser Tyr Trp Gly Gln Glu Leu Lys Asn Ser Ala Ile Asn Leu
        35                  40                  45

<210> SEQ ID NO 66
<211> LENGTH: 81
<212> TYPE: PRT
<213> ORGANISM: Human immunodeficiency virus type 1

<400> SEQUENCE: 66

Leu Ile Ala Ala Arg Thr Val Glu Leu Leu Gly Arg Arg Gly Trp Glu
1               5                   10                  15

Ala Leu Lys Tyr Leu Trp Asn Leu Leu Gln Tyr Trp Gly Gln Glu Leu
            20                  25                  30

Lys Asn Ser Ala Ile Ser Leu Leu Asp Thr Thr Ala Ile Ala Val Ala
        35                  40                  45

Glu Gly Thr Asp Arg Val Ile Glu Val Val Gln Arg Val Cys Arg Ala
    50                  55                  60

Ile Leu Asn Ile Pro Arg Arg Ile Arg Gln Gly Phe Glu Arg Ala Leu
65                  70                  75                  80

Leu

<210> SEQ ID NO 67
<211> LENGTH: 81
<212> TYPE: PRT
<213> ORGANISM: Human immunodeficiency virus type 1

<400> SEQUENCE: 67

Leu Ile Ala Ala Arg Thr Val Glu Leu Leu Gly Arg Arg Gly Trp Glu
1               5                   10                  15

Ala Leu Lys Tyr Leu Trp Asn Leu Leu Gln Tyr Trp Gly Gln Glu Leu
            20                  25                  30

Lys Asn Ser Ala Ile Ser Leu Leu Asp Thr Thr Ala Ile Ala Val Ala
        35                  40                  45

Glu Gly Thr Asp Arg Val Ile Glu Val Val Gln Arg Ala Cys Arg Ala

```
                    50                  55                  60

Ile Leu His Ile Pro Arg Arg Ile Arg Gln Gly Phe Glu Arg Ala Leu
 65                  70                  75                  80

Leu

<210> SEQ ID NO 68
<211> LENGTH: 88
<212> TYPE: PRT
<213> ORGANISM: Human immunodeficiency virus type 1

<400> SEQUENCE: 68

Leu Ile Ala Ala Arg Thr Val Glu Leu Leu Gly His Ser Ser Leu Lys
  1               5                  10                  15

Gly Leu Arg Leu Gly Trp Glu Gly Leu Lys Tyr Leu Trp Asn Leu Leu
                 20                  25                  30

Leu Tyr Trp Gly Arg Glu Leu Lys Ile Ser Ala Ile Asn Leu Val Asp
             35                  40                  45

Thr Ile Ala Ile Ala Val Ala Gly Trp Thr Asp Arg Val Ile Glu Ile
         50                  55                  60

Gly Gln Arg Ile Gly Arg Ala Ile Leu His Ile Pro Arg Arg Ile Arg
 65                  70                  75                  80

Gln Gly Leu Glu Arg Ala Leu Leu
                 85

<210> SEQ ID NO 69
<211> LENGTH: 88
<212> TYPE: PRT
<213> ORGANISM: Human immunodeficiency virus type 1

<400> SEQUENCE: 69

Leu Ile Ala Ala Arg Thr Val Glu Leu Leu Gly Arg Ser Ser Leu Lys
  1               5                  10                  15

Gly Leu Arg Leu Gly Trp Glu Gly Leu Lys Tyr Leu Trp Asn Leu Leu
                 20                  25                  30

Leu Tyr Trp Gly Arg Glu Leu Lys Ile Ser Ala Ile Asn Leu Leu Asp
             35                  40                  45

Thr Ile Ala Ile Ala Val Ala Gly Trp Thr Asp Arg Val Ile Glu Ile
         50                  55                  60

Gly Gln Arg Ile Cys Arg Ala Ile Leu Asn Ile Pro Arg Arg Ile Arg
 65                  70                  75                  80

Gln Gly Leu Glu Arg Ala Leu Leu
                 85

<210> SEQ ID NO 70
<211> LENGTH: 88
<212> TYPE: PRT
<213> ORGANISM: Human immunodeficiency virus type 1

<400> SEQUENCE: 70

Leu Ile Ala Ala Arg Thr Val Glu Leu Leu Gly His Ser Ser Leu Lys
  1               5                  10                  15

Gly Leu Arg Leu Gly Trp Glu Gly Leu Lys Tyr Leu Trp Asn Leu Leu
                 20                  25                  30

Leu Tyr Trp Gly Arg Glu Leu Lys Asn Ser Ala Ile Ser Leu Leu Asp
             35                  40                  45

Thr Ile Ala Val Ala Val Ala Glu Trp Thr Asp Arg Val Ile Glu Ile
         50                  55                  60
```

```
Gly Gln Arg Ala Cys Arg Ala Ile Leu Asn Ile Pro Arg Arg Ile Arg
 65                  70                  75                  80

Gln Gly Phe Glu Arg Ala Leu Leu
                85

<210> SEQ ID NO 71
<211> LENGTH: 81
<212> TYPE: PRT
<213> ORGANISM: Human immunodeficiency virus type 1

<400> SEQUENCE: 71

Leu Ile Val Thr Arg Ile Val Glu Leu Leu Gly Arg Arg Gly Trp Glu
 1               5                  10                  15

Val Leu Lys Tyr Trp Trp Asn Leu Leu Gln Tyr Trp Ser Gln Glu Leu
                20                  25                  30

Lys Asn Ser Ala Val Ser Leu Leu Asn Ala Thr Ala Ile Ala Val Ala
            35                  40                  45

Glu Gly Thr Asp Arg Val Ile Glu Val Val Gln Arg Ala Cys Arg Ala
        50                  55                  60

Ile Leu His Ile Pro Arg Arg Ile Arg Gln Gly Leu Glu Arg Ala Leu
 65                  70                  75                  80

Leu

<210> SEQ ID NO 72
<211> LENGTH: 81
<212> TYPE: PRT
<213> ORGANISM: Human immunodeficiency virus type 1

<400> SEQUENCE: 72

Leu Ile Val Ala Arg Ile Val Glu Leu Leu Gly Arg Arg Gly Trp Glu
 1               5                  10                  15

Ala Leu Lys Tyr Trp Trp Asn Leu Leu Gln Tyr Trp Ser Gln Glu Leu
                20                  25                  30

Lys Asn Ser Ala Val Ser Leu Leu Asn Ala Thr Ala Ile Ala Val Ala
            35                  40                  45

Glu Gly Thr Asp Arg Val Ile Glu Val Val Gln Arg Ala Cys Arg Ala
        50                  55                  60

Ile Leu His Ile Pro Arg Arg Ile Arg Gln Gly Leu Glu Arg Ala Leu
 65                  70                  75                  80

Leu

<210> SEQ ID NO 73
<211> LENGTH: 88
<212> TYPE: PRT
<213> ORGANISM: Human immunodeficiency virus type 1

<400> SEQUENCE: 73

Leu Ile Ala Ala Arg Ala Val Glu Leu Leu Gly Arg Ser Ser Leu Arg
 1               5                  10                  15

Gly Leu Gln Arg Gly Trp Glu Ala Leu Lys Tyr Leu Gly Ser Leu Val
                20                  25                  30

Gln Tyr Trp Gly Leu Glu Leu Lys Lys Ser Ala Ile Ser Leu Leu Asp
            35                  40                  45

Thr Ile Ala Ile Ala Val Ala Glu Gly Thr Asp Arg Ile Ile Glu Leu
        50                  55                  60

Ile Gln Arg Ile Cys Arg Ala Ile Arg Asn Ile Pro Arg Arg Ile Arg
 65                  70                  75                  80
```

```
Gln Gly Phe Glu Ala Ala Leu Gln
            85

<210> SEQ ID NO 74
<211> LENGTH: 88
<212> TYPE: PRT
<213> ORGANISM: Human immunodeficiency virus type 1

<400> SEQUENCE: 74

Leu Ile Ala Ala Arg Ala Val Glu Leu Leu Gly Arg Ser Ser Leu Arg
1               5                   10                  15

Gly Leu Gln Arg Gly Trp Glu Ala Leu Lys Tyr Leu Gly Ser Leu Val
            20                  25                  30

Gln Tyr Trp Gly Leu Glu Leu Lys Lys Ser Ala Ile Ser Leu Leu Asp
        35                  40                  45

Thr Ile Ala Ile Ala Val Ala Glu Gly Thr Asp Arg Ile Ile Glu Leu
    50                  55                  60

Ile Gln Arg Ile Cys Arg Ala Ile Arg Asn Ile Pro Arg Arg Ile Arg
65                  70                  75                  80

Gln Gly Phe Glu Ala Ala Leu Leu
            85

<210> SEQ ID NO 75
<211> LENGTH: 81
<212> TYPE: PRT
<213> ORGANISM: Human immunodeficiency virus type 1

<400> SEQUENCE: 75

Leu Ile Ala Ala Arg Ile Val Glu Leu Leu Gly Arg Arg Gly Trp Glu
1               5                   10                  15

Ala Leu Lys Tyr Leu Trp Asn Leu Leu Gln Tyr Trp Ile Gln Glu Leu
            20                  25                  30

Lys Asn Ser Ala Ile Ser Leu Phe Asp Thr Thr Ala Ile Ala Val Ala
            35                  40                  45

Glu Gly Thr Asp Arg Val Ile Glu Ile Val Gln Arg Ala Cys Arg Ala
    50                  55                  60

Ile Leu Asn Ile Pro Thr Arg Ile Arg Gln Gly Leu Glu Arg Ala Leu
65                  70                  75                  80

Leu

<210> SEQ ID NO 76
<211> LENGTH: 81
<212> TYPE: PRT
<213> ORGANISM: Human immunodeficiency virus type 1

<400> SEQUENCE: 76

Leu Ile Ala Ala Arg Ile Val Asp Arg Gly Leu Arg Arg Gly Trp Glu
1               5                   10                  15

Ala Leu Lys Tyr Leu Gly Asn Leu Thr Gln Tyr Trp Ser Gln Glu Leu
            20                  25                  30

Lys Asn Ser Ala Ile Ser Leu Leu Asn Thr Thr Ala Ile Val Val Ala
            35                  40                  45

Glu Gly Thr Asp Arg Val Ile Glu Ala Leu Gln Arg Ala Gly Arg Ala
    50                  55                  60

Val Leu Asn Ile Pro Arg Arg Ile Arg Gln Gly Leu Glu Arg Ala Leu
65                  70                  75                  80

Leu
```

<210> SEQ ID NO 77
<211> LENGTH: 81
<212> TYPE: PRT
<213> ORGANISM: Human immunodeficiency virus type 1

<400> SEQUENCE: 77

Leu Ile Ala Ala Arg Thr Val Asp Met Gly Leu Lys Arg Gly Trp Glu
1               5                   10                  15

Ala Leu Lys Tyr Leu Trp Asn Leu Pro Gln Tyr Trp Gly Gln Glu Leu
            20                  25                  30

Lys Asn Ser Ala Ile Ser Leu Leu Asp Thr Thr Ala Ile Ala Val Ala
        35                  40                  45

Glu Gly Thr Asp Arg Ile Ile Glu Val Leu Gln Arg Ala Gly Arg Ala
    50                  55                  60

Val Leu His Ile Pro Arg Arg Ile Arg Gln Gly Phe Glu Arg Ala Leu
65                  70                  75                  80

Leu

<210> SEQ ID NO 78
<211> LENGTH: 88
<212> TYPE: PRT
<213> ORGANISM: Human immunodeficiency virus type 1

<400> SEQUENCE: 78

Leu Ile Ala Ala Arg Thr Val Glu Leu Leu Gly Arg Ser Ser Leu Lys
1               5                   10                  15

Gly Leu Arg Leu Gly Trp Glu Gly Leu Lys Tyr Leu Trp Asn Leu Leu
            20                  25                  30

Leu Tyr Trp Gly Gln Glu Leu Lys Asn Ser Ala Ile Asn Leu Leu Asp
        35                  40                  45

Thr Ile Ala Ile Ala Val Ala Asn Trp Thr Asp Arg Val Ile Glu Val
    50                  55                  60

Ala Gln Arg Ala Cys Arg Ala Ile Leu Asn Ile Pro Arg Arg Ile Arg
65                  70                  75                  80

Gln Gly Leu Glu Arg Ala Leu Leu
            85

<210> SEQ ID NO 79
<211> LENGTH: 81
<212> TYPE: PRT
<213> ORGANISM: Human immunodeficiency virus type 1

<400> SEQUENCE: 79

Leu Ile Val Val Arg Thr Val Glu Leu Leu Gly Arg Arg Gly Arg Glu
1               5                   10                  15

Ala Leu Lys Tyr Leu Trp Asn Leu Leu Gln Tyr Trp Gly Gln Glu Leu
            20                  25                  30

Lys Asn Ser Ala Ile Asn Leu Leu Asn Thr Thr Ala Ile Ala Val Ala
        35                  40                  45

Glu Gly Thr Asp Arg Ile Ile Glu Ile Val Gln Arg Ala Trp Arg Ala
    50                  55                  60

Ile Leu His Ile Pro Arg Arg Ile Arg Gln Gly Phe Glu Arg Thr Leu
65                  70                  75                  80

Leu

<210> SEQ ID NO 80
<211> LENGTH: 88

<212> TYPE: PRT
<213> ORGANISM: Human immunodeficiency virus type 1

<400> SEQUENCE: 80

```
Leu Ile Ala Ala Arg Thr Val Glu Leu Leu Gly His Ser Ser Leu Lys
1               5                   10                  15

Gly Leu Arg Arg Gly Trp Glu Gly Leu Lys Tyr Leu Gly Asn Leu Leu
            20                  25                  30

Leu Tyr Trp Gly Gln Glu Leu Lys Ile Ser Ala Ile Ser Leu Leu Asp
        35                  40                  45

Ala Thr Ala Ile Ala Val Ala Gly Trp Thr Asp Arg Val Ile Glu Val
    50                  55                  60

Ala Gln Gly Ala Trp Arg Ala Ile Leu His Ile Pro Arg Arg Ile Arg
65                  70                  75                  80

Gln Gly Leu Glu Arg Ala Leu Leu
                85
```

<210> SEQ ID NO 81
<211> LENGTH: 88
<212> TYPE: PRT
<213> ORGANISM: Human immunodeficiency virus type 1

<400> SEQUENCE: 81

```
Leu Ile Ala Ala Arg Thr Val Glu Leu Leu Gly His Ser Ser Leu Lys
1               5                   10                  15

Gly Leu Arg Leu Gly Trp Glu Ala Leu Lys Tyr Leu Gly Asn Leu Leu
            20                  25                  30

Ser Tyr Trp Gly Gln Glu Leu Lys Asn Ser Ala Ile Asn Leu Leu Asp
        35                  40                  45

Thr Ile Ala Ile Ala Val Ala Asn Trp Thr Asp Arg Val Ile Glu Ile
    50                  55                  60

Gly Gln Arg Ala Gly Arg Ala Ile Leu Asn Ile Pro Arg Arg Ile Arg
65                  70                  75                  80

Gln Gly Leu Glu Arg Ala Leu Leu
                85
```

<210> SEQ ID NO 82
<211> LENGTH: 81
<212> TYPE: PRT
<213> ORGANISM: Human immunodeficiency virus type 1

<400> SEQUENCE: 82

```
Leu Ile Ala Ala Arg Ile Val Glu Leu Leu Gly Arg Arg Gly Trp Glu
1               5                   10                  15

Ala Leu Lys Tyr Trp Asn Leu Leu Gln Tyr Trp Ile Gln Glu Leu
            20                  25                  30

Lys Ser Ser Ala Ile Asn Leu Ile Asp Thr Ile Ala Ile Ala Val Ala
        35                  40                  45

Gly Trp Thr Asp Arg Val Ile Glu Ile Gly Gln Arg Phe Cys Arg Ala
    50                  55                  60

Ile Arg Asn Ile Pro Arg Arg Ile Arg Gln Gly Ala Glu Lys Ala Leu
65                  70                  75                  80

Gln
```

<210> SEQ ID NO 83
<211> LENGTH: 81
<212> TYPE: PRT
<213> ORGANISM: Human immunodeficiency virus type 1

<400> SEQUENCE: 83

| Leu | Ile | Val | Ala | Arg | Thr | Val | Glu | Leu | Leu | Gly | Ile | Arg | Gly | Trp | Glu |
|---|---|---|---|---|---|---|---|---|---|---|---|---|---|---|---|
| 1 | | | | 5 | | | | | 10 | | | | | 15 | |

| Ala | Leu | Lys | Tyr | Leu | Trp | Asn | Leu | Leu | Leu | Tyr | Trp | Gly | Gln | Glu | Leu |
|---|---|---|---|---|---|---|---|---|---|---|---|---|---|---|---|
| | | | 20 | | | | | 25 | | | | | 30 | | |

| Arg | Asn | Ser | Ala | Ile | Asn | Leu | Leu | Asp | Thr | Thr | Ala | Ile | Ala | Val | Ala |
|---|---|---|---|---|---|---|---|---|---|---|---|---|---|---|---|
| | | 35 | | | | | 40 | | | | | 45 | | | |

| Glu | Gly | Thr | Asp | Arg | Ile | Ile | Glu | Ala | Val | Gln | Arg | Ala | Cys | Arg | Ala |
|---|---|---|---|---|---|---|---|---|---|---|---|---|---|---|---|
| | 50 | | | | | 55 | | | | | 60 | | | | |

| Ile | Arg | Asn | Ile | Pro | Arg | Arg | Ile | Arg | Gln | Gly | Leu | Glu | Arg | Ala | Leu |
|---|---|---|---|---|---|---|---|---|---|---|---|---|---|---|---|
| 65 | | | | | 70 | | | | | 75 | | | | | 80 |

Leu

<210> SEQ ID NO 84
<211> LENGTH: 81
<212> TYPE: PRT
<213> ORGANISM: Human immunodeficiency virus type 1

<400> SEQUENCE: 84

| Leu | Ile | Ala | Ala | Arg | Thr | Val | Glu | Thr | Leu | Gly | His | Arg | Gly | Trp | Glu |
|---|---|---|---|---|---|---|---|---|---|---|---|---|---|---|---|
| 1 | | | | 5 | | | | | 10 | | | | | 15 | |

| Ile | Leu | Lys | Tyr | Leu | Gly | Asn | Leu | Val | Cys | Tyr | Trp | Gly | Gln | Glu | Leu |
|---|---|---|---|---|---|---|---|---|---|---|---|---|---|---|---|
| | | | 20 | | | | | 25 | | | | | 30 | | |

| Lys | Asn | Ser | Ala | Ile | Ser | Leu | Leu | Asp | Thr | Thr | Ala | Ile | Ala | Val | Ala |
|---|---|---|---|---|---|---|---|---|---|---|---|---|---|---|---|
| | | 35 | | | | | 40 | | | | | 45 | | | |

| Asn | Trp | Thr | Asp | Arg | Val | Ile | Glu | Val | Val | Gln | Arg | Val | Phe | Arg | Ala |
|---|---|---|---|---|---|---|---|---|---|---|---|---|---|---|---|
| | 50 | | | | | 55 | | | | | 60 | | | | |

| Phe | Leu | Asn | Ile | Pro | Arg | Arg | Ile | Arg | Gln | Gly | Phe | Glu | Arg | Ala | Leu |
|---|---|---|---|---|---|---|---|---|---|---|---|---|---|---|---|
| 65 | | | | | 70 | | | | | 75 | | | | | 80 |

Leu

<210> SEQ ID NO 85
<211> LENGTH: 87
<212> TYPE: PRT
<213> ORGANISM: Human immunodeficiency virus type 1

<400> SEQUENCE: 85

| Leu | Thr | Ala | Arg | Gly | Val | Glu | Leu | Leu | Gly | Arg | Asn | Ser | Leu | Arg | Gly |
|---|---|---|---|---|---|---|---|---|---|---|---|---|---|---|---|
| 1 | | | | 5 | | | | | 10 | | | | | 15 | |

| Leu | Gln | Arg | Gly | Trp | Glu | Ala | Leu | Lys | Tyr | Leu | Gly | Ser | Leu | Val | Gln |
|---|---|---|---|---|---|---|---|---|---|---|---|---|---|---|---|
| | | | 20 | | | | | 25 | | | | | 30 | | |

| Tyr | Trp | Gly | Leu | Glu | Leu | Lys | Lys | Ser | Thr | Ile | Ser | Leu | Val | Asp | Thr |
|---|---|---|---|---|---|---|---|---|---|---|---|---|---|---|---|
| | | | 35 | | | | | 40 | | | | | 45 | | |

| Ile | Ala | Ile | Ala | Val | Ala | Glu | Gly | Thr | Asp | Arg | Ile | Ile | Asn | Ile | Val |
|---|---|---|---|---|---|---|---|---|---|---|---|---|---|---|---|
| | 50 | | | | | 55 | | | | | 60 | | | | |

| Gln | Gly | Ile | Cys | Arg | Ala | Ile | His | Asn | Ile | Pro | Arg | Arg | Ile | Arg | Gln |
|---|---|---|---|---|---|---|---|---|---|---|---|---|---|---|---|
| 65 | | | | | 70 | | | | | 75 | | | | | 80 |

| Gly | Phe | Glu | Ala | Ala | Leu | Gln |
|---|---|---|---|---|---|---|
| | | | 85 | | | |

<210> SEQ ID NO 86
<211> LENGTH: 81
<212> TYPE: PRT
<213> ORGANISM: Human immunodeficiency virus type 1

<400> SEQUENCE: 86

```
Leu Ile Ala Thr Arg Ile Val Glu Leu Leu Gly Arg Arg Gly Trp Glu
1               5                   10                  15

Ala Ile Lys Tyr Leu Trp Asn Leu Leu Gln Tyr Trp Ile Gln Glu Leu
                20                  25                  30

Lys Asn Ser Ala Ile Ser Leu Leu Asp Thr Thr Ala Ile Ala Val Ala
            35                  40                  45

Glu Gly Thr Asp Arg Ala Ile Glu Ile Val Gln Arg Ala Val Arg Ala
        50                  55                  60

Val Leu Asn Ile Pro Thr Arg Ile Arg Gln Gly Leu Glu Arg Ala Leu
65                  70                  75                  80

Leu

<210> SEQ ID NO 87
<211> LENGTH: 81
<212> TYPE: PRT
<213> ORGANISM: Human immunodeficiency virus type 1

<400> SEQUENCE: 87

Leu Ile Ala Ala Arg Ile Val Glu Thr Leu Gly Arg Arg Gly Trp Glu
1               5                   10                  15

Ile Leu Lys Tyr Leu Gly Asn Leu Ala Gln Tyr Trp Gly Gln Glu Leu
                20                  25                  30

Lys Asn Ser Ala Ile Ser Leu Leu Asn Ala Thr Ala Ile Ala Val Ala
            35                  40                  45

Glu Gly Thr Asp Arg Ile Ile Glu Val Val His Arg Val Leu Arg Ala
        50                  55                  60

Ile Leu His Ile Pro Arg Arg Ile Arg Gln Gly Phe Glu Arg Ala Leu
65                  70                  75                  80

Leu

<210> SEQ ID NO 88
<211> LENGTH: 81
<212> TYPE: PRT
<213> ORGANISM: Human immunodeficiency virus type 1

<400> SEQUENCE: 88

Leu Ile Val Thr Arg Ile Val Glu Leu Leu Gly Arg Arg Gly Trp Glu
1               5                   10                  15

Val Leu Lys Tyr Trp Trp Asn Leu Leu Gln Tyr Trp Ser Gln Glu Leu
                20                  25                  30

Lys Asn Ser Ala Ile Ser Leu Leu Asn Thr Thr Ala Ile Val Val Ala
            35                  40                  45

Glu Gly Thr Asp Arg Val Ile Glu Ala Leu Gln Arg Val Gly Arg Ala
        50                  55                  60

Ile Leu Asn Ile Pro Arg Arg Ile Arg Gln Gly Leu Glu Arg Ala Leu
65                  70                  75                  80

Leu

<210> SEQ ID NO 89
<211> LENGTH: 88
<212> TYPE: PRT
<213> ORGANISM: Human immunodeficiency virus type 1

<400> SEQUENCE: 89

Leu Ile Ala Ala Arg Thr Val Glu Leu Leu Gly Arg Ser Ser Leu Lys
1               5                   10                  15

Gly Leu Arg Leu Gly Trp Glu Gly Leu Lys Tyr Leu Trp Asn Leu Leu
```

```
            20                  25                  30

Leu Tyr Trp Gly Arg Glu Leu Lys Asn Ser Ala Ile Asn Leu Leu Asp
            35                  40                  45

Thr Val Ala Ile Ala Val Ala Asn Trp Thr Asp Arg Ala Ile Glu Val
        50                  55                  60

Val Gln Arg Val Gly Arg Ala Val Leu Asn Ile Pro Val Arg Ile Arg
65                  70                  75                  80

Gln Gly Leu Glu Arg Ala Leu Leu
                85

<210> SEQ ID NO 90
<211> LENGTH: 39
<212> TYPE: PRT
<213> ORGANISM: Human immunodeficiency virus type 1

<400> SEQUENCE: 90

Gly Leu Ile His Ser Gln Arg Arg Gln Asp Ile Leu Asp Leu Trp Ile
1               5                   10                  15

Tyr His Thr Gln Gly Tyr Phe Pro Asp Trp Gln Asn Tyr Thr Pro Gly
            20                  25                  30

Pro Gly Val Arg Tyr Pro Leu
        35

<210> SEQ ID NO 91
<211> LENGTH: 39
<212> TYPE: PRT
<213> ORGANISM: Human immunodeficiency virus type 1

<400> SEQUENCE: 91

Gly Leu Ile His Ser Gln Arg Arg Gln Asp Ile Leu Asp Leu Trp Ile
1               5                   10                  15

Tyr His Thr Gln Gly Tyr Phe Pro Asp Trp Gln Asn Tyr Thr Pro Gly
            20                  25                  30

Pro Gly Val Arg Tyr Pro Leu
        35

<210> SEQ ID NO 92
<211> LENGTH: 39
<212> TYPE: PRT
<213> ORGANISM: Human immunodeficiency virus type 1

<400> SEQUENCE: 92

Gly Leu Ile Tyr Ser Gln Lys Arg Gln Asp Ile Leu Asp Leu Trp Val
1               5                   10                  15

Tyr His Thr Gln Gly Tyr Phe Pro Asp Trp Gln Asn Tyr Thr Pro Gly
            20                  25                  30

Pro Gly Ile Arg Tyr Pro Leu
        35

<210> SEQ ID NO 93
<211> LENGTH: 39
<212> TYPE: PRT
<213> ORGANISM: Human immunodeficiency virus type 1

<400> SEQUENCE: 93

Gly Leu Ile Trp Ser Gln Lys Arg Gln Glu Ile Leu Asp Leu Trp Val
1               5                   10                  15

Tyr His Thr Gln Gly Phe Phe Pro Asp Trp Gln Asn Tyr Thr Pro Gly
            20                  25                  30
```

```
Pro Gly Ile Arg Tyr Pro Leu
        35

<210> SEQ ID NO 94
<211> LENGTH: 39
<212> TYPE: PRT
<213> ORGANISM: Human immunodeficiency virus type 1

<400> SEQUENCE: 94

Gly Leu Ile Tyr Ser Lys Lys Arg Gln Glu Ile Leu Asp Leu Trp Val
1               5                   10                  15

Tyr His Thr Gln Gly Tyr Phe Pro Asp Trp Gln Asn Tyr Thr Pro Gly
            20                  25                  30

Pro Gly Ile Arg Tyr Pro Leu
        35

<210> SEQ ID NO 95
<211> LENGTH: 39
<212> TYPE: PRT
<213> ORGANISM: Human immunodeficiency virus type 1

<400> SEQUENCE: 95

Gly Leu Ile Tyr Ser Lys Lys Arg Gln Glu Ile Leu Asp Leu Trp Val
1               5                   10                  15

Tyr His Thr Gln Gly Tyr Phe Pro Asp Trp Gln Asn Tyr Thr Pro Gly
            20                  25                  30

Pro Gly Val Arg Tyr Pro Leu
        35

<210> SEQ ID NO 96
<211> LENGTH: 39
<212> TYPE: PRT
<213> ORGANISM: Human immunodeficiency virus type 1

<400> SEQUENCE: 96

Gly Leu Ile Tyr Ser Lys Lys Arg Gln Asp Ile Leu Asp Leu Trp Val
1               5                   10                  15

Tyr His Thr Gln Gly Tyr Phe Pro Asp Trp Gln Asn Tyr Thr Pro Gly
            20                  25                  30

Pro Gly Ile Arg Tyr Pro Leu
        35

<210> SEQ ID NO 97
<211> LENGTH: 39
<212> TYPE: PRT
<213> ORGANISM: Human immunodeficiency virus type 1

<400> SEQUENCE: 97

Gly Leu Ile Tyr Ser Lys Lys Arg Gln Glu Ile Leu Asp Leu Trp Val
1               5                   10                  15

Tyr Asn Thr Gln Gly Phe Phe Pro Asp Trp Gln Asn Tyr Thr Pro Gly
            20                  25                  30

Pro Gly Ile Arg Tyr Pro Leu
        35

<210> SEQ ID NO 98
<211> LENGTH: 39
<212> TYPE: PRT
<213> ORGANISM: Human immunodeficiency virus type 1

<400> SEQUENCE: 98
```

-continued

```
Gly Leu Ile Tyr Ser Lys Lys Arg Gln Glu Ile Leu Asp Leu Trp Val
1               5                   10                  15

Tyr His Thr Gln Gly Phe Phe Pro Asp Trp Gln Asn Tyr Thr Pro Gly
                20                  25                  30

Pro Gly Thr Arg Phe Pro Leu
                35

<210> SEQ ID NO 99
<211> LENGTH: 39
<212> TYPE: PRT
<213> ORGANISM: Human immunodeficiency virus type 1

<400> SEQUENCE: 99

Gly Leu Ile Tyr Ser Lys Lys Arg Gln Glu Ile Leu Asp Leu Trp Val
1               5                   10                  15

Tyr Asn Thr Gln Gly Phe Phe Pro Asp Trp Gln Asn Tyr Thr Pro Gly
                20                  25                  30

Pro Gly Thr Arg Phe Pro Leu
                35

<210> SEQ ID NO 100
<211> LENGTH: 39
<212> TYPE: PRT
<213> ORGANISM: Human immunodeficiency virus type 1

<400> SEQUENCE: 100

Gly Leu Ile Tyr Ser Lys Lys Arg Gln Glu Ile Leu Asp Leu Trp Val
1               5                   10                  15

Tyr Asn Thr Gln Gly Tyr Phe Pro Asp Trp Gln Asn Tyr Thr Pro Gly
                20                  25                  30

Pro Gly Glu Arg Tyr Pro Leu
                35

<210> SEQ ID NO 101
<211> LENGTH: 90
<212> TYPE: PRT
<213> ORGANISM: Human immunodeficiency virus type 2

<400> SEQUENCE: 101

Ala Pro Gln Gly Leu Ile Pro Thr Ala Pro Pro Met Asn Pro Ala Phe
1               5                   10                  15

Gly Met Thr Pro Gln Gly Ala Ile Pro Ser Ala Pro Pro Ala Asp Pro
                20                  25                  30

Ala Ala Asp Leu Leu Glu Lys Tyr Leu Gln Gln Gly Arg Lys Gln Arg
            35                  40                  45

Glu Gln Arg Glu Arg Pro Tyr Lys Glu Val Thr Glu Asp Leu Leu His
50                  55                  60

Leu Glu Gln Gly Glu Thr Pro Arg Arg Glu Ala Thr Glu Asp Leu Leu
65                  70                  75                  80

His Leu Asn Ser Leu Phe Gly Lys Asp Gln
                85                  90

<210> SEQ ID NO 102
<211> LENGTH: 109
<212> TYPE: PRT
<213> ORGANISM: Human immunodeficiency virus type 2

<400> SEQUENCE: 102

Phe Leu Ile Arg Leu Leu Ile Arg Leu Leu Ile Gly Leu Tyr Asn Ile
1               5                   10                  15
```

-continued

```
Cys Arg Thr Leu Ile Ser Lys Ser Phe Gln Thr Leu Gln Pro Ile Ser
            20                  25                  30

Gln Gly Leu Gln Arg Ala Leu Thr Ala Ile Arg Asp Trp Leu Arg Pro
        35                  40                  45

Gly Ala Ala Tyr Leu Gln Tyr Gly Cys Glu Trp Ile Gln Glu Ala Leu
    50                  55                  60

Gln Ala Phe Ala Arg Ala Thr Arg Glu Thr Leu Thr Ser Val Trp Arg
65                  70                  75                  80

Asn Phe Cys Gly Thr Met Gly Gln Ile Gly Arg Gly Ile Leu Ala Ile
                85                  90                  95

Pro Arg Arg Ile Arg Gln Gly Ala Glu Leu Ala Leu Leu
            100                 105

<210> SEQ ID NO 103
<211> LENGTH: 59
<212> TYPE: PRT
<213> ORGANISM: Human immunodeficiency virus type 2

<400> SEQUENCE: 103

Val His Gln Gly Leu Met Pro Thr Ala Pro Pro Glu Asp Pro Ala Val
1               5                   10                  15

Asp Leu Leu Lys Asn Tyr Met Gln Leu Gly Lys Gln Gln Arg Glu Lys
            20                  25                  30

Gln Arg Glu Ser Arg Glu Lys Pro Tyr Lys Glu Val Thr Glu Asp Leu
        35                  40                  45

Leu His Leu Asn Ser Leu Phe Gly Gly Asp Gln
    50                  55

<210> SEQ ID NO 104
<211> LENGTH: 72
<212> TYPE: PRT
<213> ORGANISM: Human immunodeficiency virus type 2

<400> SEQUENCE: 104

Ala Pro Gln Gly Leu Ile Pro Thr Ala Pro Pro Ala Asp Pro Ala Ala
1               5                   10                  15

Asp Leu Leu Glu Lys Tyr Leu Gln Gln Gly Arg Lys Gln Arg Glu Gln
            20                  25                  30

Arg Glu Arg Pro Tyr Lys Glu Val Thr Glu Asp Leu Leu His Leu Glu
        35                  40                  45

Gln Gly Glu Thr Pro Arg Arg Glu Ala Thr Glu Asp Leu Leu His Leu
    50                  55                  60

Asn Ser Leu Phe Gly Lys Asp Gln
65                  70

<210> SEQ ID NO 105
<211> LENGTH: 55
<212> TYPE: PRT
<213> ORGANISM: Human immunodeficiency virus type 2

<400> SEQUENCE: 105

Val His Gln Gly Leu Thr Pro Thr Ala Pro Pro Glu Glu Pro Ala Val
1               5                   10                  15

Asp Leu Leu Lys Asn Tyr Met His Leu Gly Lys Gln Gln Arg Glu Ser
            20                  25                  30

Arg Gly Lys Pro Tyr Lys Glu Val Thr Glu Asp Leu Leu His Leu Asn
        35                  40                  45
```

Ser Leu Phe Gly Gly Asp Gln
    50                  55

<210> SEQ ID NO 106
<211> LENGTH: 55
<212> TYPE: PRT
<213> ORGANISM: Human immunodeficiency virus type 2

<400> SEQUENCE: 106

Met His Gln Gly Leu Thr Pro Thr Ala Pro Pro Glu Asp Pro Ala Val
1               5                   10                  15

Asp Leu Leu Lys Asn Tyr Met Gln Leu Gly Lys Gln Gln Arg Glu Ser
            20                  25                  30

Lys Arg Lys Pro Tyr Lys Glu Val Ala Glu Asp Leu Leu His Leu Asn
        35                  40                  45

Ser Leu Phe Gly Glu Asp Gln
    50                  55

<210> SEQ ID NO 107
<211> LENGTH: 55
<212> TYPE: PRT
<213> ORGANISM: Human immunodeficiency virus type 2

<400> SEQUENCE: 107

Met Pro Gln Gly Leu Thr Pro Thr Ala Pro Pro Glu Asp Pro Ala Val
1               5                   10                  15

Asp Leu Leu Lys Asn Tyr Met Lys Val Gly Arg Arg Gln Arg Glu Asn
            20                  25                  30

Arg Glu Arg Pro Tyr Lys Glu Val Thr Glu Asp Leu Leu His Leu Asn
        35                  40                  45

Ser Leu Phe Gly Glu Asp Gln
    50                  55

<210> SEQ ID NO 108
<211> LENGTH: 73
<212> TYPE: PRT
<213> ORGANISM: Human immunodeficiency virus type 2

<400> SEQUENCE: 108

Ala Pro Gln Gly Ile Val Pro Ser Ala Pro Pro Met Asn Pro Ala Phe
1               5                   10                  15

Gly Met Thr Pro Gln Gly Ala Ile Pro Ser Ala Pro Pro Ala Asp Pro
            20                  25                  30

Ala Glu Glu Met Leu Lys Asn Tyr Met Gln Leu Gly Lys Lys Gln Lys
        35                  40                  45

Glu Asn Arg Glu Arg Pro Tyr Lys Glu Val Thr Glu Asp Leu Leu His
    50                  55                  60

Leu Asn Ser Leu Phe Gly Glu Asp Gln
65                  70

<210> SEQ ID NO 109
<211> LENGTH: 73
<212> TYPE: PRT
<213> ORGANISM: Human immunodeficiency virus type 2

<400> SEQUENCE: 109

Val Pro Gln Gly Val Thr Pro Ser Ala Pro Pro Met Asp Pro Ala Glu
1               5                   10                  15

Gly Met Thr Pro Arg Gly Ala Thr Pro Ser Ala Pro Pro Ala Asp Pro
            20                  25                  30

```
Ala Val Glu Met Leu Lys Ser Tyr Met Lys Met Gly Arg Gln Gln Arg
            35                  40                  45

Glu Ser Arg Glu Arg Pro Tyr Lys Glu Val Thr Glu Asp Leu Leu His
    50                  55                  60

Leu Asn Ser Leu Phe Gly Glu Asp Gln
65                  70
```

<210> SEQ ID NO 110
<211> LENGTH: 73
<212> TYPE: PRT
<213> ORGANISM: Human immunodeficiency virus type 2

<400> SEQUENCE: 110

```
Val Pro Gln Gly Val Thr Pro Ser Ala Pro Pro Met Asn Pro Ala Glu
1               5                   10                  15

Gly Met Thr Pro Arg Gly Ala Thr Pro Ser Ala Pro Pro Ala Asp Pro
            20                  25                  30

Ala Val Glu Met Leu Lys Ser Tyr Met Gln Met Gly Arg Gln Gln Arg
            35                  40                  45

Glu Ser Arg Glu Arg Pro Tyr Lys Glu Val Thr Glu Asp Leu Leu His
    50                  55                  60

Leu Asn Ser Leu Phe Gly Glu Asp Gln
65                  70
```

<210> SEQ ID NO 111
<211> LENGTH: 73
<212> TYPE: PRT
<213> ORGANISM: Human immunodeficiency virus type 2

<400> SEQUENCE: 111

```
Ala Pro Gln Gly Ile Leu Pro Ser Ala Pro Met Asn Pro Ala Glu
1               5                   10                  15

Asn Met Thr Pro Gln Gly Ala Met Pro Ser Ala Pro Pro Ala Asp Pro
            20                  25                  30

Ala Val Glu Met Leu Lys Asp Tyr Met Gln Leu Gly Arg Lys Gln Lys
            35                  40                  45

Gly Gly Arg Glu Lys Pro Tyr Lys Glu Val Thr Glu Asp Leu Leu His
    50                  55                  60

Leu Asn Ser Leu Phe Gly Glu Asp Gln
65                  70
```

<210> SEQ ID NO 112
<211> LENGTH: 55
<212> TYPE: PRT
<213> ORGANISM: Human immunodeficiency virus type 2
<220> FEATURE:
<221> NAME/KEY: misc_feature
<222> LOCATION: (43)..(43)
<223> OTHER INFORMATION: Xaa can be any naturally occurring amino acid

<400> SEQUENCE: 112

```
Val Pro Gln Gly Leu Thr Pro Ser Ala Pro Pro Met Asp Pro Ala Val
1               5                   10                  15

Asp Leu Leu Lys Asn Tyr Met Gln Leu Gly Arg Lys Lys Glu Gln
            20                  25                  30

Arg Asn Lys Pro Tyr Lys Glu Val Thr Glu Xaa Leu Leu His Leu Ser
        35                  40                  45

Ser Leu Phe Gly Asp Asp Gln
    50                  55
```

<210> SEQ ID NO 113
<211> LENGTH: 69
<212> TYPE: PRT
<213> ORGANISM: Human immunodeficiency virus type 2

<400> SEQUENCE: 113

Val Pro Gln Gly Leu Thr Pro Thr Ala Pro Pro Ala Glu Pro Ala Val
1               5                   10                  15

Asp Leu Leu Thr Pro Thr Ala Pro Ala Asp Pro Ala Val Asp Leu
            20                  25                  30

Leu Lys Ser Tyr Met Gln Gln Gly Lys Lys Gln Lys Glu Asn Arg Glu
        35                  40                  45

Arg Pro Tyr Lys Glu Val Thr Glu Asp Leu Leu His Leu Asn Ser Leu
    50                  55                  60

Phe Gly Asn Asp Gln
65

<210> SEQ ID NO 114
<211> LENGTH: 73
<212> TYPE: PRT
<213> ORGANISM: Human immunodeficiency virus type 2

<400> SEQUENCE: 114

Val Pro Gln Glu Ile Val Pro Ser Ala Pro Pro Met Asn Thr Ala Glu
1               5                   10                  15

Gly Lys Thr His Gln Gly Ala Ile Pro Ser Ala Pro Pro Ala Asp Pro
            20                  25                  30

Ala Val Glu Met Leu Lys Ser Tyr Met Gln Leu Gly Lys Gln Gln Arg
        35                  40                  45

Glu Lys Gln Gly Arg Pro Tyr Lys Glu Val Thr Glu Asp Leu Leu His
    50                  55                  60

Leu Asn Ser Leu Phe Gly Glu Asp Gln
65                  70

<210> SEQ ID NO 115
<211> LENGTH: 53
<212> TYPE: PRT
<213> ORGANISM: Human immunodeficiency virus type 2

<400> SEQUENCE: 115

Thr Thr Ser Leu Thr Pro Ser Ala Pro Pro Asp Pro Ala Ala Arg Ile
1               5                   10                  15

Val Lys Glu Tyr Leu Glu Lys Ala Gln Arg Glu Lys Thr Arg Arg Ser
            20                  25                  30

Arg Pro Tyr Lys Glu Val Thr Glu Asp Leu Leu His Leu Asn Ser Leu
        35                  40                  45

Phe Gly Glu Asp Gln
    50

<210> SEQ ID NO 116
<211> LENGTH: 109
<212> TYPE: PRT
<213> ORGANISM: Human immunodeficiency virus type 2

<400> SEQUENCE: 116

Phe Leu Ile Arg Gln Leu Ile Arg Leu Leu Thr Trp Leu Phe Ser Asn
1               5                   10                  15

Cys Arg Thr Leu Leu Ser Arg Val Tyr Gln Ile Leu Gln Pro Ile Leu

```
                20                  25                  30
Gln Arg Leu Ser Ala Thr Leu Gln Arg Ile Arg Glu Val Leu Arg Thr
            35                  40                  45
Glu Leu Thr Tyr Leu Gln Tyr Gly Trp Ser Tyr Phe His Glu Ala Val
        50                  55                  60
Gln Ala Val Trp Arg Ser Ala Thr Glu Thr Leu Ala Gly Ala Trp Gly
65                  70                  75                  80
Asp Leu Trp Glu Thr Leu Arg Arg Gly Gly Arg Trp Ile Leu Ala Ile
                85                  90                  95
Pro Arg Arg Ile Arg Gln Gly Leu Glu Leu Thr Leu Leu
            100                 105

<210> SEQ ID NO 117
<211> LENGTH: 109
<212> TYPE: PRT
<213> ORGANISM: Human immunodeficiency virus type 2

<400> SEQUENCE: 117

Phe Leu Ile Arg Leu Leu Ile Arg Leu Leu Ile Gly Leu Tyr Asn Ile
1               5                   10                  15
Cys Arg Thr Leu Ile Ser Lys Ser Phe Gln Thr Leu Gln Pro Ile Ser
                20                  25                  30
Gln Gly Leu Gln Arg Ala Leu Thr Ala Ile Arg Asp Trp Leu Arg Pro
            35                  40                  45
Gly Ala Ala Tyr Leu Gln Tyr Gly Cys Glu Trp Ile Gln Glu Ala Leu
        50                  55                  60
Gln Ala Phe Ala Arg Ala Thr Arg Glu Thr Leu Thr Ser Val Trp Arg
65                  70                  75                  80
Asn Phe Cys Gly Thr Met Gly Gln Ile Gly Arg Gly Ile Leu Ala Ile
                85                  90                  95
Pro Arg Arg Ile Arg Gln Gly Ala Glu Leu Ala Leu Leu
            100                 105

<210> SEQ ID NO 118
<211> LENGTH: 105
<212> TYPE: PRT
<213> ORGANISM: Human immunodeficiency virus type 2

<400> SEQUENCE: 118

Leu Leu Ile His Leu Leu Thr Arg Leu Leu Thr Gly Leu Tyr Ser Ile
1               5                   10                  15
Cys Arg Asp Leu Leu Ser Ala Asn Ser Pro Thr Arg Leu Ile Ser
                20                  25                  30
Gln Asn Leu Thr Ala Ile Arg Asp Trp Leu Arg Leu Lys Ala Ala Tyr
            35                  40                  45
Leu Gln Tyr Gly Cys Glu Trp Ile Gln Glu Ala Phe Gln Ala Ile Ala
        50                  55                  60
Arg Thr Ala Arg Glu Thr Leu Ala Gly Ala Trp Arg Gly Leu Cys Lys
65                  70                  75                  80
Ala Val Gln Arg Ile Gly Arg Gly Ile Leu Ala Val Pro Arg Arg Ile
                85                  90                  95
Arg Gln Gly Ala Glu Ile Ala Leu Leu
            100                 105

<210> SEQ ID NO 119
<211> LENGTH: 105
<212> TYPE: PRT
```

<213> ORGANISM: Human immunodeficiency virus type 2

<400> SEQUENCE: 119

Phe Leu Ile His Leu Leu Thr Arg Leu Leu Ile G

Arg Gln Gly Ala Glu Ile Ala Leu Leu
            100                 105

<210> SEQ ID NO 122
<211> LENGTH: 109
<212> TYPE: PRT
<213> ORGANISM: Human immunodeficiency virus type 2

<400> SEQUENCE: 122

Phe Leu Ile Arg Leu Leu Ile Arg Leu Leu Ile Gly Leu Tyr Asn Ile
1               5                   10                  15

Cys Arg Asp Leu Leu Ser Arg Ser Ser Leu Ile Leu Gln Pro Ile Leu
            20                  25                  30

Gln Ser Leu Gln Arg Ala Leu Thr Ala Ile Arg Asp Trp Leu Arg Leu
        35                  40                  45

Glu Ala Ala Tyr Leu Gln Tyr Gly Cys Glu Trp Ile Gln Glu Ala Leu
    50                  55                  60

Gln Ala Leu Thr Arg Ala Thr Arg Glu Thr Leu Ala Gly Ala Trp Arg
65                  70                  75                  80

Asn Leu Trp Gly Ala Leu Gln Arg Ile Gly Arg Gly Ile Leu Ala Val
                85                  90                  95

Pro Arg Arg Ile Arg Gln Gly Ala Glu Leu Ala Leu Leu
            100                 105

<210> SEQ ID NO 123
<211> LENGTH: 102
<212> TYPE: PRT
<213> ORGANISM: Human immunodeficiency virus type 2

<400> SEQUENCE: 123

Phe Leu Ile Arg Leu Leu Ile Arg Leu Leu Thr Arg Leu Tyr Asn Ser
1               5                   10                  15

Cys Arg Asp Leu Leu Ser Arg Ser Phe Leu Thr Leu Gln Pro Ile Phe
            20                  25                  30

Gln Asn Leu Arg Asp Trp Leu Arg Leu Arg Thr Ala Phe Leu Gln Tyr
        35                  40                  45

Gly Arg Gln Trp Ile Gln Glu Ala Phe Gln Ala Phe Ala Arg Ala Thr
    50                  55                  60

Arg Glu Thr Leu Thr Ser Ala Cys Arg Gly Leu Trp Arg Thr Leu Asp
65                  70                  75                  80

Asn Phe Gly Arg Gly Ile Leu Ser Ile Pro Arg Arg Ile Arg Gln Gly
                85                  90                  95

Ala Glu Ile Ala Leu Leu
            100

<210> SEQ ID NO 124
<211> LENGTH: 109
<212> TYPE: PRT
<213> ORGANISM: Human immunodeficiency virus type 2

<400> SEQUENCE: 124

Phe Leu Ile Arg Gln Leu Ile Arg Leu Leu Asn Arg Leu Tyr Asn Ile
1               5                   10                  15

Cys Arg Asp Leu Leu Ser Arg Ser Phe Gln Thr Leu Gln Leu Ile Ser
            20                  25                  30

Gln Ser Leu Arg Arg Ala Leu Thr Ala Val Arg Asp Trp Leu Arg Phe
        35                  40                  45

```
Asn Thr Ala Tyr Leu Gln Tyr Gly Gly Glu Trp Ile Gln Glu Ala Phe
 50                  55                  60

Arg Ala Phe Ala Arg Ala Thr Gly Glu Thr Leu Thr Asn Ala Trp Arg
 65                  70                  75                  80

Gly Phe Trp Gly Thr Leu Gly Gln Ile Gly Arg Gly Ile Leu Ala Val
                 85                  90                  95

Pro Arg Arg Ile Arg Gln Gly Ala Glu Ile Ala Leu Leu
            100                 105
```

<210> SEQ ID NO 125
<211> LENGTH: 102
<212> TYPE: PRT
<213> ORGANISM: Human immunodeficiency virus type 2

<400> SEQUENCE: 125

```
Phe Leu Ile Arg Gln Leu Ile Arg Leu Leu Thr Arg Leu Tyr Ser Ile
 1               5                  10                  15

Cys Arg Asp Leu Leu Ser Arg Ser Phe Leu Thr Leu Gln Leu Ile Tyr
                20                  25                  30

Gln Asn Leu Arg Asp Trp Leu Arg Leu Arg Thr Ala Phe Leu Gln Tyr
            35                  40                  45

Gly Cys Glu Trp Ile Gln Glu Ala Phe Gln Ala Ala Arg Ala Thr
 50                  55                  60

Arg Glu Thr Leu Ala Gly Ala Cys Arg Gly Leu Trp Arg Val Leu Glu
 65                  70                  75                  80

Arg Ile Gly Arg Gly Ile Leu Ala Val Pro Arg Arg Ile Arg Gln Gly
                 85                  90                  95

Ala Glu Ile Ala Leu Leu
            100
```

<210> SEQ ID NO 126
<211> LENGTH: 98
<212> TYPE: PRT
<213> ORGANISM: Human immunodeficiency virus type 2

<400> SEQUENCE: 126

```
Phe Leu Ile Arg Leu Leu Ile Arg Leu Leu Thr Arg Leu Tyr Asn Ser
 1               5                  10                  15

Cys Arg Asp Leu Leu Ser Arg Leu Tyr Leu Ile Leu Gln Pro Leu Arg
                20                  25                  30

Asp Trp Leu Arg Leu Lys Ala Ala Tyr Leu Gln Tyr Gly Cys Glu Trp
            35                  40                  45

Ile Gln Glu Ala Phe Gln Ala Leu Ala Arg Val Thr Arg Glu Thr Leu
 50                  55                  60

Thr Ser Ala Gly Arg Ser Leu Trp Gly Ala Leu Gly Arg Ile Gly Arg
 65                  70                  75                  80

Gly Ile Leu Ala Val Pro Arg Arg Ile Arg Gln Gly Ala Glu Ile Ala
                 85                  90                  95

Leu Leu
```

<210> SEQ ID NO 127
<211> LENGTH: 98
<212> TYPE: PRT
<213> ORGANISM: Human immunodeficiency virus type 2

<400> SEQUENCE: 127

```
Phe Pro Ile Arg Gln Leu Arg Asp Leu Leu Ile Trp Leu Tyr Ser Gly
 1               5                  10                  15
```

```
Cys Arg Thr Leu Leu Ser Lys Thr Phe Gln Thr Leu Gln Pro Val Leu
            20                  25                  30

Gln Pro Leu Arg Leu Pro Pro Ala Tyr Leu Arg Tyr Gly Ile Ser Trp
        35                  40                  45

Phe Gln Glu Ala Ile Gln Ala Ala Arg Ala Ala Gly Glu Thr Leu
 50                  55                  60

Ala Ser Ala Ala Arg Thr Ser Trp Gly Val Leu Arg Ala Ala Gly
 65                  70                  75                  80

Glu Ile Ile Ala Ile Pro Arg Arg Ile Arg Gln Gly Ala Glu Leu Ala
                85                  90                  95

Leu Leu

<210> SEQ ID NO 128
<211> LENGTH: 101
<212> TYPE: PRT
<213> ORGANISM: Human immunodeficiency virus type 2

<400> SEQUENCE: 128

Phe Leu Leu Arg Gln Leu Arg Asn Leu Leu Ile Trp Leu Tyr Asn Gly
 1               5                  10                  15

Cys Arg Thr Leu Leu Leu Lys Thr Phe Gln Ile Leu His Gln Ile Ser
            20                  25                  30

Thr Asn Leu Gln Pro Leu Arg Leu Pro Val Ala Tyr Leu Gln Tyr Gly
        35                  40                  45

Ile Ser Trp Phe Gln Glu Ala Leu Arg Ala Ala Arg Ala Thr Gly
 50                  55                  60

Glu Thr Leu Ala Ser Ala Gly Glu Thr Leu Trp Gln Ala Leu Arg Arg
 65                  70                  75                  80

Ala Ala Arg Ala Ile Ile Ala Ile Pro Arg Arg Ile Arg Gln Gly Leu
                85                  90                  95

Glu Leu Thr Leu Leu
            100

<210> SEQ ID NO 129
<211> LENGTH: 109
<212> TYPE: PRT
<213> ORGANISM: Human immunodeficiency virus type 2
<220> FEATURE:
<221> NAME/KEY: misc_feature
<222> LOCATION: (3)..(3)
<223> OTHER INFORMATION: Xaa can be any naturally occurring amino acid
<220> FEATURE:
<221> NAME/KEY: misc_feature
<222> LOCATION: (25)..(25)
<223> OTHER INFORMATION: Xaa can be any naturally occurring amino acid

<400> SEQUENCE: 129

Phe Leu Xaa Arg Gln Leu Gly Asn Leu Leu Thr Trp Leu Tyr Ser Asn
 1               5                  10                  15

Cys Arg Ala Leu Leu Ser Arg Ile Xaa Gln Thr Leu Gln Pro Leu Phe
            20                  25                  30

Gln Arg Ile Ser Arg Thr Leu Gln Ala Ile Arg Glu His Leu Arg Leu
        35                  40                  45

Glu Ala Ala Tyr Phe Ser Tyr Gly Phe Arg Trp Leu Gln Glu Ala Cys
 50                  55                  60

Thr Ala Ala Thr Arg Ala Ala Gln Glu Thr Leu Thr Ser Thr Trp Arg
 65                  70                  75                  80

Ala Leu Trp Lys Thr Leu Gly Arg Val Gly Arg Gly Ile Leu Ala Ile
```

```
                 85                  90                  95

Pro Arg Arg Ile Arg Gln Gly Leu Glu Leu Thr Leu Leu
            100                 105

<210> SEQ ID NO 130
<211> LENGTH: 102
<212> TYPE: PRT
<213> ORGANISM: Human immunodeficiency virus type 2

<400> SEQUENCE: 130

Phe Leu Ile His Gln Leu Ile Arg Leu Leu Thr Trp Leu Tyr Ser Ser
1               5                   10                  15

Cys Arg Asp Leu Leu Ser Arg Ile Cys Gln Ser Leu Gln Pro Leu Phe
            20                  25                  30

Gln Ser Ile Arg Glu Arg Leu His Leu Glu Ile Ala Tyr Leu Gln Tyr
        35                  40                  45

Gly Trp Gln Tyr Phe Lys Glu Ala Phe Gln Ala Phe Gly Lys Ala Ala
    50                  55                  60

Arg Glu Thr Leu Ser Arg Thr Gly Arg Glu Leu Trp Glu Thr Leu Gly
65                  70                  75                  80

Arg Val Gly Arg Trp Leu Arg Ala Ile Pro Arg Arg Ile Arg Gln Gly
                85                  90                  95

Phe Glu Leu Ala Leu Leu
            100

<210> SEQ ID NO 131
<211> LENGTH: 98
<212> TYPE: PRT
<213> ORGANISM: Human immunodeficiency virus type 2

<400> SEQUENCE: 131

Phe Leu Ile Arg Gln Leu Arg Asn Leu Leu Ile Trp Leu Tyr Asp Gly
1               5                   10                  15

Cys Arg Thr Leu Leu Leu Lys Thr Phe Gln Thr Leu Gln Pro Ala Leu
            20                  25                  30

Gln Pro Leu Arg Leu Leu Phe Ala Tyr Leu Gln Tyr Gly Ile Gly Trp
        35                  40                  45

Phe Gln Glu Ala Val Gln Ala Ala Gly Ala Thr Gly Glu Thr Leu
    50                  55                  60

Ala Ser Thr Gly Arg Thr Leu Trp Glu Ala Leu Arg Arg Thr Ala Arg
65                  70                  75                  80

Gly Ile Ile Ala Val Pro Arg Arg Ile Arg Gln Gly Leu Glu Leu Ala
                85                  90                  95

Leu Leu

<210> SEQ ID NO 132
<211> LENGTH: 92
<212> TYPE: PRT
<213> ORGANISM: Human immunodeficiency virus type 2

<400> SEQUENCE: 132

Phe Leu Ile Arg Gln Leu Ile Arg Leu Leu Thr Trp Leu Phe Ser Asn
1               5                   10                  15

Cys Arg Thr Leu Leu Ser Arg Val Tyr Gln Ile Leu Gln Pro Ile Phe
            20                  25                  30

Gln Arg Leu Ser Ala Thr Leu Gln Arg Ile Arg Glu Val Leu Arg Thr
        35                  40                  45
```

```
Glu Leu Thr Tyr Leu Gln Tyr Gly Trp Ser Tyr Phe His Glu Ala Val
 50                  55                  60

Gln Ala Val Trp Arg Ser Ala Thr Glu Thr Leu Ala Gly Ala Trp Gly
 65                  70                  75                  80

Asp Leu Trp Glu Thr Leu Arg Arg Gly Gly Arg Trp
                 85                  90

<210> SEQ ID NO 133
<211> LENGTH: 92
<212> TYPE: PRT
<213> ORGANISM: Human immunodeficiency virus type 2

<400> SEQUENCE: 133

Phe Leu Ile Arg Gln Leu Ile Arg Leu Leu Thr Trp Leu Phe Ser Asn
 1               5                  10                  15

Cys Arg Thr Leu Leu Ser Arg Val Tyr Gln Ile Leu Gln Pro Met Phe
                 20                  25                  30

Gln Gly Leu Ser Ala Thr Leu Gln Arg Ile Arg Glu Val Leu Arg Thr
             35                  40                  45

Glu Leu Thr Tyr Leu Gln Tyr Gly Trp Ser Tyr Phe His Glu Ala Val
 50                  55                  60

Gln Ala Val Trp Arg Ala Ala Thr Glu Thr Leu Ala Gly Ala Trp Gly
 65                  70                  75                  80

Asp Leu Trp Glu Thr Leu Arg Arg Gly Gly Arg Trp
                 85                  90

<210> SEQ ID NO 134
<211> LENGTH: 92
<212> TYPE: PRT
<213> ORGANISM: Human immunodeficiency virus type 2

<400> SEQUENCE: 134

Phe Leu Ile Arg Gln Leu Ile Arg Leu Leu Thr Trp Leu Phe Ser Asn
 1               5                  10                  15

Cys Arg Thr Leu Leu Ser Arg Val Tyr Gln Ile Leu Gln Pro Ile Phe
                 20                  25                  30

Gln Gly Leu Ser Ala Thr Leu Gln Arg Ile Arg Glu Val Leu Arg Thr
             35                  40                  45

Glu Leu Thr Tyr Leu Gln Tyr Gly Trp Ser Tyr Phe His Glu Ala Val
 50                  55                  60

Gln Ala Val Trp Arg Ala Ala Thr Glu Thr Leu Ala Gly Ala Trp Gly
 65                  70                  75                  80

Asp Leu Trp Glu Thr Leu Arg Arg Gly Gly Arg Trp
                 85                  90

<210> SEQ ID NO 135
<211> LENGTH: 109
<212> TYPE: PRT
<213> ORGANISM: Human immunodeficiency virus type 2

<400> SEQUENCE: 135

Phe Leu Ile Arg Gln Leu Ile Arg Leu Leu Thr Trp Leu Phe Ser Asn
 1               5                  10                  15

Cys Arg Thr Leu Leu Ser Arg Ala Tyr Gln Ile Leu Gln Pro Ile Phe
                 20                  25                  30

Gln Arg Phe Ser Thr Thr Leu Gln Arg Val Arg Glu Val Leu Arg Thr
             35                  40                  45

Glu Leu Thr Tyr Leu Gln Tyr Gly Trp Ser Tyr Phe Gln Glu Ala Val
```

```
                    50                  55                  60
Gln Val Ala Trp Arg Ser Ala Thr Glu Thr Leu Ala Gly Ala Trp Gly
 65                  70                  75                  80

Asp Leu Trp Glu Thr Leu Gly Arg Val Gly Arg Trp Ile Leu Ala Ile
                 85                  90                  95

Pro Arg Arg Ile Arg Gln Glu Leu Glu Leu Thr Leu Leu
            100                 105
```

<210> SEQ ID NO 136
<211> LENGTH: 109
<212> TYPE: PRT
<213> ORGANISM: Human immunodeficiency virus type 2

<400> SEQUENCE: 136

```
Phe Leu Ile Arg Gln Leu Ile Arg Ile Leu Thr Trp Leu Tyr Asn Asn
  1               5                  10                  15

Leu Thr Arg Leu Ala Ser Arg Ala Tyr Gln Asn Leu Gln Gln Leu Cys
                 20                  25                  30

Gln Arg Leu Ser Glu Ile Ser Gln Pro Ile Arg Glu Leu Val Arg Arg
             35                  40                  45

Glu Ala Gly Tyr Ile Arg Tyr Gly Trp Asn Tyr Phe Ile Glu Ala Cys
         50                  55                  60

Gln Glu Ala Trp Arg Ser Ala Gln Glu Ala Ile Val Gly Ala Trp Gly
 65                  70                  75                  80

Leu Ile Trp Glu Thr Leu Gly Arg Val Gly Arg Gly Ile Ala Ala Ile
                 85                  90                  95

Pro Arg Arg Ile Arg Gln Gly Leu Glu Leu Met Leu Asn
            100                 105
```

<210> SEQ ID NO 137
<211> LENGTH: 109
<212> TYPE: PRT
<213> ORGANISM: Human immunodeficiency virus type 2

<400> SEQUENCE: 137

```
Phe Leu Ile Arg Gln Leu Ile Arg Leu Leu Thr Trp Leu Phe Ser Ser
  1               5                  10                  15

Cys Arg Asp Trp Leu Leu Arg Ile Tyr Gln Ile Leu Gln Pro Val Leu
                 20                  25                  30

Gln Gly Leu Ser Arg Thr Leu Gln Arg Val Arg Glu Val Ile Arg Ile
             35                  40                  45

Glu Ile Thr Tyr Leu Gln Tyr Gly Trp Ser Tyr Phe Gln Glu Ala Ala
         50                  55                  60

Gln Ala Trp Trp Lys Phe Ala Arg Glu Thr Leu Ala Ser Ala Trp Arg
 65                  70                  75                  80

Asp Ile Trp Glu Thr Leu Gly Arg Val Gly Arg Gly Ile Leu Ala Ile
                 85                  90                  95

Pro Arg Arg Val Arg Gln Gly Leu Glu Leu Ala Leu Leu
            100                 105
```

<210> SEQ ID NO 138
<211> LENGTH: 4
<212> TYPE: PRT
<213> ORGANISM: Artificial Sequence
<220> FEATURE:
<223> OTHER INFORMATION: Peptide linker

<400> SEQUENCE: 138

```
Gly Gly Gly Cys
1

<210> SEQ ID NO 139
<211> LENGTH: 29
<212> TYPE: DNA
<213> ORGANISM: Human immunodeficiency virus type 1

<400> SEQUENCE: 139
aaaaatctct agcagtggcg cccgaacag                                29

<210> SEQ ID NO 140
<211> LENGTH: 29
<212> TYPE: DNA
<213> ORGANISM: Human immunodeficiency virus type 1

<400> SEQUENCE: 140
aagcactcaa ggcaagcttt attgaggct                                29

<210> SEQ ID NO 141
<211> LENGTH: 46
<212> TYPE: PRT
<213> ORGANISM: Human immunodeficiency virus type 1

<400> SEQUENCE: 141

Ser Arg Pro Glu Pro Thr Ala Pro Pro Ala Glu Ser Phe Arg Phe Glu
1               5                   10                  15

Glu Thr Thr Pro Ala Pro Lys Gln Glu Pro Lys Asp Arg Glu Pro Leu
            20                  25                  30

Thr Ser Leu Lys Ser Leu Phe Gly Ser Asp Pro Leu Ser Gln
        35                  40                  45
```